United States Patent
Pecker et al.

(10) Patent No.: US 12,134,638 B2
(45) Date of Patent: Nov. 5, 2024

(54) SIRPALPHA-4-1BBL VARIANT FUSION PROTEIN AND METHODS OF USE THEREOF

(71) Applicant: KAHR Medical Ltd., Jerusalem (IL)

(72) Inventors: Iris Pecker, Rishon LeZion (IL); Itai Bloch, Moshav Ramot Naftali (IL)

(73) Assignee: KAHR Medical Ltd., Modiln Makabim-ReUt (IL)

( * ) Notice: Subject to any disclaimer, the term of this patent is extended or adjusted under 35 U.S.C. 154(b) by 0 days.

(21) Appl. No.: 17/258,170

(22) PCT Filed: Jul. 11, 2019

(86) PCT No.: PCT/IL2019/050783
§ 371 (c)(1),
(2) Date: Jan. 6, 2021

(87) PCT Pub. No.: WO2020/012486
PCT Pub. Date: Jan. 16, 2020

(65) Prior Publication Data
US 2021/0214417 A1    Jul. 15, 2021

Related U.S. Application Data

(60) Provisional application No. 62/696,362, filed on Jul. 11, 2018.

(51) Int. Cl.
*C07K 14/705* (2006.01)
*A61K 38/00* (2006.01)
*A61P 35/00* (2006.01)
*A61K 39/00* (2006.01)

(52) U.S. Cl.
CPC ........ *C07K 14/70596* (2013.01); *A61P 35/00* (2018.01); *C07K 14/70578* (2013.01); *A61K 38/00* (2013.01); *A61K 39/00* (2013.01); *C07K 2319/21* (2013.01); *C07K 2319/50* (2013.01)

(58) Field of Classification Search
CPC .......... C07K 14/70596; C07K 2319/50; C07K 2319/21; C07K 14/70578; C07K 2319/00; C07K 2319/33; C07K 2319/74; C07K 14/705; A61K 38/00; A61P 35/00; C12N 15/62
See application file for complete search history.

(56) References Cited

U.S. PATENT DOCUMENTS

| | | | |
|---|---|---|---|
| 5,287,386 A | 2/1994 | Wade et al. | |
| 5,674,704 A | 10/1997 | Goodwin et al. | |
| 6,046,048 A | 4/2000 | Ashkenazi et al. | |
| 6,740,739 B1 | 5/2004 | Ashkenazi et al. | |
| 7,142,018 B2 | 11/2006 | Masleid et al. | |
| 7,279,925 B1 | 10/2007 | Richmond et al. | |
| 7,569,663 B2 | 8/2009 | Tykocinski et al. | |
| 8,039,437 B2 | 10/2011 | Tykocinski et al. | |
| 8,216,805 B2 | 7/2012 | Carter et al. | |
| 9,562,087 B2 | 2/2017 | Ring et al. | |
| 10,040,841 B2 | 8/2018 | Dranitzki Elhalel et al. | |
| 10,183,060 B2 | 1/2019 | Schreiber et al. | |
| 10,464,981 B2 | 11/2019 | Amann et al. | |
| 11,130,796 B2 * | 9/2021 | Shani ................... | C12N 5/0638 |
| 11,702,458 B2 | 7/2023 | Tykocinski | |
| 2003/0216546 A1 | 11/2003 | Tykocinski et al. | |
| 2007/0036783 A1 | 2/2007 | Humeau et al. | |
| 2007/0110746 A1 | 5/2007 | Chung | |
| 2012/0189625 A1 | 7/2012 | Wang et al. | |
| 2013/0039911 A1 | 2/2013 | Bedi et al. | |
| 2013/0094307 A1 | 4/2013 | Cheng | |
| 2013/0287802 A1 | 10/2013 | Govindappa et al. | |
| 2015/0183881 A1 | 7/2015 | Bedi et al. | |
| 2015/0353642 A1 | 12/2015 | Tykocinski | |
| 2015/0376260 A1 | 12/2015 | Elhalel et al. | |
| 2016/0039903 A1 | 2/2016 | Ring et al. | |
| 2016/0200833 A1 * | 7/2016 | Amann ............... | C07K 16/3007 |
| | | | 435/254.2 |
| 2017/0095531 A1 * | 4/2017 | Schreiber ............... | C07K 14/00 |
| 2017/0107270 A1 * | 4/2017 | Pons ...................... | A61P 31/04 |
| 2017/0327588 A1 | 11/2017 | Baca et al. | |
| 2019/0016782 A1 | 1/2019 | Dranitzki Elhalel et al. | |
| 2019/0151413 A1 | 5/2019 | Schreiber et al. | |
| 2019/0315834 A1 | 10/2019 | Shani | |
| 2019/0330304 A1 | 10/2019 | Shani et al. | |
| 2019/0352371 A1 | 11/2019 | Tykocinski et al. | |

(Continued)

FOREIGN PATENT DOCUMENTS

| | | |
|---|---|---|
| CN | 104968364 | 10/2015 |
| CN | 107001485 | 8/2017 |

(Continued)

OTHER PUBLICATIONS

US_20170095531_ABSS sequence comparison findings 102; generated by examiner on May 17, 2022 using the ABSS application: http://abss.uspto.gov/abss4examiners/. (Year: 2022).*
US_20160200833_ABSS_Sequence_Comparisons; generated by examiner on May 17, 2022 using the ABSS application: http://abss.uspto.gov/abss4examiners/. (Year: 2022).*
WO_2014121093_ABSS_Sequence_Comparison; generated by examiner on May 16-17, 2022 using the ABSS application: http://abss.uspto.gov/abss4examiners/. (Year: 2022).*

(Continued)

*Primary Examiner* — Lianko G Garyu
*Assistant Examiner* — John Cronin

(57) ABSTRACT

SIRPalpha-4-1BBL variant fusion proteins are provided. Also provided are isolated polypeptides comprising a SIRPalpha variant. Also provided are polynucleotides and nucleic acid constructs encoding the SIRPalpha-41BBL fusion protein or the isolated polypeptide, host-cells expressing same and methods of use thereof.

10 Claims, 35 Drawing Sheets
(13 of 35 Drawing Sheet(s) Filed in Color)
Specification includes a Sequence Listing.

(56) References Cited

U.S. PATENT DOCUMENTS

| | | | |
|---|---|---|---|
| 2019/0352372 A1* | 11/2019 | Shani | A61K 47/65 |
| 2020/0087377 A1 | 3/2020 | Yue et al. | |
| 2020/0317773 A1 | 10/2020 | Clark et al. | |
| 2021/0284711 A1 | 9/2021 | Pecker et al. | |
| 2021/0301020 A1 | 9/2021 | Yu et al. | |
| 2021/0371500 A1* | 12/2021 | Shani | C07K 14/70575 |
| 2022/0204586 A1 | 6/2022 | Shani et al. | |
| 2023/0048361 A1 | 2/2023 | Muthuswamy et al. | |
| 2023/0048719 A1 | 2/2023 | Muthuswamy et al. | |
| 2023/0220040 A1 | 7/2023 | Shani et al. | |
| 2024/0010700 A1 | 1/2024 | Tykocinski et al. | |
| 2024/0109952 A1 | 4/2024 | Shani | |

FOREIGN PATENT DOCUMENTS

| | | | |
|---|---|---|---|
| CN | 107857819 | | 3/2018 |
| CN | 108350055 | | 7/2018 |
| CN | 110128550 | | 8/2019 |
| JP | 2017-060462 | | 3/2017 |
| RU | 2636342 | | 11/2017 |
| WO | WO 01/049318 | | 7/2001 |
| WO | WO 01/75067 | | 10/2001 |
| WO | WO 01/86003 | | 11/2001 |
| WO | WO 03/046581 | | 6/2003 |
| WO | WO 2005/087797 | | 9/2005 |
| WO | WO 2010/027828 | | 3/2010 |
| WO | WO 2010/070047 | | 6/2010 |
| WO | WO 2011/109789 | | 9/2011 |
| WO | WO 2012/042480 | | 4/2012 |
| WO | WO 2013/064700 | | 5/2013 |
| WO | WO 2013/109752 | | 7/2013 |
| WO | WO 2013/112986 | | 8/2013 |
| WO | WO 2013/144704 | | 10/2013 |
| WO | WO 2014/072534 | | 5/2014 |
| WO | WO 2014/106839 | | 7/2014 |
| WO | WO 2014/121093 | | 8/2014 |
| WO | WO-2014121093 A1 * | 8/2014 | ......... C07K 14/4703 |
| WO | WO 2014/180288 | | 11/2014 |
| WO | WO 2015/148416 | | 10/2015 |
| WO | WO 2016/022994 | | 2/2016 |
| WO | WO 2016/023001 | | 2/2016 |
| WO | WO 2016/024021 | | 2/2016 |
| WO | WO 2016/063233 | | 4/2016 |
| WO | WO 2016/090312 | | 6/2016 |
| WO | WO 2016/139668 | | 9/2016 |
| WO | WO 2016/169261 | | 10/2016 |
| WO | WO 2016/187226 | | 11/2016 |
| WO | WO 2017/012770 | | 1/2017 |
| WO | WO 2017/019846 | | 2/2017 |
| WO | WO 2017/027422 | | 2/2017 |
| WO | WO 2017/059168 | | 4/2017 |
| WO | WO 2017/068192 | | 4/2017 |
| WO | WO 2017/152132 | | 9/2017 |
| WO | WO 2017/181119 | | 10/2017 |
| WO | WO 2017/194641 | | 11/2017 |
| WO | WO 2017/207775 | | 12/2017 |
| WO | WO 2018/006881 | | 1/2018 |
| WO | WO 2018/032793 | | 2/2018 |
| WO | WO 2018/053885 | | 3/2018 |
| WO | WO 2018/085358 | | 5/2018 |
| WO | WO 2018/091580 | | 5/2018 |
| WO | WO 2018/114754 | | 6/2018 |
| WO | WO 2018/127916 | | 7/2018 |
| WO | WO 2018/127916 A9 | | 7/2018 |
| WO | WO 2018/127917 | | 7/2018 |
| WO | WO 2018/127918 | | 7/2018 |
| WO | WO 2018/127918 A9 | | 7/2018 |
| WO | WO 2018/127919 | | 7/2018 |
| WO | WO 2018/127919 A9 | | 7/2018 |
| WO | WO 2019/086499 | | 5/2019 |
| WO | WO 2020/012485 | | 1/2020 |
| WO | WO 2020/012486 | | 1/2020 |
| WO | WO 2020/012485 A9 | | 5/2020 |
| WO | WO 2020/146423 | | 7/2020 |
| WO | WO 2020/242919 | | 12/2020 |
| WO | WO 2021/005599 | | 1/2021 |
| WO | WO 2022/153307 | | 7/2022 |
| WO | WO 2023/119295 | | 6/2023 |

OTHER PUBLICATIONS

U.S. Appl. No. 16/473,631—1_pep_vs_U.S. Appl. No. 17/258,170—13_pep_align; generated by examiner on May 18, 2022 using the ABSS application: http://abss.uspto.gov/abss4examiners/ (Year: 2022).*

U.S. Appl. No. 17/400,179—2_pep_vs_U.S. Appl. No. 17/258,170—13_pep_align; generated by examiner on May 18, 2022 using the ABSS application: http://abss.uspto.gov/abss4examiners/. (Year: 2022).*

Itoh, et al., Optimization of the inter-domain structure of galectin-9 for recombinant production Glycobiology vol. 23 No. 8 pp. 920-925: doi:10.1093/glycob/cwt023. (Year: 2013).*

Chichili et al., 2012, Linkers in the structural biology of protein protein interactions, Protein Science, 22: 153-167 (Year: 2012).*

Supplementary European Search Report and the European Search Opinion Dated Dec. 20, 2021 From the European Patent Office Re. Application No. 21179906.9. (8 Pages).

Notice of Reason(s) for Rejection Dated Sep. 28, 2021 From the Japan Patent Office Re. Application No. 2019-536286 and Its Translation Into English. (11 Pages).

Kornbluth et al. "Multimeric Soluble 4-1BBL as a T Cell Stimulator for Adoptive Immunotherapy", The Journal of Immunology, 198(1) Suppl., May 1, 2017.

Search Report and Written Opinion Dated Mar. 23, 2022 From the Intellectual Property Office of Singapore Re. Application No. 11202013167U. (10 Pages).

Supplementary European Search Report and the European Search Opinion Dated Mar. 23, 2022 From the European Patent Office Re. Application No. 19833260.3. (7 Pages).

Cendrowicz et al. "DSP107 Combines Inhibition of CD47/SIRP Alpha Axis With Activation of 4-1BB to Trigger Anticancer Immunity", Journal of Experimental & Clinical Cancer Research, 41(1): 97-1-97-16, Mar. 14, 2022.

Restriction Official Action Dated Mar. 28, 2022 from US Patent and Trademark Office Re. U.S. Appl. No. 16/475,139. (10 pages).

Supplementary European Search Report and the European Search Opinion Dated Mar. 7, 2022 From the European Patent Office Re. Application No. 19833103.5.(10 Pages).

Official Action Dated Mar. 2, 2022 from US Patent and Trademark Office Re. U.S. Appl. No. 16/475,705. (79 pages).

Uni Prot "Programmed Cell Death Protein 1", Uni Prot/NCBI Accession Q15116, Sequence Updated Apr. 17, 2017, 9 P., Accessed on Line Feb. 23, 2022.

UniProt "Tumor Necrosis Factor Ligand Superfamily Member 9", UniProt/NCBI Accession P41273, 4 P., Accessed Online Feb. 23, 2022, Sequence Updated Feb. 1, 1995.

Search Report and Written Opinion Dated Mar. 23, 2022 From the Intellectual Property Office of Singapore, IPOS Re. Application No. 11202013170R. (10 Pages).

Official Action Dated Jul. 7, 2021 from the US Patent and Trademark Office Re. U.S. Appl. No. 16/475,683. (46 pages).

Examination Report Dated Feb. 25, 2022 From the Intellectual Property Office of Singapore, IPOS Re. Application No. 11201905679S. (6 pages).

Invitation to Pay Additional Fees, Communication Relating to the Results of the Partial International Search Dated Mar. 10, 2022 From the International Searching Authority Re. Application No. PCT/IL2022/050055. (7 Pages).

Notice of Eligibility for Grant Dated Feb. 28, 2022 From the Intellectual Property Office of Singapore, IPOS Re. Application No. 11201905679S. (1 page).

Communication Pursuant to Article 94(3) EPC Dated Oct. 1, 2021 From the European Patent Office Re. Application No. 18736642.2. (7 Pages).

Notice of Reason(s) for Rejection Dated Sep. 28, 2021 From the Japan Patent Office Re. Application No. 2019-536308 and Its Translation Into English. (8 Pages).

(56) References Cited

OTHER PUBLICATIONS

Translation Dated Oct. 1, 2021 of Request for Examination Dated Sep. 8, 2021 From the (Rospatent), Federal Government Institution of Industrial Property of the Federal Service of Intellectual Property, Patents and Trademark of the Russian Federation Re. Application No. 2019124678. (8 Pages).
Translation Dated Oct. 5, 2021 of Request for Examination Dated Sep. 8, 2021 From the Federal Government Institution, Federal Institute of Industrial Property of the Federal Service of Intellectual Property, Patents and Trademarks of the Russian Federation, FIPS Re. Application No. 2019124676. (11 Pages).
Written Opinion Dated Sep. 28, 2021 From the Intellectual Property Office of Singapore Re. Application No. 11201905679S. (9 Pages).
International Preliminary Report on Patentability Dated Jan. 20, 2022 From the International Bureau of WIPO Re. Application No. PCT/IL2020/050762. (8 Pages).
Restriction Official Action Dated Jul. 3, 2019 from US Patent and Trademark Office Re. U.S. Appl. No. 16/475,705. (8 pages).
Amiot et al. "Biology of HLA-G in Cancer: A Candidate Molecule for Therapeutic Intervention?", Cellular and Molecular Life Sciences, 68(3): 417-431, Published Online Nov. 10, 2010.
Anna et al. "First Immunotherapeutic CAR-T Cells Against the Immune Checkpoint Protein HLA-G", Journal for Immuno Therapy of Cancer, 9(3): e001998-1-e001998-14, Mar. 2021.
Blaschitz et al. "Reaction Patterns of Monoclonal Antibodies to HLA-G in Human Tissues and on Cell Lines: A Comparative Study", Human Immunology, 61(11): 1074-1085, Nov. 2000.
Carosella et al. "Beyond the Increasing Complexity of the Immunomodulatory HLA-G Molecule", Blood, 111(10): 4862-4870, Published Online Mar. 11, 2008.
Carosella et al. "HLA-G: An Immune Checkpoint Molecule", Advances in Immunology, 127: 33-144, Published Online May 27, 2015.
Carosella et al. "HLA-G: From Biology to Clinical Benefits", Trends in Immunology, 29(3): 125-132, Available Online Feb. 4, 2008.
Clements et al. "Crystal Structure of HLA-G: A Nonclassical MHC Class I Molecule Expressed at the Fetal-Maternal Interface", Proc. Natl. Acad. Sci. USA, PNAS, 102(9): 3360-3365, Mar. 1, 2005.
Kang et al. "Inhibitory Leukocyte Immunoglobulin-Like Receptors: Immune Checkpoint Proteins and Tumor Sustaining Factors", Cell Cycle, 15(1): 25-40, Jan. 2, 2016.
Katz "Inhibition of Inflammatory Responses by Leukocyte Ig-Like Receptors", Advances in Immunology, 91: 251-272, Jan. 2006.
Lin et al. "Human Leukocyte Antigen-G (HLA-G) Expression in Cancers: Roles in Immune Evasion, Metastasis and Target for Therapy", Molecular Medicine, 21(1): 782-791, Published Online Aug. 24, 2015.
Menier et al. "Characterization of Monoclonal Antibodies Recognizing HLA-G or HLA-E: New Tools to Analyze the Expression of Nonclassical HLA Class I Molecules", Human Immunology, 64(3): 315-326, Mar. 2003.
Shiroishi et al. "Efficient Leukocyte Ig-Like Receptor Signalling and Crystal Structure of Disulfide-Linked HLA-G Dimer", The Journal of Biological Chemistry, 281(15): 10439-10447, Published Online Feb. 2, 2006.
Shiroishi et al. "Human Inhibitory Receptors Ig-Like Transcript 2 (ILT2) and ILT4 Compete With CD8 for MHC Class I Binding and Bind Preferentially to HLA-G", Proc. Natl. Acad. Sci. USA, PNAS, 100(15): 8856-8861, Jul. 22, 2003.
Shiroishi et al. "Structural Basis for Recognition of the Nonclassical MHC Molecule HLA-G by the Leukocyte Ig-Like Receptor B2 (LILRB2 / LIR2 / ILT4 / CD85d)", Proc. Natl. Acad. Sci. USA, PNAS, 103(44): 16412-16417, Oct. 31, 2006.
Yan "HLA-G Expression in Cancers: Potential Role in Diagnosis, Prognosis and Therapy", Endocrine, Metabolic & Immune Disorders - Drug Targets, 11(1): 76-89, Mar. 2011.
Written Opinion Dated Jan. 18, 2022 From the Intellectual Property Office of Singapore, IPOS Re. Application No. 11201905681W. (8 Pages).

Persson et al. "Transforming Growth Factor (TGF-b)-specific Signaling by Chimeric TGF-b Type II Receptor with Intracellular Domain of Activin Type IIB Receptor", Cell Biologt and Metabolism, 272(34): 1187-21194, Aug. 1997.
Interview Summary Dated Aug. 5, 2021 from the US Patent and Trademark Office Re. U.S. Appl. No. 16/027,382. (2 pages).
Kadagidze et al. Targeted Immunotherapy in Oncology, Allergiology and Immunology, 16(4):352, Nov. 2015, Abstract with English Translation.
Prokofieva et al. "Course of Lectures on General Pharmacology: Teaching Aid, Ulyanovsk", Ulyanovsk State University, 155 p. pp. 65-77. 2017, with its Translation into English.
Official Action Dated Jan. 21, 2022 from US Patent and Trademark Office Re. U.S. Appl. No. 16/027,382. (21 pages).
International Search Report and the Written Opinion Dated May 9, 2022 From the International Searching Authority Re. Application No. PCT/IL2022/050055. (19 Pages).
Notice of Reasons for Rejection Dated Apr. 26, 2022 From the Japan Patent Office Re. Application No. 2019-536286 and Its Translation Into English.(12 pages).
Chajut et al. "790 DSP502—A Novel Approach for Targeting TIGIT and PD1 Pathways for Cancer Immunotherapy", Journal for Immunotherapy of Cancer, 9(2): A825-A825, Nov. 30, 2021.
Hung et al. "TIGIT and PD-1 Dual Checkpoint Blockade Enhances Antitumor Immunity and Survival in GBM", OncoImmunology, 7(8): e1466769-1-e1466769-14, May 24, 2018.
Nguyen "Blocking 'Don't Eat Me' Signals CD47 and LILRB2 to Enhance Macrophage-and Granulocyte-Mediated Phagocytosis of Cancer Cells", Thesis, 1-31 P., Jul. 31, 2019.
Zak et al. "Structure of the Complex of Human Programmed Death 1, PD-1, and Its Ligand PD-L1", Structure, 23(12): 2341-2348,Dec. 1, 2015.
Tokuriki et al. "Stability Effects of Mutations and Protein Evolvability", Current Opinion in Structural Biology, 19(5):596-604, Oct. 2009.
Communication Pursuant to Article 94(3) EPC Dated May 9, 2022 From the European Patent Office Re. Application No. 18736642.2. (8 Pages).
English Translation Dated May 9, 2022 of Notice of Reasons for Rejection Dated Apr. 26, 2022 From the Japan Patent Office Re. Application No. 2019-5363308. (4 Pages).
Official Action Dated Sep. 7, 2022 from US Patent and Trademark Office Re. U.S. Appl. No. 16/475,705. (34 pages).
Official Action Dated Aug. 5, 2022 from US Patent and Trademark Office Re. U.S. Appl. No. 16/027,382. (37 pages).
Communication Pursuant to Article 94(3) EPC Dated Jun. 1, 2017 From the European Patent Office Re. Application No. 13827047.5. (4 Pages).
Communication Pursuant to Article 94(3) EPC Dated Feb. 6, 2018 From the European Patent Office Re. Application No. 13827047.5. (5 Pages).
Communication Pursuant to Article 94(3) EPC Dated Sep. 26, 2016 From the European Patent Office Re. Application No. 13827047.5. (3 Pages).
Examination Report Dated Jul. 11, 2017 From the Australian Government, IP Australia Re. Application No. 2013371826.(4 Pages).
Examination Report Dated Mar. 28, 2018 From the Australian Government, IP Australia Re. Application No. 2013371826.(2 Pages).
Final Official Action Dated May 12, 2021 From the US Patent and Trademark Office Re. U.S. Appl. No. 16/027,382. (15 Pages).
International Preliminary Report on Patentability Dated Jul. 16, 2015 From the International Bureau of WIPO Rc. Application No. PCT/IL2013/051098. (14 Pages).
International Preliminary Report on Patentability Dated Jul. 18, 2019 From the International Bureau of WIPO Re. Application No. PCT/IL2018/050014. (7 Pages).
International Preliminary Report on Patentability Dated Jul. 18, 2019 From the International Bureau of WIPO Re. Application No. PCT/IL2018/050015. (7 Pages).
International Preliminary Report on Patentability Dated Jul. 18, 2019 From the International Bureau of WIPO Re. Application No. PCT/IL2018/050016. (7 Pages).

(56) References Cited

OTHER PUBLICATIONS

International Preliminary Report on Patentability Dated Jul. 18, 2019 From the International Bureau of WIPO Re. Application No. PCT/IL2018/050017. (7 Pages).
International Preliminary Report on Patentability Dated Jan. 21, 2021 From the International Bureau of WIPO Re. Application No. PCT/IL2019/050782. (9 Pages).
International Preliminary Report on Patentability Dated Jan. 21, 2021 From the International Bureau of WIPO Re. Application No. PCT/IL2019/050783. (8 Pages).
International Search Report and the Written Opinion Dated Oct. 6, 2020 From the International Searching Authority Re. Application No. PCT/IL2020/050762. (13 Pages).
International Search Report and the Written Opinion Dated Mar. 13, 2018 From the International Searching Authority Re. Application No. PCT/IL2018/050015. (11 Pages).
International Search Report and the Written Opinion Dated Mar. 13, 2018 From the International Searching Authority Re. Application No. PCT/IL2018/050016. (11 Pages).
International Search Report and the Written Opinion Dated May 15, 2014 From the International Searching Authority Re. Application No. PCT/IL2013/051098. (19 Pages).
International Search Report and the Written Opinion Dated Sep. 16, 2019 From the International Searching Authority Re. Application No. PCT/IL2019/050783. (15 Pages).
International Search Report and the Written Opinion Dated Sep. 18, 2019 From the International Searching Authority Re. Application No. PCT/IL2019/050782. (16 Pages).
International Search Report and the Written Opinion Dated Feb. 25, 2018 From the International Searching Authority Re. Application No. PCT/IL2018/050017. (11 Pages).
International Search Report and the Written Opinion Dated Feb. 27, 2018 From the International Searching Authority Re. Application No. PCT/IL2018/050014. (11 Pages).
Notification of Office Action and Search Report Dated Dec. 15, 2017 From the State Intellectual Property Office of the People's Republic of China Re. Application No. 201380074192.4. (7 Pages).
Notification of Office Action Dated Jul. 10, 2018 From The State Intellectual Property Office of the People's Republic of China Re. Application No. 201380074192.4. and Its Summary in English. (5 Pages).
Office Action Dated Aug. 14, 2018 From the Israel Patent Office Re. Application No. 239671 and Its Translation Into English. (7 Pages).
Official Action Dated Oct. 6, 2017 From the US Patent and Trademark Office Re. U.S. Appl. No. 14/655,752. (9 pages).
Official Action Dated Nov. 13, 2020 from the US Patent and Trademark Office Re. U.S. Appl. No. 16/027,382. (41 pages).
Official Action Dated Mar. 29, 2021 From the US Patent and Trademark Office Re. U.S. Appl. No. 16/473,631. (34 Pages).
Official Action Dated Mar. 30, 2017 From the US Patent and Trademark Office Re. U.S. Appl. No. 14/655,752. (12 Pages).
Patent Examination Report Dated Apr. 6, 2021 From the Australian Government, IP Australia Re. Application No. 2018205890.(4 Pages).
Patent Examination Report Dated Mar. 26, 2021 From the Australian Government, IP Australia Re. Application No. 2018205888. (4 Pages).
Request for Examination and Search Report Dated Apr. 9, 2021 From the (ROSPATENT), Federal Government Institution of Industrial Property of the Federal Service of Intellectual Property, Patents and Trademark of the Russian Federation Re. Application No. 2019124676 and Its Translation Into English. (40 Pages).
Request for Examination Dated Apr. 9, 2021 Fom the (ROSPATENT), Federal Government Institution of Industrial Property of the Federal Service of Intellectual Property, Patents and Trademark of the Russian Federation Re. Application No. 2019124678 and Its Translation Into English. (33 Pages).
Restriction Official Action Dated Jun. 15, 2016 From the US Patent and Trademark Office Re. U.S. Appl. No. 14/655,752. (7 Pages).
Restriction Official Action Dated May 15, 2020 from the US Patent and Trademark Office Re. U.S. Appl. No. 16/027,382. (10 pages).
Restriction Official Action Dated Nov. 2, 2020 From the US Patent and Trademark Office Re. U.S. Appl. No. 16/473,631. (14 Pages).
Restriction Official Action Dated Mar. 26, 2021 from the US Patent and Trademark Office Re. U.S. Appl. No. 16/475,683. (9 pages).
Search Report and Written Opinion Dated Apr. 25, 2020 From the Intellectual Property Office of Singapore Re. Application No. 11201905679S.
Search Report and Written Opinion Dated Apr. 25, 2020 From the Intellectual Propery Office of Singapore Re. Application No. 11201905681W. (10 Pages).
Supplementary European Search Report and the European Search Opinion Dated Oct. 12, 2020 From the European Patent Office Re. Application No. 18735930.2. (8 Pages).
Supplementary European Search Report and the European Search Opinion Dated Nov. 19, 2020 From the European Patent Office Re. Application No. 18736642.2. (12 Pages).
Translation Dated Jul. 25, 2018 of Notification of Office Action Dated Jul. 10, 2018 From The State Intellectual Property Office of the People's Republic of China Re. Application No. 201380074192.4. (5 Pages).
Translation of Notification of Office Action and Search Report Dated Dec. 15, 2017 From the State Intellectual Property Office of the People's Republic of China Re. Application No. 201380074192.4. (9 Pages).
Absolute Antibody "Antibody Sequencing, Engineering & Recombinant Expression", Absolute Antibody, Home Products, Website, 3 P., 2019.
Absolute Antibody "Bispecific and Trispecific Antibodies", Absolute Antibody, Website, Home Products, Website, 3 P., 2019.
Absolute Antibody "Products Archive", Absolute Antibody, Home Products, Website, 2 P., 2019.
Antoniou et al. "Transgenes Excompassing Dual-Promoter CpG Islands From the Human TBPand HNRPA2B1 Loci Are Resistant to Heterochromatin-Mediated Silencing", Genomics, 82(3): 269-279, Sep. 2003.
Arora et al. "Belatacept: A New Biological Agent for Maintenance Immunosuppression in Kidney Transplantation", Expert Opinion on Biological Therapy, 12(7): 965-979, Published Online May 8, 2012.
Ascierto et al. "Clinical Experiences With Anti-CD137 and Anti-PD1 Therapeutic Antibodies", Seminars in Oncology, XP008175440, 27(5): 508-516, Oct. 1, 2010.
Bcha et al. "IL-15-Based Trifunctional Antibody-Fusion Proteins With Costimulatory TNF-Superfamily Ligands in the Single-Chain Format for Cancer Immunotherapy", Molecular Cancer Therapeutics, p. 1-35, Published Ahead of Print Apr. 30, 2019.
Berry et al. "Substitution of Cysteine for Selenocysteine in Type I Iodothyronine Deiodinase Reduces the Catalytic Efficiency of the Protein But Enhances its Translation", Endocrinology, 131(4): 1848-1852, Oct. 1, 1992.
Chen et al. "Fusion Protein Linkers: Property, Design and Functionality", Advanced Drug Delivery Reviews, 65(10): 1357-1369, Oct. 15, 2013.
Dranitzki-Elhalel et al. CD40•FasL Inhibits Human T Cells: Evidence for An Auto-Inhibitory Loop-Back Mechanism, International Immunology, XP001668353, 19(4): 355-363, Advance Access Publication Feb. 20, 2007.
Eisele et al. "APO010, A Synthetic Hexameric CD95 Ligand, Induces Human Glioma Cell Death In Vitro and In Vivo", Neuro-Oncology, 13(2): 155-164, Published Online Dec. 22, 2010.
Fellermeier et al. "Advancing Targeted Co-Stimulation With Antibody-Fusion Proteins by Introducing TNF Superfamily Members in a Single-Chain Format", Oncoimmunology, 5(11): e1238540-1-e1238540-11, Sep. 27, 2016.
Feng et al. "CTLA4-Fas Ligand Gene Transfer Mediated by Adenovirus Induce Long-Time Survival of Murine Cardiac Allografts", Transplantation Proceedings, 37(5): 2379-2381, Jun. 2005.
Frankel et al. Characterization Of Diphtheria Fusion Proteins Targeted to the Human Interleukin-3 Receptor, Protein Engineering, Design and Selection, 13(8);575-581, Aug. 1, 2000.
Gasser et al. "Antibody Production With Yeasts and Filamentous Fungi: On the Road to Large Scale?", Biotechnology Letters, 29: 201-212, Nov. 22, 2006.

(56) References Cited

OTHER PUBLICATIONS

Gozlan et al. "Abstract A076: DSP107-A novel SIRPα-4-1 BBL Dual Signaling Protein (DSP) for Cancer Immunotherapy",Cancer Immunology Research, XP55734527A,7(2): 2P., Feb. 2019.

Grewal et al. "CD40 and CD154 in Cell-Mediated Immunity", Annual Review of Immunology, 16:111-135, Publication date: Apr. 1998.

Halin et al. "Synergistic Therapeutic Effects of a Tumor Targeting Antibody Fragment, Fused to Interleukin 12 and to Tumor Necrosis Factor α", Cancer Research, 63(12):3202-3210, Jun. 15, 2003.

Herrero-Beaumont et al. "Abatacept Mechanism of Action: Concordance With Its Clinical Profile?", Reumatologia Clinica, 8(2): 78-83, Available Online Feb. 15, 2012.

Holler et al. "Two Adjacent Trimeric Fas Ligands Are Required for Fas Signaling and Formation of a Death-Inducing Signaling Complex", Molecular and Cellular Biology, XP002258597, 23(4): 1428-1440, Feb. 2003. Abstract.

Huang et al. "CTLA-4-Fas Ligand Functions as a Trans Signal Converter Protein in Bridging Antigen-Presenting Cells and T Cells", International Immunology, XP001147390, 13(4): 529-539, Apr. 1, 2001. p. 537, r-h Col., Last Para, Fig. 1.

Jin et al. "Simultaneous Stimulation of Fas-Mediated Apoptosis and Blockade of Costimualtion Prevent Autoimmune Diabetes in Mice Induced by Multiple Low-Dose Streptozotocin", Gene Therapy, 11(12): 982-991, Published Online Mar. 25, 2004.

Kahr Medical "DSP105 (PD1-41BBL): Targeted Immune Activation Leading to T-Cell Mediated Tumor Destruction", Kahr Medical, Product Description, p. 1-4, Apr. 29, 2018.

Kaiko et al. "Immunological Decision-Making: How Does The Immune System Decide to Mount a Helper T-Cell Response?", Immunology,123(3):326-338, Jan. 18, 2008.

Kontermann et al. "Bispecific Antibodies", Drug Discovery Today, 20(7): 838-847, Jul. 2015.

Lazar-Molnar et al. "Crystal Structure of the Complex Between Programmed Death-1 (PD-1) and Its Ligand PD-2", Proc. Natl. Acad. Sci. USA, PNAS, 105(30): 10483-10488, Jul. 29, 2008.

Locksley et al. "The TNF and TNF Receptor Superfamilies: Integrating Mammalian Biology", Cell, 104(4): 487-501, Feb. 23, 2001.

Maeda et al. "Engineering of Functional Chimeric Protein G-VargulaLuciferase", Analytical Biochemistry, 249(2): 147-152, Jul. 1, 1997.

Maute et al. "Engineering High-Affinity PD-1 Variants for Optimized Immunotherapy and Ommuno-PET Omaging", Proceedings of the National Academy of Sciences, 112 (47): E6506-E6514, Published Online Nov. 10, 2015.

Merchant et al. "An Efficient Route to Human Bispecific IgG", Nature Biotechnology, 16(7): 677-681, Jul. 1998.

Muller et al. "Spliceosomal peptide P140 forImmunotherapy of Systemic Lupus Erythematosus: Results of an Early Phase II Clinical Trial*", Arthritis and Rheumatology, 58(12): 3873-3883, Nov. 26, 2008.

Nalamalpu et al. "Booster for Driving Long Onchip Interconnects—Design Issues, Interconnect Synthesis, and Comparison With Repeaters", IEEE Transactions on Computer-Aided Design of Integrated Circuits and Systems, 21(1): 50-62, Jan. 2002.

Orbach et al. "CD40.FasL and CTLA-4•FasL Fusion Proteins Induce Apoptosis in Malignant Cell Lines by Dual Signaling", The American Journal of Pathology, XP009155963, 177(6): 3159-3168, Dec. 2010. Abstract.

Orbach et al. "CTLA-4 • FasL Induces Early Apoptosis of Activated T Cells by Interfering With Anti-Apoptotic Signals", The Journal of Immunology, XP002668354, 179(11): 7287-7294, Dec. 1, 2007.

Pereg "Kahr Medical Dual Signaling Proteins (DSP) Platform—The Next Generation of Cancer Immunotherapy", Kahr Medical, Abstract Template for Company Presentations, 1 P., May 11, 2018.

Sanmamed et al. "Agonists of Co-Stimulation in Cancer Immunotherapy Directed Against CD137, OX40, GITR, CD27, CD28, and ICOS", Seminars in Oncology, XP055410294, 42(4): 640-655, Aug. 1, 2015.

Shi et al. "Prolongation of Corneal Allograft Survival by CTLA4-FasL in a Murine Model", Graefe's Archive for Clinical and Experimental Ophthalmology, XP019542074, 245(11): 1691-1697, Published Online May 31, 2007.

Shrimali et al. "Concurrent PD-1 Blockade Negates the Effects of OX40 Agonist in Combination Immunotherapy Through Inducing T-Cell Apoptosis", Cancer Immunology Research, 5(9): 755-766, Published Online Aug. 28, 2017.

Slavin et al. "Spontaneous Murine B-Cell Leukaemia", Nature, 272(5654): 624-626, Apr. 13, 1978.

Tansey et al. "The TNF Superfamily in 2009: New Pathways, New Indications, and New Drugs", Drug Discovery Today, 14(23/24): 1082-1088, Dec. 2009.

Weiskopf et al. "Engineered SIRP-alpha Variants as Immunotherapeutic Adjuvants to Anti-cancer Antibodies," Science, 341 (6141): 88-91, Jul. 5, 2013.

Wyzgol ct al. "Trimer Stabilization, Oligomerization, and Antibody-Mediated Cell Surface Immobilization Improve the Activity of Soluble Trimers of CD27L, CD40L, 41BBL, and Glucocorticoid-InducedTNF Receptor Ligands", The Journal of Immunology, 183(3): 1851-1861, Published Online Jun. 13, 2009.

Xiao et al. "Soluble PD-1 Facilitates 4-1BBL-Triggered Antitumor Immunity Against Murine H22 Hepatocarcinoma In Vivo", Clinical Cancer Research, XP055144430, 13(6): 1823-1830, Published Online Feb. 26, 2007.

Yang et al. "High-Level Expression And Deletion Mutagenesis of Human Tryptophan Hydroxylase", Proceedings of the National Academy of Sciences ofthe United States of America, 91(14): 6659-6663, Jul. 5, 1994.

Yu et al. "The Surface Protein TIGIT Suppresses T Cell Activation by Promoting the Generation of Mature Immunoregulatory Dendritic Cells", Nature Immunology, 10: 48-57, 2009.

Zhang et al. "Intraarticular Gene Delivery of CTLA4-FasL Suppresses Experimental Arthritis", International Immunology, 24(6): 379-388, Advance Access Publicaiton Feb. 21, 2012.

Zhang et al. "Targeted and Untargeted CD137L Fusion Proteins for the Immunotherapy of Experimental Solid Tumors", Clinical Cancer Research, XP055186494, 13(9): 2758-2767, May 1, 2007.

Translation Dated Nov. 17, 2022 of Notification of Office Action Dated Sep. 28, 2022 From the State Intellectual Property Office of the People's Republic of China Re. Application No. 201880015833.1. (9 Pages).

Official Action Dated Jun. 24, 2022 from US Patent and Trademark Office Re. U.S. Appl. No. 16/475,139. (97 pages).

Examination Report Under Sections 12 & 13 of the Patents Act, 1970 and the Patents Rules, 2003 Dated Jul. 18, 2022 From the Government of India, Intellectual Property India, Patents Designs, Trade Marks, Geographical Indications the Patent Office Re. Application No. 202127002771. (6 Pages).

Notification of Office Action and Search Report Dated Oct. 9, 2022 From the State Intellectual Property Office of the People's Republic of China Re Application No. 201880016069.X. (13 Pages).

Official Action Dated Oct. 17, 2022 from US Patent and Trademark Office Re. U.S. Appl. No. 16/027,382. (16 pages).

Summary Dated Oct. 18, 2022 of Notification of Office Action Dated Sep. 28, 2022 From the State Intellectual Property Office of the People's Republic of China Re. Application No. 201880015833.1. (1 Pages).

Summary Dated Nov. 4, 2022 of Notification of Office Action Dated Oct. 9, 2022 From the State Intellectual Property Office of the People's Republic of China Re. Application No. 201880016069.X. (5 Pages).

Notification of Office Action and Search Report Dated Sep. 28, 2022 From the State Intellectual Property Office of the People's Republic of China Re. Application No. 201880015833.1. (9 Pages).

Office Action Dated Sep. 28, 2022 From the Israel Patent Office Re. Application No. 267861. (3 Pages).

Office Action Dated Sep. 29, 2022 From the Israel Patent Office Re. Application No. 267862. (3 Pages).

Official Action Dated Sep. 29, 2022 from US Patent and Trademark Office Re. U.S. Appl. No. 17/400,179. (104 pages).

Aaron "Overview of Fungal Skin Infections", Merck Manual, 1-2, accessed Feb. 19, 2019.

(56) References Cited

OTHER PUBLICATIONS

Bowie et al. "Deciphering the Message in Protein Sequences: Tolerance to Amino Acid Substitutions", Science 247(4948): 1306-1310, Mar. 16, 1990.
Burgess et al. "Possible Dissociation of the Heparin-binding and Mitogenic Activities of Heparin-binding (acidic fibroblast) Growth Factor-1 from its Receptor-binding Activities by Site-directed Mutagenesis of a Single Lysine Residue", Jurnal of Cell Biology (1990) 111 (5): 2129-2138, Nov. 1, 1990.
CDC "Types of Fungal Diseases", Center for Disease Control and Prevention, 1-2, accessed May 21, 2021.
Doron "Bacterial Infections: Overview", International Encyclopedia of Public Healthy, 2008 : 273-282, PMC7149789, Aug. 26, 2008.
Gregory "Neuroblastoma", Merck Manual, 1-4, accessed Dec. 3, 2017.
Hershman "Thyroid cancers", 1-4, Dec. 3, 2017.
Kleinsmith et al. "Understanding Cancer and Related Topics—Understanding Cancer", National Cancer Institute, 1-63, 2007, accessed Aug. 21, 2014.
Kramer "Overview of Viruses", Merck Manual, 1-6, accessed Feb. 19, 2019.
Lazar et al. "Transforming Growth Factor: Mutation of Aspartic Acid 47 and Leucine 48 Results in Different Boiological Activities", Molecular and Cellular Biology, 8(3): 1247-1252, Mar. 1998.
Master "Renal Cell Carcinoma", Merck Manual, 1-6, accessed Dec. 3, 2017.
merckmanuals.com "Bladder Cancer", Merck Manual, 1-2, accessed Aug. 21, 2014.
merckmanuals.com "Colorectal Cancer", Merck Manual, 1-5, accessed on-line Aug. 21, 2014.
merckmanuals.com "Overview of Fungal Infections", Merck Manual, 1-3, accessed Oct. 21, 2020.
merckmanuals.com "Overview of Leukemia", Merck Manual, 1-2, accessed Aug. 21, 2014.
merckmanuals.com "Overview of Lymphoma", Merck Manual, 1, accessed Aug. 21, 2014.
merckmanuals.com "Prostate Cancer", Merck Manual, 1-8, accessed Aug. 21, 2014.
NIH "Antimicrobial Resistance Threats", Natinal Institute of Allergy and Infectious Diseases, 1-3, 2020.
Pearson "Approach to Parasitic Infections", Merck Manual, 1-10, accessed Oct. 22, 2020.
Shanks et al. "Are animal models predictive for humans?", Philosophy, Ethics, and Humanities in Medicine, 4(2):1-20, Jan. 15, 2009.
Tsao Lung Carcinoma (Lung Cancer), Merck Manual, 1-18, accessed Dec. 3, 2017.
Notice of the Results of the Patent Fee Check Dated May 30, 2022 From the Federal Government Institution, Federal Institute of Industrial Property of the Federal Service of Intellectual Property, Patents and Trademarks of the Russian Federation, FIPS Re. 2021101108. (3 Pages).
Notice of Allowance Dated Sep. 30, 2022 from US Patent and Trademark Office Re. U.S. Appl. No. 16/475,139. (11 pages).
International Search Report and the Written Opinion Dated Feb. 16, 2023 From the International Searching Authority Re. Application No. PCT/IL2022/051378 (11 Pages).
Interview Summary Dated Feb. 17, 2023 from the US Patent and Trademark Office Re. U.S. Appl. No. 16/027,382. (2 pages).
Notice of Allowance Dated Feb. 24, 2023 from the US Patent and Trademark Office Re. U.S. Appl. No. 16/475,705. (21 pages).
Request for Examination Dated May 11, 2022 From the (Rospatent), Federal Government Institution of Industrial Property of the Federal Service of Intellectual Property, Patents and Trademark of the Russian Federation Re. Application No. 2022103192 and Its Translation Into English. (5 Pages).
Jones et al. "Leukocyte Immunoglobulin-like Receptor Subfamily B Member 2 Soluble Isoform [*Homo sapiens*]", Database NCBI [Online], GenBank: ACK56072.1, Database Accession No. ACK56072, 3 pages, Feb. 18, 2010.
Search Report and Written Opinion Dated Feb. 24, 2023 From the Intellectual Property Office of Singapore, IPOS Re. Application No. 11202200041R. (15 Pages).
Notice of Reason(s) for Rejection Dated Nov. 25, 2022 From the Japan Patent Office Re. Application No. 2019-536286 and Its Translation Into English.(7 pages).
Official Action Dated Dec. 14, 2022 from the US Patent and Trademark Office Re. U.S. Appl. No. 16/475,705. (7 pages).
Request for Examination and Search Report Dated Dec. 5, 2022 From the (Rospatent), Federal Government Institution of Industrial Property of the Federal Service of Intellectual Property, Patents and Trademark of the Russian Federation Re. Application No. 2021101108 and Its Summary in English. (16 Pages).
Request for Examination and Search Report Dated Jan. 12, 2023 From the (Rospatent), Federal Government Institution of Industrial Property of the Federal Service of Intellectual Property, Patents and Trademark of the Russian Federation Re. Application No. 2021101091. (13 Pages).
Translation Dated Dec. 23, 2022 of Request for Examination Dated Dec. 5, 2022 From the (Rospatent), Federal Government Institution of Industrial Property of the Federal Service of Intellectual Property, Patents and Trademark of the Russian Federation Re. Application No. 2021101108. (10 pages).
Translation Dated Jan. 30, 2023 of Request for Examination and Search Report Dated Jan. 12, 2023 From the (Rospatent), Federal Government Institution of Industrial Property of the Federal Service of Intellectual Property, Patents and Trademark of the Russian Federation Re. Application No. 2021101091. (9 pages).
Edgar "T cell immunodeficiency", Journal of Clinical Pathology, 61(9): 988-993, Aug. 28, 2008.
Keskin et al. "A New, Structurally Nonredundant, Diverse Data Set of Protein-Protein Interfaces and Its Implications", Protein Science, 13(4): 1043-1055, Apr. 2004.
Kosobokova et al. "Antibody-cytokine Fusion Proteins: Production, Functionality and Application Prospects in Oncology", Contemporary Technologies in Medicine 2013—5(4): 102-111, Jun. 27, 2013.
Pakula et al. "Genetic Analysis of Protein Stability and Function", Annual Review of Genetics, 23(1): 289-310, Dec. 1989.
Grounds of Reason of Rejection Dated Mar. 7, 2023 From the Korean Intellectual Property Office Re. Application No. 10-2019-7022848 (6 Pages).
Office Action Dated Aug. 7, 2023 From the Israel Patent Office Re. Application No. 267862. (3 Pages).
International Preliminary Report on Patentability Dated Jul. 27, 2023 From the International Bureau of WIPO Re. Application No. PCT/IL2022/050055 (10 Pages).
Official Action Dated Oct. 19, 2023 from the US Patent and Trademark Office Re. U.S. Appl. No. 17/258,220. (167 pages).
Chichili et al. "Linkers in The Structural Biology of Protein-Protein Interactions", Protein Science, 22(2): 153-167, Dec. 6, 2012.
Translation Dated May 12, 2023 of Notification of Office Action Dated Apr. 21, 2023 From the State Intellectual Property Office of the People's Republic of China Re. Application No. 201880015833.1 (6 pages).
Translation Dated Jul. 14, 2023 of Notice of Reason(s) for Rejection Dated Jun. 27, 2023 From the Japan Patent Office Re. Application No. 2021-500820. (4 pages).
Notification of Office Action Dated Apr. 21, 2023 From the State Intellectual Property Office of the People's Republic of China Re. Application No. 201880015833.1 (5 pages).
Translation Dated Mar. 22, 2023 of Grounds of Reason of Rejection Dated Mar. 7, 2023 From the Korean Intellectual Property Office Re. Application No. 10-2019-7022848. (5 Pages).
Translation Dated Apr. 27, 2023 of Grounds of Reason of Rejection Dated Apr. 5, 2023 From the Korean Intellectual Property Office Re. Application No. 10-2019-7022855. (3 Pages).
Translation Dated Oct. 10, 2023 of Request for Examination and Search Report Dated Sep. 13, 2023 From the Federal Government Institution, Federal Institute of Industrial Property of the Federal

(56) References Cited

OTHER PUBLICATIONS

Service of Intellectual Property, Patents and Trademarks of the Russian Federation, FIPS Re. Application No. 2022103192. (6 pages).
Grounds of Reason of Rejection Dated Apr. 5, 2023 From the Korean Intellectual Property Office Re. Application No. 10-2019-7022855. (4 Pages).
English Summary Dated Jun. 16, 2023 of Notification of Office Action Dated Jun. 1, 2023 From the State Intellectual Property Office of the People's Republic of China Re. Application No. 201980052864.9. (3 pages).
English Summary Dated Jun. 19, 2023 of Notification of Office Action and Search Report Dated Jun. 2, 2023 From the State Intellectual Property Office of the People's Republic of China Re. Application No. 201980052845.6. (3 pages).
Official Action Dated Jun. 12, 2023 from the US Patent and Trademark Office Re. U.S. Appl. No. 16/027,382. (49 pages).
Requisition by the Examiner Dated Jun. 20, 2023 From the Innovation, Science and Economic Development Canada, Canadian Intellectual Property Office Re. Application No. 3,146,248. (8 pages).
Translation Dated Jun. 15, 2023 of Notice of Reason(s) for Rejection Dated May 23, 2023 From the Japan Patent Office Re. Application No. 2021-500829. (3 pages).
English Summary Dated Jul. 4, 2023 of Notification of Office Action Dated Jun. 7, 2023 From the State Intellectual Property Office of the People's Republic of China Re. Application No. 202080063464.0. (4 pages).
Office Action Dated Jul. 6, 2023 From the Israel Patent Office Re. Application No. 267861. (3 Pages).
Ha et al. "Immunoglobulin Fc Heterodimer Platform Technology: From Design to Applications in Therapeutic Antibodies and Proteins", Frontiers in Immunology, 7(394): Oct. 1-16, 2016.
Requisition by the Examiner Dated Aug. 3, 2023 From the Innovation, Science and Economic Development Canada, Canadian Intellectual Property Office Re. Application No. 3,104,780. (9 Pages).
Notice of Reason(s) for Rejection Dated Jul. 25, 2023 From the Japan Patent Office Re. Application No. 2022-132987 and Its Translation Into English. (7 Pages).
English Summary Dated May 11, 2023 of Notification of Office Action Dated Apr. 27, 2023 From the State Intellectual Property Office of the People's Republic of China Re. Application No. 201880016069.X (3 pages).
Notification of Office Action Dated Apr. 27, 2023 From the State Intellectual Property Office of the People's Republic of China Re. Application No. 201880016069.X (7 pages).
Official Action Dated May 8, 2023 from the US Patent and Trademark Office Re. U.S. Appl. No. 17/400,179. (48 pages).
Request for Examination Dated Apr. 14, 2023 From the Federal Government Institution, Federal Institute of Industrial Property of the Federal Service of Intellectual Property, Patents and Trademarks of the Russian Federation, FIPS Re. Application No. 2021101108. (7 Pages).
Barclay et al. "The Interaction Between Signal Regulatory Protein Alpha (SIRPα) and CD47: Structure, Function, and Therapeutic Target", Annual Review of Immunology, 32: 25-50, Nov. 6, 2013.
Willingham et al. "The CD47-Signal Regulatory Protein Alpha (SIRPα) Interaction is a Therapeutic Target for Human Solid Tumors", PNAS, 109(17): 6662-6667, Mar. 26, 2012.
Won et al. "The Structure of the Trimer of Human 4-1 BB Ligand Is Unique Among Members of the Tumor necrosis factor Superfamily", The Journal of Biological Chemistry, 285(12): 9202-9210, Mar. 19, 2010.
Translation Dated May 15, 2023 of Request for Examination Dated Apr. 14, 2023 From the Federal Government Institution, Federal Institute of Industrial Property of the Federal Service of Intellectual Property, Patents and Trademarks of the Russian Federation, FIPS Re. Application No. 2021101108. (4 Pages).
Notification on the Results of Checking the Patentability of an Invention Dated Aug. 25, 2023 From the Federal Government Institution, Federal Institute of Industrial Property of the Federal Service of Intellectual Property, Patents and Trademarks of the Russian Federation, FIPS Re. Application No. 2021101108 and Its Translation Into English. (7 pages).
Badri et al. "Optimization of Radiation Dosing Schedules for Proneural Glioblastoma", Journal of Mathematical Biology, 72(5): 1301-1336, Jun. 21, 2015.
Baylot et al. "TCTP Has a Crucial Role in the Different Stages of Prostate Cancer Malignant 4 Progression 5 ", Results and Problems in Cell Differentiation, TCTP/tpt1—Remodeling Signaling from Stem Cell to Disease, 255-261, Nov. 18, 2017.
Written Opinion Dated Oct. 9, 2023 From the Intellectual Property Office of Singapore, IPOS Re. Application No. 11201905681W. (7 Pages).
Notice of Allowance Dated Aug. 22, 2023 From the US Patent and Trademark Office Re. U.S. Appl. No. 17/400,179. (32 Pages).
English summary dated Jul. 3, 2023 of Request for Examination Dated Jun. 7, 2023 From the Federal Government Institution, Federal Institute of Industrial Property of the Federal Service of Intellectual Property, Patents and Trademarks of the Russian Federation, FIPS Re. Application No. 2021101091.
Restriction Official Action Dated Jun. 29, 2023 from the US Patent and Trademark Office Re. U.S. Appl. No. 17/258,220. (13 pages).
English Summary Dated Nov. 10, 2023 of Request for Examination and Search Report Dated Nov. 2, 2023 From the (Rospatent), Federal Government Institution of Industrial Property of the Federal Service of Intellectual Property, Patents and Trademark of the Russian Federation Re. Application No. 2021101091. (4 Pages).
English Summary Dated Dec. 11, 2023 of Notification of Office Action Dated Nov. 23, 2023 From the State Intellectual Property Office of the People's Republic of China Re. Application No. 201980052864.9. (2 Pages).
Examination Report Under Sections 12 & 13 of the Patents Act, 1970 and the Patents Rules, 2003 Dated Dec. 1, 2023 From the Government of India, Intellectual Property India, Patents, Designs, Trade Marks, Geographical Indications, The Patent Office Re. Application No. 201927030333. (5 pages).
Machine Translation Dated Nov. 28, 2023 of Notification of Office Action Dated Nov. 23, 2023 From the State Intellectual Property Office of the People's Republic of China Re. Application No. 201980052864.9. (9 Pages).
Machine Translation Dated Nov. 29, 2023 of Notification of Office Action Dated Nov. 25, 2023 From the State Intellectual Property Office of the People's Republic of China Re. Application No. 201980052845.6. (5 Pages).
Notice of Reason(s) for Rejection Dated Nov. 28, 2023 From the Japan Patent Office Re. Application No. 2021-500829. (2 pages).
Notification of Office Action Dated Nov. 23, 2023 From the State Intellectual Property Office of the People's Republic of China Re. Application No. 201980052864.9. (4 Pages).
Notification of Office Action Dated Nov. 25, 2023 From the State Intellectual Property Office of the People's Republic of China Re. Application No. 201980052845.6. (5 Pages).
Official Action Dated Nov. 6, 2023 from the US Patent and Trademark Office Re. U.S. Appl. No. 17/695,898. (159 pages).
Request for Examination and Search Report Dated Nov. 2, 2023 From the (Rospatent), Federal Government Institution of Industrial Property of the Federal Service of Intellectual Property, Patents and Trademark of the Russian Federation Re. Application No. 2021101091. (9 Pages).
Requisition by the Examiner Dated Nov. 7, 2023 From the Innovation, Science and Economic Development Canada, Canadian Intellectual Property Office Re. Application No. 3,104,778. (5 Pages).
Requisition by the Examiner Dated Nov. 15, 2023 From the Innovation, Science and Economic Development Canada, Canadian Intellectual Property Office Re. Application No. 3,047,707. (9 Pages).

(56) References Cited

OTHER PUBLICATIONS

Requisition by the Examiner Dated Sep. 27, 2023 From the Innovation, Science and Economic Development Canada, Canadian Intellectual Property Office Re. Application No. 3,047,708. (5 Pages).
Summary Dated Dec. 5, 2023 of Notification of Office Action Dated Nov. 25, 2023 From the State Intellectual Property Office of the People's Republic of China Re. Application No. 201980052845.6. (2 Pages).
Translation Dated Dec. 12, 2023 of Notice of Reason(s) for Rejection Dated Nov. 28, 2023 From the Japan Patent Office Re. Application No. 2021-500829. (2 pages).
Translation Dated Nov. 22, 2023 of Request for Examination and Search Report Dated Nov. 2, 2023 From the (Rospatent), Federal Government Institution of Industrial Property of the Federal Service of Intellectual Property, Patents and Trademark of the Russian Federation Re. Application No. 2021101091. (7 Pages).
Official Action Dated Mar. 20, 2024 from the US Patent and Trademark Office Re. U.S. Appl. No. 17/258,220. (125 pages).
English Summary Dated Dec. 27, 2023 of Notification of Office Action Dated Dec. 14, 2023 From the State Intellectual Property Office of the People's Republic of China Re. Application No. 202080063464.0. (5 Pages).
Notification of Office Action Dated Dec. 14, 2023 From the State Intellectual Property Office of the People's Republic of China Re. Application No. 202080063464.0 and Its Machine Translation Into English. (13 Pages).
Written Opinion Dated Feb. 1, 2024 From the Intellectual Property Office of Singapore, IPOS Re. Application No. 11202013170R. (6 Pages).
Written Opinion Dated Jan. 8, 2024 From the Intellectual Property Office of Singapore, IPOS Re. Application No. 11202013167U. (8 Pages).
Written Opinion Dated Jan. 8, 2024 From the Intellectual Property Office of Singapore, IPOS Re. Application No. 11202200041R. (10 Pages).
Advisory Action Before the Filing of an Appeal Brief Dated Jun. 10, 2024 from US Patent and Trademark Office Re. U.S. Appl. No. 17/258,220. (2 pages).
Machine Translation Dated Jun. 10, 2024 of Notice of Reasons for Rejection Dated May 28, 2024 From the Japan Patent Office Re. Application No. 2019-536286.(2 pages).
Notice of Reasons for Rejection Dated May 28, 2024 From the Japan Patent Office Re. Application No. 2019-536286.(3 pages).
Restriction Official Action Dated Jun. 11, 2024 from the US Patent and Trademark Office Re. U.S. Appl. No. 18/101,601. (9 pages).

* cited by examiner

FIG. 1

MGWSCIILFLVATATGVHSEEELQVIQPDKSVLVAAGETATLRCTATSLIPVGPIQWFRGAGPGRELIY
NQKEGHFPRVTTVSDLTKRNNMDFSIRIGNITPADAGTYYCVKFRKGSPDDVEFKSGAGTELSVRAKPS
APVVSGPAARATPQHTVSFTCESHGFSPRDITLKWFKNGNELSDFQTNVDPVGESVSYSIHSTAKVVLT
REDVHSQVICEVAHVTLQGDPLRGTANLSETIRVPPTLEVTQQPVRAENQVNVTCQVRKFYPQRLQLTW
LENGNVSRTETASTVTENKDGTYNWMSWLLVNVSAHRDDVKLTCQVEHDGQPAVSKSHDLKVSAHPKEQ
GSNTAAENTGSNERNIYGACPWAVSGARASPGSAASPRLREGPELSPDDPAGLLDLRQGMFAQLVAQNV
LLIDGPLSWYSDPGLAGVSLTGGLSYKEDTKELVVAKAGVYYVFFQLELRRVVAGEGSGSVSLALHLQP
LRSAAGAAALALTVDLPPASSEARNSAFGFQGRLLHLSAGQRLGVHLHTEARARHAWQLTQGATVLGLF
RVTPEIPAGLPSPRSEHHHHHH

FIG. 2A

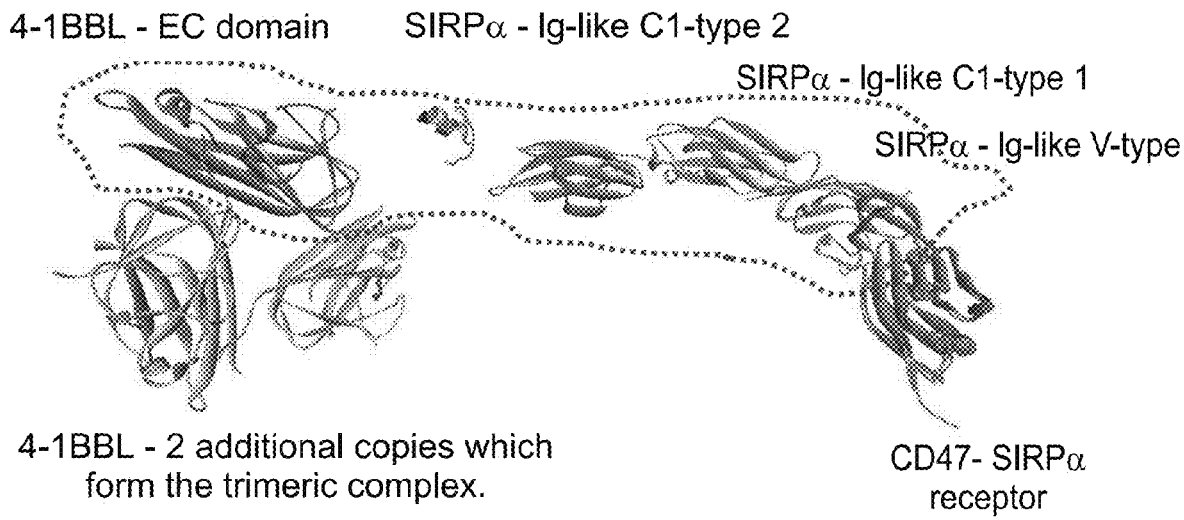

FIG. 2B
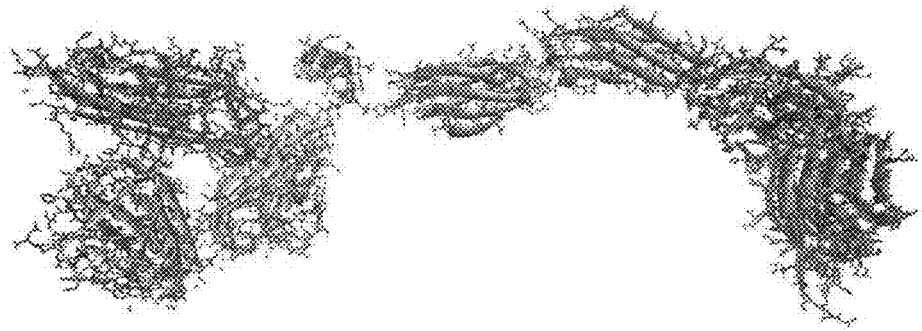
FIG. 2C
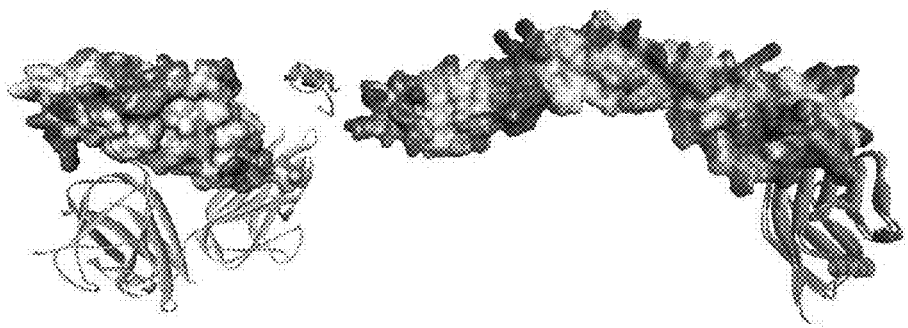
FIG. 3

FIG. 4
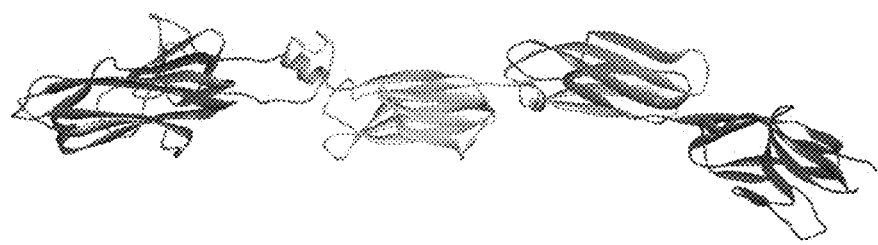

FIG. 5
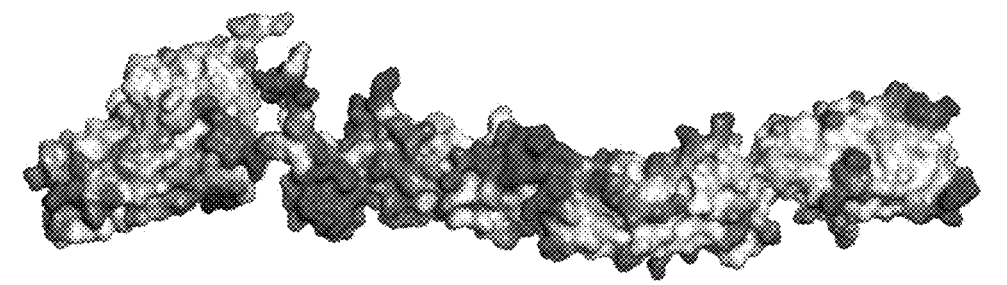
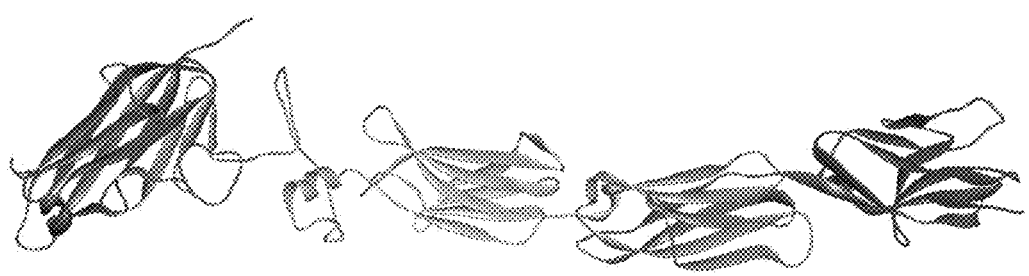
FIG. 6
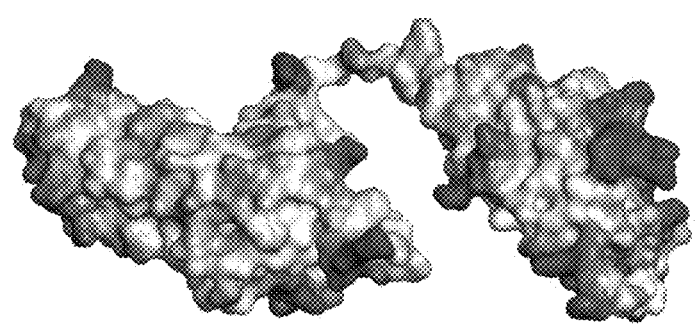
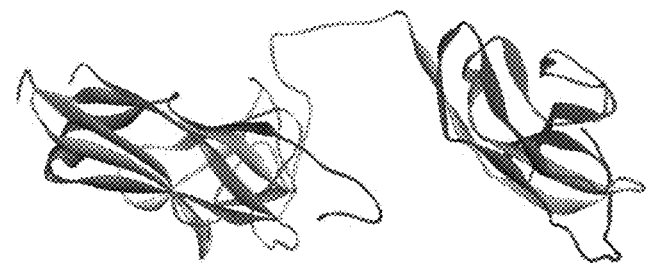

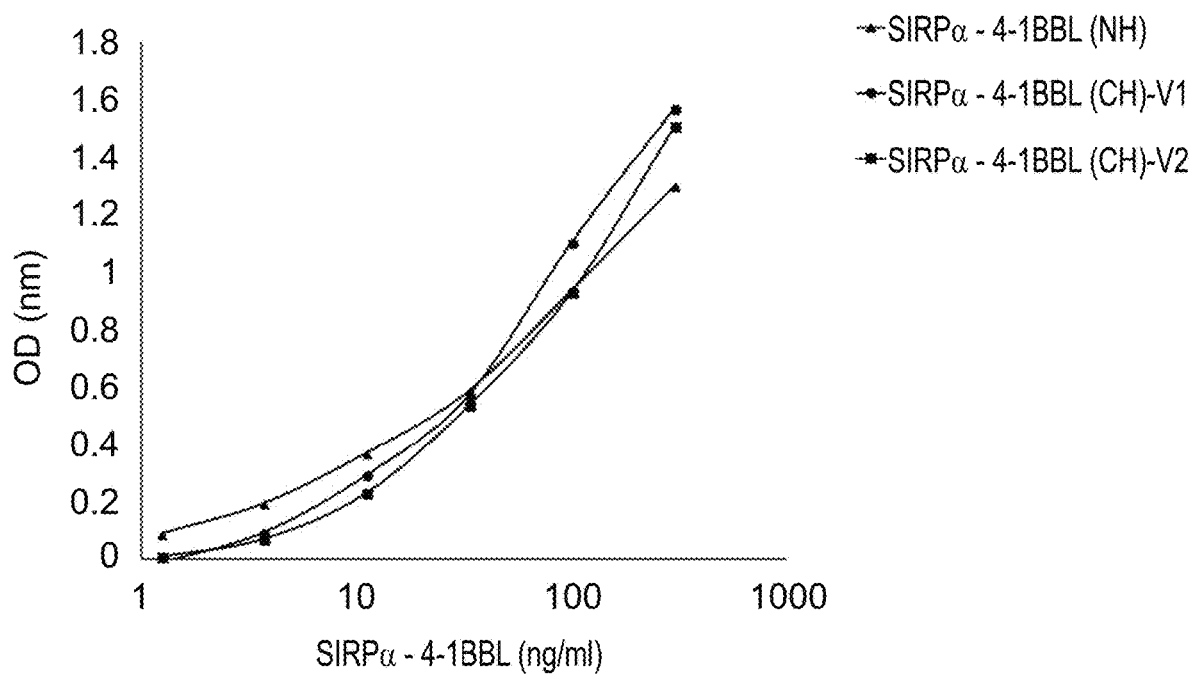

FIG. 21B
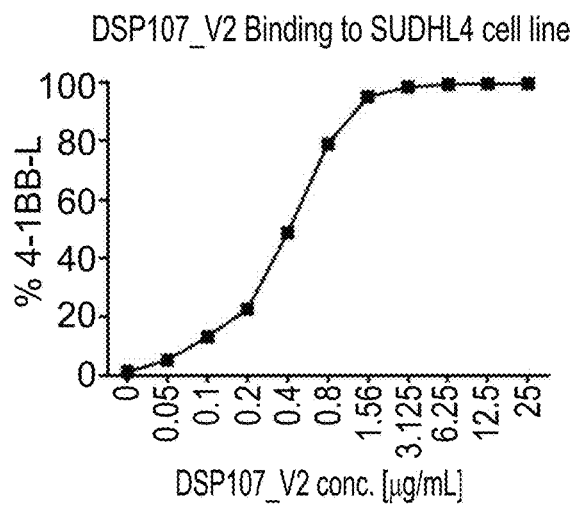
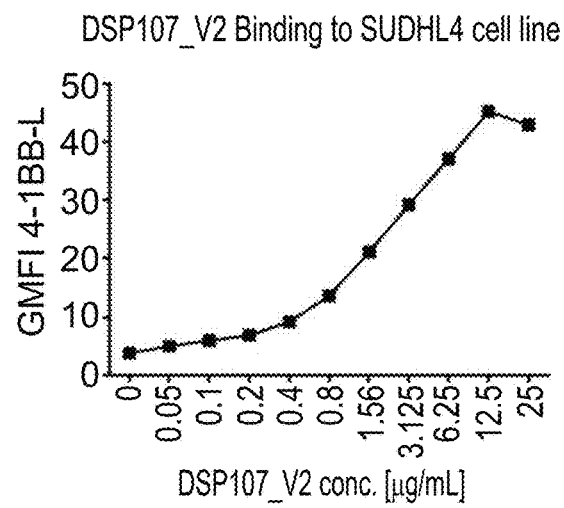
FIG. 22A
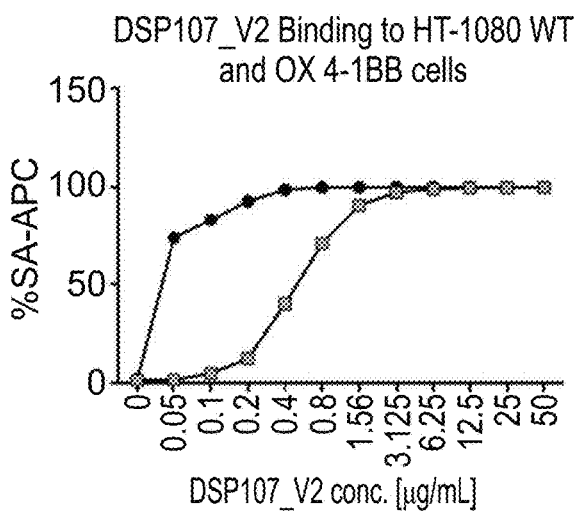
FIG. 22B
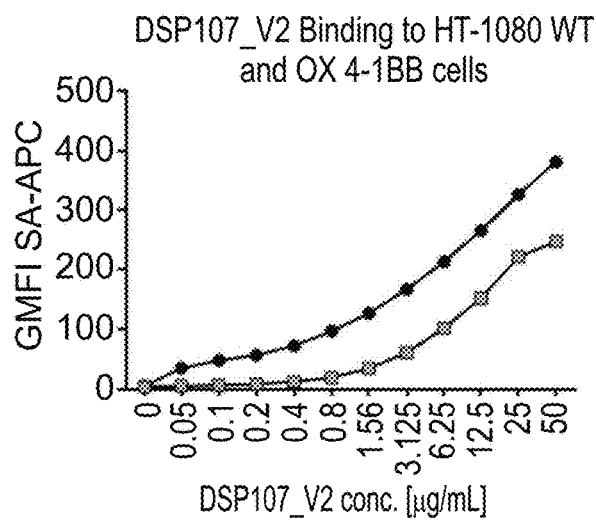

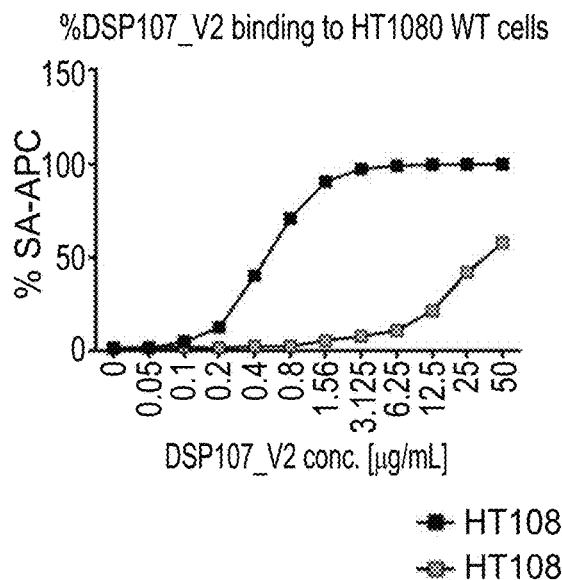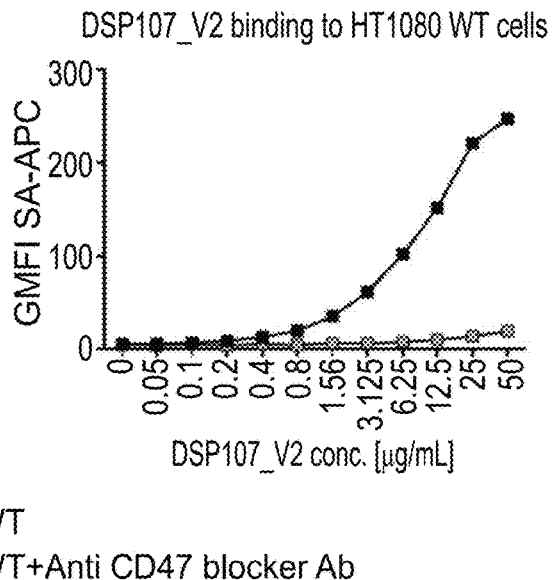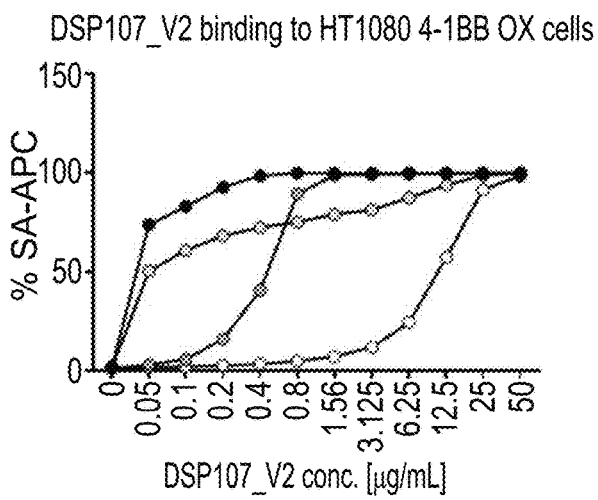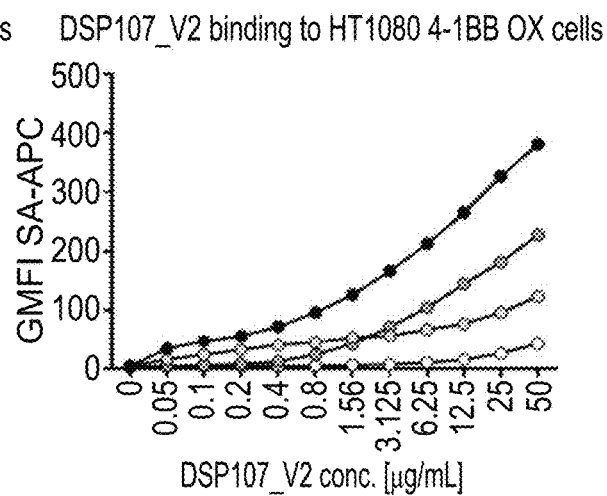

SIRPALPHA-4-1BBL VARIANT FUSION PROTEIN AND METHODS OF USE THEREOF

RELATED APPLICATIONS

This application is a National Phase of PCT Patent Application No. PCT/IL2019/050783 having International filing date of Jul. 11, 2019, which claims the benefit of priority under 35 USC § 119(e) of U.S. Provisional Patent Application No. 62/696,362 filed on Jul. 11, 2018. The contents of the above applications are all incorporated by reference as if fully set forth herein in their entirety.

SEQUENCE LISTING STATEMENT

The ASCII file, entitled 85833SequenceListing.txt, created on Jan. 5, 2021, comprising 191,735 bytes, submitted concurrently with the filing of this application is incorporated herein by reference. The sequence listing submitted herewith is identical to the sequence listing forming part of the international application.

FIELD AND BACKGROUND OF THE INVENTION

The present invention, in some embodiments thereof, relates to a SIRPα-4-1BBL variant fusion protein and methods of use thereof.

Dual Signaling Proteins (DSP), also known as Signal-Converting-Proteins (SCP), which are currently known in the art as bi-functional fusion proteins that link an extracellular portion of a type I membrane protein (extracellular amino-terminus), to an extracellular portion of a type II membrane protein (extracellular carboxyl-terminus), forming a fusion protein with two active sides (see e.g. U.S. Pat. Nos. 7,569,663 and 8,039,437).

SIRPα (signal-regulatory protein alpha) is a cell surface receptor of the immunoglobulin superfamily. SIRPα is expressed mainly on the surface of immune cells from the phagocyte lineage like macrophages and dendritic cells (DC). CD47 is the ligand of SIRPα. CD47 is a cell surface molecule in the immunoglobulin superfamily. CD47 functions as an inhibitor of phagocytosis through ligation of SIRPα expressed on phagocytes. CD47 is widely expressed on a majority of normal tissues. In this way, CD47 serves as a "don't eat me signal" and a marker of self, as loss of CD47 leads to homeostatic phagocytosis of aged or damaged cells. CD47 has been found to be expressed on multiple human tumor types. Tumors evade macrophage phagocytosis through the expression of antiphagocytic signals, including CD47. While CD47 is ubiquitously expressed at low levels on normal cells, multiple tumors express increased levels of CD47 compared to their normal cell counterparts and overexpression of CD47 enables tumors to escape innate immune system surveillance through evasion of phagocytosis.

4-1BBL is the activating ligand of the 4-1BB receptor (CD137), a member of the TNF receptor superfamily and a potent activation-induced T cell costimulatory molecule. 4-1BBL naturally forms a homo-trimer but signaling via 4-1BB requires significant oligomerization of 4-1BBL. 4-1BBL is present on a variety of antigen presenting cells (APCs), including dendritic cells (DCs), B cells, and macrophages. The 4-1BB receptor is not detected (<3%) on resting T cells or T cell lines, however, 4-1BB is stably upregulated when T cells are activated. 4-1BB activation upregulates survival genes, enhances cell division, induces cytokine production and prevents activation induced cell death in T-cells.

Additional background art includes:
Weiskopf K et al. Science. (2013); 341(6141):88-91;
International Patent Application Publication No. WO 2017027422;
International Patent Application Publication No. WO 2001086003;
International Patent Application Publication No. WO 2001075067;
International Patent Application Publication No. WO 2017194641;
International Patent Application Publication No. WO 2014180288;
International Patent Application Publication No. WO2017059168;
International Patent Application Publication No. WO2001/049318;
International Patent Application Publication No. WO2016/139668;
International Patent Application Publication No. WO2014/106839;
International Patent Application Publication No. WO2012/042480;
US Patent Application Publication No. 20150183881;
US Patent Application Publication No. US20070110746;
US Patent Application Publication No. US20070036783; and
U.S. Pat. No. 9,562,087.

SUMMARY OF THE INVENTION

According to an aspect of some embodiments of the present invention there is provided a SIRPα-4-1BBL fusion protein comprising a SIRPα amino acid sequence and a 4-1BBL amino acid sequence, wherein the SIRPα amino acid sequence is 100-119 amino acids in length having at least 95% identity to an amino acid sequence selected from the group consisting of SEQ ID NOs: 24 and 26, and/or wherein the 4-1BBL amino acid sequence:

(a) is 185-202 amino acids in length having at least 95% identity to an amino acid sequence selected from the group consisting of SEQ ID NOs: 22, 23, 27 and 28, is 170-197 amino acids in length having at least 80% identity to an amino acid sequence selected from the group consisting of SEQ ID NO: 74 and 76 and does not comprise an amino acid segment G198-E205 corresponding to SEQ ID NO: 3, is 170-182 amino acids in length having at least 80% identity to SEQ ID NO: 72 and does not comprise an amino acid segment A1-E23 corresponding to SEQ ID NO: 3 or is 184 amino acids in length having at least 80% identity to SEQ ID NO: 70; and/or (b) comprises three repeats of a 4-1BBL amino acid sequence; and wherein the fusion protein is capable of at least one of:
(i) binding CD47 and 4-1BB;
(ii) activating the 4-1BB signaling pathway in a cell expressing the 4-1BB;
(iii) co-stimulating immune cells expressing the 4-1BB; and/or
(iv) enhancing phagocytosis of pathologic cells expressing the CD47 by phagocytes compared to same in the absence of the SIRPα-4-1BBL fusion protein.

According to an aspect of some embodiments of the present invention there is provided a SIRPα-4-1BBL fusion protein comprising a SIRPα amino acid sequence and a 4-1BBL amino acid sequence, wherein the SIRPα amino acid sequence is 100-119 amino acids in length having at least 95% identity to an amino acid sequence selected from the group consisting of SEQ ID NOs: 24 and 26, and/or wherein the 4-1BBL amino acid sequence is 185-202 amino acids in length having at least 95% identity to an amino acid sequence selected from the group consisting of SEQ ID NOs: 22, 23, 27 and 28; and wherein the fusion protein is capable of at least one of:

(i) binding CD47 and 4-1BB;
(ii) activating the 4-1BB signaling pathway in a cell expressing the 4-1BB;
(iii) co-stimulating immune cells expressing the 4-1BB; and/or
iv) enhancing phagocytosis of pathologic cells expressing the CD47 by phagocytes compared to same in the absence of the SIRPα-4-1BBL fusion protein.

According to an aspect of some embodiments of the present invention there is provided an isolated polypeptide comprising a SIRPα amino acid sequence, wherein the SIRPα amino acid sequence is 100-119 amino acids in length having at least 95% identity to an amino acid sequence selected from the group consisting of SEQ ID NOs: 24 and 26; and wherein the polypeptide is capable of binding CD47.

According to an aspect of some embodiments of the present invention there is provided an isolated polypeptide comprising a 4-1BBL amino acid sequence, wherein the 4-1BBL amino acid sequence is 185-202 amino acids in length having at least 95% identity to an amino acid sequence selected from the group consisting of SEQ ID NOs: 22, 23, 27 and 28; and wherein the polypeptide is capable of at least one of:

(i) binding 4-1BB,
(ii) activating the 4-1BB signaling pathway in a cell expressing the 4-1BB; and/or
(iii) co-stimulating immune cells expressing the 4-1BB.

According to some embodiments of the invention, the SIRPα amino acid sequence is at least 115 amino acids in length.

According to some embodiments of the invention, the SIRPα amino acid sequence is 116 amino acids in length.

According to some embodiments of the invention, the SIRPα amino acid sequence comprises a mutation at an amino acid residue selected from the group consisting of L4, A27, E47 and V92 corresponding to SEQ ID NO: 2.

According to some embodiments of the invention, the mutation is selected from the group consisting of L4I, A27I, E47V and V92I corresponding to SEQ ID NO: 2.

According to some embodiments of the invention, the SIRPα amino acid sequence does not comprise any of amino acid residues K117-Y343 corresponding to SEQ ID NO: 2.

According to some embodiments of the invention, the SIRPα amino acid sequence comprises the SEQ ID NO: 24 or 26.

According to some embodiments of the invention, the SIRPα amino acid sequence consists of the SEQ ID NO: 24 or 26.

According to some embodiments of the invention, the 4-1BBL amino acid sequence has at least 95% identity to an amino acid sequence selected from the group consisting of SEQ ID NO: 22-23.

According to some embodiments of the invention, the 4-1BBL amino acid sequence does not comprise any of amino acid residues A1-V6 or A1-G14 corresponding to SEQ ID NO: 3.

According to some embodiments of the invention, the 4-1BBL amino acid sequence comprises the SEQ ID NO: 22, 23, 27 or 28.

According to some embodiments of the invention, the 4-1BBL amino acid sequence consists of the SEQ ID NO: 22, 23, 27 or 28.

According to some embodiments of the invention:
(i) the SIRPα amino acid sequence is as set forth in SEQ ID NO: 2 or 25 and the 4-1BBL amino acid sequence is as set forth in SEQ ID NO: 22, 23, 27 or 28; or
(ii) the SIRPα amino acid sequence is as set forth in SEQ ID NO: 24 or 26 and the 4-1BBL amino acid sequence is as set forth in SEQ ID NO: 3, 22, 23, 27 or 28.

According to some embodiments of the invention:
(i) the SIRPα amino acid sequence is as set forth in SEQ ID NO: 2 and the 4-1BBL amino acid sequence is as set forth in SEQ ID NO: 22 or 23; or
(ii) the SIRPα amino acid sequence is as set forth in SEQ ID NO: 24 and the 4-1BBL amino acid sequence is as set forth in SEQ ID NO: 22.

According to some embodiments of the invention, the 4-1BBL amino acid sequence comprises the SEQ ID NO: 72, 74 or 76.

According to some embodiments of the invention, the 4-1BBL amino acid sequence consists of the SEQ ID NO: 72, 74 or 76.

According to some embodiments of the invention, the 4-1BBL amino acid sequence comprises the SEQ ID NO: 70.

According to some embodiments of the invention, the 4-1BBL amino acid sequence consists of the SEQ ID NO: 70.

According to some embodiments of the invention, the SIRPα-4-1BBL fusion protein comprises a linker between the SIRPα and the 4-1BBL.

According to some embodiments of the invention, the SIRPα-4-1BBL fusion protein comprising a linker between each of the three repeats of the 4-1BBL amino acid sequence.

According to some embodiments of the invention, the linker has a length of one to six amino acids.

According to some embodiments of the invention, the linker is a single amino acid linker.

According to some embodiments of the invention, the linker is glycine.

According to some embodiments of the invention, the linker is not an Fc domain of an antibody or a fragment thereof.

According to some embodiments of the invention, the linker is an Fc domain of an antibody or a fragment thereof.

According to some embodiments of the invention, the SIRPα-4-1BBL fusion protein being in a form of at least a homo-trimer.

According to some embodiments of the invention, the at least homo-trimer is at least 100 kD in molecular weight as determined by SEC-MALS.

According to some embodiments of the invention, the SIRPα-4-1BBL fusion protein or the isolated polypeptide being soluble.

According to some embodiments of the invention, the production yield of the fusion protein is at least 1.5 fold higher than the production yield of SEQ ID NO: 5 under the same production conditions, the production conditions comprise expression in a mammalian cell and culturing at 32-37° C., 5-10% $CO_2$ for 5-13 days.

According to some embodiments of the invention, the SIRPα-4-1BBL fusion protein amino acid sequence comprises an amino acid sequence having at least 95% identity to an amino acid sequence selected from the group consisting of SEQ ID NO: 11, 13, 15, 16, 18-21 and 45-49.

According to some embodiments of the invention, the SIRPα-4-1BBL fusion protein amino acid sequence comprises an amino acid sequence having at least 95% identity to an amino acid sequence selected from the group consisting of SEQ ID NO: 11, 13 and 16.

According to some embodiments of the invention, the SIRPα-4-1BBL fusion protein amino acid sequence comprises an amino acid sequence selected from the group consisting of SEQ ID NO: 11, 13, 15, 16, 18-21 and 45-49.

According to some embodiments of the invention, the SIRPα-4-1BBL fusion protein amino acid sequence comprises an amino acid sequence selected from the group consisting of SEQ ID NO: 11, 13 and 16.

According to some embodiments of the invention, the SIRPα-4-1BBL fusion protein amino acid sequence consists of an amino acid sequence selected from the group consisting of SEQ ID NO: 11, 13, 15, 16, 18-21 and 45-49.

According to some embodiments of the invention, the SIRPα-4-1BBL fusion protein amino acid sequence consists of an amino acid sequence selected from the group consisting of SEQ ID NO: 11, 13 and 16.

According to an aspect of some embodiments of the present invention there is provided a polynucleotide encoding the SIRPα-4-1BBL fusion protein or the polypeptide.

According to an aspect of some embodiments of the present invention there is provided a nucleic acid construct comprising the polynucleotide, and a regulatory element for directing expression of the polynucleotide in a host cell.

According to some embodiments of the invention, the polynucleotide comprises a nucleic acid sequence selected from the group consisting of SEQ ID NO: 55-66 and 68.

According to some embodiments of the invention, the polynucleotide comprises a nucleic acid sequence selected from the group consisting of SEQ ID NO: 55, 56 and 58.

According to an aspect of some embodiments of the present invention there is provided a host cell comprising the SIRPα-4-1BBL fusion protein or the polypeptide or the polynucleotide or the nucleic acid construct.

According to an aspect of some embodiments of the present invention there is provided a method of producing a SIRPα-4-1BBL fusion protein or a polypeptide, the method comprising expressing in a host cell the polynucleotide or the nucleic acid construct.

According to some embodiments of the invention, the method comprising isolating the fusion protein or the polypeptide.

According to an aspect of some embodiments of the present invention there is provided a method of treating a disease that can benefit from activating immune cells comprising administering to a subject in need thereof the SIRPα-4-1BBL fusion protein or the isolated polypeptide, the polynucleotide or the nucleic acid construct or the host cell.

According to some embodiments of the invention, the method further comprising administering to the subject a therapeutic agent for treating the disease.

According to an aspect of some embodiments of the present invention there is provided the SIRPα-4-1BBL fusion protein or the isolated polypeptide, the polynucleotide or the nucleic acid construct or the host cell, for use in treating a disease that can benefit from activating immune cells.

According to some embodiments of the invention, the composition further comprising a therapeutic agent for treating the disease.

According to an aspect of some embodiments of the present invention there is provided an article of manufacture comprising a packaging material packaging a therapeutic agent for treating a disease that can benefit from activating immune cells; and the SIRPα-4-1BBL fusion protein or the isolated polypeptide, the polynucleotide or the nucleic acid construct or the host cell.

According to some embodiments of the invention, the cells of the disease express CD47.

According to some embodiments of the invention, the disease comprises a hyper-proliferative disease.

According to some embodiments of the invention, the hyper-proliferative disease comprises sclerosis or fibrosis, Idiopathic pulmonary fibrosis, psoriasis, systemic sclerosis/scleroderma, primary biliary cholangitis, primary sclerosing cholangitis, liver fibrosis, prevention of radiation-induced pulmonary fibrosis, myelofibrosis or retroperitoneal fibrosis.

According to some embodiments of the invention, the hyper-proliferative disease comprises cancer.

According to some embodiments of the invention, the cancer is selected from the group consisting of lymphoma, leukemia and carcinoma.

According to some embodiments of the invention, the disease comprises a disease associated with immune suppression or medication induced immunosuppression.

According to some embodiments of the invention, the comprises HIV, Measles, influenza, LCCM, RSV, Human Rhinoviruses, EBV, CMV or Parvo viruses.

According to some embodiments of the invention, the disease comprises an infection.

According to an aspect of some embodiments of the present invention there is provided a method of activating immune cells, the method comprising in-vitro activating immune cells in the presence of the SIRPα-4-1BBL fusion protein or the isolated polypeptide, the polynucleotide or the nucleic acid construct or the host cell.

According to some embodiments of the invention, the activating is in the presence of cells expressing CD47 or exogenous CD47.

According to some embodiments of the invention, the cells expressing the CD47 comprise pathologic cells.

According to some embodiments of the invention, the pathologic cells comprise cancer cells.

According to some embodiments of the invention, the activating is in the presence of an anti-cancer agent.

According to some embodiments of the invention, the therapeutic agent for treating the disease or the anti-cancer agent comprises an antibody.

According to some embodiments of the invention, the antibody is selected from the group consisting rituximab, cetuximab, trastuzumab, edrecolomab, almetuzumab, gemtuzumab, ibritumomab, panitumumab, Belimumab, Bevacizumab, Bivatuzumab mertansine, Blinatumomab, Blontuvetmab, Brentuximab vedotin, Catumaxomab, Cixutumumab, Daclizumab, Adalimumab, Bezlotoxumab, Certolizumab pegol, Citatuzumab bogatox, Daratumumab, Dinutuximab, Elotuzumab, Ertumaxomab, Etaracizumab, Gemtuzumab ozogamicin, Girentuximab, Necitumumab, Obinutuzumab, Ofatumumab, Pertuzumab, Ramucirumab, Siltuximab, Tositumomab, Trastuzumab, Nivolumab, Pembrolizumab, Durvalumab, Atezolizumab, Avelumab and ipilimumab.

According to some embodiments of the invention, the antibody is selected from the group consisting of rituximab, cetuximab and almetuzumab.

According to some embodiments of the invention, the therapeutic agent for treating the disease or the anti-cancer agent comprises an IMiD (e.g. Thalidomide, Lenalidomie, Pomalidomide).

According to some embodiments of the invention, the method comprising adoptively transferring the immune cells following the activating to a subject in need thereof.

According to some embodiments of the invention, the immune cells comprise T cells.

According to some embodiments of the invention, the immune cells comprise phagocytes.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1 is a schematic representation of the SIRPα-4-1BBL fusion protein referred to herein as "DSP107" (SEQ ID NO: 5) comprising an N-terminal signal peptide and a C-terminal his-tag (SEQ ID NO 43). Shown the signal peptide (underlined, SEQ ID NO: 4), the SIRPα domain (red, SEQ ID NO: 2), the glycine linker (black), the 4-1BBL domain (blue, SEQ ID NO: 3) and the C-terminal His-tag (black bold).

FIGS. 2A-C demonstrate the predicted 3D structure of DSP107 (SEQ ID NO: 5). FIG. 2A is a schematic 3D model. SIRPα is shown in grey ribbons, CD47 (SIRPα receptor) is shown in green ribbons, 4-1BBL is shown in blue ribbons and 2 additional copies of 4-1BBL (forming the trimer) are shown in light blue. FIG. 2B is a schematic, full atomic 3D model. FIG. 2C is a schematic 3D model. The X-ray resolved domains are represented by its surface and colored by a hydrophobicity scale-blue (most hydrophilic) to Brown (Hydrophobic). 4-1BBL shows a higher level of exposed hydrophobic areas.

FIG. 3 is a schematic representation of the domain and segments identified in DSP107 (SEQ ID NO: 5). An Ig-like V type domain is highlighted in light blue, an Ig-like C1-type1 domain is highlighted in yellow, an Ig-like C1-type2 domain is highlighted in green, an X-ray resolved part is highlighted in grey and flanking/unstructured regions are marked with red boxes.

FIG. 4 demonstrates the predicted 3D structure of SIRPα-4-1BBL variant fusion protein referred to herein as "DSP107_var1" (SEQ ID NO: 11). The upper panel shows the 3D structure in surface representation and colored by hydrophobicity scale: hydrophilic in blue and hydrophobic surface in brown. The lower panel shows the 3D structure in ribbons representation colored by sequence position from the N-terminal (in blue) to the C-terminal (red).

FIG. 5 demonstrates the predicted 3D structure of SIRPα-4-1BBL variant fusion protein referred to herein as "DSP107_var2" (SEQ ID NO: 13). The upper panel shows the 3D structure in surface representation and colored by hydrophobicity scale: hydrophilic in blue and hydrophobic surface in brown. The lower panel shows the 3D structure in ribbons representation colored by sequence position from the N-terminal (in blue) to the C-terminal (red).

FIG. 6 demonstrates the predicted 3D structure of SIRPα-4-1BBL variant fusion protein referred to herein as "DSP107_var3.1" (SEQ ID NO: 15). The upper panel shows the 3D structure in surface representation and colored by hydrophobicity scale: hydrophilic in blue and hydrophobic surface in brown. The lower panel shows the 3D structure in ribbons representation colored by sequence position from the N-terminal (in blue) to the C-terminal (red).

Figure 7A:
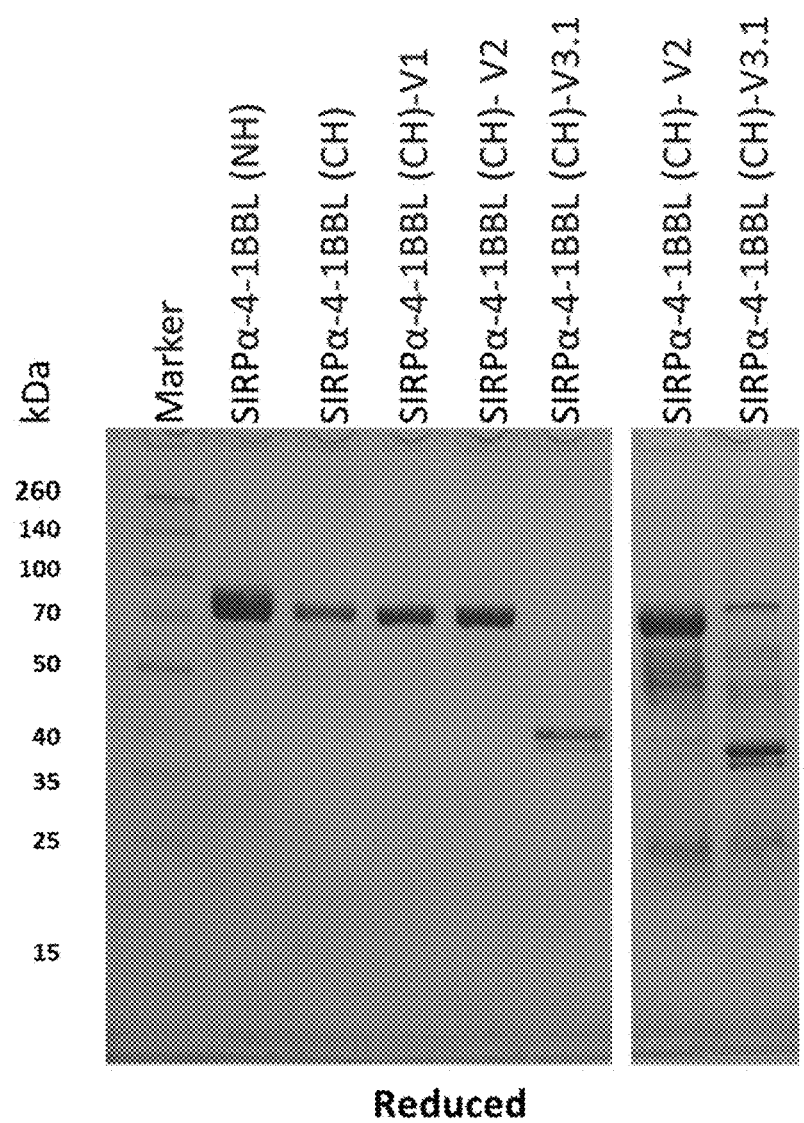
Figure 7B:
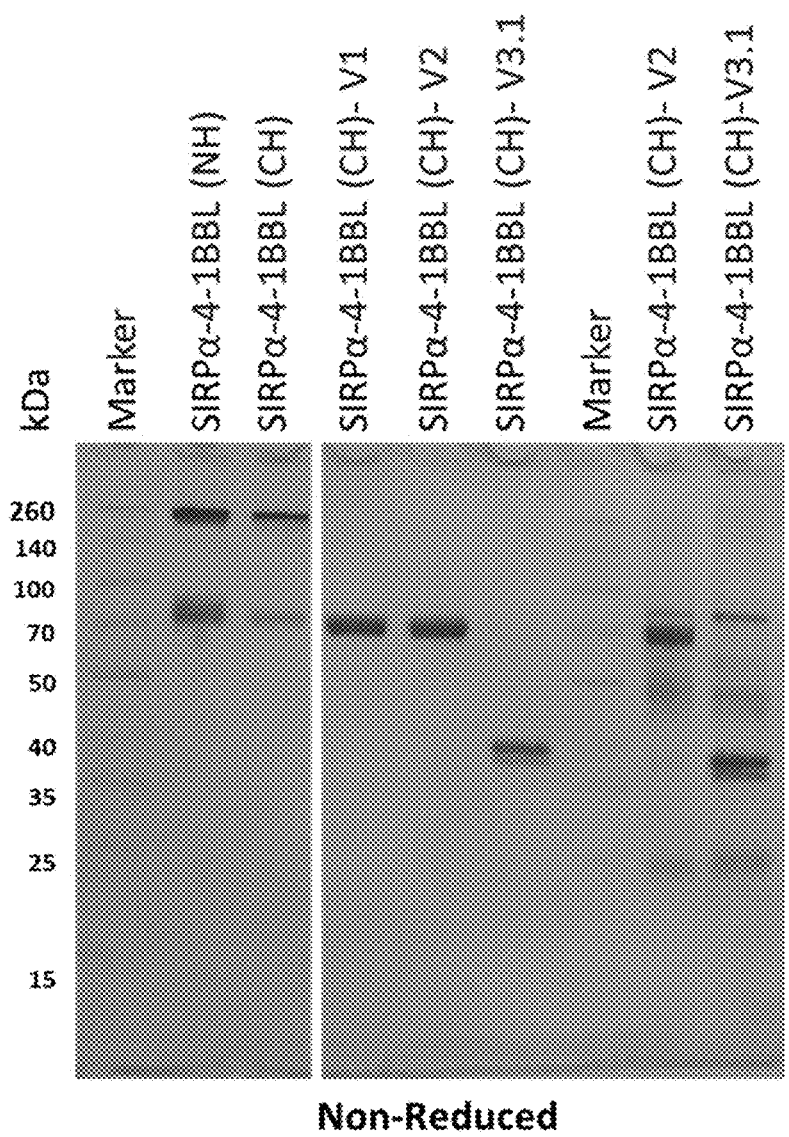

FIGS. 7A-B demonstrate SDS-PAGE analysis of the SIRPα-4-1BBL fusion proteins produced. N-terminal his-tagged DSP107 [marked as (NH), SEQ ID NO: 44], C-terminal his-tagged DSP107 [marked as (CH), SEQ ID NO: 1] and C-terminal his-tagged DSP107 variants [marked as (CH)-V1, (CH)-V2 and (CH)-V3.1 (SEQ ID NO 12, 14 and 17, respectively)] (2 μg/well) were separated on 4-20% SDS-PAGE at reducing (FIG. 7A) and non-reducing (FIG. 7B) conditions. Proteins migration on the gel was visualized by staining with e-Stain peds. A molecular size proteins marker was also separated in the same gel and the sizes are indicated.

Figure 8A:
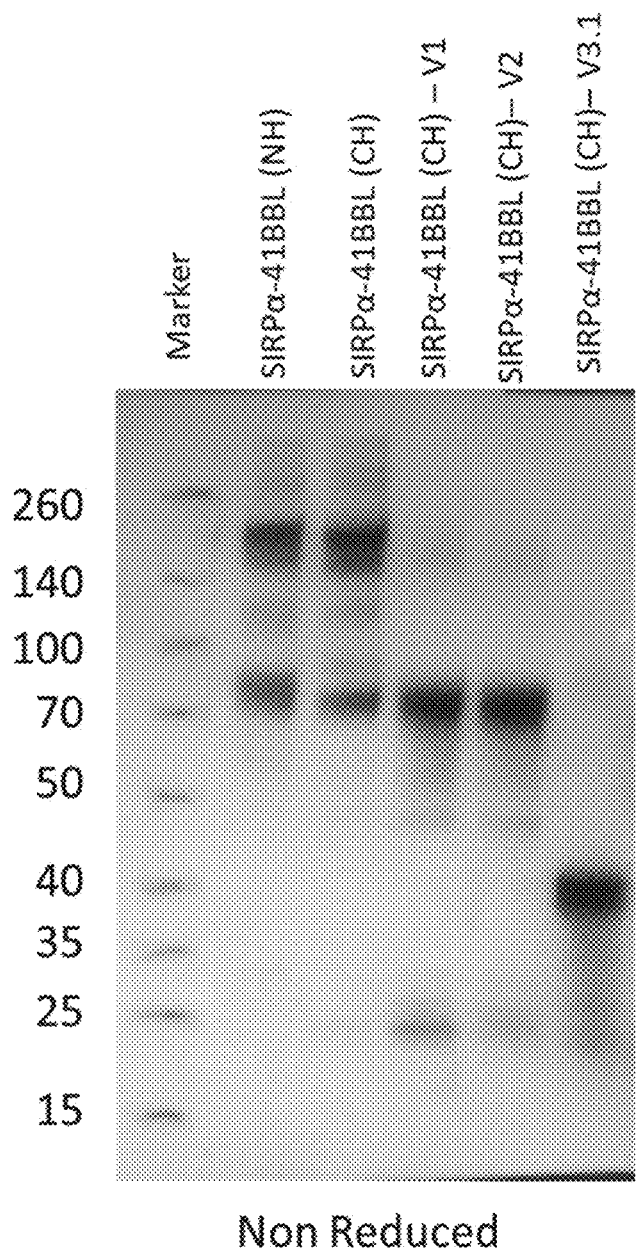
Figure 8B:
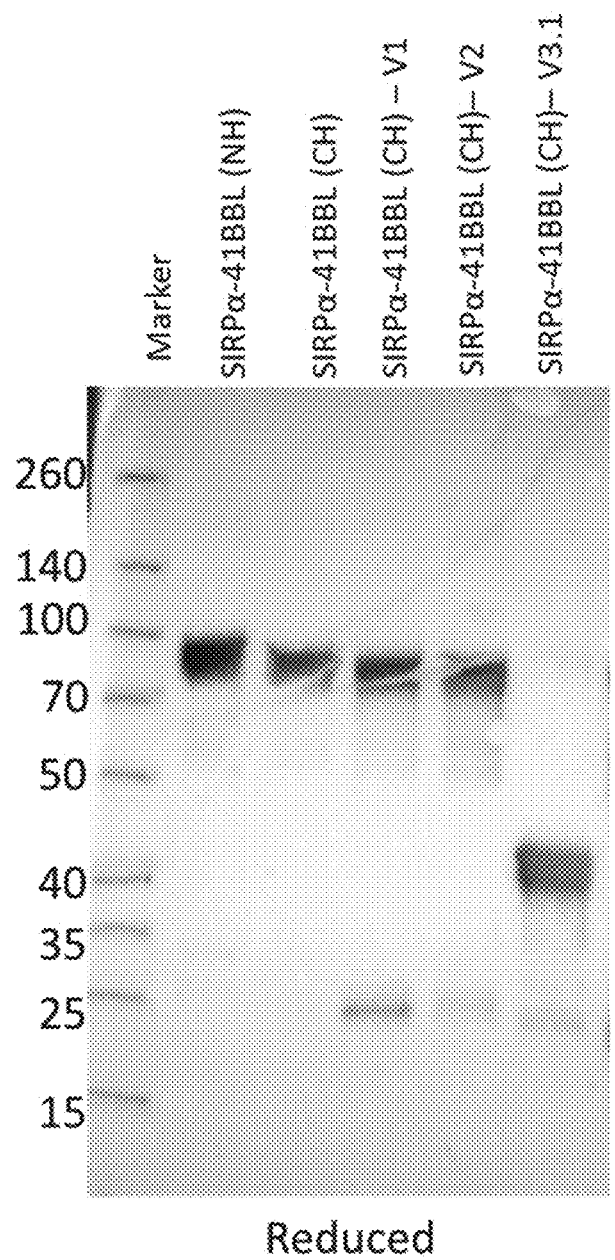
Figure 8C:
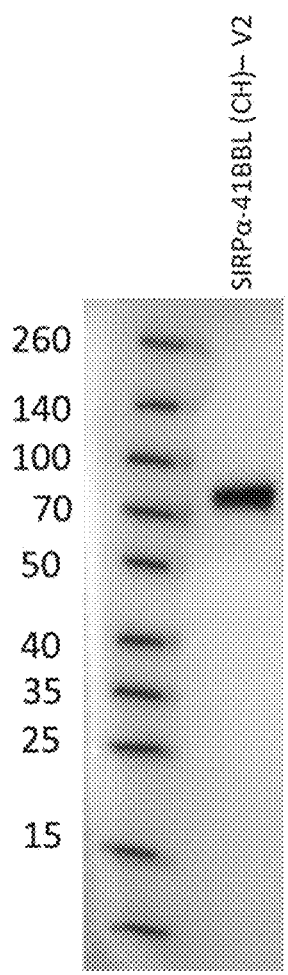

FIGS. 8A-C demonstrate western blot analysis of the SIRPα-4-1BBL fusion proteins produced. N-terminal his-tagged DSP107 [marked as (NH), SEQ ID NO: 44], C-terminal his-tagged DSP107 [marked as (CH), SEQ ID NO: 1, C-terminal his-tagged DSP107_V1 [marked as (CH)-V1, SEQ ID NO: 12], C-terminal his-tagged DSP107_V2 [marked as (CH)-V2), SEQ ID NO: 14] and C-terminal his-tagged DSP107_V3.1 [marked as (CH)-V3.1, SEQ ID NO 17] (500 ng/well) were separated on SDS-PAGE at non reducing (FIG. 8A) and reducing (FIG. 8B) conditions, followed by immunoblotting with anti 4-1BBL antibody. C-terminal his-tagged DSP107_V2 [marked as (CH)-V2), SEQ ID NO: 14] (50 ng/well) was also separated on SDS-PAGE at reducing conditions, followed by immunoblotting with anti SIRPα antibody (FIG. 8C).

FIG. 9 is a graph demonstrating binding of N-terminal his-tagged DSP107 [marked as (NH), SEQ ID NO: 44], C-terminal his-tagged DSP107_V1 [marked as (CH)-V1, SEQ ID NO: 12] and C-terminal his-tagged DSP107_V2 [marked as (CH)-V2, SEQ ID NO: 14] to SIRPα and 4-1BBL in a similar dose response manner as determined by a sandwich ELISA, using anti 4-1BBL antibody for binding and SIRPα-biotinylated antibody for detection.

Figure 10:
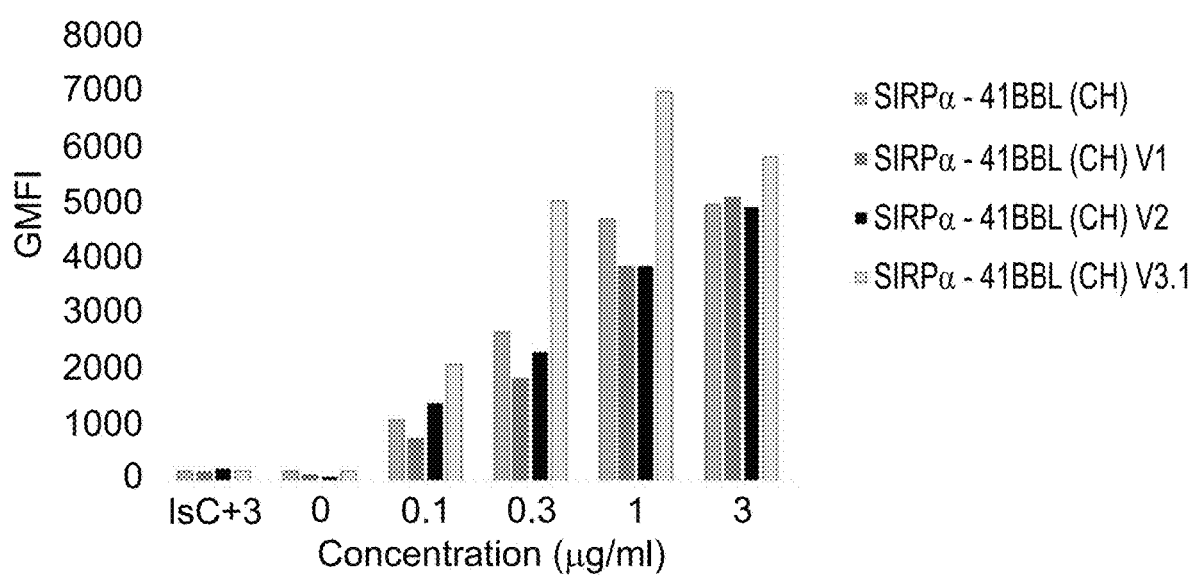

FIG. 10 is a bar graph demonstrating binding of the SIRPα moiety of C-terminal his-tagged DSP107 [marked as (CH), SEQ ID NO: 1, C-terminal his-tagged DSP107_V1 [marked as (CH)-V1), SEQ ID NO: 12], C-terminal his-tagged DSP107_V2 [marked as (CH)-V2, SEQ ID NO: 14] and C-terminal his-tagged DSP107_V3.1 [marked as (CH)-V3.1, SEQ ID NO 17] as determined by flow cytometry analysis. Shown are GMFI values.

Figure 11:
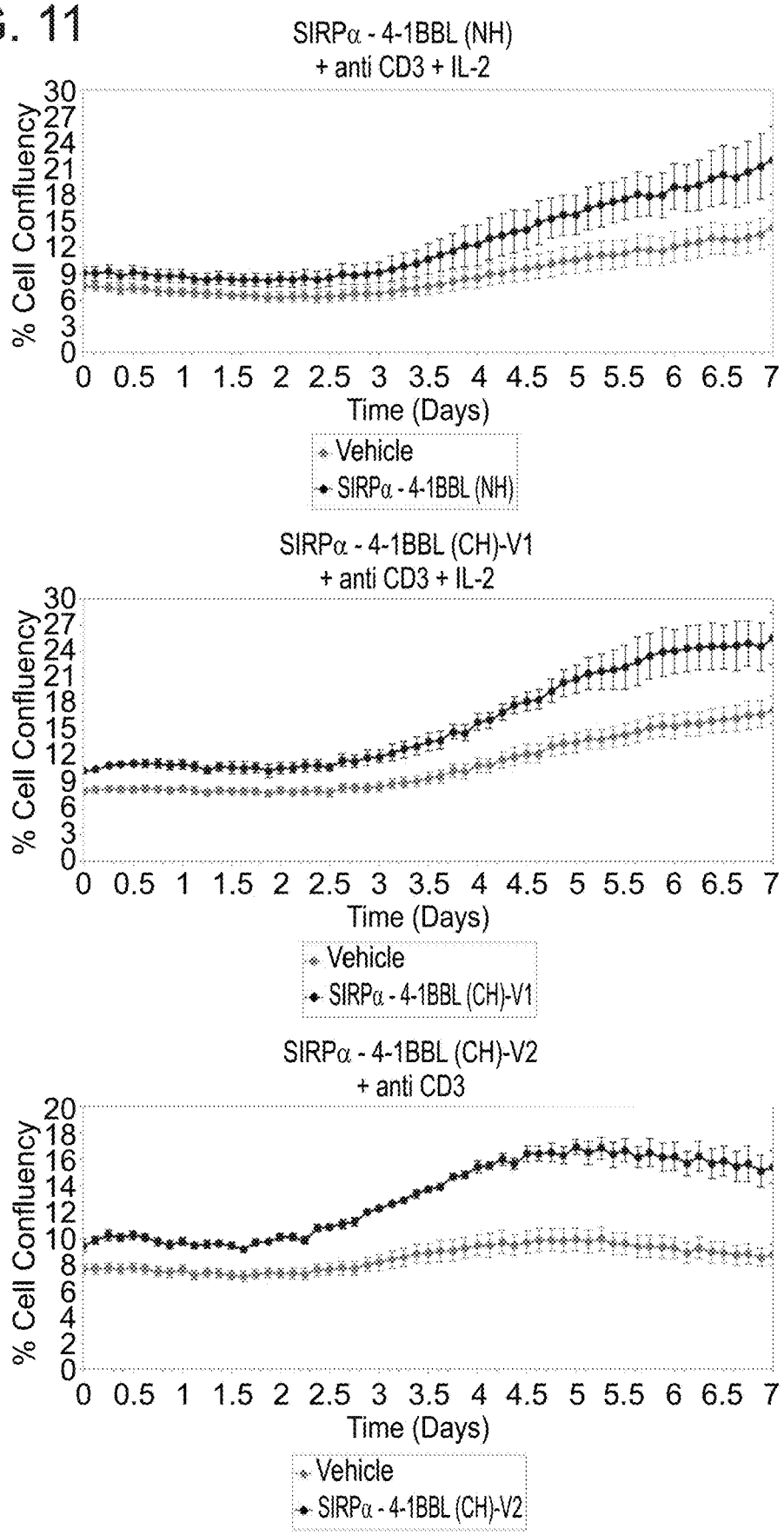

FIG. 11 shows graphs demonstrating that the SIRPα-4-1BBL fusion proteins produced promote T cell proliferation.

PBMCs were incubated with 0.01 μg/ml N-terminal his-tagged DSP107 [marked as (NH), SEQ ID NO: 44], C-terminal his-tagged DSP107_V1 [marked as (CH)-V1, SEQ ID NO: 12] or C-terminal his-tagged DSP107_V2 [marked as (CH)-V2, SEQ ID NO: 17] in the presence of anti-CD3, with or without IL-2, as indicated; and proliferation was determined at the indicated time points by confluency measurement.

Figure 12:
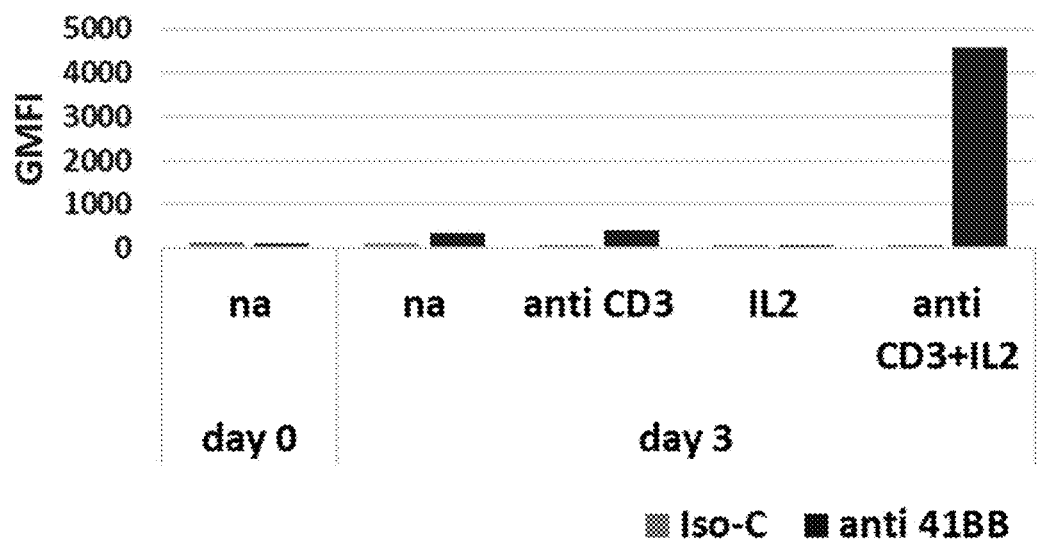

FIG. 12 is a bar graph demonstrating 4-1BB expression on human PBMCs following stimulation in the presence of sub-optimal concentrations of anti-CD3 and/or IL-2 as compared to unstimulated cells (na) at the indicated time points. Shown are GMFI values.

Figure 13A:
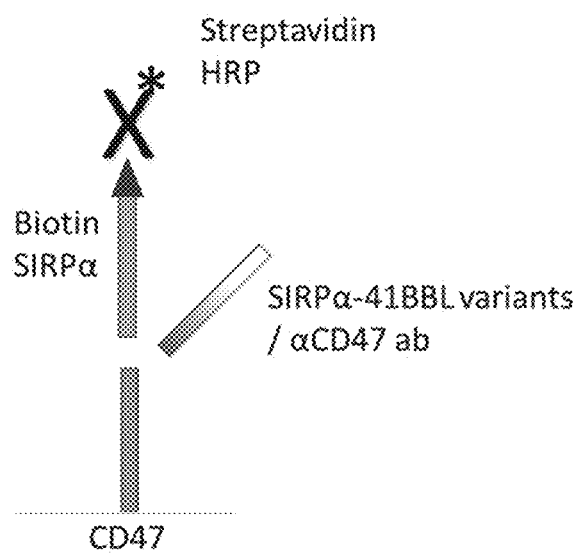
Figure 13B:
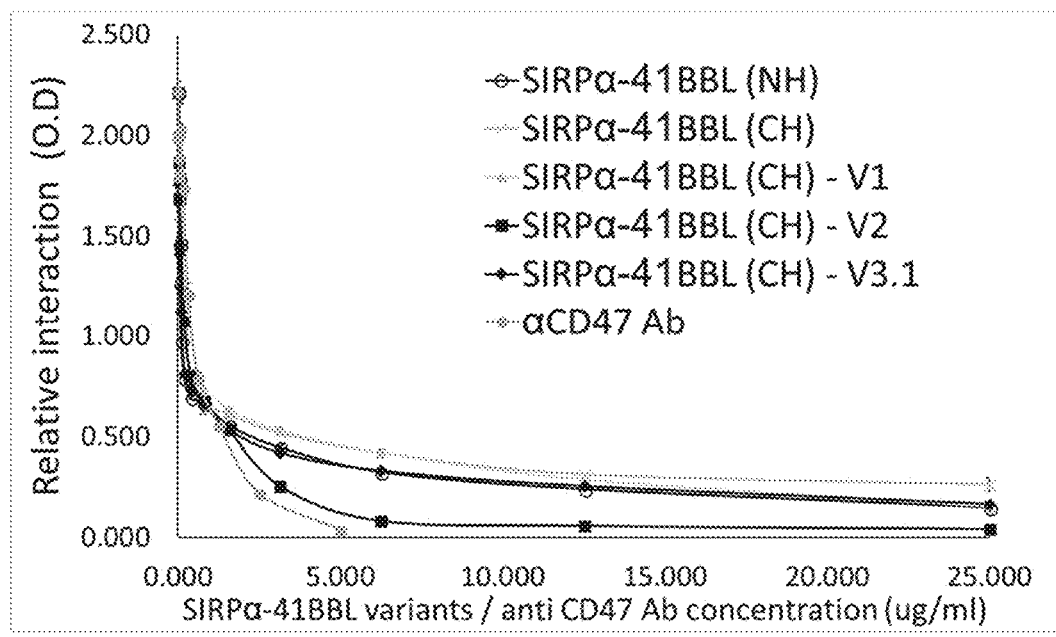
Figure 13C:
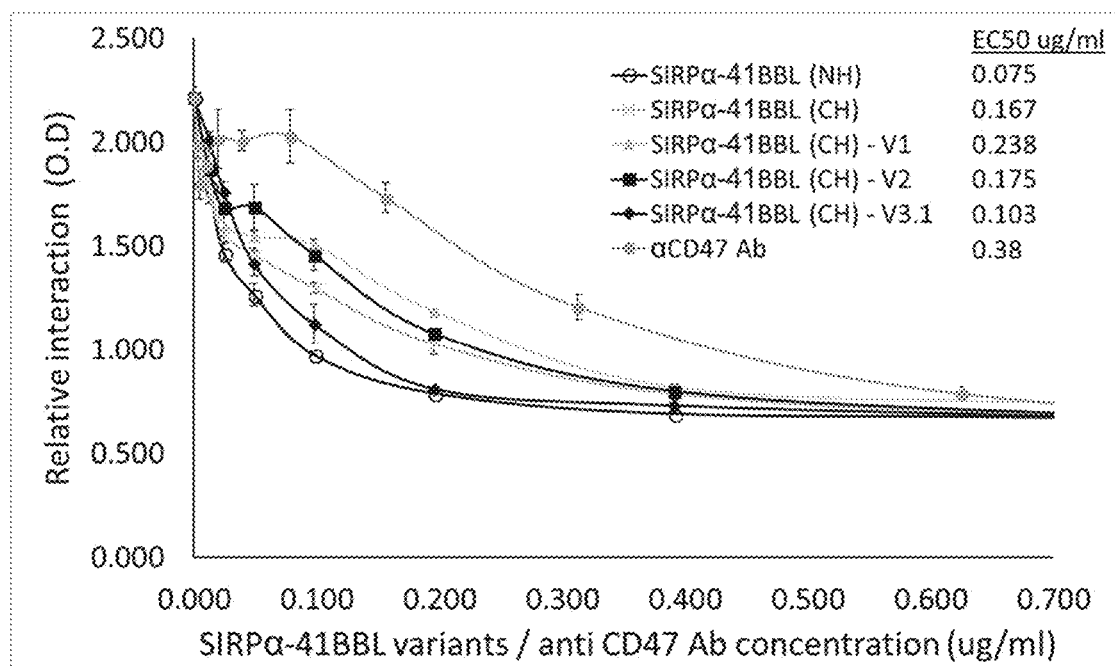

FIGS. 13A-C demonstrate that the SIRPα-4-1BBL fusion proteins produced block interaction of SIRPα with 4-1BBL. FIG. 13A shows the assay design: Recombinant human CD47 was bound to ELISA plate. SIRPα-4-1BBL fusion protein, or a positive control anti CD47 antibody were added to the plate. Following wash biotinylated recombinant human SIRPα was added followed by streptavidin HRP and TMB substrate. Interaction of SIRPα with CD47 was measured by absorbance at 450 nm. FIG. 13B is a graph demonstrating blockade of the SIRPα interaction by N-terminal his-tagged DSP107 [marked as (NH), SEQ ID NO: 44], C-terminal his-tagged DSP107 [marked as (CH), SEQ ID NO: 1], C-terminal his-tagged DSP107_V1 [marked as (CH-V1, SEQ ID NO: 12, C-terminal his-tagged DSP107_V2 [marked as (CH)-V2, SEQ ID NO: 14] and C-terminal his-tagged DSP107_V3.1 [marked as (CH)-V3.1, SEQ ID NO: 17] as compared to the blocking antibody positive control. FIG. 13C is a graph showing EC50 values calculated for a limited range of concentrations.

Figure 14A:
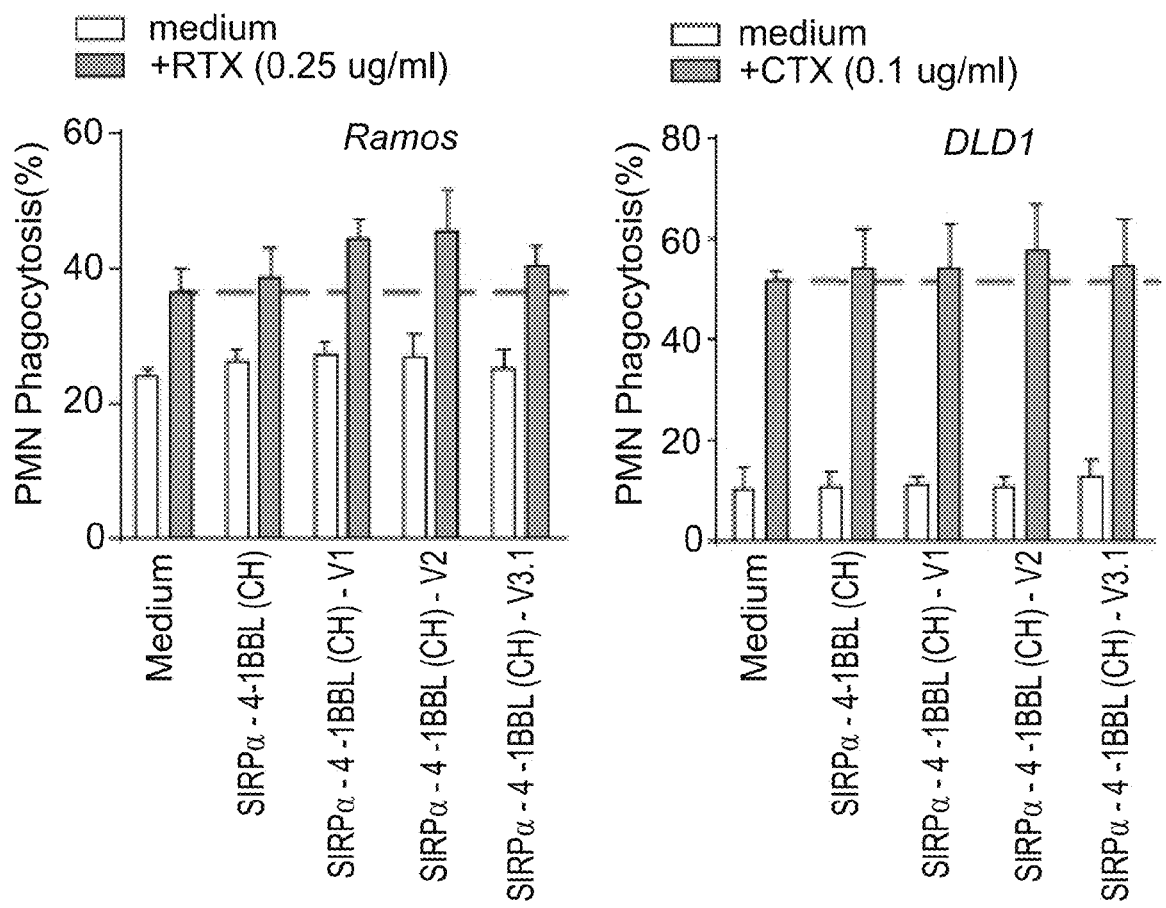
Figure 14B:
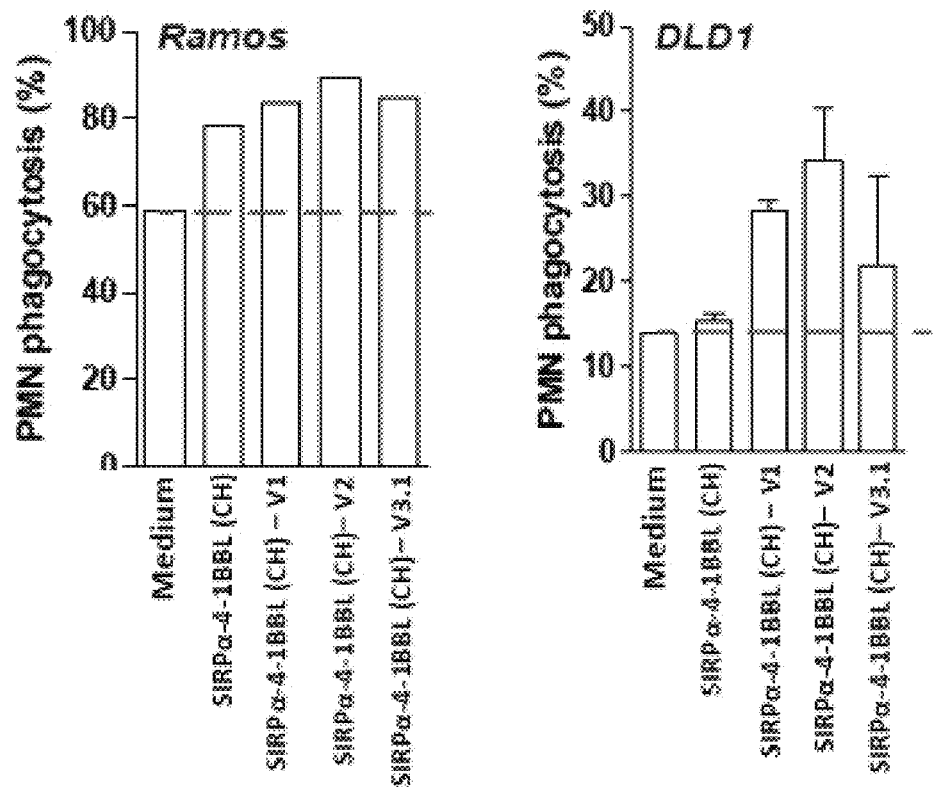

FIGS. 14A-B are bar graphs demonstrating that the SIRPα-4-1BBL fusion proteins produced enhance polymorphonuclear (PMNs) mediated phagocytosis of human cancer cells. Shown % phagocytosis following 2 hours (FIG. 14A) or 18 hours (FIG. 14B) incubation of PMNs and Ramos or DLD1 cancer cells with C-terminal his-tagged DSP107 [marked as (CH), SEQ ID NO: 1, C-terminal his-tagged DSP107_V1 [marked as (CH)-V1, SEQ ID NO: 12], C-terminal his-tagged DSP107_V2 [marked as (CH)-V2, SEQ ID NO: 14] or C-terminal his-tagged DSP107_V3.1 [marked as (CH)-V3.1, SEQ ID NO: 17]; alone or in combination with Rituximab (RTX) or Cetuximab (CTX), as indicated.

Figure 15:
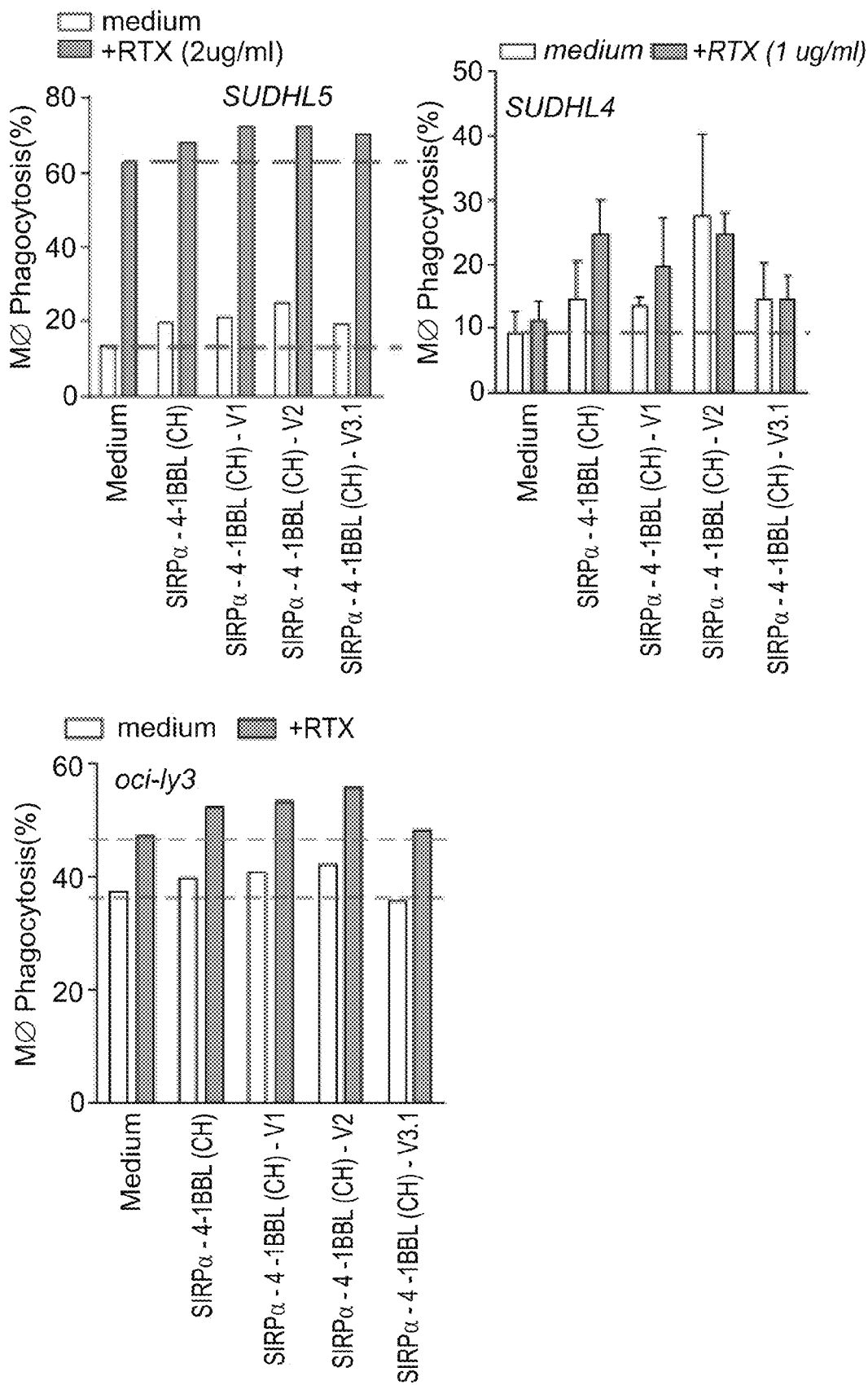

FIG. 15 shows bar graphs demonstrating that the SIRPα-4-1BBL fusion proteins produced enhance macrophages mediated phagocytosis of human lymphoma cells. Shown % phagocytosis following 2 hours incubation of macrophages and SUDHL5, SUDHL4 and OCI-LY3 cancer cells with C-terminal his-tagged DSP107 [marked as (CH), SEQ ID NO: 1], C-terminal his-tagged DSP107_V1 [marked as (CH)-V1, SEQ ID NO: 12], C-terminal his-tagged DSP107_V2 [marked as (CH)-V2, SEQ ID NO: 14] or C-terminal his-tagged DSP107_V3.1 [marked as (CH)-V3.1, SEQ ID NO: 17); alone or in combination with Rituximab (RTX), as indicated.

Figure 16:
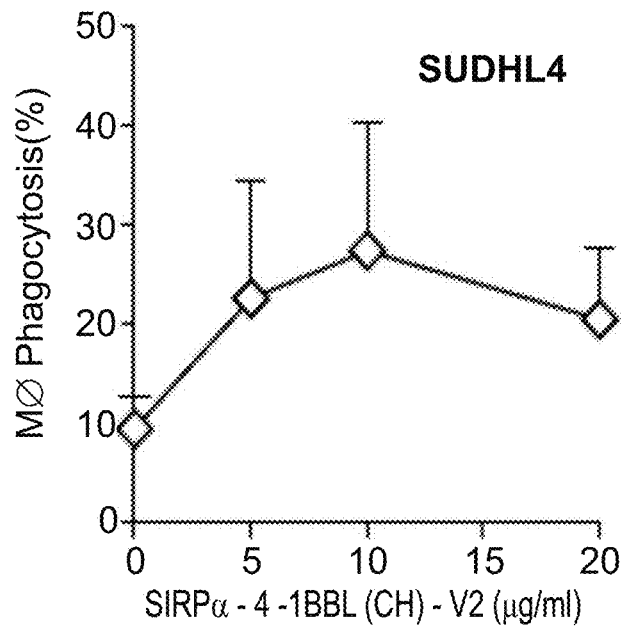

FIG. 16 is a graph demonstrating that C-terminal his-tagged DSP107_V2 [marked as (CH)-V2, SEQ ID NO: 14] enhance macrophages mediated phagocytosis of SUDHL4 cancer cells following 2 hours of incubation, in a dose depended manner.

Figure 17:
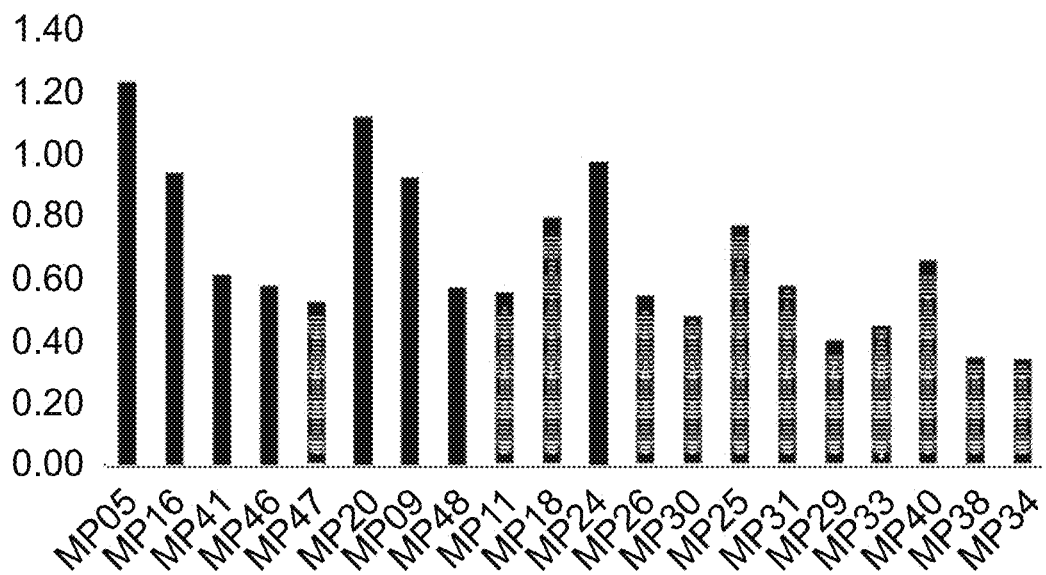

FIG. 17 is a bar graph demonstrating DSP107_V2 (SEQ ID NO: 13) concentration in minipools' samples taken at day 11 from fed batch cultures, as determined by Dual side ELISA.

Figure 18:
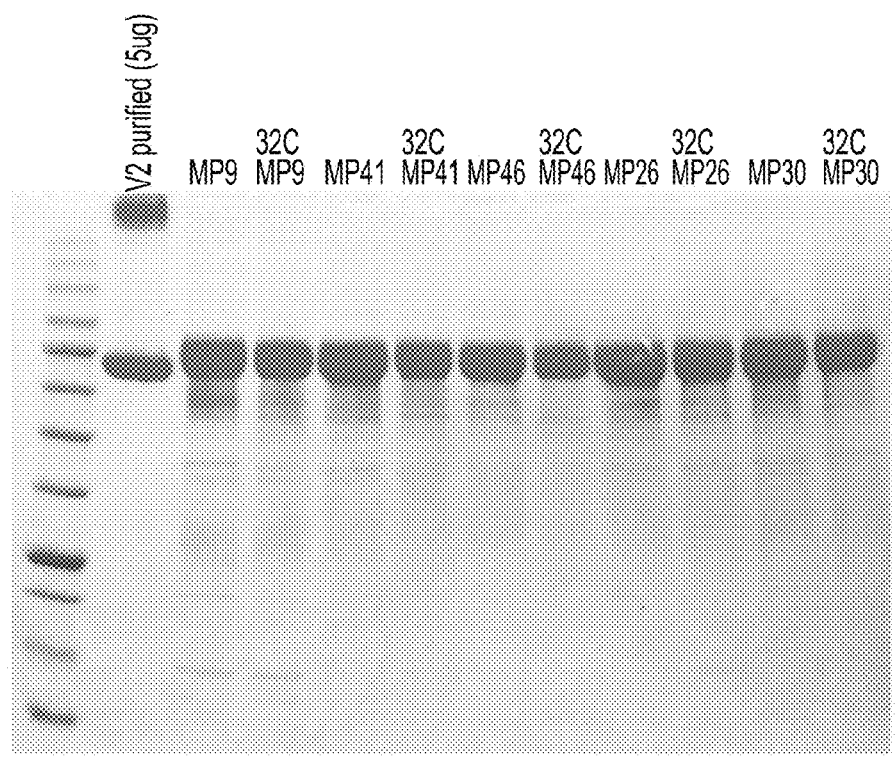

FIG. 18 demonstrates SDS-PAGE analysis of DSP107_V2 (SEQ ID NO: 13). Purified DSP107_V2 (5 mg) and minipools' samples taken at day 11 from fed batch cultures (5 μl) were separated on 4-20% SDS-PAGE at reducing conditions, followed by Coomassie staining.

Figure 19A:
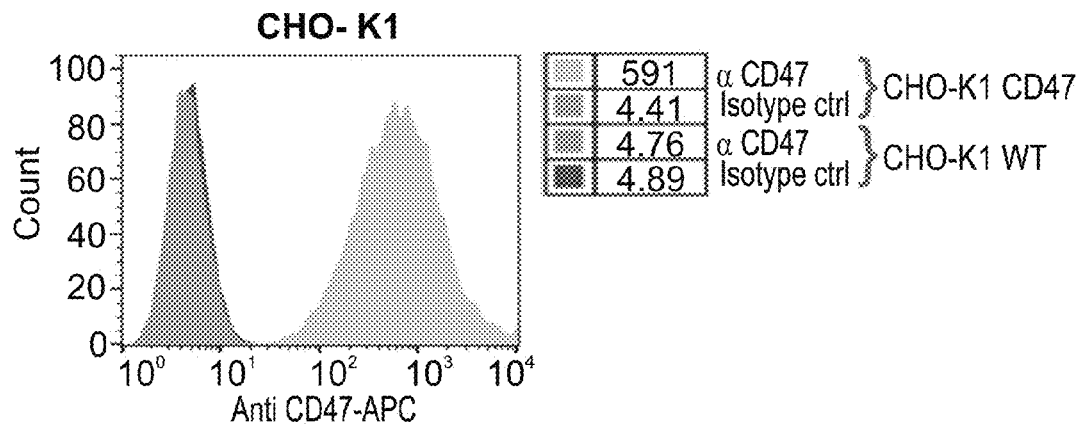
Figure 19B:
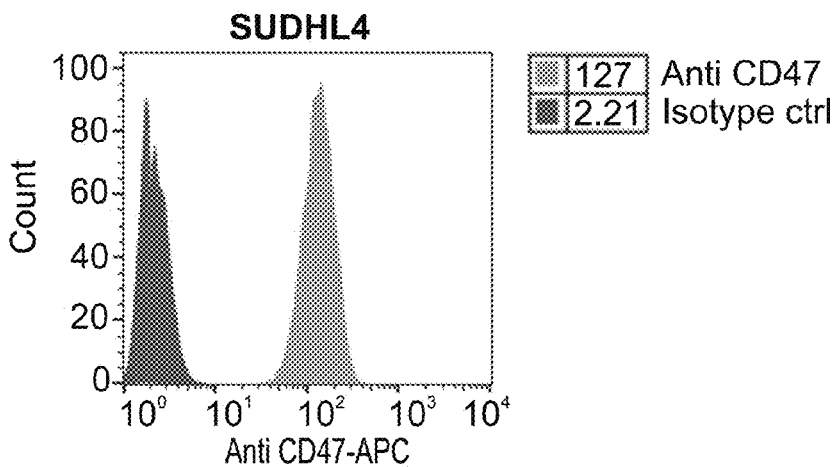

FIGS. 19A-B show histograms demonstrating membrane expression of CD47 on CHO-K1 overexpressing (OX) human CD47 cells (FIG. 19A) and SUDHL4 cells (FIG. 19B), and no expression on CHO-K1 cells (FIG. 19A), as determined by flow cytometry analysis.

Figure 20:
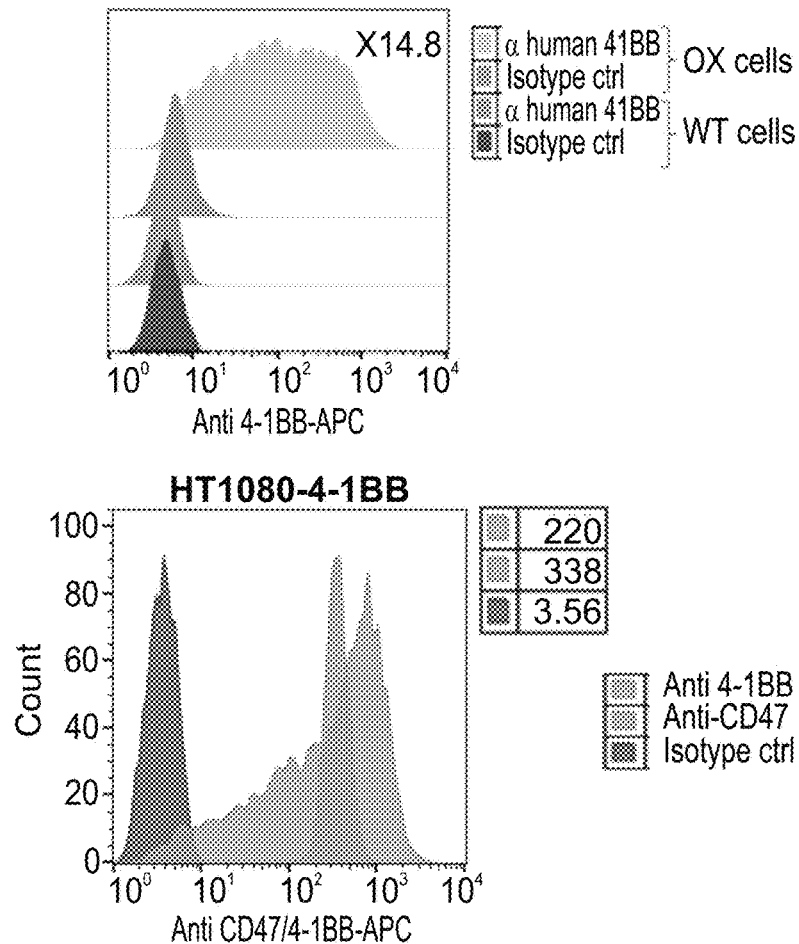

FIG. 20 shows histograms demonstrating membrane expression of 4-1BB and CD47 on HT1080 cells OX 4-1BB, and no expression of 4-1BB on HT1080 parental (WT) cells as determined by flow cytometry analysis.

Figure 21A:
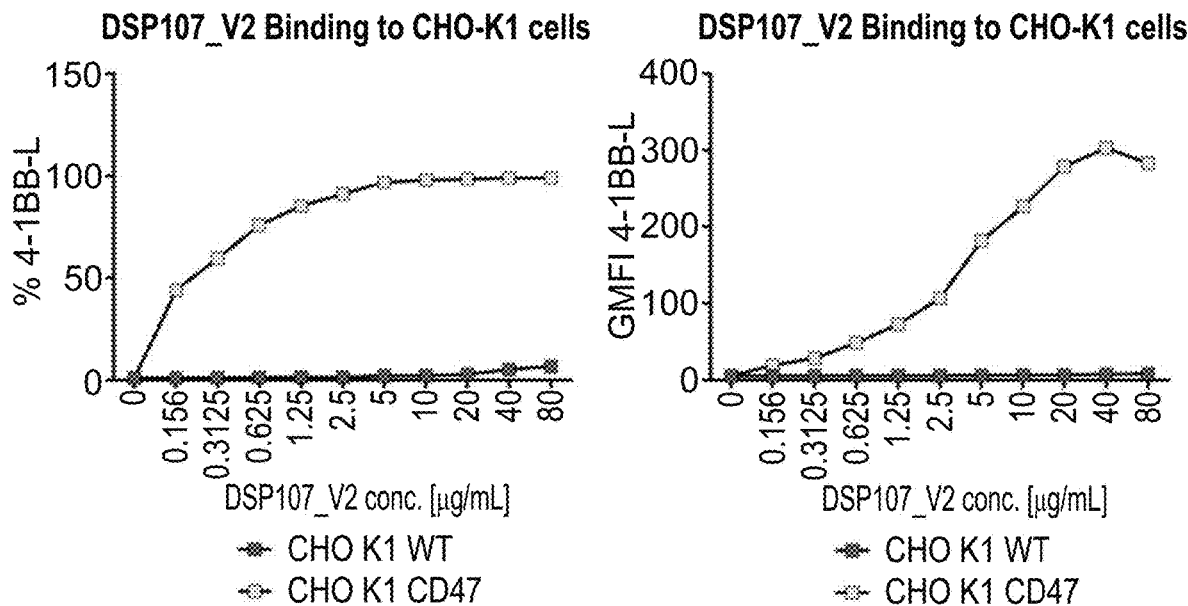

FIGS. 21A-B show graphs demonstrating binding of the SIRPα moiety of DSP107_V2 (SEQ ID NO: 13), to CHO-K1-CD47 cells (FIG. 21A) and SUDHL4 cells (FIG. 21B) and no binding to CHO-K1 parental cells, as determined by flow cytometry analysis. Shown are percentages of positively stained cells or GMFI values.

FIGS. 22A-F demonstrate binding of both arms of DSP107_V2 (SEQ ID NO: 13) to HT1080 cells overexpressing 4-1BB (FIGS. 22A-B, E-F), or binding of the SIRPα arm to CD47 on HT1080 WT cells (FIGS. 22C-D), as determined by flow cytometry analysis. Addition of an anti-CD47 antibody and/or anti-4-1BB antibody, where indicated, was used to determine specific binding. Shown are percentages of positively stained cells and GMFI values.

Figure 23A:
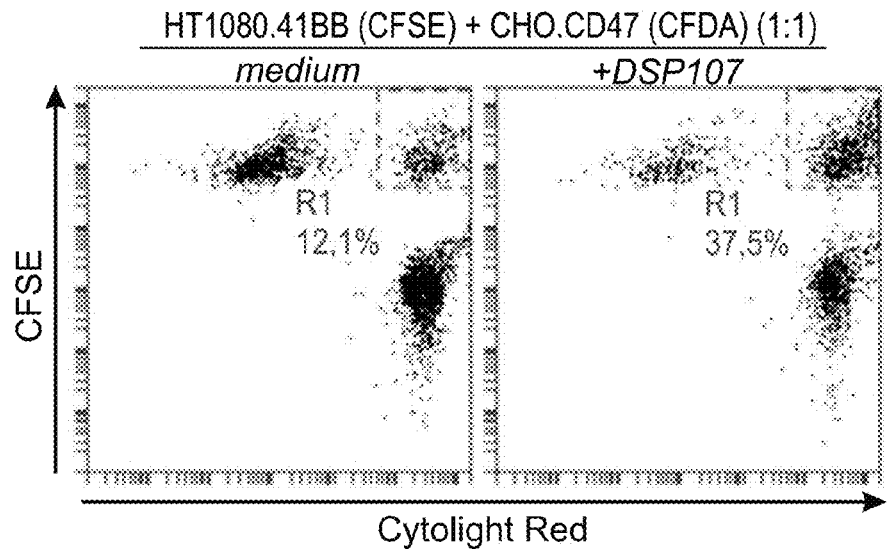
Figure 23B:
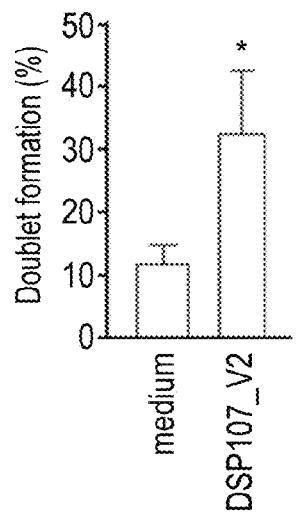

FIGS. 23A-B demonstrate simultaneous binding of DSP107_V2 (SEQ ID NO: 13) to CHO K1-CD47 and HT1080-4-1BB cells. DSP107_V2 (SEQ ID NO: 13) was incubated with CFSE-labeled HT1080 4-1BB OX cells and CytoLight Red-labelled CHO-K1 CD47 OX cells and doublet formation was determined by flow cytometry. FIG. 23A shows representative flow cytometry plots of CFSE vs. of CytoLight Red following incubation of the labeled cells with DSP107_V2 (SEQ ID NO: 13) as compared to medium control. FIG. 23B is a graph 10 demonstrating the mean results of doublet formation from three independent experiments.

Figure 24:
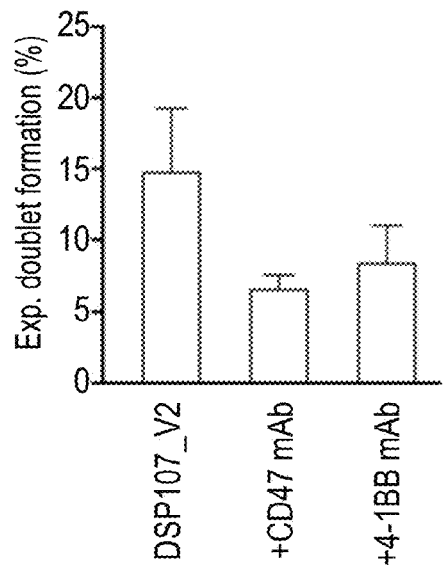

FIG. 24 demonstrates simultaneous binding of DSP107_V2 (SEQ ID NO: 13) to CHO K1-CD47 and HT1080-4-1BB cells. DSP107_V2 (SEQ ID NO: 13) was incubated with CFSE-labeled HT1080 4-1BB OX cells and CytoLight Red-labelled CHO-K1 CD47 OX cells with or without an anti-CD47 antibody of an anti-4-1BB antibody, and doublet formation was determined by flow cytometry. Shown the mean results of doublet formation from two independent experiments after subtracting medium effect.

Figure 25A:
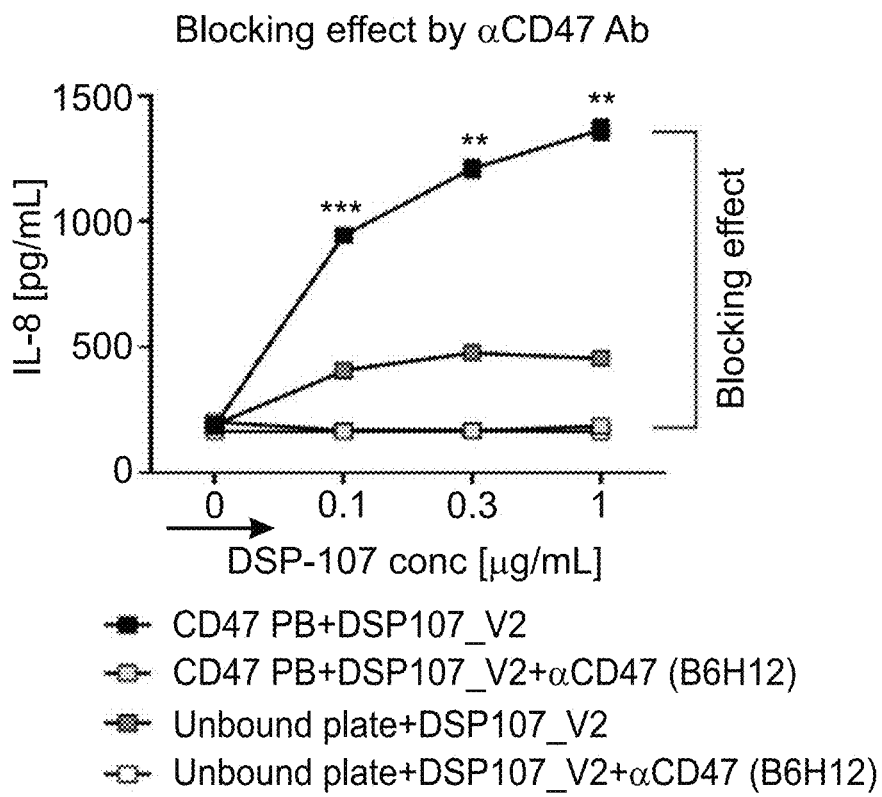
Figure 25B:
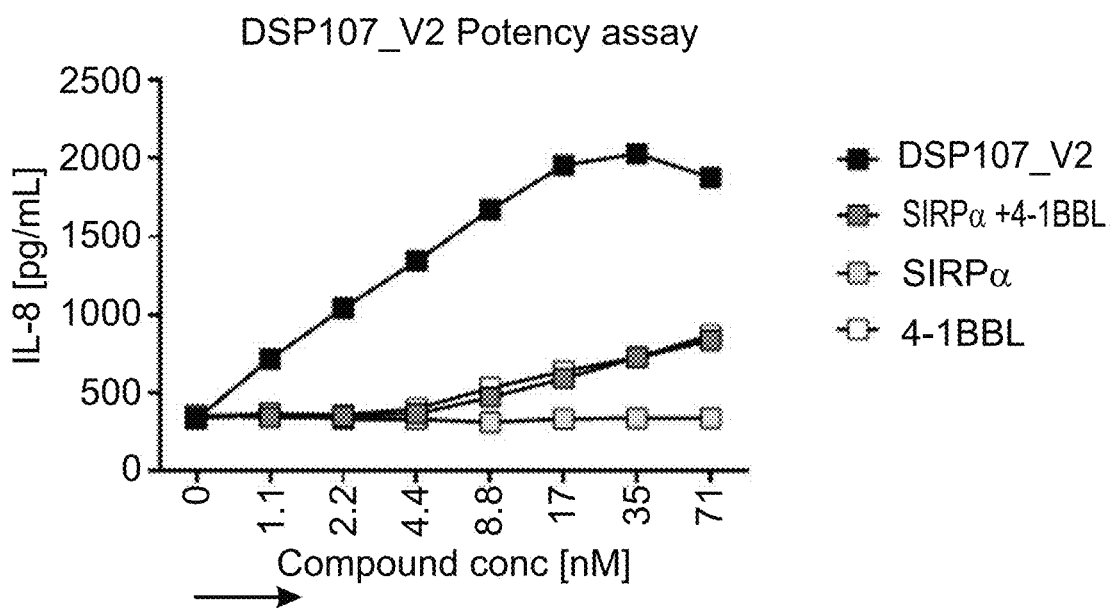

FIGS. 25A-B demonstrate activation of 4-1BB by DSP107_V2 (SEQ ID NO: 13), as determined by IL8 secretion from HT1018-4-1BB cells in the single-culture assay.

Figure 26:
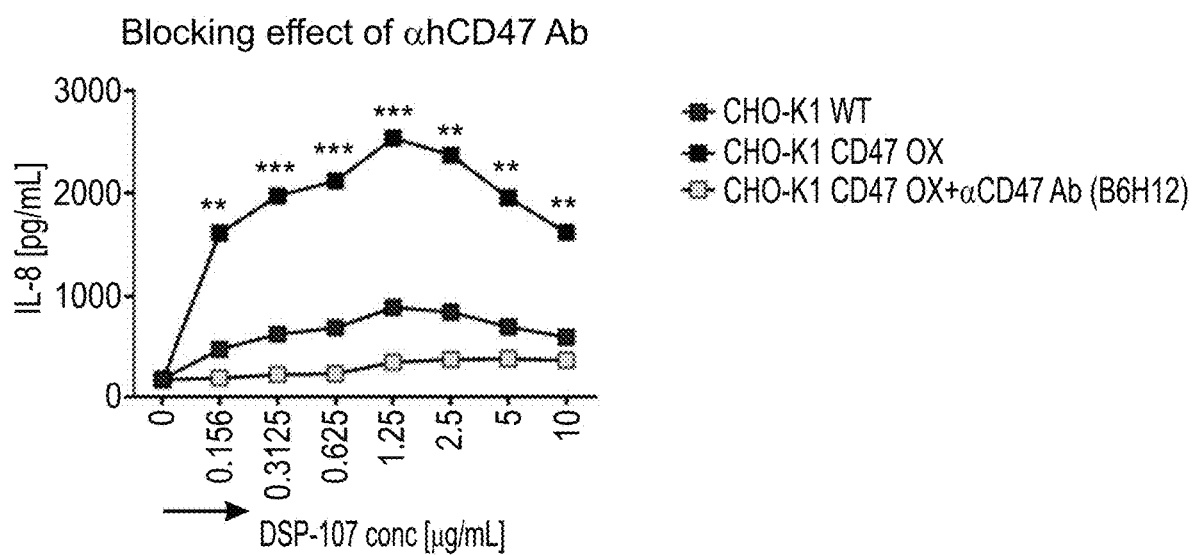

FIG. 26 demonstrates activation of 4-1BB by DSP107_V2 (SEQ ID NO: 13), as determined by IL8 secretion from HT1018-4-1BB cells in the co-culture assay.

Figure 27:
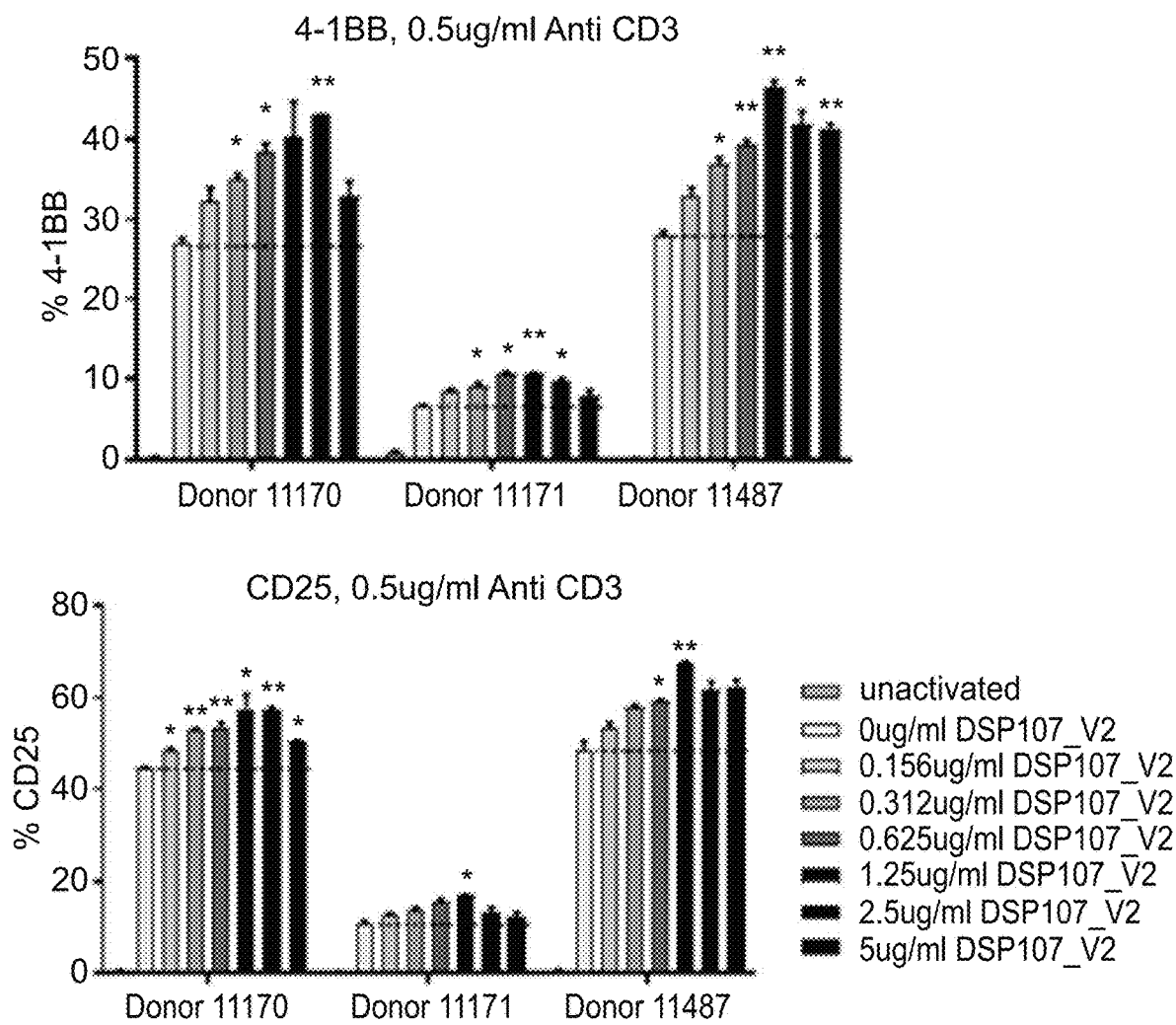

FIG. 27 shows bar graphs demonstrating that DSP107_V2 (SEQ ID NO: 13) induces T cell activation in a dose dependent manner, as determined by expression of the activation markers CD25 and 4-1BB. PBMCs from three donors were incubated with the indicated concentrations of DSP107_V2 (SEQ ID NO: 13) in the presence of plate-bound anti-CD3; and CD25 or 4-1BB expression was determined following 48 hours of incubation by flow cytometry.

Figure 28:
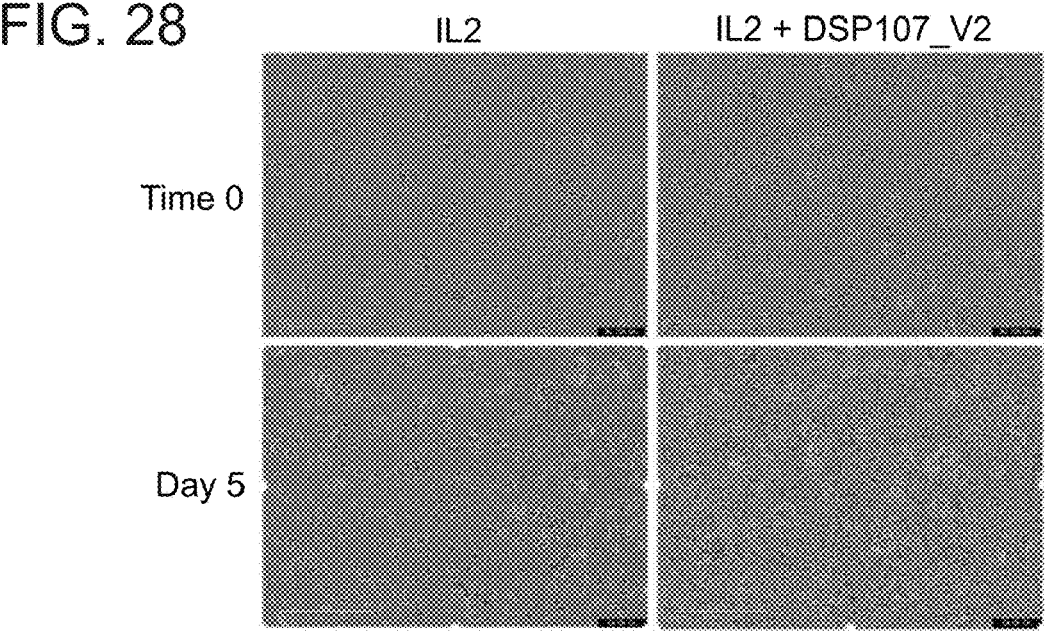

FIG. 28 shows representative images demonstrating the effect of DSP107-V2 (SEQ ID NO: 13) on PBMC proliferation, as determined by Incucyte.

Figure 29:
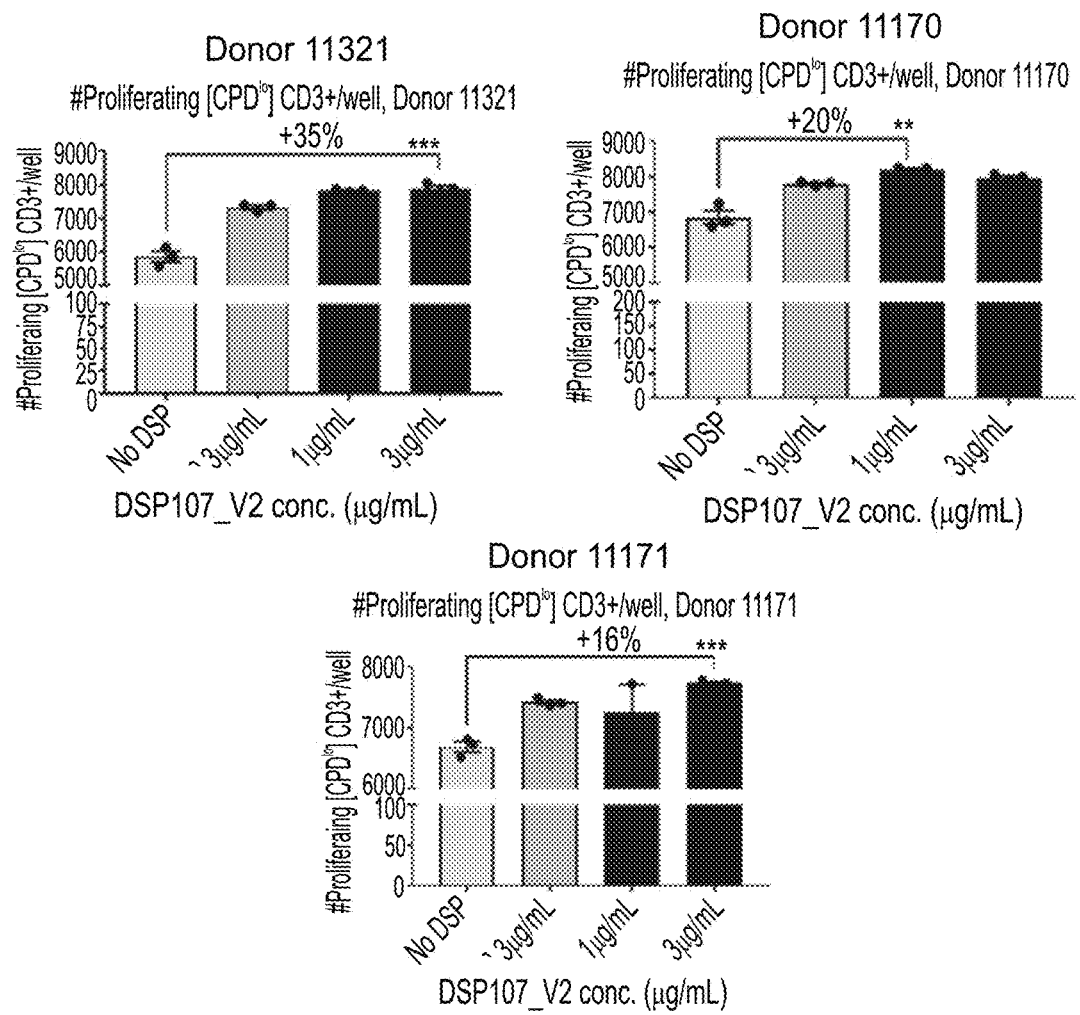

FIG. 29 shows bar graphs demonstrating the effect of DSP107_V2 (SEQ ID NO: 13) on proliferation of CPD-stained T cells obtained from three human donors, as determined by flow cytometry.

Figure 30A:
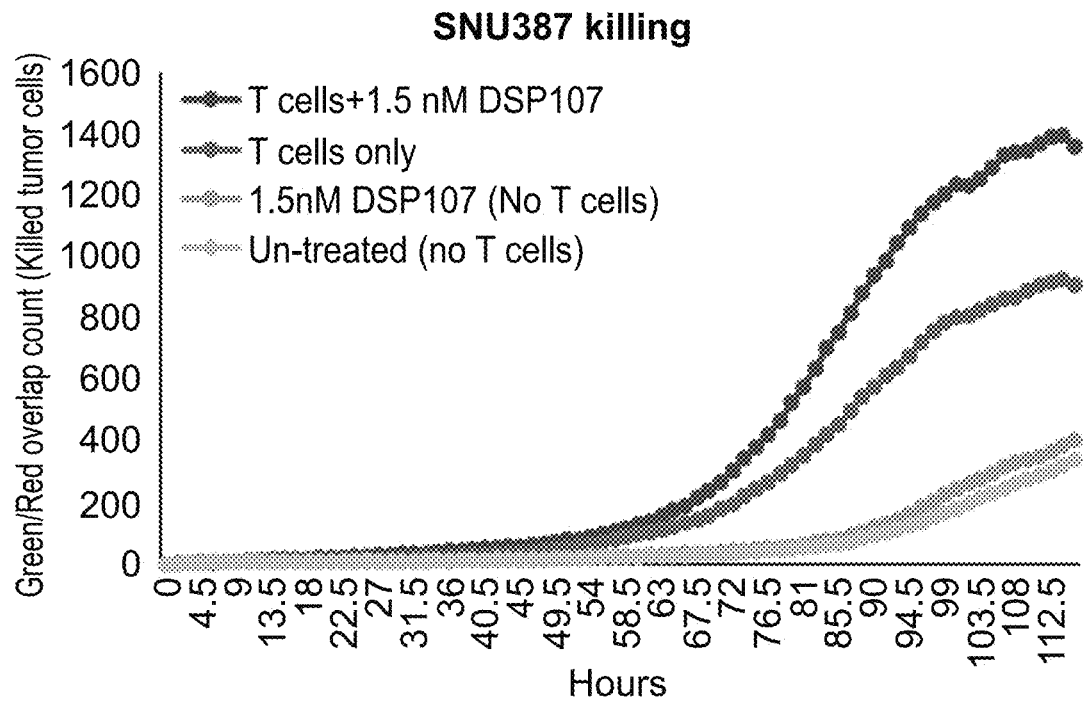
Figure 30B:
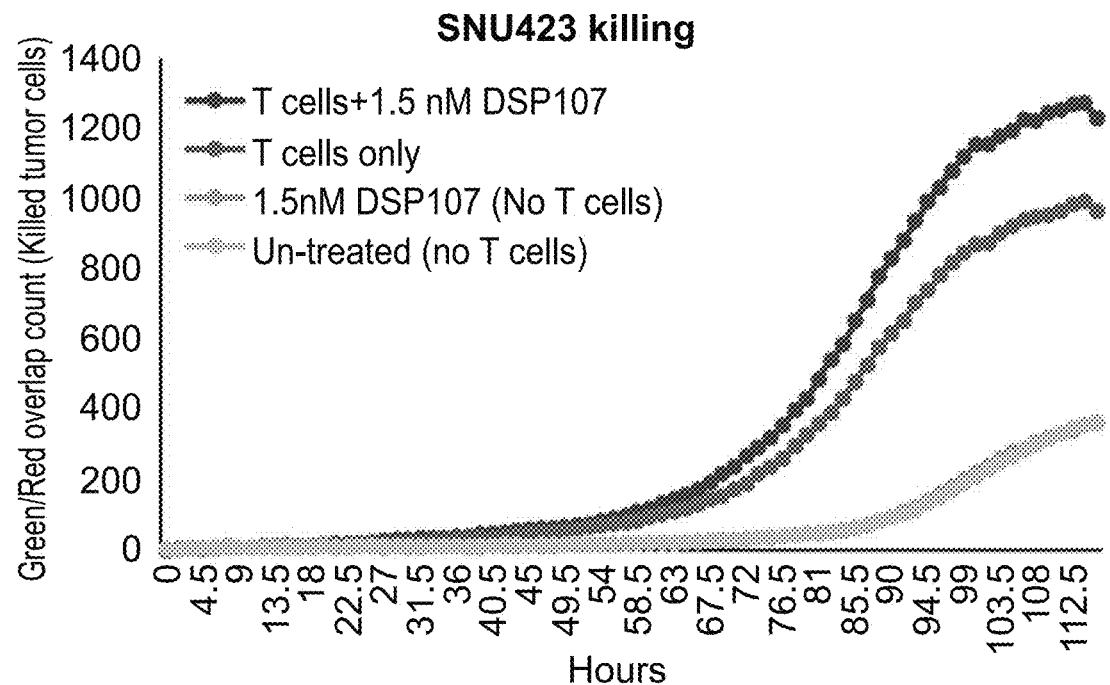
Figure 30C:
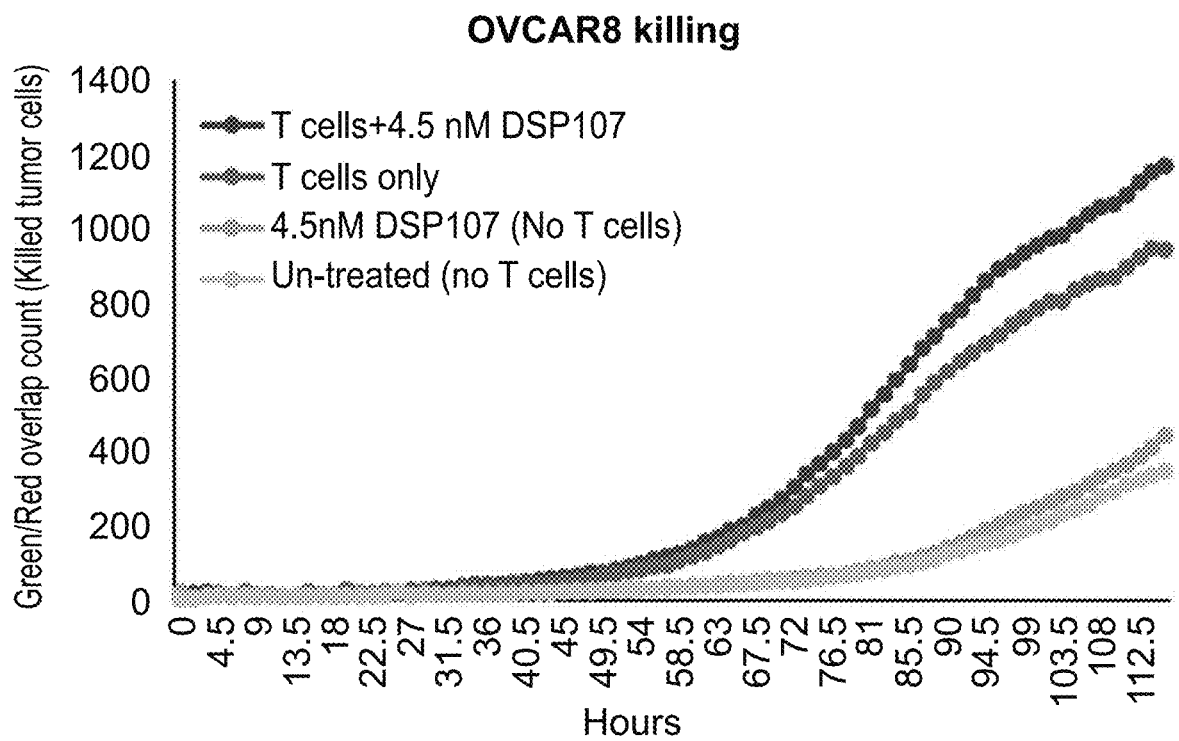

FIGS. 30A-C demonstrate the effect of DSP107-V2 (SEQ ID NO: 13) on T-cell mediated killing of SNU387 (FIG. 30A), SNU423 (FIG. 30B) and Ovcar8 (FIG. 30C) cancer cells, as determined by Incucyte.

Figure 31A:
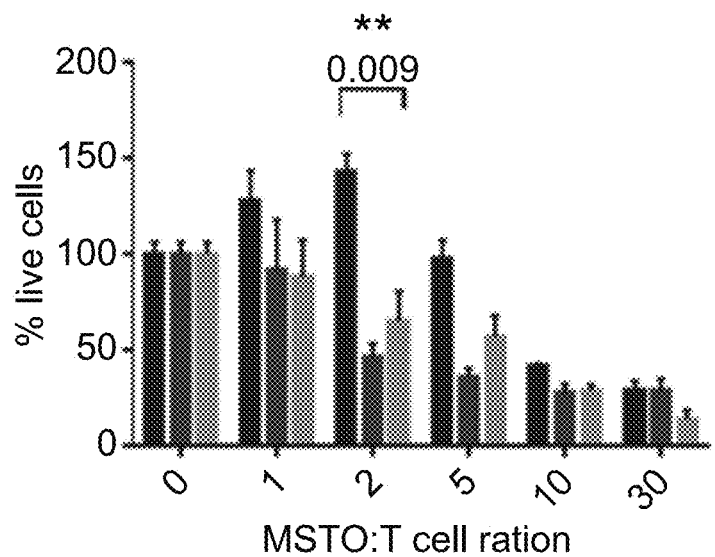
Figure 31B:
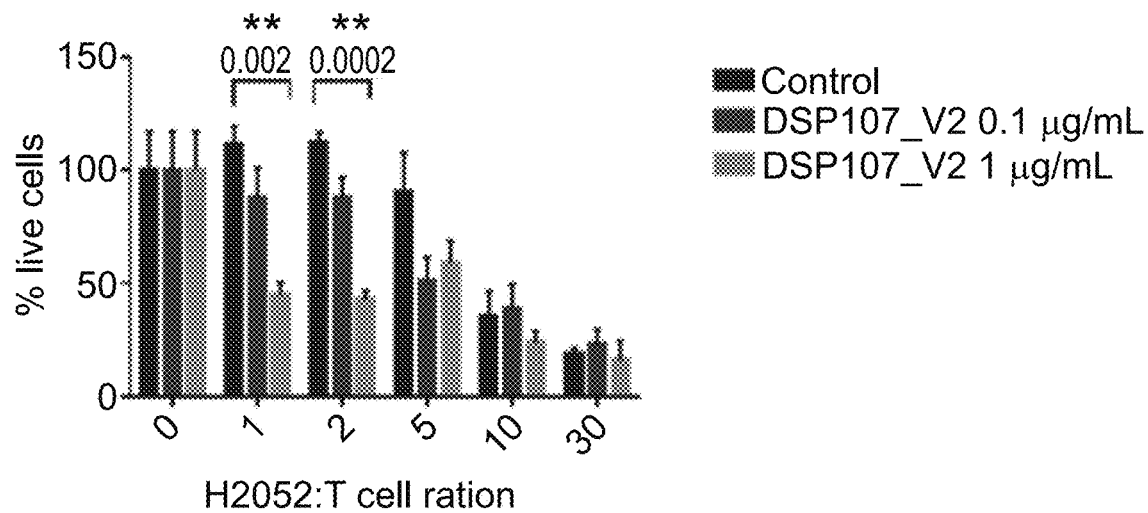

FIGS. 31A-B demonstrate the effect of DSP107-V2 (SEQ ID NO: 13) on T-cell mediated killing of MSTO (FIG. 31A) and H2052 (FIG. 31B) mesothelioma cells, as determined by flow cytometry.

Figure 32A:
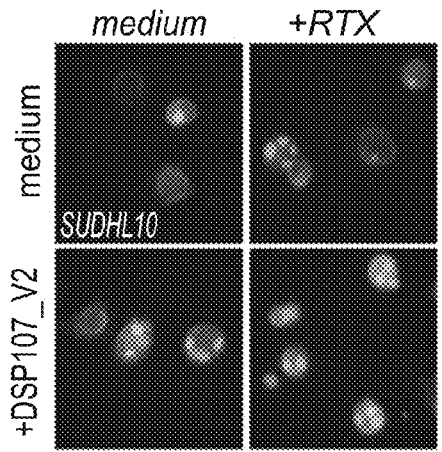
Figure 32B:
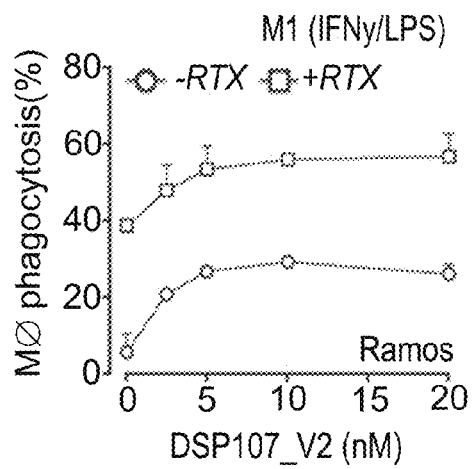
Figure 32C:
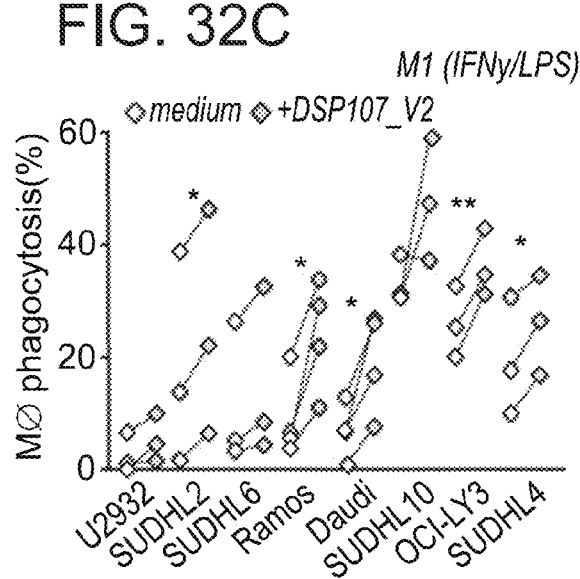
Figure 32D:
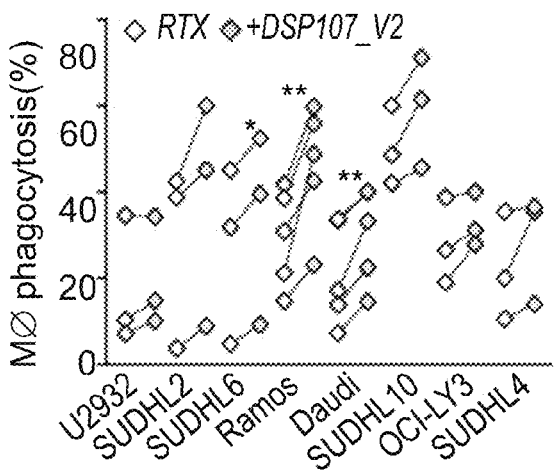
Figure 32E:
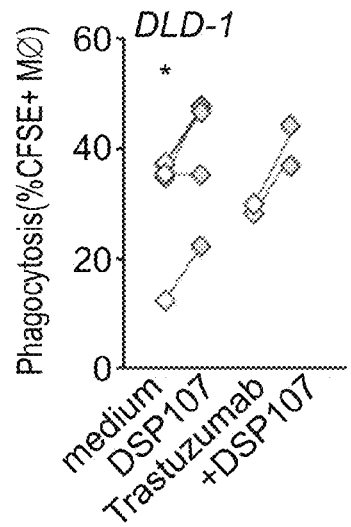

FIGS. 32A-E show a representative image (FIG. 32A) and graphs (FIGS. 32B-E) demonstrating that the DSP107_V2 (SEQ ID NO: 13) enhances M1-macrophages mediated phagocytosis of different lymphoma cell lines (FIG. 32B-D) and DLD-1 colon cancer cell line (FIG. 32E).

Figure 33A:
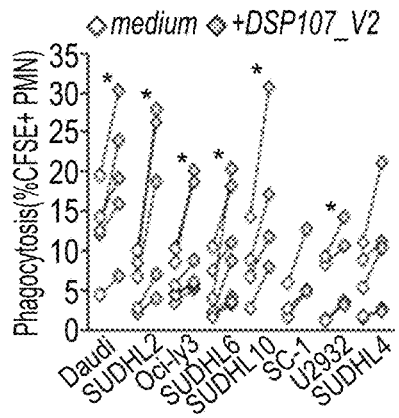
Figure 33B:
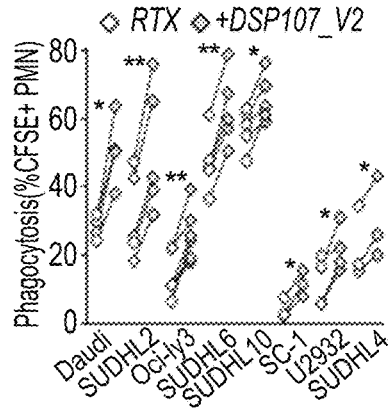
Figure 33C:
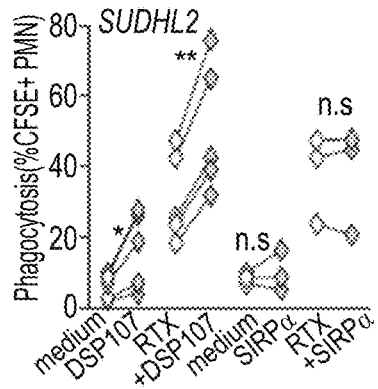
Figure 33D:
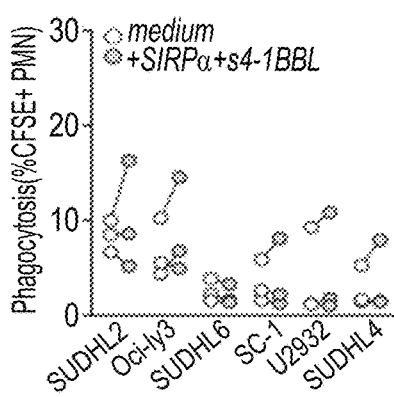
Figure 33E:
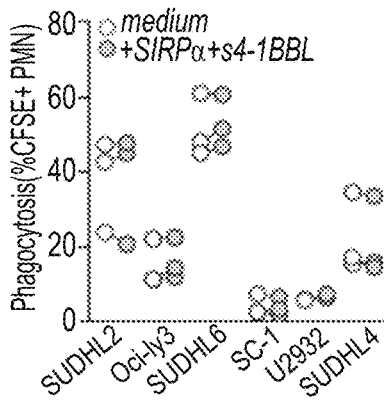
Figure 33F:
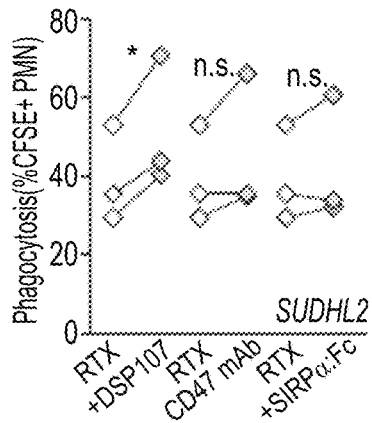
Figure 33G:
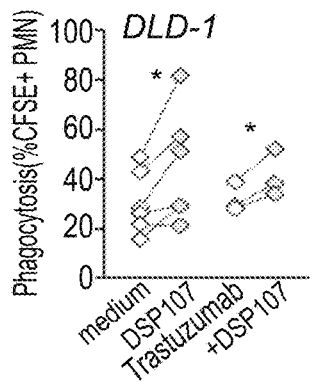
Figure 33H:
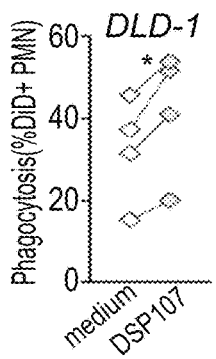

FIGS. 33A-H demonstrate the effect of DSP107_V2 (SEQ ID NO: 13 on granulocyte-mediated phagocytosis of different lymphoma cell lines as monotherapy and in combination with Rituximab (FIGS. 33A-D), as compared to soluble SIRPα, soluble 4-1BBL or combination of both (FIGS. 33D-F). Phagocytosis of DLD1 colon carcinoma cell line by granulocytes by DSP107_V2 in monotherapy and in combination with Trastuzumab (FIGS. 33G-H).

Figure 34:
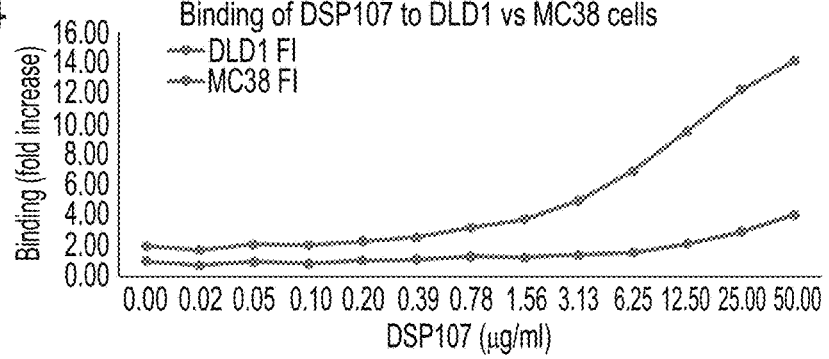

FIG. 34 represents the binding to DSP107_V2 (SEQ ID NO: 13) to MC38 (mouse) and DLD1 (human) colon carcinoma cell lines.

Figure 35A:
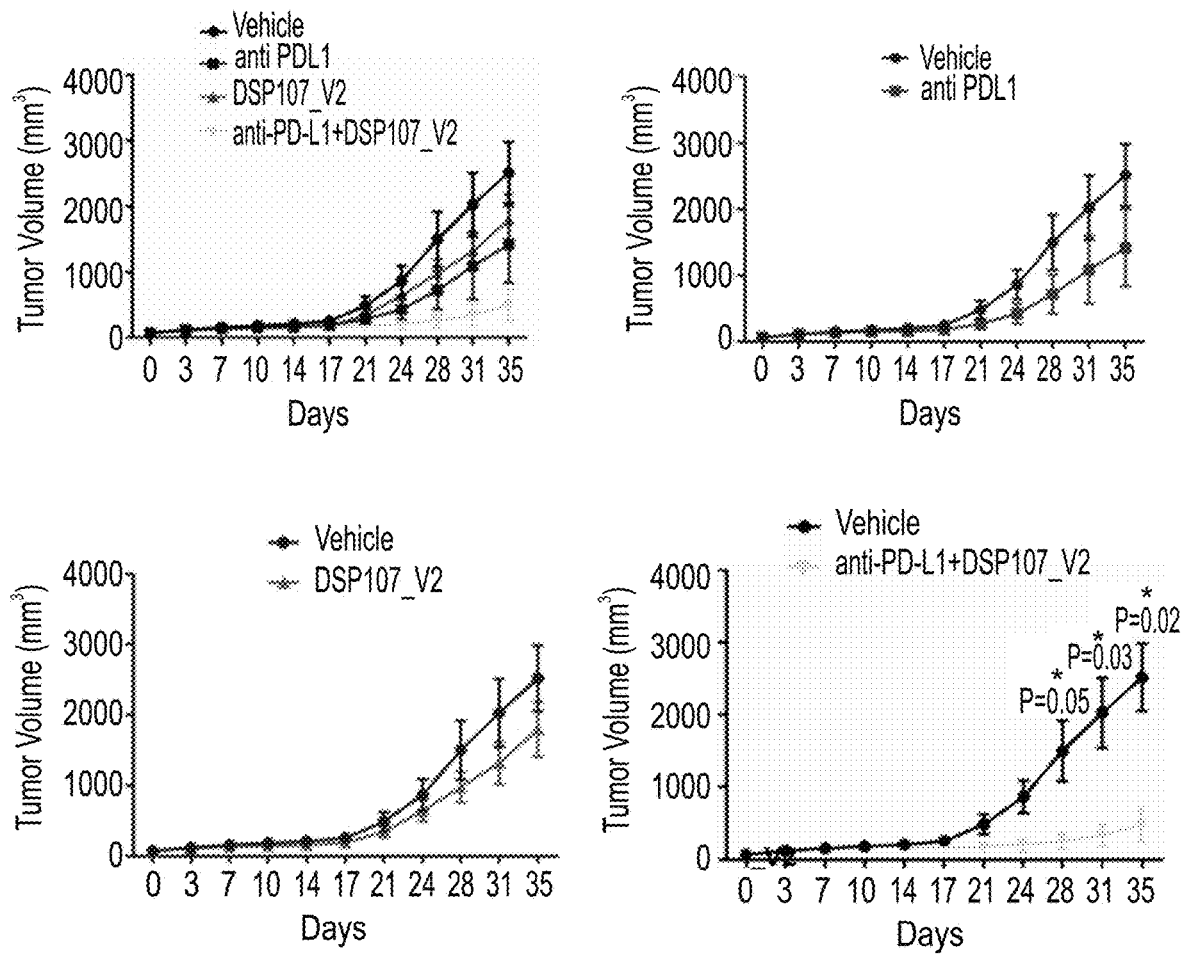
Figure 35B:
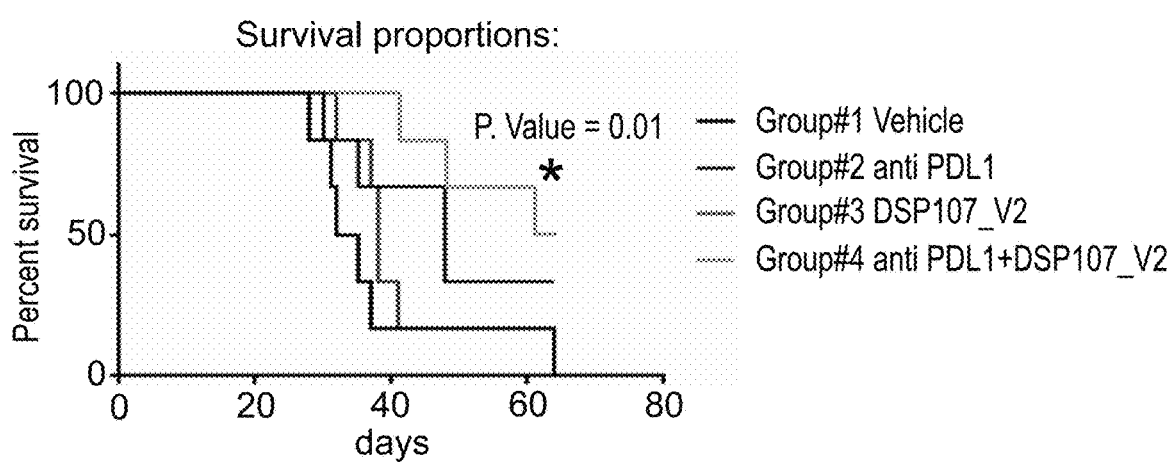

FIGS. 35A-B demonstrate the in-vivo effect of DSP107_V2 (SEQ ID NO: 13) and anti-mouse PD-L1 antibody on hCD47 MC38 tumors growth (FIG. 35A) and survival (FIG. 35B) in h4-1BB knock-in mice.

Figure 36A:
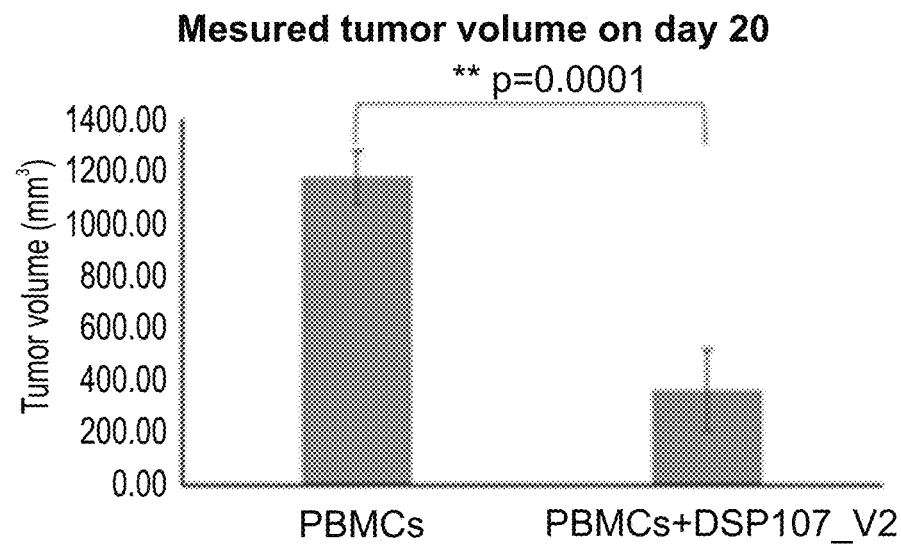
Figure 36B:
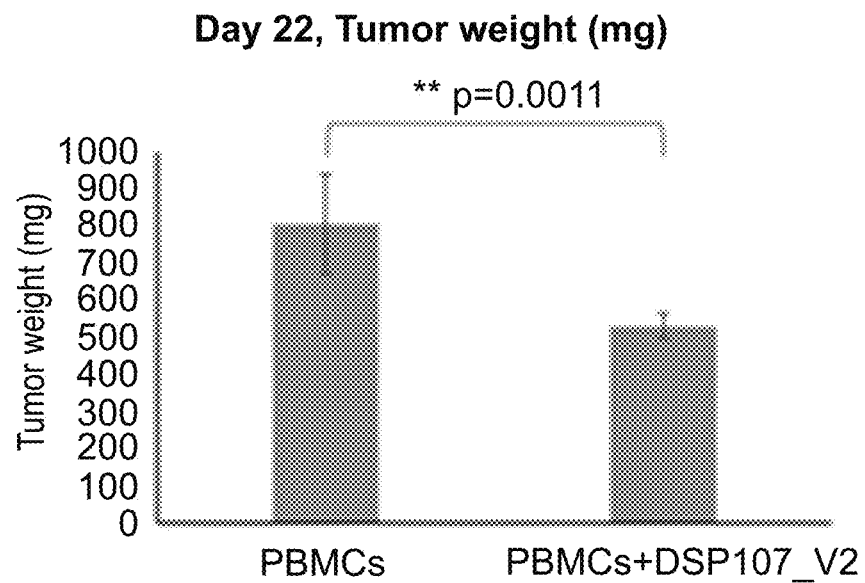

FIGS. 36A-B demonstrate the in-vivo effect of DSP107_V2 (SEQ ID NO: 13) on SUDHL6 DLBCL tumors in humanized NSG mice. FIG. 36A shows average tumor weight, determined following mice sacrifice on day 22. FIG. 36B shows average tumor volume determined prior to mice sacrifice on day 20.

Figure 37A:
Figure 37B:
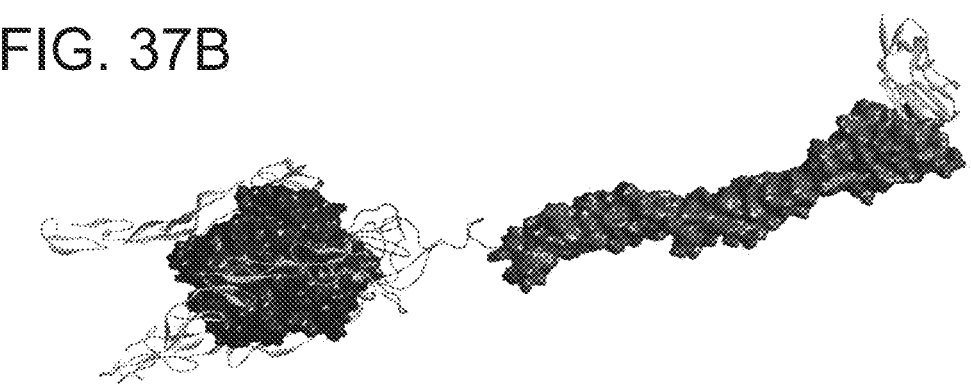

FIGS. 37A-B demonstrate the predicted 3D structure of a SIRPα-4-1BBL variant fusion comprising SIRPα (SEQ ID NO: 2) and three repeats of a 4-1BBL amino acid sequence (SEQ ID NO: 78) in the presence of its binding counterparts (CD47 and 4-1BB). FIG. 37A is a schematic 3D model and FIG. 37B is a full atomic 3D model. SIRP is represented in a dark grey ribbons display (upper right-hand side). 4-1BBL is represented in dark grey ribbons (left-hand side). Spacer'/ 'linker' segments are represented in Grey and white ribbons between the structural elements of SIRPox and 4-1BBL. CD47 is represented in grey ribbons (upper right-hand side) and three 4-1BB receptors are represented in grey ribbons in complex with 4-1BBL (left-hand side).

Figure 38:
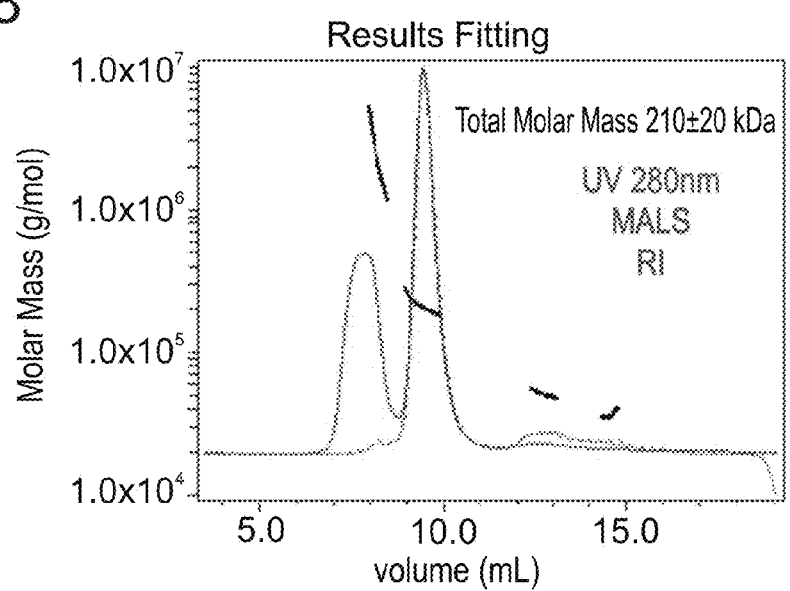

FIG. 38 demonstrates SEC-MALS analysis of DSP107-V2 (SEQ ID NO: 13). Protein (150 μg) was loaded on a Superdex 200 Increase column (GE Healthcare) and ran at a flow rate of 0.8 ml/min with 10 mM KPO4 pH 8.0+150 mM NaCl as mobile phase. Detection was performed by UV, MALS and RI using AKTA Explorer (GE)+MiniDawn TREOS+OPTILAB T-reX (WYATT).

DESCRIPTION OF DETAILED EMBODIMENTS OF THE INVENTION

The present invention, in some embodiments thereof, relates to a SIRPα-4-1BBL variant fusion protein and methods of use thereof.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Dual Signaling Proteins (DSP), also known as Signal-Converting-Proteins (SCP), which are currently known in the art as bi-functional fusion proteins that link an extracellular portion of a type I membrane protein (extracellular amino-terminus), to an extracellular portion of a type II membrane protein (extracellular carboxyl-terminus), forming a fusion protein with two active sides.

Employing structural-functional tools, the present inventors were able to generate SIRPα-4-1BBL fusion proteins comprising a SIRPα variant and/or a 4-1BBL variant with improved production characteristics (e.g. higher yield); and which can be advantageously used for activating immune cells (via co-stimulation) in general and treating diseases that can benefit from activating immune cells (e.g. cancer) in particular.

Without being bound by theory, the following is suggested by the inventors as a mode of action of the SIRPα-4-1BBL fusion protein of some embodiments of the invention in the treatment of cancer as an example:

Due to the relatively high expression of CD47 on the surface of tumor cells and in the tumor micro-environment, the SIRPα moiety of the SIRPα-4-1BBL fusion targets the molecule to tumor and metastasis sites, leading to binding of the fusion protein to CD47 within the tumor micro-environment.

Targeting the fusion protein to the tumor cells or/and tumor micro-environment facilitates an increase in SIRPα-4-1BBL concertation in the tumor micro-environment and subsequent immobilization and oligomerization of the 4-1BBL moiety of the fusion protein at the tumor site; thereby delivering a 4-1BB co-stimulatory signal that promotes activation of T cells, B cells, NK cells, especially Tumor-Infiltrating Lymphocytes (TILs) and other immune cells at the tumor site, to kill cancer cells.

In addition to the 4-1BBL-4-1BB co-stimulatory signal, the binding of the fusion protein's SIRPα moiety to CD47 in the tumor site competes with the endogenous SIRPα expressed on macrophages and dendritic cells, thus, removing the inhibition on these cells and further contributing to the phagocytosis of tumor cells and to activation of dendritic cells and T cells in the tumor micro-environment.

The above activities of the SIRPα-4-1BBL fusion protein are expected to lead to a synergistic effect on the activation of TILs, dendritic cells and macrophages within the tumor micro-environment, which is expected to be more specific and robust effect as compared to the effect of each moiety separately, as well as when using the two different moieties thereof in combination.

Thus, according to an aspect of the present invention, there is provided a SIRPα-4-1BBL fusion protein comprising a SIRPα amino acid sequence and a 4-1BBL amino acid sequence, wherein said SIRPα amino acid sequence is 100-119 amino acids in length having at least 95% identity to an amino acid sequence selected from the group consisting of SEQ ID NOs: 24 and 26, and/or wherein said 4-1BBL amino acid sequence:
  (a) is 185-202 amino acids in length having at least 95% identity to an amino acid sequence selected from the group consisting of SEQ ID NOs: 22, 23, 27 and 28, is 170-197 amino acids in length having at least 80% identity to an amino acid sequence selected from the group consisting of SEQ ID NO: 74 and 76 and does not comprise an amino acid segment G198-E205 corresponding to SEQ ID NO: 3, is 170-182 amino acids in length having at least 80% identity to SEQ ID NO: 72 and does not comprise an amino acid segment A1-E23 corresponding to SEQ ID NO: 3 or is 184 amino acids in length having at least 80% identity to SEQ ID NO: 70; and/or
(b) comprises three repeats of a 4-1BBL amino acid sequence; and wherein said fusion protein is capable of at least one of:
  (i) binding CD47 and 4-1BB;
  (ii) activating said 4-1BB signaling pathway in a cell expressing said 4-1BB;
  (iii) co-stimulating immune cells expressing said 4-1BB; and/or
  (iv) enhancing phagocytosis of pathologic cells expressing said CD47 by phagocytes compared to same in the absence of said SIRPα-4-1BBL fusion protein.

According to an alternative or an additional aspect of the present invention, there is provided a SIRPα-4-1BBL fusion protein comprising a SIRPα amino acid sequence and a 4-1BBL amino acid sequence, wherein said SIRPα amino acid sequence is 100-119 amino acids in length having at least 95% identity to an amino acid sequence selected from the group consisting of SEQ ID NOs: 24 and 26, and/or wherein said 4-1BBL amino acid sequence is 185-202 amino acids in length having at least 95% identity to an amino acid sequence selected from the group consisting of SEQ ID NOs: 22, 23, 27 and 28; and wherein said fusion protein is capable of at least one of:
  (i) binding CD47 and 4-1BB;
  (ii) activating said 4-1BB signaling pathway in a cell expressing said 4-1BB;
  (iii) co-stimulating immune cells expressing said 4-1BB; and/or
  (iv) enhancing phagocytosis of pathologic cells expressing said CD47 by phagocytes compared to same in the absence of said SIRPα-4-1BBL fusion protein.

According to an alternative or an additional aspect of the present invention, there is provided an isolated polypeptide comprising a SIRPα amino acid sequence, wherein said SIRPα amino acid sequence is 100-119 amino acids in length having at least 95% identity to an amino acid sequence selected from the group consisting of SEQ ID NOs: 24 and 26; and wherein said polypeptide is capable of binding CD47.

According to an alternative or an additional aspect of the present invention, there is provided an isolated polypeptide comprising a 4-1BBL amino acid sequence, wherein said 4-1BBL amino acid sequence is 185-202 amino acids in length having at least 95% identity to an amino acid sequence selected form the group consisting of SEQ ID NOs: 22, 23, 27 and 28, is 170-197 amino acids in length having at least 80% identity to an amino acid sequence selected from the group consisting of SEQ ID NO: 74 and 76 and does not comprise an amino acid segment G198-E205 corresponding to SEQ ID NO: 3, or is 170-182 amino acids in length having at least 80% identity to SEQ ID NO: 72 and does not comprise an amino acid segment A1-E23 corresponding to SEQ ID NO: 3; and optionally comprises three repeats of said 4-1BBL amino acid sequence; and wherein said polypeptide is capable of at least one of:
  (i) binding 4-1BB,
  (ii) activating said 4-1BB signaling pathway in a cell expressing said 4-1BB; and/or
  (iii) co-stimulating immune cells expressing said 4-1BB.

According to an alternative or an additional aspect of the present invention, there is provided an isolated polypeptide comprising a 4-1BBL amino acid sequence, wherein said 4-1BBL amino acid sequence is 185-202 amino acids in length having at least 95% identity to an amino acid sequence selected from the group consisting of SEQ ID NOs: 22, 23, 27 and 28; and wherein said polypeptide is capable of at least one of:
  (i) binding 4-1BB,
  (ii) activating said 4-1BB signaling pathway in a cell expressing said 4-1BB; and/or
  (iii) co-stimulating immune cells expressing said 4-1BB.

As used herein the term "SIRPα (Signal Regulatory Protein Alpha, also known as CD172a)" refers to the polypeptide of the SIRPA gene (Gene ID 140885) or a functional homolog e.g., functional fragment thereof. According to specific embodiments, the term "SIRPα" refers to a functional homolog of SIRPα polypeptide. According to specific embodiments, SIRPα is human SIRPα. According to a specific embodiment, the SIRPα protein refers to the human protein, such as provided in the following GenBank Number NP_001035111, NP_001035112, NP_001317657 or NP_542970.

As use herein, the phrase "functional homolog" or "functional fragment" when related to SIRPα, refers to a portion of the polypeptide which maintains the activity of the full length SIRPα e.g., CD47 binding.

According to a specific embodiment, the CD47 protein refers to the human protein, such as provided in the following GenBank Numbers NP_001768 or NP_942088.

Assays for testing binding are well known in the art and include, but not limited to flow cytometry, BiaCore, biolayer interferometry Blitz® assay, HPLC.

According to specific embodiments, the SIRPα binds CD47 with a Kd of 0.1-100 µM, 0.1-10 µM, 1-10 µM, 0.1-5 µM, or 1-2 µM as determined by SPR, each possibility represents a separate embodiment of the present invention.

According to specific embodiments, the SIRPα comprises an extracellular domain of said SIRPα or a functional fragment thereof.

According to specific embodiments, SIRPα amino acid sequence comprises SEQ ID NO: 29.

According to specific embodiments, SIRPα amino acid sequence consists of SEQ ID NO: 29.

According to specific embodiments, SIRPα nucleic acid sequence comprises SEQ ID NO: 30.

According to specific embodiments, SIRPα nucleic acid sequence consists of SEQ ID NO: 30.

According to specific embodiments, SIRPα amino acid sequence comprises SEQ ID NO: 2.

According to specific embodiments, SIRPα amino acid sequence consists of SEQ ID NO: 2.

According to specific embodiments, SIRPα nucleic acid sequence comprises SEQ ID NO: 31 or 67.

According to specific embodiments, SIRPα nucleic acid sequence consists of SEQ ID NO: 31 or 67.

The term "SIRPα" also encompasses functional homologues (naturally occurring or synthetically/recombinantly produced), which exhibit the desired activity (i.e., binding CD47). Such homologues can be, for example, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identical or homologous to the polypeptide SEQ ID NO: 2 or 29; or at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identical to the polynucleotide sequence encoding same (as further described hereinbelow).

According to specific embodiments the SIRPα functional homologues are at least 95%, at least 96%, at least 97%, at least 98%, at least 99% or 100% identical or homologous to the polypeptide SEQ ID NO: 2 or 29; or at least 95%, at least 96%, at least 97%, at least 98%, at least 99% or 100% identical to the polynucleotide sequence encoding same (as further described hereinbelow).

As used herein, "identity" or "sequence identity" refers to global identity, i.e., an identity over the entire amino acid or nucleic acid sequences disclosed herein and not over portions thereof.

Sequence identity or homology can be determined using any protein or nucleic acid sequence alignment algorithm such as Blast, ClustalW, and MUSCLE. The homolog may also refer to an ortholog, a deletion, insertion, or substitution variant, including an amino acid substitution, as further described hereinbelow.

According to specific embodiments, the SIRPα polypeptide may comprise conservative and non-conservative amino acid substitutions (also referred to herein as mutations). Such substitutions are known in the art and disclosed e.g. in Weiskopf K et al. Science. (2013); 341(6141):88-91, the contents of which are fully incorporated herein by reference.

When percentage of sequence identity is used in reference to proteins it is recognized that residue positions which are not identical often differ by conservative amino acid substitutions, where amino acid residues are substituted for other amino acid residues with similar chemical properties (e.g. charge or hydrophobicity) and therefore do not change the functional properties of the molecule. Where sequences differ in conservative substitutions, the percent sequence identity may be adjusted upwards to correct for the conservative nature of the substitution. Sequences which differ by such conservative substitutions are considered to have "sequence similarity" or "similarity". Means for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Henikoff S and Henikoff JG. [Amino acid substitution matrices from protein blocks. Proc. Natl. Acad. Sci. U.S.A. 1992, 89(22): 10915-9].

According to specific embodiments, one or more amino acid mutations are located at an amino acid residue selected from: L4, V6, A21, A27, 131, E47, K53, E54, H56, V63, L66, K68, V92 and F96 corresponding to the SIRPα amino acid sequence set forth in SEQ ID NO: 2.

According to specific embodiments, the SIRPα amino acid sequence comprises a mutation at an amino acid residue selected from the group consisting of LA, A27, E47 and V92 corresponding to the SIRPα amino acid sequence set forth in SEQ ID NO: 2.

According to specific embodiments, one or more amino acid mutations are selected from the group consisting of: L4V or L4I, V61 or V6L, A21V, A27I or A27L, I31F or I31T, E47V or E47L, K53R, E54Q, H56P or H56R, V63I, L66T or L66G, K68R, V92I and F94L or F94V corresponding to the SIRPα amino acid sequence set forth in SEQ ID NO: 2.

According to specific embodiments, the SIRPα amino acid sequence comprises a mutation selected from the group consisting of L4I, A27I, E47V and V92I corresponding to the SIRPα amino acid sequence set forth in SEQ ID NO: 2.

As used herein, the phrase "corresponding to the SIRPα amino acid sequence set forth in SEQ ID NO: 2" or "corresponding to SEQ ID NO: 2" intends to include the corresponding amino acid residue relative to any other SIRPα amino acid sequence.

According to specific embodiments, the SIRPα amino acid sequence comprises SEQ ID NO: 25.

According to specific embodiments, the SIRPα amino acid sequence consists of SEQ ID NO: 25.

According to specific embodiments, the SIRPα nucleic acid sequence comprises SEQ ID NO: 35.

According to specific embodiments, the SIRPα nucleic acid sequence consists of SEQ ID NO: 35.

Additional description on conservative amino acid and non-conservative amino acid substitutions is further provided hereinbelow.

The SIRPα of some embodiments of the present invention is at least 95%, at least 96%, at least 97%, at least 98%, at least 99% or 100% identical or homologous to the polypeptide SEQ ID NO: 24 or 26; or at least 95%, at least 96%, at least 97%, at least 98%, at least 99% or 100% identical to the polynucleotide sequence encoding same (as further described hereinbelow).

According to specific embodiments, the SIRPα amino acid sequence has at least 95% identity to SEQ ID NOs: 24 and/or 26.

According to specific embodiments, the SIRPα amino acid sequence has at least 96%, at least 97%, at least 98%, at least 99% or 100% identity to SEQ ID NO: 24 and/or 26, each possibility represents a separate embodiment of the present invention.

According to specific embodiments, the SIRPα amino acid sequence has at least 95%, at least 96%, at least 97%, at least 98%, at least 99% or 100% identity to SEQ ID NO: 24.

According to specific embodiments, the SIRPα amino acid sequence has at least 95%, at least 96%, at least 97%, at least 98%, at least 99% or 100% identity to SEQ ID NO: 26.

According to specific embodiments, the SIRPα amino acid sequence does not comprise the amino acid segment K117-Y343 corresponding to SEQ ID NO: 2.

According to specific embodiments, the SIRPα amino acid sequence does not comprise any of amino acid residues K117-Y343 corresponding to SEQ ID NO: 2.

According to specific embodiments, the SIRPα amino acid sequence does not comprise SEQ ID NO: 32 or any fragment thereof.

According to specific embodiments, the SIRPα amino acid sequence does not comprise SEQ ID NO: 32.

According to specific embodiments, the C-terminal of the SIRPα amino acid sequence ends with SEQ ID NO: 8.

According to specific embodiments, the SIRPα amino acid sequence comprises SEQ ID NO: 24 or 26.

According to specific embodiments, the SIRPα amino acid sequence comprises SEQ ID NO: 24.

According to specific embodiments, the SIRPα amino acid sequence comprises SEQ ID NO: 26.

According to specific embodiments, the SIRPα amino acid sequence consists of SEQ ID NO: 24 or 26.

According to specific embodiments, the SIRPα amino acid sequence consists of SEQ ID NO: 24.

According to specific embodiments, the SIRPα amino acid sequence consists of SEQ ID NO: 26.

According to specific embodiments, the SIRPα nucleic acid sequence has at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identity to SEQ ID NO: 33 and/or 34, each possibility represents a separate embodiment of the present invention.

According to specific embodiments, the SIRPα nucleic acid sequence has at least 95% identity to SEQ ID NO: 33 and/or 34.

According to specific embodiments, the SIRPα nucleic acid sequence has at least 96%, at least 97%, at least 98%, at least 99% or 100% identity to SEQ ID NO: 33 and/or 34.

According to specific embodiments, the SIRPα nucleic acid sequence has at least 95%, at least 96%, at least 97%, at least 98%, at least 99% or 100% identity to SEQ ID NO: 33.

According to specific embodiments, the SIRPα nucleic acid sequence has at least 95%, at least 96%, at least 97%, at least 98%, at least 99% or 100% identity to SEQ ID NO: 34.

According to specific embodiments, the SIRPα nucleic acid sequence comprises SEQ ID NO: 33 or 34.

According to specific embodiments, the nucleic acid sequence comprises SEQ ID NO: 33.

According to specific embodiments, the SIRPα nucleic acid sequence comprises SEQ ID NO: 34.

According to specific embodiments, the SIRPα nucleic acid sequence consists of SEQ ID NO: 33 or 34.

According to specific embodiments, the SIRPα nucleic acid sequence consists of SEQ ID NO: 33.

According to specific embodiments, the SIRPα nucleic acid sequence consists of SEQ ID NO: 34.

According to specific embodiments, SIRPα amino acid sequence comprises 100-500 amino acids, 150-450 amino acids, 200-400 amino acids, 250-400 amino acids, 300-400 amino acids, 320-420 amino acids, 340-350 amino acids, each possibility represents a separate embodiment of the present invention.

According to specific embodiments, SIRPα amino acid sequence is 300-400 amino acids in length.

According to specific embodiments, SIRPα amino acid sequence is 340-450 amino acids in length.

According to specific embodiments, SIRPα amino acid sequence is 343 amino acids in length.

According to specific embodiments, SIRPα amino acid sequence comprises 100-200 amino acids, 100-150 amino acids, 100-125 amino acids, 100-120 amino acids, 100-119 amino acids, each possibility represents a separate embodiment of the present invention.

According to specific embodiments, SIRPα amino acid sequence is 100-119 amino acids in length.

According to specific embodiments, SIRPα amino acid sequence is 105-119 amino acids, 110-119 amino acids, 115-119 amino acids, 105-118 amino acids, 110-118 amino acids, 115-118 amino acids, 105-117 amino acids, 110-117 amino acids, 115-117 amino acids, each possibility represents a separate embodiment of the present invention.

According to specific embodiments, SIRPα amino acid sequence is at least 115 amino acids in length.

According to specific embodiments, SIRPα amino acid sequence is 115-119 amino acids in length.

According to specific embodiments, SIRPα amino acid sequence is 116 amino acids in length.

As used herein the term "4-1BBL (also known as CD137L and TNFSF9)" refers to the polypeptide of the TNFSF9 gene (Gene ID 8744) or a functional homolog e.g., functional fragment thereof. According to specific embodiments, the term "4-1BBL" refers to a functional homolog of 4-1BBL polypeptide. According to specific embodiments, 4-1BBL is human 4-1BBL. According to a specific embodiment, the 4-1BBL protein refers to the human protein, such as provided in the following GenBank Number NP_003802.

As use herein, the phrase "functional homolog" or "functional fragment" when related to 4-1BBL, refers to a portion of the polypeptide which maintains the activity of the full length 4-1BBL e.g., (i) binding 4-1BB, (ii) activating 4-1BB signaling pathway, (iii) activating immune cells expressing 4-1BB, (iv) forming a homotrimer.

According to specific embodiments, the functional homolog when related to 4-1BBL is capable of (i), (ii), (iii), (i)+(ii), (i)+(iii), (ii)+(iii).

According to specific embodiments, the functional homolog when related to 4-1BBL is capable of (i)+(ii)+(iii).

According to specific embodiments, the functional homolog when related to 4-1BBL is capable of (iv), (i)+(iv), (ii)+(iv), (iii)+(iv), (i)+(ii)+(iv), (i)+(iii)+(iv), (ii)+(iii)+(iv). According to specific embodiments, the functional homolog when related to 4-1BBL is capable of (i)+(ii)+(iii)+(iv).

According to a specific embodiment, the 4-1BB protein refers to the human protein, such as provided in the following GenBank Number NP_001552.

Assays for testing binding are well known in the art and are further described hereinabove According to specific embodiments, the 4-1BBL binds 4-1BB with a Kd of about 0.1-1000 nM, 0.1-100 nM, 1-100 nM, or 55.2 nM as determined by SPR, each possibility represents a separate embodiment of the claimed invention.

Assays for testing trimerization are well known in the art and include, but not limited to NATIVE-PAGE, SEC-HPLC 2D gels, gel filtration, SEC-MALS, Analytical ultracentrifugation (AUC) Mass spectrometry (MS), capillary gel electrophoresis (CGE).

As used herein the terms "activating" or "activation" refer to the process of stimulating an immune cell (e.g. T cell, B cell, NK cell, phagocytic cell) that results in cellular proliferation, maturation, cytokine production, phagocytosis and/or induction of regulatory or effector functions.

According to specific embodiments, activating comprises co-stimulating.

As used herein the term "co-stimulating" or "co-stimulation" refers to transmitting a secondary antigen independent stimulatory signal (e.g. 4-1BB signal) resulting in activation of the immune cell.

According to specific embodiments, activating comprises suppressing an inhibitory signal (e.g. CD47 signal) resulting in activation of the immune cell.

Methods of determining signaling of a stimulatory or inhibitory signal are well known in the art and also disclosed in the Examples section which follows, and include, but are not limited to, binding assay using e.g. BiaCore, HPLC or flow cytometry, enzymatic activity assays such as kinase activity assays, and expression of molecules involved in the signaling cascade using e.g. PCR, Western blot, immunoprecipitation and immunohistochemistry. Additionally or alternatively, determining transmission of a signal (co-stimulatory or inhibitory) can be effected by evaluating immune cell activation or function. Methods of evaluating immune cell activation or function are well known in the art and include, but are not limited to, proliferation assays such as CFSE staining, MTS, Alamar blue, BRDU and thymidine incorporation, cytotoxicity assays such as CFSE staining, chromium release, Calcin AM, cytokine secretion assays such as intracellular cytokine staining, ELISPOT and ELISA, expression of activation markers such as CD25, CD69, CD137, CD107a, PD1, and CD62L using flow cytometry.

According to specific embodiments, determining the signaling activity or activation is effected in-vitro or ex-vivo e.g. in a mixed lymphocyte reaction (MLR), as further described hereinbelow.

For the same culture conditions the signaling activity or the immune cell activation or function are generally expressed in comparison to the signaling, activation or function in a cell of the same species but not contacted with the SIRPα-4-1BBL fusion protein, a polynucleotide encoding same or a host cell encoding same; or contacted with a vehicle control, also referred to as control.

According to specific embodiments, the 4-1BBL comprises an extracellular domain of said 4-1BBL or a functional fragment thereof.

According to specific embodiments, 4-1BBL amino acid sequence comprises SEQ ID NO: 36.

According to specific embodiments, 4-1BBL amino acid sequence consists of SEQ ID NO: 36.

According to specific embodiments, 4-1BBL nucleic acid sequence comprises SEQ ID NO: 37.

According to specific embodiments, 4-1BBL nucleic acid sequence consists of SEQ ID NO: 37.

According to specific embodiments, 4-1BBL amino acid sequence comprises SEQ ID NO: 3.

According to specific embodiments, 4-1BBL amino acid sequence consists of SEQ ID NO: 3.

According to specific embodiments, 4-1BBL nucleic acid sequence comprises SEQ ID NO: 38.

According to specific embodiments, 4-1BBL nucleic acid sequence consists of SEQ ID NO: 38.

The term "4-1BBL" also encompasses functional homologues (naturally occurring or synthetically/recombinantly produced), which exhibit the desired activity (as defined hereinabove). Such homologues can be, for example, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identical or homologous to the polypeptide SEQ ID NO: 3, 36; or at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identical to the polynucleotide sequence encoding same (as further described hereinbelow).

According to specific embodiments the 4-1BBL functional homologues are at least 95%, at least 96%, at least 97%, at least 98%, at least 99% or 100% identical or homologous to the polypeptide SEQ ID NO: 3, 36; or at least 95%, at least 96%, at least 97%, at least 98%, at least 99% or 100% identical to the polynucleotide sequence encoding same (as further described hereinbelow).

According to specific embodiments, the 4-1BBL polypeptide may comprise conservative amino acid substitutions, as further described hereinabove and below.

The 4-1BBL of some embodiments of the present invention is at least 95%, at least 96%, at least 97%, at least 98%, at least 99% or 100% identical or homologous to the polypeptide SEQ ID NO: 22, 23, 27 or 28; or at least 95%, at least 96%, at least 97%, at least 98%, at least 99% or 100% identical to the polynucleotide sequence encoding same (as further described hereinbelow).

According to specific embodiments, the 4-1BBL amino acid sequence has at least 95% identity to an amino acid sequence selected from the group consisting of SEQ ID NOs: 22, 23, 27 and 28, each possibility represents a separate embodiment of the present invention.

According to specific embodiments, the 4-1BBL amino acid sequence has at least 96%, at least 97%, at least 98%, at least 99% or 100% identity to SEQ ID NO: 22, 23, 27 and/or 28, each possibility represents a separate embodiment of the present invention.

According to specific embodiments, the 4-1BBL amino acid sequence has at least 95%, at least 96%, at least 97%, at least 98%, at least 99% or 100% identity to SEQ ID NO: 22 and/or 23.

According to specific embodiments, the 4-1BBL amino acid sequence has at least 95%, at least 96%, at least 97%, at least 98%, at least 99% or 100% identity to SEQ ID NO: 22.

According to specific embodiments, the 4-1BBL amino acid sequence has at least 95%, at least 96%, at least 97%, at least 98%, at least 99% or 100% identity to SEQ ID NO: 23.

According to specific embodiments, the 4-1BBL amino acid sequence has at least 95%, at least 96%, at least 97%, at least 98%, at least 99% or 100% identity to SEQ ID NO: 27.

According to specific embodiments, the 4-1BBL amino acid sequence has at least 95%, at least 96%, at least 97%, at least 98%, at least 99% or 100% identity to SEQ ID NO: 28.

According to specific embodiments, the 4-1BBL amino acid sequence does not comprise the amino acid segment A1-V6 corresponding to SEQ ID NO: 3.

According to specific embodiments, the 4-1BBL amino acid sequence does not comprise the amino acid segment A1-G14 corresponding to SEQ ID NO: 3.

According to specific embodiments, the 4-1BBL amino acid sequence does not comprise any of amino acid residues A1-V6 or A1-G14 corresponding to SEQ ID NO: 3.

As used herein, the phrase "corresponding to SEQ ID NO: 3" intends to include the corresponding amino acid residue relative to any other 4-1BBL amino acid sequence.

According to specific embodiments, the 4-1BBL amino acid sequence does not comprise SEQ ID NO: 6 or 7 or any fragment thereof.

According to specific embodiments, the 4-1BBL amino acid sequence does not comprise SEQ ID NO: 6 or 7.

According to specific embodiments, the 4-1BBL amino acid sequence comprises SEQ ID NO: 22, 23, 27 or 28.

According to specific embodiments, the 4-1 BBL amino acid sequence comprises SEQ ID NO: 22 or 23.

According to specific embodiments, the 4-1BBL amino acid sequence comprises SEQ ID NO: 22.

According to specific embodiments, the 4-1BBL amino acid sequence comprises SEQ ID NO: 23.

According to specific embodiments, the 4-1BBLα amino acid sequence comprises SEQ ID NO: 27.

According to specific embodiments, the 4-1BBL amino acid sequence comprises SEQ ID NO: 28.

According to specific embodiments, the 4-1BBL amino acid sequence consists of SEQ ID NO: 22, 23, 27 or 28.

According to specific embodiments, the 4-1BBL amino acid sequence consists of SEQ ID NO: 22 or 23.

According to specific embodiments, the 4-1BBL amino acid sequence consists of SEQ ID NO: 22.

According to specific embodiments, the 4-1BBL amino acid sequence consists of SEQ ID NO: 23.

According to specific embodiments, the 4-1BBLα amino acid sequence consists of SEQ ID NO: 27.

According to specific embodiments, the 4-1BBL amino acid sequence consists of SEQ ID NO: 28.

According to specific embodiments, the 4-1BBL amino acid sequence has at least 80% identity to an amino acid sequence selected from the group consisting of SEQ ID NOs: 74 and 76, each possibility represents a separate embodiment of the present invention.

According to specific embodiments, the 4-1BBL amino acid sequence has at least 85% identity to an amino acid sequence selected from the group consisting of SEQ ID NOs: 74 and 76, each possibility represents a separate embodiment of the present invention.

According to specific embodiments, the 4-1BBL amino acid sequence has at least 90% identity to an amino acid sequence selected from the group consisting of SEQ ID NOs: 74 and 76, each possibility represents a separate embodiment of the present invention.

According to specific embodiments, the 4-1BBL amino acid sequence has at least 91%, at least 92%, at least 93%, at least 94%, at least 95%, at least 96%, at least 97%, at least 98%, at least 99% or 100% identity to an amino acid sequence selected from the group consisting of SEQ ID NOs: 74 and 76, each possibility represents a separate embodiment of the present invention.

According to specific embodiments, the 4-1BBL amino acid sequence has at least 95% identity to an amino acid sequence selected from the group consisting of SEQ ID NOs: 74 and 76, each possibility represents a separate embodiment of the present invention.

According to specific embodiments, the 4-1BBL amino acid sequence has at least 96%, at least 97%, at least 98%, at least 99% or 100% identity to an amino acid sequence selected from the group consisting of SEQ ID NOs: 74 and 76, each possibility represents a separate embodiment of the present invention.

According to specific embodiments, the 4-1BBL amino acid sequence does not comprise the amino acid segment G198-E205 corresponding to SEQ ID NO: 3.

According to specific embodiments, the 4-1BBL amino acid sequence does not comprise any of amino acid residues G198-E205 corresponding to SEQ ID NO: 3.

According to specific embodiments, the 4-1BBL amino acid sequence does not comprise SEQ ID NO: 97 or any fragment thereof.

According to specific embodiments, the 4-1BBL amino acid sequence does not comprise SEQ ID NO: 97.

According to specific embodiments, the 4-1BBL amino acid sequence comprises SEQ ID NOs: 74 or 76.

According to specific embodiments, the 4-1BBL amino acid sequence consists of SEQ ID NOs: 74 or 76.

According to specific embodiments, the 4-1BBL amino acid sequence has at least 80% identity to SEQ ID NO: 72.

According to specific embodiments, the 4-1BBL amino acid sequence has at least 85% identity SEQ ID NO: 72.

According to specific embodiments, the 4-1BBL amino acid sequence has at least 90% identity to SEQ ID NO: 72.

According to specific embodiments, the 4-1BBL amino acid sequence has at least 91%, at least 92%, at least 93%, at least 94%, at least 95%, at least 96%, at least 97%, at least 98%, at least 99% or 100% identity to SEQ ID NO: 72.

According to specific embodiments, the 4-1BBL amino acid sequence has at least 95% identity to SEQ ID NO: 72.

According to specific embodiments, the 4-1BBL amino acid sequence has at least 96%, at least 97%, at least 98%, at least 99% or 100% identity to SEQ ID NO: 72.

According to specific embodiments, the 4-1BBL amino acid sequence does not comprise the amino acid segment A1-E23 corresponding to SEQ ID NO: 3.

According to specific embodiments, the 4-1BBL amino acid sequence does not comprise any of amino acid residues A1-E23 corresponding to SEQ ID NO: 3.

According to specific embodiments, the 4-1BBL amino acid sequence does not comprise SEQ ID NO: 98 or any fragment thereof.

According to specific embodiments, the 4-1BBL amino acid sequence does not comprise SEQ ID NO: 98.

According to specific embodiments, the 4-1BBL amino acid sequence comprises SEQ ID NO: 72.

According to specific embodiments, the 4-1 BBL amino acid sequence consists of SEQ ID NO: 72.

According to specific embodiments, the 4-1BBL amino acid sequence has at least 80% identity to SEQ ID NO: 70.

According to specific embodiments, the 4-1BBL amino acid sequence has at least 85% identity SEQ ID NO: 70.

According to specific embodiments, the 4-1BBL amino acid sequence has at least 90% identity to SEQ ID NO: 70.

According to specific embodiments, the 4-1BBL amino acid sequence has at least 91%, at least 92%, at least 93%, at least 94%, at least 95%, at least 96%, at least 97%, at least 98%, at least 99% or 100% identity to SEQ ID NO: 70.

According to specific embodiments, the 4-1BBL amino acid sequence has at least 95% identity to SEQ ID NO: 70.

According to specific embodiments, the 4-1BBL amino acid sequence has at least 96%, at least 97%, at least 98%, at least 99% or 100% identity to SEQ ID NO: 70.

According to specific embodiments, the 4-1BBL amino acid sequence comprises SEQ ID NO: 70.

According to specific embodiments, the 4-1BBL amino acid sequence consists of SEQ ID NO: 70.

According to specific embodiments, the 4-1BBL nucleic acid sequence has at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identity to SEQ ID NO: 39, 40, 41 and/or 42, each possibility represents a separate embodiment of the present invention.

According to specific embodiments, the 4-1BBL nucleic acid sequence has at least 95% identity to SEQ ID NO: 39, 40, 41 and/or 42.

According to specific embodiments, the 4-1BBL nucleic acid sequence has at least 96%, at least 97%, at least 98%, at least 99% or 100% identity to SEQ ID NO: 39, 40, 41 and/or 42.

According to specific embodiments, the 4-1BBL nucleic acid sequence has at least 95%, at least 96%, at least 97%, at least 98%, at least 99% or 100% identity to SEQ ID NO: 39 and/or 40.

According to specific embodiments, the 4-1BBL nucleic acid sequence comprises SEQ ID NO: 39, 40, 41 or 42.

According to specific embodiments, the 4-1BBL nucleic acid sequence comprises SEQ ID NO: 39 or 40.

According to specific embodiments, the 4-1BBL nucleic acid sequence comprises SEQ ID NO: 39.

According to specific embodiments, the 4-1BBL nucleic acid sequence comprises SEQ ID NO: 40.

According to specific embodiments, the 4-1BBL nucleic acid sequence comprises SEQ ID NO: 41.

According to specific embodiments, the 4-1BBL nucleic acid sequence comprises SEQ ID NO: 42.

According to specific embodiments, the 4-1BBL nucleic acid sequence consists of SEQ ID NO: 39, 40, 41 or 42.

According to specific embodiments, the 4-1BBL nucleic acid sequence consists of SEQ ID NO: 39 or 40.

According to specific embodiments, the 4-1BBL nucleic acid sequence consists of SEQ ID NO: 39.

According to specific embodiments, the 4-1BBL nucleic acid sequence consists of SEQ ID NO: 40.

According to specific embodiments, the 4-1BBLα nucleic acid sequence consists of SEQ ID NO: 41.

According to specific embodiments, the 4-1BBL nucleic acid sequence consists of SEQ ID NO: 42.

According to specific embodiments, the 4-1BBL nucleic acid sequence has at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identity to SEQ ID NO: 75 and/or 77, each possibility represents a separate embodiment of the present invention.

According to specific embodiments, the 4-1BBL nucleic acid sequence has at least 95% identity to SEQ ID NO: 75 and/or 77.

According to specific embodiments, the 4-1BBL nucleic acid sequence has at least 96%, at least 97%, at least 98%, at least 99% or 100% identity to SEQ ID NO: 75 and/or 77.

According to specific embodiments, the 4-1BBL nucleic acid sequence comprises SEQ ID NO: 75 or 77.

According to specific embodiments, the 4-1BBL nucleic acid sequence consists of SEQ ID NO: 75 or 77.

According to specific embodiments, the 4-1BBL nucleic acid sequence has at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identity to SEQ ID NO: 73.

According to specific embodiments, the 4-1BBL nucleic acid sequence has at least 95% identity to SEQ ID NO: 73.

According to specific embodiments, the 4-1BBL nucleic acid sequence has at least 96%, at least 97%, at least 98%, at least 99% or 100% identity to SEQ ID NO: 73.

According to specific embodiments, the 4-1BBL nucleic acid sequence comprises SEQ ID NO: 73.

According to specific embodiments, the 4-1BBL nucleic acid sequence consists of SEQ ID NO: 73.

According to specific embodiments, the 4-1BBL nucleic acid sequence bas at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identity to SEQ ID NO: 71.

According to specific embodiments, the 4-1BBL nucleic acid sequence has at least 95% identity to SEQ ID NO: 71.

According to specific embodiments, the 4-1BBL nucleic acid sequence has at least 96%, at least 97%, at least 98%, at least 99% or 100% identity to SEQ ID NO: 71.

According to specific embodiments, the 4-1BBL nucleic acid sequence comprises SEQ ID NO: 71.

According to specific embodiments, the 4-1BBL nucleic acid sequence consists of SEQ ID NO: 71.

According to specific embodiments, 4-1BBL amino acid sequence comprises 100-300 amino acids, 150-250 amino acids, 100-250 amino acids, 150-220 amino acids, 180-220 amino acids, 180-210 amino acids, 185-205 amino acids, 190-210 amino acids, each possibility represents a separate embodiment of the present invention.

According to specific embodiments, 4-1BBL amino acid sequence is 190-210 amino acids in length.

According to specific embodiments, 4-1BBL amino acid sequence is 204 amino acids in length.

According to specific embodiments, 4-1BBL amino acid sequence is 185-202 amino acids in length.

According to specific embodiments, 4-1BBL amino acid sequence is 185-200 amino acids in length.

According to specific embodiments, 4-1BBL amino acid sequence is 185-199 amino acids in length.

According to specific embodiments, 4-1BBL amino acid sequence is 170-197 amino acids in length.

According to specific embodiments, 4-1BBL amino acid sequence is 170-182 amino acids in length.

According to specific embodiments, 4-1BBL amino acid sequence is 184 amino acids in length.

According to specific embodiments, 4-1BBL amino acid sequence is 185, 191, 197 or 199 amino acids in length, each possibility represents a separate embodiment of the present invention.

According to specific embodiments, 4-1BBL amino acid sequence is 184 amino acids in length.

According to specific embodiments, 4-1BBL amino acid sequence is 183 amino acids in length.

According to specific embodiments, 4-1BBL amino acid sequence is 182 amino acids in length.

According to specific embodiments, 4-1BBL amino acid sequence is 176 amino acids in length.

According to specific embodiments, the 4-1BBL amino acid sequence comprised in the SIRPα-1BBL fusion protein or the 4-1BBL polypeptide disclosed herein comprises three repeats of a 4-1BBL amino acid sequence.

According to specific embodiments, each of the three repeats is capable of at least one of: (i) binding 4-1BB, (ii) activating 4-1BB signaling pathway, (iii) activating immune cells expressing 4-1BB, (iv) forming a homotrimer.

According to specific embodiments, the 4-1BBL amino acid sequence does not comprise a linker between each of the three repeats of said 4-1BBL amino acid sequence.

According to other specific embodiments, the 4-1 BBL amino acid sequence comprises a linker between each of the three repeats of the 4-1BBL amino acid sequence. Any linker known in the art can be used with specific embodiments of the invention. Non-limiting examples of linkers that can be used are described in details hereinbelow.

According to a specific embodiment, the linker is a (GGGGS)x2+GGGG (SEQ ID NO: 82) linker.

According to specific embodiments, the repeated sequence can be any of the 4-1BBL as defined herein.

According to specific embodiments, the three repeats have an identical 4-1BBL amino acid sequence.

According to other specific embodiments, the three repeats are distinct, i.e. have different 4-1BBL amino acid sequences.

According to other specific embodiments, two of the three repeats have an identical 4-1BBL amino acid sequence.

According to specific embodiments, at least one of the repeats comprises a 4-1BBL amino acid sequence disclosed herein.

According to specific embodiments, at least one of the repeats consists of a 4-1BBL amino acid sequence disclosed herein.

According to specific embodiments, the 4-1BBL amino acid sequence comprises three repeats of an amino acid sequence comprising SEQ ID NO: 23.

According to specific embodiments, the 4-1BBL amino acid sequence comprises three repeats of an amino acid sequence consisting of SEQ ID NO: 23.

Thus, according to specific embodiments, the 4-1BBL amino acid sequence comprises an amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identity to SEQ ID NO: 78.

According to specific embodiments, the 4-1BBL amino acid sequence comprises an amino acid sequence having at least 80% identify to SEQ ID NO: 78.

According to specific embodiments, the 4-1BBL amino acid sequence comprises an amino acid sequence having at least 85% identify to SEQ ID NO: 78.

According to specific embodiments, the 4-1BBL amino acid sequence comprises an amino acid sequence having at least 90% identify to SEQ ID NO: 78.

According to specific embodiments, the 4-1BBL amino acid sequence comprises an amino acid sequence having at least 95% identify to SEQ ID NO: 78.

According to specific embodiments, the 4-1BBL amino acid sequence comprises SEQ ID NO: 78.

According to specific embodiments, the 4-1BBL amino acid sequence consists of SEQ ID NO: 78.

According to specific embodiments, the 4-1BBL nucleic acid sequence has at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identity to SEQ ID NO: 79.

According to specific embodiments, the 4-1BBL nucleic acid sequence has at least 95% identity to SEQ ID NO: 79.

According to specific embodiments, the 4-1BBL nucleic acid sequence has at least 96%, at least 97%, at least 98%, at least 99% or 100% identity to SEQ ID NO: 79.

According to specific embodiments, the 4-1BBL nucleic acid sequence comprises SEQ ID NO: 79.

According to specific embodiments, the 4-1BBL nucleic acid sequence consists of SEQ ID NO: 79.

The terms "DSP" and "fusion protein", "chimeric protein" or "chimera" are used herein interchangeably, and refer to an amino acid sequence having two or more parts which are not found together in a single amino acid sequence in nature.

The fusion protein of some embodiments of the present invention comprises a SIRPα amino acid sequence and a 4-1BBL amino acid sequence (referred to herein as a SIRPα-4-1BBL fusion protein).

According to specific embodiments, the SIRPα is N-terminal to the 4-1BBL.

According to other specific embodiments, the SIRPα is C-terminal to the 4-1BBL.

The SIRPα-1BBL fusion protein of some embodiments of the present invention can comprise any SIRPα as defined herein; and any 4-1BBL amino acid sequence:

(a) being 185-202 amino acids in length and having at least 95% identity to an amino acid sequence selected form the group consisting of SEQ ID NOs: 22, 23, 27 and 28, being 170-197 amino acids in length having at least 80% identity to an amino acid sequence selected from the group consisting of SEQ ID NO: 74 and 76 and not comprising an amino acid segment G198-E205 corresponding to SEQ ID NO: 3, being 170-182 amino acids in length having at least 80% identity to SEQ ID NO: 72 and not comprising an amino acid segment A1-E23 corresponding to SEQ ID NO: 3 or being 184 amino acids in length having at least 80% identity to SEQ ID NO: 70; and/or (b) comprising three repeats of a 4-1BBL amino acid sequence; such as e.g. disclosed herein, each possibility represents a separate embodiment of the present invention. The SIRPα-4-1BBL fusion protein of some embodiments of the present invention can comprise any SIRPα as defined herein; and any 4-1BBL amino acid sequence being 185-202 amino acids in length and having at least 95% identity to an amino acid sequence selected from the group consisting of SEQ ID NOs: 22, 23, 27 and 28 such as e.g. disclosed herein, each possibility represents a separate embodiment of the present invention.

The SIRPα-4-1BBL fusion protein of some embodiments of the present invention can comprise any SIRPα amino acid sequence being 100-119 amino acids in length and having at least 95% identity to SEQ ID NOs: 24 and/or 26 such as e.g. disclosed herein; and any 4-1BBL as defined herein, each possibility represents a separate embodiment of the present invention.

The SIRPα-4-1BBL fusion protein of some embodiments of the present invention can comprise any SIRPα amino acid sequence being 100-119 amino acids in length and having at least 95% identity to SEQ ID NOs: 24 and/or 26 such as e.g. disclosed herein; and any 4-1BBL amino acid sequence:

(a) being 185-202 amino acids in length and having at least 95% identity to an amino acid sequence selected form the group consisting of SEQ ID NOs: 22, 23, 27 and 28, being 170-197 amino acids in length having at least 80% identity to an amino acid sequence selected from the group consisting of SEQ ID NO: 74 and 76 and not comprising an amino acid segment G198-E205 corresponding to SEQ ID NO: 3, being 170-182 amino acids in length having at least 80% identity to SEQ ID NO: 72 and not comprising an amino acid segment A1-E23 corresponding to SEQ ID NO: 3 or being 184 amino acids in length having at least 80% identity to SEQ ID NO: 70; and/or (b) comprising three repeats of a 4-1BBL amino acid sequence; such as e.g. disclosed herein, each possibility represents a separate embodiment of the present invention.

The SIRPα-4-1BBL fusion protein of some embodiments of the present invention can comprise any SIRPα amino acid sequence being 100-119 amino acids in length and having at least 95% identity to SEQ ID NOs: 24 and/or 26 such as e.g. disclosed herein; and any 4-1BBL amino acid sequence being 185-202 amino acids in length and having at least 95% identity to an amino acid sequence selected from the group consisting of SEQ ID NOs: 22, 23, 27 and 28 such as e.g. disclosed herein, each possibility represents a separate embodiment of the present invention.

According to specific embodiments, the SIRPα amino acid sequence has at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identity to SEQ ID NO: 2, 24-26 and/or 29; and the 4-1BBL amino acid sequence:
  (a) is 185-202 amino acids in length and having at least 95%, at least 96%, at least 97%, at least 98%, at least 99% or 100% identity to an amino acid sequence selected form the group consisting of SEQ ID NOs: 22, 23, 27 and 28, is 170-197 amino acids in length having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identity to an amino acid sequence selected from the group consisting of SEQ ID NO: 74 and 76 and not comprising an amino acid segment G198-E205 corresponding to SEQ ID NO: 3, is 170-182 amino acids in length having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identity to SEQ ID NO: 72 and not comprising an amino acid segment A1-E23 corresponding to SEQ ID NO: 3 or is 184 amino acids in length having at least 80% identity to SEQ ID NO: 70; and/or
  (b) comprises three repeats of a 4-1BBL amino acid sequence; each possibility represents a separate embodiment of the present invention.

According to specific embodiments, the SIRPα amino acid sequence comprises SEQ ID NO: 2, 24-26 or 29; and the 4-1BBL amino acid sequence:
  (a) is 185-202 amino acids in length comprising SEQ ID NOs: 22, 23, 27 and 28, is 170-197 amino acids in length comprising SEQ ID NO: 74 and 76, is 170-182 amino acids in length comprising SEQ ID NO: 72 or is 184 amino acids in length comprising SEQ ID NO: 70; and/or
  (b) comprises three repeats of a 4-1BBL amino acid sequence; each possibility represents a separate embodiment of the present invention.

According to specific embodiments, the SIRPα amino acid sequence is as set forth in SEQ ID NO: 2, 24-26 or 29; and the 4-1BBL amino acid sequence is as set forth in SEQ ID NOs: 22, 23, 27, 28, 74, 76, 72 or 70, each possibility represents a separate embodiment of the present invention.

According to specific embodiments, the SIRPα amino acid sequence has at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identity to SEQ ID NO: 2, 24-26 and/or 29; and the 4-1BBL amino acid sequence is 185-202 amino acids in length having at least 95%, at least 96%, at least 97%, at least 98%, at least 99% or 100% identity to SEQ ID NOs: 22, 23, 27 and/or 28, each possibility represents a separate embodiment of the present invention.

According to specific embodiments, the SIRPα amino acid sequence comprises SEQ ID NO: 2, 24-26 or 29; and the 4-1BBL amino acid sequence is 185-202 amino acids in length comprising SEQ ID NOs: 22, 23, 27 or 28, each possibility represents a separate embodiment of the present invention.

According to specific embodiments, the SIRPα amino acid sequence is as set forth in SEQ ID NO: 2, 24-26 or 29; and the 4-1BBL amino acid sequence is as set forth in SEQ ID NOs: 22, 23, 27 or 28, each possibility represents a separate embodiment of the present invention.

According to specific embodiments, the SIRPα amino acid sequence has at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identity to SEQ ID NO: 2 or 25; and the 4-1BBL amino acid sequence is 185-202 amino acids in length having at least 95%, at least 96%, at least 97%, at least 98%, at least 99% or 100% identity to SEQ ID NOs: 22, 23, 27 and/or 28.

According to specific embodiments, the SIRPα amino acid sequence comprises SEQ ID NO: 2 or 25; and the 4-1BBL amino acid sequence is 185-202 amino acids in length comprising SEQ ID NOs: 22, 23, 27 or 28.

According to specific embodiments, the SIRPα amino acid sequence is as set forth in SEQ ID NO: 2 or 25 and the 4-1BBL amino acid sequence is as set forth in SEQ ID NO: 22, 23, 27 or 28.

According to specific embodiments, the SIRPα amino acid sequence has at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identity to SEQ ID NO: 2; and the 4-1BBL amino acid sequence is 185-202 amino acids in length having at least 95%, at least 96%, at least 97%, at least 98%, at least 99% or 100% identity to SEQ ID NOs: 22 or 23.

According to specific embodiments, the SIRPα amino acid sequence comprises SEQ ID NO: 2; and the 4-1BBL amino acid sequence is 185-202 amino acids in length comprising SEQ ID NOs: 22 or 23.

According to specific embodiments, the SIRPα amino acid sequence is as set forth in SEQ ID NO: 2 and the 4-1BBL amino acid sequence is as set forth in SEQ ID NO: 22 or 23.

According to specific embodiments, the SIRPα amino acid sequence is 100-119 amino acids in length having at least 95%, at least 96%, at least 97%, at least 98%, at least 99% or 100% identity to SEQ ID NO: 24 and/or 26; and the 4-1BBL amino acid sequence has at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identity to SEQ ID NO: 3, 22, 23, 27, 28 and/or 36, each possibility represents a separate embodiment of the present invention.

According to specific embodiments, the SIRPα amino acid sequence is 100-119 amino acids in length comprising SEQ ID NO: 24 and/or 26; and the 4-1BBL amino acid sequence comprises SEQ ID NO: 3, 22, 23, 27, 28 and/or 36, each possibility represents a separate embodiment of the present invention.

According to specific embodiments, the SIRPα amino acid sequence is as set forth in SEQ ID NO: 24 and/or 26; and the 4-1BBL amino acid sequence is as set forth in SEQ ID NO: 3, 22, 23, 27, 28 and/or 36.

According to specific embodiments, the SIRPα amino acid sequence is 100-119 amino acids in length having at least 95%, at least 96%, at least 97%, at least 98%, at least 99% or 100% identity to SEQ ID NO: 24 or 26; and the 4-1BBL amino acid sequence has at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identity to SEQ ID NO: 3, 22, 23, 27 or 28.

According to specific embodiments, the SIRPα amino acid sequence is 100-119 amino acids in length comprising SEQ ID NO: 24 and/or 26; and the 4-1BBL amino acid sequence comprises SEQ ID NO: 3, 22, 23, 27 or 28.

According to specific embodiments, the SIRPα amino acid sequence is as set forth in SEQ ID NO: 24 or 26 and the 4-1BBL amino acid sequence is as set forth in SEQ ID NO: 3, 22, 23, 27 or 28.

According to specific embodiments, the SIRPα amino acid sequence is 100-119 amino acids in length having at least 95%, at least 96%, at least 97%, at least 98%, at least 99% or 100% identity to SEQ ID NO: 24 and/or 26; and the 4-1BBL amino acid sequence is 185-202 amino acids in length having at least 95%, at least 96%, at least 97%, at least 98%, at least 99% or 100% identity to SEQ ID NOs: 22, 23, 27 and/or 28, each possibility represents a separate embodiment of the present invention.

According to specific embodiments, the SIRPα amino acid sequence is 100-119 amino acids in length comprising SEQ ID NO: 24 and/or 26; and the 4-1BBL amino acid sequence is 185-202 amino acids in length comprising SEQ ID NOs: 22, 23, 27 and/or 28, each possibility represents a separate embodiment of the present invention.

According to specific embodiments, the SIRPα amino acid sequence is as set forth in SEQ ID NO: 24 and/or 26; and the 4-1BBL amino acid sequence is as set forth in SEQ ID NOs: 22, 23, 27 and/or 28.

According to specific embodiments, the SIRPα amino acid sequence is 100-119 amino acids in length having at least 95%, at least 96%, at least 97%, at least 98%, at least 99% or 100% identity to SEQ ID NO: 24; and the 4-1BBL amino acid sequence is 185-202 amino acids in length having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identity to SEQ ID NO: 22.

According to specific embodiments, the SIRPα amino acid sequence is 100-119 amino acids in length comprising SEQ ID NO: 24; and the 4-1BBL amino acid sequence is 185-202 amino acids in length comprising SEQ ID NO: 22.

According to specific embodiments, the SIRPα amino acid sequence is as set forth in SEQ ID NO: 24 and the 4-1BBL amino acid sequence is as set forth in SEQ ID NO: 22.

Non-limiting examples of specific combinations of SIRPα amino acid sequence and 4-1BBL amino acid sequence which can be used with specific embodiments of the present invention are provided in Table 4 of the Examples section which follows, which serves as an integral part of the specification.

According to specific embodiments, the isolated polypeptide comprising the SIRPα amino acid sequence or the isolated polypeptide comprising the 4-1BBL amino acid sequence is soluble (i.e., not immobilized to a synthetic or a naturally occurring surface).

According to specific embodiments, the isolated polypeptide comprising the SIRPα amino acid sequence or the isolated polypeptide comprising the 4-1BBL amino acid sequence is immobilized to a synthetic or a naturally occurring surface.

According to specific embodiments, the SIRPα-4-1BBL fusion protein is soluble (i.e., not immobilized to a synthetic or a naturally occurring surface).

According to specific embodiments, the SIRPα-4-1BBL fusion protein is immobilized to a synthetic or a naturally occurring surface.

According to specific embodiments, the SIRPα-4-1BBL fusion protein is in a form of at least a homo-trimer.

According to specific embodiments, at least 10%, at least 20%, at least 30%, at least 40%, at least 50%, at least 60%, at least 70%, at least 80%, at least 90%, at least 95% of the SIRPα-4-1BBL fusion protein is in a form of at least a homo-trimer, each possibility represents a separate embodiment of the present invention.

According to specific embodiments, the at least homo-trimer comprises a homo-trimer.

According to specific embodiments, the at least homo-trimer comprises a homo-tetramer.

According to specific embodiments, the at least homo-trimer comprises a homo-pentamer.

According to specific embodiments, the at least homo-trimer comprises a homo-hexamer.

Methods of determining trimerization are well known in the art and include, but are not limited to NATIVE-PAGE, SEC-HPLC, 2D gels, gel filtration, SEC MALS, Analytical ultracentrifugation (AUC) Mass spectrometry (MS), capillary gel electrophoresis (CGE).

According to specific embodiments the at least homo-trimer is at least 100 Kd, at least 140 kD, at least 160 kD, at least 180 kD at least 200 kD, at least 220 kD, at least 240 kD, at least 250 kD in molecular weight as determined by SEC MALS.

According to specific embodiments the at least homo-trimer is at least 100 kD in molecular weight as determined by SEC MALS.

According to specific embodiments, the at least homo-trimer is at least 240 kD in molecular weight as determined by SEC MALS.

According to specific embodiments, the at least homo-trimer is about 250-270 kD in molecular weight as determined by SEC MALS.

According to specific embodiments, the SIRPα-4-1BBL does not comprise a linker between the SIRPα and the 4-1BBL.

According to specific embodiments the SIRPα-4-1BBL fusion protein comprises a linker between said SIRPα and said 4-1BBL.

Any linker known in the art can be used with specific embodiments of the invention.

According to specific embodiments, the linker may be derived from naturally-occurring multi-domain proteins or is an empirical linker as described, for example, in Chichili et al., (2013), Protein Sci. 22(2): 153-167, Chen et al., (2013), Adv Drug Deliv Rev. 65(10): 1357-1369, the entire contents of which are hereby incorporated by reference. In some embodiments, the linker may be designed using linker designing databases and computer programs such as those described in Chen et al., (2013), Adv Drug Deliv Rev. 65(10): 1357-1369 and Crasto et al (2000), Protein Eng. 13(5):309-312, the entire contents of which are hereby incorporated by reference.

According to specific embodiments, the linker is a synthetic linker such as PEG.

According to specific embodiments, the linker is an Fc domain or the hinge region of an antibody (e.g., of IgG, IgA, IgD) or IgE) or a fragment thereof.

According to other specific embodiments, the linker is not an Fc domain or a hinge region of an antibody or a fragment thereof.

According to specific embodiments, the linker is an Fc domain or the hinge region of human IgG4.

According to specific embodiments, the Fc domain linker comprises SEQ ID NO: 95.

According to specific embodiments, the linker is an Fc domain or the hinge region of human IgG1.

According to specific embodiments, the Fc domain linker comprises SEQ ID NO: 96.

According to specific embodiments, the Fc domain or the hinge region linker may comprise conservative and non-conservative amino acid substitutions (also referred to herein as mutations). Such substitutions are known in the art. According to specific embodiments, the linker may be functional. For example, without limitation, the linker may function to improve the folding and/or stability, improve the expression, improve the pharmacokinetics, and/or improve the bioactivity of the SIRPα-4-1BBL fusion protein. In another example, the linker may function to target the SIRPα-4-1BBL fusion protein to a particular cell type or location.

According to specific embodiments, the linker is a polypeptide.

Non-limiting examples of polypeptide linkers include linkers having the sequence LE, GGGGS (SEQ ID NO: 85), (GGGGS)$_n$ (n=1-4) (SEQ ID NO: 84), GGGGSGGGG (SEQ ID NO: 83), (GGGGS)x2 (SEQ ID NO: 86), (GGGGS)x2+GGGG (SEQ ID NO: 82), (Gly)$_8$, (Gly)$_6$, (EAAAK)$_n$ (n=1-3) (SEQ ID NO: 87), A(EAAAK)$_n$A (n=2-5) (SEQ ID NO: 88), AEAAAKEAAAKA (SEQ ID NO: 89), A(EAAAK)$_4$ALEA(EAAAK)$_4$A (SEQ ID NO: 90), PAPAP (SEQ ID NO: 91), K ESGSVSS EQ LAQ FRS LD (SEQ ID NO: 92), EGKSSGSGSESKST (SEQ ID NO: 93), GSAGSAAGSGEF (SEQ ID NO: 94), and (XP)», with X designating any amino acid, e.g., Ala, Lys, or Glu.

According to specific embodiments, the linker is selected from the group consisting of GGGGS (SEQ ID NO: 85), (GGGGS), (n=1-4) (SEQ ID NO: 84), GGGGSGGGG (SEQ ID NO: 83), (GGGGS)x2 (SEQ ID NO: 86), (GGGGS)x2+GGGG (SEQ ID NO: 82).

According to specific embodiments, the linker is a (GGGGS)$_n$(n=1-4) (SEQ ID NO: 84) linker.

According to specific embodiments, the linker is GGGGSx2 (SEQ ID NO: 86) linker. According to specific embodiments, the linker is a GGGGSGGGG (SEQ ID NO: 83) linker.

According to specific embodiments, the linker is a (GGGGS)x2+GGGG (SEQ ID NO: 82) linker.

In some embodiments, the SIRPα-4-1BBL comprises a linker at a length of one to six amino acids.

According to specific embodiments, the linker is substantially comprised of glycine and/or serine residues (e.g. about 30%, or about 40%, or about 50%, or about 60%, or about 70%, or about 80%, or about 90%, or about 95%, or about 97% or 100% glycines and serines). According to specific embodiments, the linker is a single amino acid linker.

In some embodiments of the invention, the amino acid which links SIRPα and 4-1BBL is glycine, also referred to herein as SIRPα-G-4-1BBL fusion protein.

According to specific embodiments, the SIRPα-4-1BBL fusion protein amino acid sequence comprises an amino acid sequence having at least 95% identity to an amino acid sequence selected from the group consisting of SEQ ID NO: 11, 13, 15, 16 and 18-21 and 45-49, each possibility represents a separate embodiment of the present invention.

According to specific embodiments, the SIRPα-4-1BBL fusion protein amino acid sequence comprises an amino acid sequence having at least 96%, at least 97%, at least 98%, at least 99% identity to an amino acid sequence selected from the group consisting of SEQ ID NO: 11, 13, 15, 16 and 18-21 and 45-49, each possibility represents a separate embodiment of the present invention.

According to specific embodiments, the SIRPα-4-1BBL fusion protein amino acid sequence comprises an amino acid sequence having at least 95% identity to an amino acid sequence selected from the group consisting of SEQ ID NO: 11, 13, 15, 16 and 18-21.

According to specific embodiments, the SIRPα-4-1BBL fusion protein amino acid sequence comprises an amino acid sequence having at least 96%, at least 97%, at least 98%, at least 99% identity to an amino acid sequence selected from the group consisting of SEQ ID NO: 11, 13, 15, 16 and 18-21.

According to specific embodiments, the SIRPα-4-1BBL fusion protein amino acid sequence comprises an amino acid sequence having at least 95% identity to an amino acid sequence selected from the group consisting of SEQ ID NO: 11, 13 and 16.

According to specific embodiments, the SIRPα-4-1BBL fusion protein amino acid sequence has at least 95% identity to SEQ ID NO: 11.

According to specific embodiments, the SIRPα-4-1BBL fusion protein amino acid sequence has at least 95% identity to SEQ ID NO: 13.

According to specific embodiments, the SIRPα-4-1BBL fusion protein amino acid sequence has at least 95% identity to SEQ ID NO: 16.

According to specific embodiments, the SIRPα-4-1BBL fusion protein amino acid sequence comprises an amino acid sequence having at least 96%, at least 97%, at least 98%, at least 99% identity to an amino acid sequence selected from the group consisting of SEQ ID NO: 11, 13 and 16.

According to specific embodiments, the SIRPα-4-1BBL fusion protein amino acid sequence comprises an amino acid sequence selected from the group consisting of SEQ ID NO: 11, 13, 15, 16, 18-21 and 45-49, each possibility represents a separate embodiment of the present invention.

According to specific embodiments, the SIRPα-4-1BBL fusion protein amino acid sequence comprises an amino acid sequence selected from the group consisting of SEQ ID NO: 11, 13, 15, 16 and 18-21.

According to specific embodiments, the SIRPα-4-1BBL fusion protein amino acid sequence comprises an amino acid sequence selected from the group consisting of SEQ ID NO: 11, 13 and 16.

According to specific embodiments, the SIRPα-4-1BBL fusion protein amino acid sequence comprises SEQ ID NO: 11.

According to specific embodiments, the SIRPα-4-1BBL fusion protein amino acid sequence comprises SEQ ID NO: 13.

According to specific embodiments, the SIRPα-4-1BBL fusion protein amino acid sequence comprises SEQ ID NO: 16.

According to specific embodiments, the SIRPα-4-1BBL fusion protein amino acid sequence consists of an amino acid sequence selected from the group consisting of SEQ ID NO: 11, 13, 15, 16, 18-21 and 45-49, each possibility represents a separate embodiment of the present invention.

According to specific embodiments, the SIRPα-4-1BBL fusion protein amino acid sequence consists of an amino acid sequence selected from the group consisting of SEQ ID NO: 11, 13, 15, 16 and 18-21.

According to specific embodiments, the SIRPα-4-1BBL fusion protein amino acid sequence consists of an amino acid sequence selected from the group consisting of SEQ ID NO: 11, 13 and 16.

According to specific embodiments, the SIRPα-4-1BBL fusion protein amino acid sequence consists of SEQ ID NO: 11.

According to specific embodiments, the SIRPα-4-1BBL fusion protein amino acid sequence consists of SEQ ID NO: 13.

According to specific embodiments, the SIRPα-4-1BBL fusion protein amino acid sequence consists of SEQ ID NO: 16.

According to specific embodiments, the SIRPα-4-1BBL fusion protein is 200-900 amino acids, 200-800 amino acids, 200-700 amino acids, 250-650 amino acids, 250-600 amino acids, 250-550 amino acids in length, each possibility represents a separate embodiment of the present invention.

According to a specific embodiment, the SIRPα-4-1BBL fusion protein is 270-750 amino acids in length.

According to a specific embodiment, the SIRPα-4-1BBL fusion protein is 290-750 amino acids in length.

According to a specific embodiment, the SIRPα-4-1BBL fusion protein is 290-550 amino acids in length.

According to a specific embodiment, the SIRPα-4-1BBL fusion protein is 297-543 amino acids in length.

According to a specific embodiment, the SIRPα-4-1BBL fusion protein is 296-542 amino acids in length.

Non-limiting examples of specific SIRPα-4-1BBL fusion proteins which can be used with specific embodiments of the present invention are provided in Table 4 of the Examples section which follows, which serves as an integral part of the specification.

According to specific embodiments, the production yield of the SIRPα-4-1BBL fusion protein of some embodiments of the present invention is at least 1.5 fold, at least 2 fold, at least 2.5 fold, at least 3 fold, at least 5 fold higher than the production yield of a SIRPα-4-1BBL fusion protein comprising a SIRPα amino acid sequence as set forth in SEQ ID NO: 2 and a 4-1BBL amino acid sequence as set forth in SEQ ID NO: 3, under the same production conditions, each possibility represents a separate embodiment of the present invention.

According to specific embodiments, the production yield of the SIRPα-4-1BBL fusion protein of some embodiments of the present invention is at least 1.5 fold higher than the production yield of a SIRPα-4-1BBL fusion protein comprising a SIRPα amino acid sequence as set forth in SEQ ID NO: 2 and a 4-1BBL amino acid sequence as set forth in SEQ ID NO: 3, under the same production conditions.

According to specific embodiments, the production yield of the SIRPα-4-1BBL fusion protein of some embodiments of the present invention is at least 2 fold higher than the production yield of a SIRPα-4-1BBL fusion protein comprising a SIRPα amino acid sequence as set forth in SEQ ID NO: 2 and a 4-1BBL amino acid sequence as set forth in SEQ ID NO: 3, under the same production conditions.

According to specific embodiments, the production yield of the SIRPα-4-1BBL fusion protein of some embodiments of the present invention is at least 1.5 fold, at least 2 fold, at least 2.5 fold, at least 3 fold, at least 5 fold higher than the production yield of a SEQ ID NO: 5, under the same production conditions each possibility represents a separate embodiment of the present invention.

According to specific embodiments, the production yield of the SIRPα-4-1BBL fusion protein of some embodiments of the present invention is at least 1.5 fold higher than the production yield of SEQ ID NO: 5 under the same production conditions.

According to specific embodiments, the production yield of the SIRPα-4-1BBL fusion protein of some embodiments of the present invention is at least 2 fold higher than the production yield of a SEQ ID NO: 5 under the same production conditions.

According to specific embodiments, the production yield of the isolated polypeptide comprising the SIRPα amino acid sequence of some embodiments of the present invention is at least 1.5 fold, at least 2 fold, at least 2.5 fold, at least 3 fold, at least 5 fold higher than the production yield of SEQ ID NO: 2, under the same production conditions, each possibility represents a separate embodiment of the present invention.

According to specific embodiments, the production yield of the isolated polypeptide comprising the 4-1BBL amino acid sequence of some embodiments of the present invention is at least 1.5 fold, at least 2 fold, at least 2.5 fold, at least 3 fold, at least 5 fold higher than the production yield of SEQ ID NO: 3, under the same production conditions, each possibility represents a separate embodiment of the present invention.

According to specific embodiments, the amount of aggregates of the SIRPα-4-1BBL fusion protein of some embodiments of the present invention is at least 20%, at least 30%, at least 40%, at least 50%, at least 60%, at least 70%, at least 80%, at least 90% or at least 95% lower than the amount of aggregates of a SIRPα-4-1BBL fusion protein comprising a SIRPα amino acid sequence as set forth in SEQ ID NO: 2 and a 4-1BBL amino acid sequence as set forth in SEQ ID NO: 3, under the same production conditions, each possibility represents a separate embodiment of the present invention.

According to specific embodiments, the amount of aggregates of the SIRPα-4-1BBL fusion protein of some embodiments of the present invention is at least 20%, at least 30%, at least 40%, at least 50%, at least 60%, at least 70%, at least 80%, at least 90% or at least 95% lower than the amount of aggregates of a SEQ ID NO: 5, under the same production conditions each possibility represents a separate embodiment of the present invention.

According to specific embodiments, the amount of aggregates of the SIRPα-4-1BBL fusion protein of some embodiments of the present invention is at least 20% lower than the amount of aggregates of a SEQ ID NO: 5, under the same production conditions each possibility represents a separate embodiment of the present invention.

According to specific embodiments, the amount of aggregates of the SIRPα-4-1BBL fusion protein of some embodiments of the present invention is at least 50% lower than the amount of aggregates of a SEQ ID NO: 5, under the same production conditions each possibility represents a separate embodiment of the present invention.

According to specific embodiments, the activity of the SIRPα-4-1BBL fusion protein of some embodiments of the present invention is at least 1.5 fold, at least 2 fold, at least 2.5 fold, at least 3 fold, at least 5 fold higher than the activity of a SIRPα-4-1BBL fusion protein comprising a SIRPα amino acid sequence as set forth in SEQ ID NO: 2 and a 4-1BBL amino acid sequence as set forth in SEQ ID NO: 3, e.g. under the same production conditions, each possibility represents a separate embodiment of the present invention.

According to specific embodiments, the activity of the SIRPα-4-1BBL fusion protein of some embodiments of the present invention is at least 1.5 fold, at least 2 fold, at least 2.5 fold, at least 3 fold, at least 5 fold higher than the activity of a SEQ ID NO: 5, e.g. under the same production conditions each possibility represents a separate embodiment of the present invention.

According to specific embodiments, the activity of the isolated polypeptide comprising the SIRPα amino acid sequence of some embodiments of the present invention is at least 1.5 fold, at least 2 fold, at least 2.5 fold, at least 3 fold, at least 5 fold higher than the activity of SEQ ID NO: 2, e.g. under the same production conditions, each possibility represents a separate embodiment of the present invention.

According to specific embodiments, the activity of the isolated polypeptide comprising the 4-1 BBL amino acid sequence of some embodiments of the present invention is at least 1.5 fold, at least 2 fold, at least 2.5 fold, at least 3 fold, at least 5 fold higher than the activity of SEQ ID NO: 3, e.g. under the same production conditions, each possibility represents a separate embodiment of the present invention.

According to specific embodiments, the stability of the SIRPα-4-1BBL fusion protein of some embodiments of the present invention is at least 1.5 fold, at least 2 fold, at least 2.5 fold, at least 3 fold, at least 5 fold higher than the stability of a SIRPα-4-1BBL fusion protein comprising a SIRPα amino acid sequence as set forth in SEQ ID NO: 2 and a 4-1BBL amino acid sequence as set forth in SEQ ID NO: 3, under the same production conditions, each possibility represents a separate embodiment of the present invention.

According to specific embodiments, the stability of the SIRPα-4-1BBL fusion protein of some embodiments of the present invention is at least 1.5 fold, at least 2 fold, at least 2.5 fold, at least 3 fold, at least 5 fold higher than the stability of a SEQ ID NO: 5, under the same production conditions each possibility represents a separate embodiment of the present invention.

According to specific embodiments, the stability of the isolated polypeptide comprising the SIRPα amino acid sequence of some embodiments of the present invention is at least 1.5 fold, at least 2 fold, at least 2.5 fold, at least 3 fold, at least 5 fold higher than the stability of SEQ ID NO: 2, under the same production conditions, each possibility represents a separate embodiment of the present invention.

According to specific embodiments, the stability of the isolated polypeptide comprising the 4-1BBL amino acid sequence of some embodiments of the present invention is at least 1.5 fold, at least 2 fold, at least 2.5 fold, at least 3 fold, at least 5 fold higher than the stability of SEQ ID NO: 3, under the same production conditions, each possibility represents a separate embodiment of the present invention.

According to specific embodiments, the safety of the SIRPα-4-1BBL fusion protein of some embodiments of the present invention is at least 1.5 fold, at least 2 fold, at least 2.5 fold, at least 3 fold, at least 5 fold higher than the safety of a SIRPα-4-1BBL fusion protein comprising a SIRPα amino acid sequence as set forth in SEQ ID NO: 2 and a 4-1BBL amino acid sequence as set forth in SEQ ID NO: 3, under the same production conditions, each possibility represents a separate embodiment of the present invention.

According to specific embodiments, the safety of the SIRPα-4-1BBL fusion protein of some embodiments of the present invention is at least 1.5 fold, at least 2 fold, at least 2.5 fold, at least 3 fold, at least 5 fold higher than the safety of a SEQ ID NO: 5, under the same production conditions each possibility represents a separate embodiment of the present invention.

According to specific embodiments, the safety of the isolated polypeptide comprising the SIRPα amino acid sequence of some embodiments of the present invention is at least 1.5 fold, at least 2 fold, at least 2.5 fold, at least 3 fold, at least 5 fold higher than the safety of SEQ ID NO: 2, under the same production conditions, each possibility represents a separate embodiment of the present invention.

According to specific embodiments, the safety of the isolated polypeptide comprising the 4-1 BBL amino acid sequence of some embodiments of the present invention is at least 1.5 fold, at least 2 fold, at least 2.5 fold, at least 3 fold, at least 5 fold higher than the safety of SEQ ID NO: 3, under the same production conditions, each possibility represents a separate embodiment of the present invention.

According to specific embodiments, the production condition comprises expression in a mammalian cell and culturing at 32-37° C., 5-10% $CO_2$ for 5-13 days.

Non-limiting examples of production conditions that can be used with specific embodiments of the invention are disclosed in the Examples section which follows.

Thus, for example an expression vector encoding the fusion protein, the isolated polypeptide comprising the SIRPα amino acid sequence or the isolated polypeptide comprising the 4-1BBL amino acid sequence including an artificial signal peptide (e.g. SEQ ID NO: 4) in the N terminus and His-tag and a stop codon in the C terminus, is expressed in mammalian cells such as Expi293F or ExpiCHO cells. The transduced cells are then cultured at 32-37° C. 5-10% $CO_2$ in cell-specific culture medium according to the Expi293F or ExpiCHO cells manufacturer instructions (Thermo) and following at least 5 days in culture the proteins are collected from the supernatant and purified.

According to specific embodiments the culture is operated in a batch, split-batch, fed-batch, or perfusion mode.

According to specific embodiments, the culture is operated under fed-batch conditions.

According to specific embodiments, the culturing is effected at 37° C.

According to specific embodiments, the culturing it effected at 37° C. with a term shift to 32° C. This tem shift can be effected to slow down cells metabolism prior to reaching a stationary phase.

According to specific embodiments, the isolated polypeptide comprising the SIRPα amino acid sequence is capable of binding CD47.

According to specific embodiments, the isolated polypeptide comprising the SIRPα amino acid sequence is capable of enhancing phagocytosis of pathologic cells expressing CD47 by phagocytes compared to same in the absence of the isolated polypeptide comprising the SIRPα amino acid sequence.

According to specific embodiments, the isolated polypeptide comprising the SIRPα amino acid sequence of some embodiments of the present invention has an enhanced activity as disclosed herein compared to SEQ ID NO: 2.

According to specific embodiments, the isolated polypeptide comprising the 4-1BBL amino acid sequence is capable of at least one of:
(i) binding 4-1BB,
(ii) activating said 4-1BB signaling pathway in a cell expressing said 4-1BB; and/or
(iii) co-stimulating immune cells expressing said 4-1BB.

According to specific embodiments, the isolated polypeptide comprising the 4-1BBL amino acid sequence of some embodiments of the present invention has an enhanced activity as disclosed herein compared to SEQ ID NO: 3.

According to specific embodiments, the isolated polypeptide comprising the 4-1BBL amino acid sequence is capable of (i), (ii), (iii), (i)+(ii), (i)+(iii), (ii)+(iii), (i)+(ii)+(iii).

According to specific embodiments, the SIRPα-4-1BBL fusion protein is capable of least one of:
(i) binding CD47 and 4-1BB,
(ii) activating 4-1BB signaling pathway in an immune cell (e.g. T cell) expressing 4-1BB;
(iii) activating immune cells (e.g. T cells) expressing said 4-1BB; and/or
(iv) enhancing phagocytosis of pathologic cells expressing CD47 by phagocytes compared to same in the absence of SIRPα-4-1BBL fusion protein.

According to specific embodiments, the SIRPα-4-1BBL fusion protein of some embodiments of the present invention has an enhanced activity as disclosed herein compared to a fusion protein comprising a SIRPα amino acid sequence as set forth in SEQ ID NO: 2 and a 4-1BBL amino acid sequence as set forth in SEQ ID NO: 3.

According to specific embodiments, the SIRPα-4-1BBL fusion protein of some embodiments of the present invention has an enhanced activity as disclosed herein compared to SEQ ID NO: 5.

According to specific embodiments, the SIRPα-4-1BBL fusion protein is capable of (i), (ii), (iii), (iv), (i)+(ii), (i)+(iii), (i)+(iv), (ii)+(iii), (ii)+(iv), (i)+(ii)+(iii), (i)+(ii)+(iv), (ii)+(iii)+(iv).

According to specific embodiments, the SIRPα-4-1BBL fusion protein is capable of (i)+(ii)+(iii)+(iv).

Methods of determining binding, activating 4-1BB signaling pathway and activating immune cells are well known in the art and are further described hereinabove and below and in the Examples section which follows.

According to specific embodiments, the SIRPα-4-1BBL fusion protein or the isolated polypeptide comprising the SIRPα amino acid sequence enhances phagocytosis of pathologic cells expressing CD47 by phagocytes.

Methods of analyzing phagocytosis are well known in the art and are also disclosed in Experiment 4 in the Examples section which follows; and include for examples killing assays, flow cytometry and/or microscopic evaluation (live cell imaging, fluorescent microscopy confocal microscopy, electron microscopy).

According to specific embodiments the enhancement in phagocytosis is at least 1.5 fold, at least 2 fold, at least 3 fold, at least 5 fold, at least 10 fold, or at least 20 fold as compared to same in the absence of the SIRPα-4-1BBL fusion protein or the isolated polypeptide comprising the SIRPα amino acid sequence, the polynucleotide or nucleic acid construct encoding same or the host cell expressing same of the present invention, as determined by e.g. flow cytometry or microscopic evaluation.

According to other specific embodiments the increase in survival is by at least 5%, by at least a 10%, at least 20%, at least 30%, at least 40%, at least 50%, at least 60%, at least 70%, at least 80%, at least 90%, at least 95% or at least 100% as compared to same in the absence of the SIRPα-4-1BBL fusion protein or the isolated polypeptide comprising the SIRPα amino acid sequence, the polynucleotide or nucleic acid construct encoding same or the host cell expressing same of the present invention, as determined by e.g. flow cytometry or microscopic evaluation.

As the compositions of some embodiments of present invention (e.g. the fusion protein, the isolated polypeptide comprising the SIRPα amino acid sequence, the isolated polypeptide comprising the 4-1BBL amino acid sequence, a polynucleotide or nucleic acid encoding same or a host cell expressing same) are capable of activating immune cells, they can be used in methods of activating immune cells, in-vitro, ex-vivo and/or in-vivo.

Thus, according to an aspect of the present invention, there is provided a method of activating immune cells, the method comprising in-vitro or ex-vivo activating immune cells in the presence of the SIRPα-4-1BBL fusion protein, the isolated polypeptide comprising the SIRPα amino acid sequence and/or the isolated polypeptide comprising the 4-1BBL amino acid sequence disclosed herein, a polynucleotide encoding same, a nucleic acid construct encoding same or a host cell expressing same.

According to another aspect of the present invention, there is provided a method of activating T cells, the method comprising in-vitro or ex-vivo activating T cells in the presence of the SIRPα-4-1BBL fusion protein disclosed herein and cells expressing CD47.

According to another aspect of the present invention, there is provided a method of activating phagocytes, the method comprising in-vitro or ex-vivo activating phagocytes in the presence of the SIRPα-4-1BBL fusion protein and/or the isolated polypeptide comprising the SIRPα amino acid sequence disclosed herein and cells expressing CD47.

According to specific embodiments, the activating is in the presence of the SIRPα-4-1BBL fusion protein, a polynucleotide encoding same, a nucleic acid construct encoding same or a host cell expressing same.

According to specific embodiments, the activating is in the presence of the isolated polypeptide comprising the SIRPα amino acid sequence, a polynucleotide encoding same, a nucleic acid construct encoding same or a host cell expressing same.

According to specific embodiments, the activating is in the presence of the isolated polypeptide comprising the 4-1BBL amino acid sequence, a polynucleotide encoding same, a nucleic acid construct encoding same or a host cell expressing same.

According to specific embodiments, the activating is in the presence of the isolated polypeptide comprising the SIRPα amino acid sequence, a polynucleotide encoding same, a nucleic acid construct encoding same or a host cell expressing same; and the 4-1BBL amino acid sequence, a polynucleotide encoding same, a nucleic acid construct encoding same or a host cell expressing same.

According to specific embodiments, the immune cells express 4-1BB.

According to specific embodiments, the immune cells comprise peripheral mononuclear blood cells (PBMCs).

As used herein the term "peripheral mononuclear blood cells (PBMCs)" refers to a blood cell having a single nucleus and includes lymphocytes, monocytes and dendritic cells (DCs).

According to specific embodiments, the PBMCs are selected from the group consisting of dendritic cells (DCs), T cells, B cells, NK cells and NKT cells.

According to specific embodiments, the PBMCs comprise T cells, B cells, NK cells and NKT cells.

Methods of obtaining PBMCs are well known in the art, such as drawing whole blood from a subject and collection in a container containing an anti-coagulant (e.g. heparin or citrate); and apheresis. Following, according to specific embodiments, at least one type of PBMCs is purified from the peripheral blood. There are several methods and reagents known to those skilled in the art for purifying PBMCs from whole blood such as leukapheresis, sedimentation, density gradient centrifugation (e.g. ficoll), centrifugal elutriation, fractionation, chemical lysis of e.g. red blood cells (e.g. by ACK), selection of specific cell types using cell surface markers (using e.g. FACS sorter or magnetic cell separation techniques such as are commercially available e.g. from Invitrogen, Stemcell Technologies, Cellpro, Advanced Magnetics, or Miltenyi Biotec.), and depletion of specific cell types by methods such as eradication (e.g. killing) with specific antibodies or by affinity based purification based on negative selection (using e.g. magnetic cell separation techniques, FACS sorter and/or capture ELISA labeling). Such methods are described for example in THE HANDBOOK OF EXPERIMENTAL IMMUNOLOGY, Volumes 1 to 4, (D. N. Weir, editor) and FLOW CYTOMETRY AND CELL SORTING (A. Radbruch, editor, Springer Verlag, 2000).

According to specific embodiments, the immune cells comprise tumor infiltrating lymphocytes.

As used herein the term "tumor infiltrating lymphocytes (TILs) refers to mononuclear white blood cells that have lest the bloodstream and migrated into a tumor.

According to specific embodiments, the TILs are selected from the group consisting of T cells, B cells, NK cells and monocytes.

Methods of obtaining TILs are well known in the art, such as obtaining tumor samples from a subject by e.g. biopsy or necropsy and preparing a single cell suspension thereof. The single cell suspension can be obtained in any suitable manner, e.g., mechanically (disaggregating the tumor using, e.g., a gentleMACS™ Dissociator, Miltenyi Biotec, Auburn, Calif.) or enzymatically (e.g., collagenase or DNase). Following, the at least one type of TILs can be purified from the cell suspension. There are several methods and reagents known to those skilled in the art for purifying the desired type of TILs, such as selection of specific cell types using cell surface markers (using e.g. FACS sorter or magnetic cell separation techniques such as are commercially available e.g. from Invitrogen, Stemcell Technologies, Cellpro, Advanced Magnetics, or Miltenyi Biotec.), and depletion of specific cell types by methods such as eradication (e.g. killing) with specific antibodies or by affinity based purification based on negative selection (using e.g. magnetic cell separation techniques, FACS sorter and/or capture ELISA labeling). Such methods are described for example in THE HANDBOOK OF EXPERIMENTAL IMMUNOLOGY, Volumes 1 to 4, (D. N. Weir, editor) and FLOW CYTOMETRY AND CELL SORTING (A. Radbruch, editor, Springer Verlag, 2000).

According to specific embodiments, the immune cells comprise phagocytes.

As used herein, the term "phagocytes" refer to a cell that is capable of phagocytosis and include both professional and non-professional phagocytes. Methods of analyzing phagocytosis are well known in the art and are further disclosed hereinabove and below. According to specific embodiments, the phagocytic cells are selected from the group consisting of monocytes, dendritic cells (DCs) and granulocytes.

According to specific embodiments, the phagocytes comprise granulocytes.

According to specific embodiments, the phagocytes comprise monocytes.

According to specific embodiments, the immune cells comprise monocytes.

According to specific embodiments, the term "monocytes" refers to both circulating monocytes and to macrophages (also referred to as mononuclear phagocytes) present in a tissue.

According to specific embodiments, the monocytes comprise macrophages. Typically, cell surface phenotype of macrophages include CD14, CD40, CD11b, CD64, F4/80 (mice)/EMRI (human), lysozyme M, MAC-1/MAC-3 and CD68.

According to specific embodiments, the monocytes comprise circulating monocytes. Typically, cell surface phenotypes of circulating monocytes include CD14 and CD16 (e.g. CD14++CD16−, CD14+CD16++, CD14++CD16+).

According to specific embodiments, the immune cells comprise DCs.

As used herein the term "dendritic cells (DCs)" refers to any member of a diverse population of morphologically similar cell types found in lymphoid or non-lymphoid tissues. DCs are a class of professional antigen presenting cells, and have a high capacity for sensitizing HLA-restricted T cells. DCs include, for example, plasmacytoid dendritic cells, myeloid dendritic cells (including immature and mature dendritic cells), Langerhans cells, interdigitating cells, follicular dendritic cells. Dendritic cells may be recognized by function, or by phenotype, particularly by cell surface phenotype. These cells are characterized by their distinctive morphology having veil-like projections on the cell surface, intermediate to high levels of surface HLA-class II expression and ability to present antigen to T cells, particularly to naive T cells (See Steinman R, et al., Ann. Rev. Immunol. 1991; 9:271-196.). Typically, cell surface phenotype of DCs include CD1a+, CD4+, CD86+, or HLA-DR. The term DCs encompasses both immature and mature DCs.

According to specific embodiments, the immune cells comprise granulocytes.

As used herein, the tern "granulocytes" refer to polymorphonuclear leukocytes characterized by the presence of granules in their cytoplasm.

According to specific embodiments, the granulocytes comprise neutrophils.

According to specific embodiments, the granulocytes comprise mast-cells.

According to specific embodiments the immune cells comprise T cells.

As used herein, the term "T cells" refers to a differentiated lymphocyte with a CD3+, T cell receptor (TCR)+ having either CD4+ or CD8+ phenotype. The T cell may be either an effector or a regulatory T cell.

As used herein, the term "effector T cells" refers to a T cell that activates or directs other immune cells e.g. by producing cytokines or has a cytotoxic activity e.g., CD4+, Th1/Th2, CD8+ cytotoxic T lymphocyte.

As used herein, the term "regulatory T cell" or "Treg" refers to a T cell that negatively regulates the activation of other T cells, including effector T cells, as well as innate immune system cells. Treg cells are characterized by sustained suppression of effector T cell responses. According to a specific embodiment, the Treg is a CD4+CD25+Foxp3+ T cell.

According to specific embodiments, the T cells are CD4+ T cells.

According to other specific embodiments, the T cells are CD8+ T cells.

According to specific embodiments, the T cells are memory T cells. Non-limiting examples of memory T cells include effector memory CD4+ T cells with a CD3+/CD4+/

CD45RA−/CCR7− phenotype, central memory CD4+ T cells with a CD3+/CD4+/CD45RA−/CCR7+ phenotype, effector memory CD8+ T cells with a CD3+/CD8+CD45RA−/CCR7− phenotype and central memory CD8+ T cells with a CD3+/CD8+CD45RA−/CCR7+ phenotype.

According to specific embodiments, the T cells comprise engineered T cells transduced with a nucleic acid sequence encoding an expression product of interest.

According to specific embodiments, the expression product of interest is a T cell receptor (TCR) or a chimeric antigen receptor (CAR).

As used herein the phrase "transduced with a nucleic acid sequence encoding a TCR" or "transducing with a nucleic acid sequence encoding a TCR" refers to cloning of variable α- and β-chains from T cells with specificity against a desired antigen presented in the context of MHC. Methods of transducing with a TCR are known in the art and are disclosed e.g. in Nicholson et al. Adv Hematol. 2012; 2012:404081; Wang and Rivière Cancer Gene Ther. 2015 March; 22(2):85-94); and Lamers et al, Cancer Gene Therapy (2002) 9, 613-623.

As used herein, the phrase "transduced with a nucleic acid sequence encoding a CAR" or "transducing with a nucleic acid sequence encoding a CAR" refers to cloning of a nucleic acid sequence encoding a chimeric antigen receptor (CAR), wherein the CAR comprises an antigen recognition moiety and a T-cell activation moiety. A chimeric antigen receptor (CAR) is an artificially constructed hybrid protein or polypeptide containing an antigen binding domain of an antibody (e.g., a single chain variable fragment (scFv)) linked to T-cell signaling or T-cell activation domains. Method of transducing with a CAR are known in the art and are disclosed e.g. in Davila et al. Oncoimmunology. 2012 Dec. 1; 1(9):1577-1583; Wang and Rivière Cancer Gene Ther. 2015 March; 22(2):85-94); Maus et al. Blood. 2014 Apr. 24;123(17):2625-35; Porter DL The New England journal of medicine. 2011, 365(8):725-733; Jackson H J, Nat Rev Clin Oncol. 2016; 13(6):370-383; and Globerson-Levin et al. Mol Ther. 2014; 22(5):1029-1038.

According to specific embodiments, the immune cells comprise B cells.

As used herein the term "B cells" refers to a lymphocyte with a B cell receptor (BCR)+, CD19+ and or B220+ phenotype. B cells are characterized by their ability to bind a specific antigen and elicit a humoral response.

According to specific embodiments, the immune cells comprise NK cells.

As used herein the term "NK cells" refers to differentiated lymphocytes with a CD16+CD56+ and/or CD57+ TCR− phenotype. NK are characterized by their ability to bind to and kill cells that fail to express "self" MHC/HLA antigens by the activation of specific cytolytic enzymes, the ability to kill tumor cells or other diseased cells that express a ligand for NK activating receptors, and the ability to release protein molecules called cytokines that stimulate or inhibit the immune response.

According to specific embodiments, the immune cells comprise NKT cells.

As used herein the term "NKT cells" refers to a specialized population of T cells that express a semi-invariant αβ T-cell receptor, but also express a variety of molecular markers that are typically associated with NK cells, such as NK1.1. NKT cells include NK1.1+ and NK1.1−, as well as CD4+, CD4−, CD8+ and CD8-cells. The TCR on NKT cells is unique in that it recognizes glycolipid antigens presented by the MHC I-like molecule CD1d. NKT cells can have either protective or deleterious effects due to their abilities to produce cytokines that promote either inflammation or immune tolerance.

According to specific embodiments, the immune cells are obtained from a healthy subject.

According to specific embodiments, the immune cells are obtained from a subject suffering from a pathology (e.g. cancer).

According to specific embodiments, the activating is in the presence of cells expressing CD47 or exogenous CD47.

According to specific embodiments, the activating is in the presence of exogenous CD47.

According to specific embodiments, the exogenous CD47 is soluble.

According to other specific embodiments, the exogenous CD47 is immobilized to a solid support.

According to specific embodiments, the activating is in the presence of cells expressing CD47.

According to specific embodiments, the cells expressing the CD47 comprise pathologic (diseased) cells.

According to specific embodiments, the cells expressing the CD47 comprise cancer cells.

According to specific embodiments, the activating is in the presence of a stimulatory agent capable of at least transmitting a primary activating signal [e.g. ligation of the T-Cell Receptor (TCR) with the Major Histocompatibility Complex (MHC)/peptide complex on the Antigen Presenting Cell (APC)] resulting in cellular proliferation, maturation, cytokine production, phagocytosis and/or induction of regulatory or effector functions of the immune cell. According to specific embodiments, the stimulator agent can also transmit a secondary co-stimulatory signal.

Methods of determining the amount of the stimulatory agent and the ratio between the stimulatory agent and the immune cells are well within the capabilities of the skilled in the art and thus are not specified herein.

The stimulatory agent can activate the immune cells in an antigen-dependent or -independent (i.e. polyclonal) manner.

According to specific embodiments, stimulatory agent comprises an antigen non-specific stimulator.

Non-specific stimulators are known to the skilled in the art. Thus, as a non-limiting example, when the immune cells comprise T cells, antigen non-specific stimulator can be an agent capable of binding to a T cell surface structure and induce the polyclonal stimulation of the T cell, such as but not limited to anti-CD3 antibody in combination with a co-stimulatory protein such as anti-CD28 antibody. Other non-limiting examples include anti-CD2, anti-CD137, anti-CD134, Notch-ligands, e.g. Delta-like 1/4, Jagged1/2 either alone or in various combinations with anti-CD3. Other agents that can induce polyclonal stimulation of T cells include, but not limited to mitogens, PHA, PMA-ionomycin, CEB and CytoStim (Miltenyi Biotech). According to specific embodiments, the antigen non-specific stimulator comprises anti-CD3 and anti-CD28 antibodies. According to specific embodiments, the T cell stimulator comprises anti-CD3 and anti-CD28 coated beads, such as the CD3CD28 MACSiBeads obtained from Miltenyi Biotec.

According to specific embodiments, the stimulatory agent comprises an antigen-specific stimulator.

Non-limiting examples of antigen specific T cell stimulators include an antigen-loaded antigen presenting cell [APC, e.g. dendritic cell] and peptide loaded recombinant MHC. Thus, for example, a T cells stimulator can be a dendritic cell preloaded with a desired antigen (e.g. a tumor antigen) or transfected with mRNA coding for the desired antigen.

According to specific embodiments, the antigen is a cancer antigen.

As used herein, the term "cancer antigen" refers to an antigen overexpressed or solely expressed by a cancerous cell as compared to a non-cancerous cell. A cancer antigen may be a known cancer antigen or a new specific antigen that develops in a cancer cell (i.e. neoantigens).

Non-limiting examples for known cancer antigens include MAGE-AI, MAGE-A2, MAGE-A3, MAGE-A4, MAGE-AS, MAGE-A6, MAGE-A7, MAGE-AS, MAGE-A9, MAGE-AIO, MAGE-All, MAGE-A12, GAGE-I, GAGE-2, GAGE-3, GAGE-4, GAGE-5, GAGE-6, GAGE-7, GAGE-8, BAGE-1, RAGE-1, LB33/MUM-1, PRAME, NAG, MAGE-Xp2 (MAGE-B2), MAGE-Xp3 (MAGE-B3), MAGE-Xp4 (MAGE-B4), MAGE-Cl/CT7, MAGE-C2, NY-ESO-1, LAGE-1, SSX-1, SSX-2(HOM-MEL-40), SSX-3, SSX-4, SSX-5, SCP-1 and XAGE, melanocyte differentiation antigens, p53, ras, CEA, MUCI, PMSA, PSA, tyrosinase, Melan-A, MART-I, gplOO, gp75, alphaactinin-4, Bcr-Abl fusion protein, Casp-8, beta-catenin, cdc27, cdk4, cdkn2a, coa-1, dek-can fusion protein, EF2, ETV6-AMLI fusion protein, LDLR-fucosyltransferaseAS fusion protein, HLA-A2, HLA-All, hsp70-2, KIAA0205, Mart2, Mum-2, and 3, neo-PAP, myosin class I, OS-9, pml-RAR alpha fusion protein, PTPRK, K-ras, N-ras, Triosephosphate isomerase, GnTV, Herv-K-mel, NA-88, SP17, and TRP2-Int2, (MART-I), E2A-PRL, H4-RET, IGH-IGK, MYL-RAR, Epstein Barr virus antigens, EBNA, human papillomavirus (HPV) antigens E6 and E7, TSP-180, MAGE-4, MAGE-5, MAGE-6, p185erbB2, plSOerbB-3, c-met, nm-23Hl, PSA, TAG-72-4, CA 19-9, CA 72-4, CAM 17.1, NuMa, K-ras, alpha.-fetoprotein, 13HCG, BCA225, BTAA, CA 125, CA 15-3 (CA 27.29\BCAA), CA 195, CA 242, CA-50, CAM43, CD68\KPI, CO-029, FGF-5, 0250, Ga733 (EpCAM), HTgp-175, M344, MA-50, MG7-Ag, MOV18, NB\170K, NYCO-I, RCASI, SDCCAG16, TA-90 (Mac-2 binding protein\cyclophilin C-associated protein), TAAL6, TAG72, TLP, TPS, tyrosinase related proteins, TRP-1, or TRP-2.

Other tumor antigens that may be expressed are well-known in the art (see for example WO00/20581; Cancer Vaccines and Immunotherapy (2000) Eds Stern, Beverley and Carroll, Cambridge University Press, Cambridge). The sequences of these tumor antigens are readily available from public databases but are also found in WO 1992/020356 AI, WO 1994/005304 AI, WO 1994/023031 AI, WO 1995/020974 AI, WO 1995/023874 AI & WO 1996/026214 AI.

Alternatively, or additionally, a tumor antigen may be identified using cancer cells obtained from the subject by e.g. biopsy.

Thus, according to specific embodiments, the stimulatory agent comprises a cancer cell.

According to specific embodiments, the activating is in the presence of an anti-cancer agent.

According to specific embodiments, the immune cells are purified following the activation.

Thus, the present invention also contemplates isolated immune cells obtainable according to the methods of the present invention.

According to specific embodiments, the immune cells used and/or obtained according to the present invention can be freshly isolated, stored e.g., cryopreserved (i.e. frozen) at e.g. liquid nitrogen temperature at any stage for long periods of time (e.g., months, years) for future use; and cell lines.

Methods of cryopreservation are commonly known by one of ordinary skill in the art and are disclosed e.g. in International Patent Application Publication Nos. WO2007054160 and WO 2001039594 and US Patent Application Publication No. US20120149108.

According to specific embodiments, the cells obtained according to the present invention can be stored in a cell bank or a depository or storage facility.

Consequently, the present teachings further suggest the use of the isolated immune cells and the methods of the present invention as, but not limited to, a source for adoptive immune cells therapies for diseases that can benefit from activating immune cells e.g. a hyper-proliferative disease; a disease associated with immune suppression and infections.

Thus, according to specific embodiments, method of the present invention comprise adoptively transferring the immune cells following said activating to a subject in need thereof.

According to specific embodiments, there is provided the immune cells obtainable according to the methods of the present invention for use in adoptive cell therapy.

The cells used according to specific embodiments of the present invention may be autologous or non-autologous; they can be syngeneic or non-syngeneic: allogeneic or xenogeneic to the subject; each possibility represents a separate embodiment of the present invention.

The present teachings also contemplate the use of the compositions of the present invention (e.g. the fusion protein, the isolated polypeptide comprising the SIRPα amino acid sequence, the isolated polypeptide comprising the 4-1BBL amino acid sequence, a polynucleotide or nucleic acid construct encoding same or a host cell expressing same) in methods of treating a disease that can benefit from activating immune cells.

Thus, according to another aspect of the present invention, there is provided a method of treating a disease that can benefit from activating immune cells comprising administering to a subject in need thereof the SIRPα-4-1BBL fusion protein, the isolated polypeptide comprising the SIRPα amino acid sequence and/or the isolated polypeptide comprising the 4-1BBL amino acid sequence disclosed herein, a polynucleotide or nucleic acid construct encoding same or a host cell encoding same.

According to another aspect of the present invention, there is provided the SIRPα-4-1BBL fusion protein, the isolated polypeptide comprising the SIRPα amino acid sequence and/or the isolated polypeptide comprising the 4-1BBL amino acid sequence disclosed herein, a polynucleotide or nucleic acid construct encoding same or a host cell encoding same for use in the treatment of a disease that can benefit from activating immune cells.

According to specific embodiments, the treating or the treatment is with the SIRPα-4-1BBL fusion protein, a polynucleotide encoding same, a nucleic acid construct encoding same or a host cell expressing same.

According to specific embodiments, the treating or the treatment is with the isolated polypeptide comprising the SIRPα amino acid sequence, a polynucleotide encoding same, a nucleic acid construct encoding same or a host cell expressing same.

According to specific embodiments, the treating or the treatment is with the isolated polypeptide comprising the 4-1BBL amino acid sequence, a polynucleotide encoding same, a nucleic acid construct encoding same or a host cell expressing same.

According to specific embodiments, the treating or the treatment is with the SIRPα amino acid sequence, a polynucleotide encoding same, a nucleic acid construct encoding same or a host cell expressing same; and the 4-1BBL amino acid sequence, a polynucleotide encoding same, a nucleic acid construct encoding same or a host cell expressing same.

The term "treating" or "treatment" refers to inhibiting, preventing or arresting the development of a pathology (disease, disorder or medical condition) and/or causing the reduction, remission, or regression of a pathology or a symptom of a pathology. Those of skill in the art will understand that various methodologies and assays can be used to assess the development of a pathology, and similarly, various methodologies and assays may be used to assess the reduction, remission or regression of a pathology.

As used herein, the term "subject" includes mammals, e.g., human beings at any age and of any gender. According to specific embodiments, the term "subject" refers to a subject who suffers from the pathology (disease, disorder or medical condition). According to specific embodiments, this term encompasses individuals who are at risk to develop the pathology.

According to specific embodiments, the subject is afflicted with a disease associated with cells expressing CD47.

According to specific embodiments, diseased cells of the subject express CD47.

As used herein the phrase "a disease that can benefit from activating immune cells" refers to diseases in which the subject's immune response activity may be sufficient to at least ameliorate symptoms of the disease or delay onset of symptoms, however for any reason the activity of the subject's immune response in doing so is less than optimal.

Non-limiting examples of diseases that can benefit from activating immune cells include hyper-proliferative diseases, diseases associated with immune suppression, immunosuppression caused by medication (e.g. mTOR inhibitors, calcineurin inhibitor, steroids) and infections.

According to specific embodiments, the disease comprises a hyper-proliferative disease.

According to specific embodiments, the hyper-proliferative disease comprises sclerosis or fibrosis, Idiopathic pulmonary fibrosis, psoriasis, systemic sclerosis/scleroderma, primary biliary cholangitis, primary sclerosing cholangitis, liver fibrosis, prevention of radiation-induced pulmonary fibrosis, myelofibrosis or retroperitoneal fibrosis.

According to other specific embodiments, the hyper-proliferative disease comprises cancer.

Thus, according to another aspect of the present invention, there is provided a method of treating cancer comprising administering the SIRPα-4-1BBL fusion protein, the isolated polypeptide comprising the SIRPα amino acid sequence and/or the isolated polypeptide comprising the 4-1BBL amino acid sequence disclosed herein to a subject in need thereof.

As used herein, the term cancer encompasses both malignant and pre-malignant cancers.

With regard to pre-malignant or benign forms of cancer, optionally the compositions and methods thereof may be applied for halting the progression of the pre-malignant cancer to a malignant form.

Cancers which can be treated by the methods of some embodiments of the invention can be any solid or non-solid cancer and/or cancer metastasis.

According to specific embodiments, the cancer comprises malignant cancer.

Examples of cancer include but are not limited to, carcinoma, lymphoma, blastoma, sarcoma, and leukemia. More particular examples of such cancers include squamous cell cancer, lung cancer (including small-cell lung cancer, non-small-cell lung cancer, adenocarcinoma of the lung, and squamous carcinoma of the lung), cancer of the peritoneum, hepatocellular cancer, gastric or stomach cancer (including gastrointestinal cancer), pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney or renal cancer, liver cancer, prostate cancer, vulvar cancer, thyroid cancer, hepatic carcinoma and various types of head and neck cancer, as well as B-cell lymphoma (including low grade/follicular non-Hodgkin's lymphoma (NHL); Burkitt lymphoma, Diffused large B cell lymphoma (DLBCL), small lymphocytic (SL) NHL; intermediate grade/follicular NHL; intermediate grade diffuse NHL; high grade immunoblastic NHL; high grade lymphoblastic NHL; high-grade small non-cleaved cell NHL; bulky disease NHL; mantle cell lymphoma; AIDS-related lymphoma; and Waldenstrom's Macroglobulinemia); T cell lymphoma, Hodgkin lymphoma, chronic lymphocytic leukemia (CLL); acute lymphoblastic leukemia (ALL); Acute myeloid leukemia (AML), Acute promyelocytic leukemia (APL), Hairy cell leukemia; chronic myeloblastic leukemia (CML); and post-transplant lymphoproliferative disorder (PTLD), as well as abnormal vascular proliferation associated with phakomatoses, edema (such as that associated with brain tumors), and Meigs' syndrome. Preferably, the cancer is selected from the group consisting of breast cancer, colorectal cancer, rectal cancer, non-small cell lung cancer, non-Hodgkins lymphoma (NHL), renal cell cancer, prostate cancer, liver cancer, pancreatic cancer, soft-tissue sarcoma, Kaposi's sarcoma, carcinoid carcinoma, head and neck cancer, melanoma, ovarian cancer, mesothelioma, and multiple myeloma. The cancerous conditions amenable for treatment of the invention include metastatic cancers.

According to specific embodiments, the cancer comprises pre-malignant cancer.

Pre-malignant cancers (or pre-cancers) are well characterized and known in the art (refer, for example, to Berman J J. and Henson D E., 2003. Classifying the precancers: a metadata approach. BMC Med Inform Decis Mak. 3:8). Classes of pre-malignant cancers amenable to treatment via the method of the invention include acquired small or microscopic pre-malignant cancers, acquired large lesions with nuclear atypia, precursor lesions occurring with inherited hyperplastic syndromes that progress to cancer, and acquired diffuse hyperplasias and diffuse metaplasias. Examples of small or microscopic pre-malignant cancers include HGSIL. (High grade squamous intraepithelial lesion of uterine cervix), AIN (anal intraepithelial neoplasia), dysplasia of vocal cord, aberrant crypts (of colon), PIN (prostatic intraepithelial neoplasia). Examples of acquired large lesions with nuclear atypia include tubular adenoma, AILD (angioimmunoblastic lymphadenopathy with dysproteinemia), atypical meningioma, gastric polyp, large plaque parapsoriasis, myelodysplasia, papillary transitional cell carcinoma in-situ, refractory anemia with excess blasts, and Schneiderian papilloma. Examples of precursor lesions occurring with inherited hyperplastic syndromes that progress to cancer include atypical mole syndrome, C cell adenomatosis and MEA. Examples of acquired diffuse hyperplasias and diffuse metaplasias include AIDS, atypical lymphoid hyperplasia, Paget's disease of bone, post-transplant lymphoproliferative disease and ulcerative colitis.

According to specific embodiments, the cancer is Leukemia, Chronic myelomonocytic leukemia (CMML), Chronic myelogenous leukemia (CML), Acute myeloid leukemia (AML), Non Hodgkin lymphoma (NHL), Diffuse Large B Cell Lymphoma (DLBCL), B cell Chronic Lymphocytic Leukemia (B-CLL), Mantle Cell Lymphoma (MCL), Follicular Lymphoma (FL), Marginal Zone Lymphoma (MZL), Pre-B acute lymphoblastic leukemia (pre-B ALL), Leiomyosarcoma, Ovarian cancer, Breast cancer, Colon cancer, Bladder cancer, Glioblastoma, Hepatocellular carcinoma, Prostate cancer, Acute lymphoblastic leukemia (ALL), Multiple Myeloma, Non-small-cell lung carcinoma (NSCLC), Colorectal cancer, Melanoma, Head and Neck Cancer, Marginal Zone B-cell Lymphoma, Pancreatic Ductal Adenocarcinoma or Brain cancer According to some embodiments the cancer is Acute myeloid leukemia, Bladder Cancer, Breast Cancer, chronic lymphocytic leukemia, Chronic myelogenous leukemia, Colorectal cancer, Diffuse large B-cell lymphoma, Epithelial Ovarian Cancer, Epithelial Tumor, Fallopian Tube Cancer, Follicular Lymphoma, Glioblastoma multiform, Hepatocellular carcinoma, Head and Neck Cancer, Leukemia, Lymphoma, Mantle Cell Lymphoma, Melanoma, Mesothelioma, Multiple Myeloma, Nasopharyngeal Cancer, Non Hodgkin lymphoma, Non-small-cell lung carcinoma, Ovarian Cancer, Prostate Cancer or Renal cell carcinoma.

According to specific embodiments, the cancer is selected from the group consisting of lymphoma, leukemia and carcinoma.

According to specific embodiments, the cancer is selected from the group consisting of lymphoma, leukemia, colon cancer, pancreatic cancer, ovarian cancer, lung cancer and squamous cell carcinoma.

According to specific embodiments, the cancer is colon carcinoma.

According to specific embodiments, the cancer is ovarian carcinoma.

According to specific embodiments, the cancer is lung carcinoma.

According to specific embodiments, the cancer is head and neck carcinoma.

According to specific embodiments, the cancer is leukemia.

According to specific embodiments, the leukemia is selected from the group consisting of acute nonlymphocytic leukemia, chronic lymphocytic leukemia, acute granulocytic leukemia, chronic granulocytic leukemia, acute promyelocytic leukemia, adult T-cellleukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, ( )ross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, plasmacytic leukemia, promyelocytic leukemia, Rieder cell leukemia, Schilling's leukemia, stem cell leukemia, subleukemic leukemia, and undifferentiated cell leukemia.

According to specific embodiments, the leukemia is promyelocytic leukemia, acute myeloid leukemia or chronic myelogenous leukemia.

According to specific embodiments, the cancer is lymphoma.

According to specific embodiments, the lymphoma is B cell lymphoma

According to specific embodiments, the lymphoma is T cell lymphoma.

According to other specific embodiments, the lymphoma is Hodgkins lymphoma.

According to specific embodiments, the lymphoma is non-Hodgkins lymphoma.

According to specific embodiments, the non-Hodgkin's Lymphoma is a selected from the group consisting of aggressive NHL, transformed NHL, indolent NHL, relapsed NHL, refractory NHL, low grade non-Hodgkin's Lymphoma, follicular lymphoma, large cell lymphoma, B-cell lymphoma, T-cell lymphoma, Mantle cell lymphoma, Burkitt's lymphoma, NK cell lymphoma, diffuse large B-cell lymphoma, acute lymphoblastic lymphoma, and cutaneous T cell cancer, including mycosis fungoides/Sezry syndrome.

According to specific embodiments, the cancer is multiple myeloma.

According to at least some embodiments, the multiple myeloma is selected from the group consisting of multiple myeloma cancers which produce light chains of kappa-type and/or light chains of lambda-type; aggressive multiple myeloma, including primary plasma cell leukemia (PCL); benign plasma cell disorders such as MGUS (monoclonal gammopathy of undetermined significance), Waldenstrom's macroglobulinemia (WM, also known as lymphoplasmacytic lymphoma) which may proceed to multiple myeloma; smoldering multiple myeloma (SMM), indolent multiple myeloma, premalignant forms of multiple myeloma which may also proceed to multiple myeloma; primary amyloidosis.

According to specific embodiments, the cancer is defined by the presence of tumors that have tumor-infiltrating lymphocytes (TILs) in the tumor micro-environment and/or tumors with a relatively high expression of CD47 in the tumor micro-environment.

According to specific embodiments, cells of the cancer express CD47.

According to specific embodiments, the disease comprises a disease associated with immune suppression or immunosuppression caused by medication (e.g. mTOR inhibitors, calcineurin inhibitor, steroids).

According to specific embodiments, the disease comprises HIV, Measles, influenza, LCCM, RSV, Human Rhinoviruses, EBV, CMV, Parvo viruses.

According to specific embodiments, the disease comprises an infection.

As used herein, the term "infection" of "infectious disease" refers to a disease induced by a pathogen. Specific examples of pathogens include, viral pathogens, bacterial pathogens e.g., intracellular mycobacterial pathogens (such as, for example, *Mycobacterium tuberculosis*), intracellular bacterial pathogens (such as, for example, *Listeria monocytogenes*), or intracellular protozoan pathogens (such as, for example, *Leishmania* and *Trypanosoma*).

Specific types of viral pathogens causing infectious diseases treatable according to the teachings of the present invention include, but are not limited to, retroviruses, circoviruses, parvoviruses, papovaviruses, adenoviruses, herpesviruses, iridoviruses, poxviruses, hepadnaviruses, picornaviruses, caliciviruses, togaviruses, flaviviruses, reoviruses, orthomyxoviruses, paramyxoviruses, rhabdoviruses, bunyaviruses, coronaviruses, arenaviruses, and filoviruses.

Specific examples of viral infections which may be treated according to the teachings of the present invention include, but are not limited to, human immunodeficiency virus (HIV)-induced acquired immunodeficiency syndrome (AIDS), influenza, rhinoviral infection, viral meningitis, Epstein-Barr virus (EBV) infection, hepatitis A, B or C virus infection, measles, papilloma virus infection/warts, cytomegalovirus (CMV) infection, Herpes simplex virus infection, yellow fever, Ebola virus infection, rabies, etc.

According to specific embodiments, the compositions disclosed herein (e.g. SIRPα-4-1BBL fusion protein, polypeptide comprising a SIRPα amino acid sequence, polypeptide comprising a 4-1BBL amino acid sequence, polynucleotide or nucleic acid construct encoding same and/or host-cell expressing same) can be administered to a subject in combination with other established or experimental therapeutic regimen to treat a disease that can benefit from activating immune cells (e.g. cancer) including, but not limited to analgesics, chemotherapeutic agents, radiotherapeutic agents, cytotoxic therapies (conditioning), hormonal therapy, antibodies and other treatment regimens (e.g., surgery) which are well known in the art.

According to specific embodiments, the compositions disclosed herein (e.g. SIRPα-4-1BBL fusion protein, polypeptide comprising SIRPα amino acid sequence, polypeptide comprising 4-1BBL amino acid sequence, polynucleotide or nucleic acid construct encoding same and/or host-cell expressing same) can be administered to a subject in combination with adoptive cell transplantation such as, but not limited to transplantation of bone marrow cells, hematopoietic stem cells, PBMCs, cord blood stem cells and/or induced pluripotent stem cells.

According to specific embodiments, the therapeutic agent administered in combination with the composition of some embodiments of the invention comprises an anti-cancer agent.

Thus, according to another aspect of the present invention, there is provided a method of treating cancer comprising administering to a subject in need thereof an anti-cancer agent; and the SIRPα-4-1BBL fusion protein, the isolated polypeptide comprising the SIRPα amino acid sequence and/or the polypeptide comprising the 4-1BBL amino acid sequence disclosed herein, a polynucleotide encoding same, a nucleic acid construct encoding same or a host cell expressing same.

Anti-cancer agents that can be use with specific embodiments of the invention include, but are not limited to the anti-cancer drugs Acivicin; Aclarubicin; Acodazole Hydrochloride; Acronine; Adriamycin; Adozelesin; Aldesleukin; Altretamine; Ambomycin; Ametantrone Acetate; Aminoglutethimide; Amsacrine; Anastrozole; Anthramycin; Asparaginase; Asperlin; Azacitidine; Azetepa; Azotomycin; Batimastat; Benzodepa; Bicalutamide; Bisantrene Hydrochloride; Bisnafide Dimesylate; Bizelesin; Bleomycin Sulfate; Brequinar Sodium; Bropirimine; Busulfan; Cactinomycin; Calusterone; Caracemide; Carbetimer; Carboplatin; Carmustine; Carubicin Hydrochloride; Carzelesin; Cedefingol; Chlorambucil; Cirolemycin; Cisplatin; Cladribine; Crisnatol Mesylate; Cyclophosphamide; Cytarabine; Dacarbazine; Dactinomycin; Daunorubicin Hydrochloride; Decitabine; Dexormaplatin; Dezaguanine; Dezaguanine Mesylate; Diaziquone; Docetaxel; Doxorubicin; Doxorubicin Hydrochloride; Droloxifene; Droloxifene Citrate; Dromostanolone Propionate; Duazomycin; Edatrexate; Eflornithine Hydrochloride; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Etoposide; Etoposide Phosphate; Etoprine; Fadrozole Hydrochloride; Fazarabine; Fenretinide; Floxuridine; Fludarabine Phosphate; Fluorouracil; Flurocitabine; Fosquidone; Fostriecin Sodium; Gemcitabine; Gemcitabine Hydrochloride; Hydroxyurea; Idarubicin Hydrochloride; Ifosfamide; Ilmofosine; Interferon Alfa-2a; Interferon Alfa-2b; Interferon Alfa-n1; Interferon Alfa-n3; Interferon Beta-I a; Interferon Gamma-I b; Iproplatin; Irinotecan Hydrochloride; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Metoprine; Meturedepa; Mitindomide; Mitocarcin; Mitocromin; Mitogillin; Mitomalcin; Mitomycin; Mitosper; Mitotane; Mitoxantrone Hydrochloride; Mycophenolic Acid; Nocodazole; Nogalamycin; Ormaplatin; Oxisuran; Paclitaxel; Pegaspargase; Peliomycin; Pentamustine; Peplomycin Sulfate; Perfosfamide; Pipobroman; Piposulfan; Piroxantrone Hydrochloride; Plicamycin; Plomestane; Porfimer Sodium; Porfiromycin; Prednimustine; Procarbazine Hydrochloride; Puromycin; Puromycin Hydrochloride; Pyrazofurin; Riboprine; Rogletimide; Safingol; Safingol Hydrochloride; Semustine; Simtrazene; Sparfosate Sodium; Sparsomycin; Spirogermanium Hydrochloride; Spiromustine; Spiroplatin; Streptonigrin; Streptozocin; Sulofenur; Talisomycin; Taxol; Tecogalan Sodium; Tegafur; Teloxantrone Hydrochloride; Temoporfin; Teniposide; Teroxirone; Testolactone; Thiamiprine; Thioguanine; Thiotepa; Tiazofuirin; Tirapazamine; Topotecan Hydrochloride; Toremifene Citrate; Trestolone Acetate; Triciribine Phosphate; Trimetrexate; Trimetrexate Glucuronate; Triptorelin; Tubulozole Hydrochloride; Uracil Mustard; Uredepa; Vapreotide; Verteporfin; Vinblastine Sulfate; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; Zorubicin Hydrochloride. Additional antineoplastic agents include those disclosed in Chapter 52, Antineoplastic Agents (Paul Calabresi and Bruce A. Chabner), and the introduction thereto, 1202-1263, of Goodman and Gilman's "The Pharmacological Basis of Therapeutics", Eighth Edition, 1990, McGraw-Hill, Inc. (Health Professions Division).

According to specific embodiments, the anti-cancer agent comprises an antibody.

According to specific embodiments, the antibody is selected from the group consisting rituximab, cetuximab, trastuzumab, edrecolomab, alemtuzumab, gemtuzumab, ibritumomab, panitumumab, Belimumab, Bevacizumab, Bivatuzumab mertansine, Blinatumomab, Blontuvetmab, Brentuximab vedotin, Catumaxomab, Cixutumumab, Daclizumab, Adalimumab, Bezlotoxumab, Certolizumab pegol, Citatuzumab bogatox, Daratumumab, Dinutuximab, Elotuzumab, Ertumaxomab, Etaracizumab, Gemtuzumab ozogamicin, Girentuximab, Necitumumab, Obinutuzumab, Ofatumumab, Pertuzumab, Ramucirumab, Siltuximab, Tositumomab, Trastuzumab, Nivolumab, Pembrolizumab, Durvalumab, Atezolizumab, Avelumab and ipilimumab.

According to specific embodiments, the antibody is selected from the group consisting of rituximab and cetuximab.

According to specific embodiments, the therapeutic agent or the anti-cancer agent comprises an IMiD (e.g. Thalidomide, Lenalidomie, Pomalidomide).

According to specific embodiments, the IMID is selected from the group consisting of Thalidomide, Lenalidomie and Pomalidomide.

According to specific embodiments, the therapeutic agent administered in combination with the composition of some embodiments of the invention comprises an anti-infection agent (e.g. antibiotics and anti-viral agents).

According to specific embodiments, the therapeutic agent administered in combination with the composition of some embodiments of the invention comprises an immune suppressor agent (e.g. GCSF and other bone marrow stimulators, steroids).

According to specific embodiments the combination therapy has an additive effect.

According to specific embodiments, the combination therapy has a synergistic effect.

According to another aspect of the present invention there is provided an article of manufacture comprising a packaging material packaging a therapeutic agent for treating a disease that can benefit from activating immune cells; and the SIRPα-4-1BBL fusion protein, the isolated polypeptide comprising the SIRPα amino acid sequence and/or the isolated polypeptide comprising the 4-1BBL amino acid sequence disclosed herein, a polynucleotide encoding same, a nucleic acid construct encoding same or a host cell expressing same. According to specific embodiments, the article of manufacture is identified for the treatment of a disease that can benefit from activating immune cells.

According to specific embodiments, the therapeutic agent for treating said disease; and the SIRPα-4-1BBL fusion protein, the isolated polypeptide comprising the SIRPα amino acid sequence and/or the isolated polypeptide comprising the 4-1BBL amino acid sequence, the polynucleotide encoding same, the nucleic acid construct encoding same or the host cell expressing same are packaged in separate containers.

According to specific embodiments, the therapeutic agent for treating said disease; and the SIRPα-4-1BBL fusion protein, the isolated polypeptide comprising the SIRPα amino acid sequence and/or the isolated polypeptide comprising the 4-1BBL amino acid sequence, the polynucleotide or the nucleic acid encoding same, the nucleic acid construct encoding same or the host cell expressing same are packaged in a co-formulation.

According to specific embodiments, the article of manufacture comprises the SIRPα-4-1BBL fusion protein, a polynucleotide encoding same, a nucleic acid construct encoding same or a host cell expressing same.

According to specific embodiments, the article of manufacture comprises the isolated polypeptide comprising the SIRPα amino acid sequence, a polynucleotide encoding same, a nucleic acid construct encoding same or a host cell expressing same.

According to specific embodiments, the article of manufacture comprises the isolated polypeptide comprising the 4-1BBL amino acid sequence, a polynucleotide encoding same, a nucleic acid construct encoding same or a host cell expressing same.

According to specific embodiments, the article of manufacture comprises the SIRPα amino acid sequence, a polynucleotide encoding same, a nucleic acid construct encoding same or a host cell expressing same; and the 4-1BBL amino acid sequence, a polynucleotide encoding same, a nucleic acid construct encoding same or a host cell expressing same.

Thus, according to another aspect of the present invention there is provided an article of manufacture comprising a packaging material packaging the isolated polypeptide comprising the SIRPα amino acid sequence disclosed herein, a polynucleotide encoding same, a nucleic acid construct encoding same or a host cell expressing same; and the isolated polypeptide comprising the 4-1BBL amino acid sequence disclosed herein, a polynucleotide encoding same, a nucleic acid construct encoding same or a host cell expressing same.

According to specific embodiments, the isolated polypeptide comprising the SIRPα amino acid sequence disclosed herein, a polynucleotide encoding same, a nucleic acid construct encoding same or a host cell expressing same; and the isolated polypeptide comprising the 4-1BBL amino acid sequence disclosed herein, a polynucleotide encoding same, a nucleic acid construct encoding same or a host cell expressing same are packaged in separate containers.

According to specific embodiments, the isolated polypeptide comprising the SIRPα amino acid sequence disclosed herein, a polynucleotide encoding same, a nucleic acid construct encoding same or a host cell expressing same; and the isolated polypeptide comprising the 4-1BBL amino acid sequence disclosed herein, a polynucleotide encoding same, a nucleic acid construct encoding same or a host cell expressing same are packaged in a co-formulation.

According to specific embodiments, the isolated polypeptide comprising the SIRPα amino acid sequence; and/or the isolated polypeptide comprising the 4-1BBL amino acid sequence is attached to or comprises a heterologous therapeutic moiety. The therapeutic moiety may be any molecule, including small molecule chemical compounds and polypeptides.

Non-limiting examples of therapeutic moieties which can be used with specific embodiments of the invention include a cytotoxic moiety, a toxic moiety, a cytokine moiety, an immunomodulatory moiety, a polypeptide, an antibody, a drug, a chemical and/or a radioisotope.

According to some embodiments of the invention, the therapeutic moiety is conjugated by translationally fusing the polynucleotide encoding the polypeptide of some embodiments of the invention with the nucleic acid sequence encoding the therapeutic moiety.

Additionally or alternatively, the therapeutic moiety can be chemically conjugated (coupled) to the polypeptide of some embodiments of the invention, using any conjugation method known to one skilled in the art. For example, a peptide can be conjugated to an agent of interest, using a 3-(2-pyridyldithio)propionic acid Nhydroxysuccinimide ester (also called N-succinimidyl 3-(2pyridyldithio) propionate) ("SDPD") (Sigma, Cat. No. P-3415; see e.g., Cumber et al. 1985, Methods of Enzymology 112: 207-224), a glutaraldehyde conjugation procedure (see e.g., G. T. Hermanson 1996, "Antibody Modification and Conjugation, in Bioconjugate Techniques, Academic Press, San Diego) or a carbodiimide conjugation procedure [see e.g., J. March, Advanced Organic Chemistry: Reaction's, Mechanism, and Structure, pp. 349-50 & 372-74 (3d ed.), 1985; B. Neises et al. 1978, Angew Chem., Int. Ed. Engl. 17:522; A. Hassner et al. 1978, Tetrahedron Lett. 4475; E. P. Boden et al. 1986, J. Org. Chem. 50:2394 and L. J. Mathias 1979, Synthesis 561].

A therapeutic moiety can be attached, for example, to the polypeptide of some embodiments of the invention using standard chemical synthesis techniques widely practiced in the art [see e.g., hypertexttransferprotocol://worldwideweb (dot) chemistry (dot) org/portal/Chemistry)], such as using any suitable chemical linkage, direct or indirect, as via a peptide bond (when the functional moiety is a polypeptide), or via covalent bonding to an intervening linker element, such as a linker peptide or other chemical moiety, such as an organic polymer. Chimeric peptides may be linked via bonding at the carboxy (C) or amino (N) termini of the peptides, or via bonding to internal chemical groups such as straight, branched or cyclic side chains, internal carbon or nitrogen atoms, and the like.

As used herein, the terms "protein", "peptide" and "polypeptide", which are interchangeably used herein, encompass native peptides (either degradation products, synthetically synthesized peptides or recombinant peptides) and peptidomimetics (typically, synthetically synthesized peptides), as well as peptoids and semipeptoids which are peptide analogs, which may have, for example, modifications rendering the peptides more stable while in a body or more capable of penetrating into cells. Such modifications include, but are not limited to N terminus modification, C terminus modification, peptide bond modification, backbone modifications, and residue modification. Methods for preparing peptidomimetic compounds are well known in the art and are specified, for example, in Quantitative Drug Design, C. A. Ramsden Gd., Chapter 17.2, F. Choplin Pergamon Press (1992), which is incorporated by reference as if fully set forth herein. Further details in this respect are provided hereinunder.

Peptide bonds (—CO—NH—) within the peptide may be substituted, for example, by N-methylated amide bonds (—N(CH3)-CO—), ester bonds (—C(=O)—O—), ketomethylene bonds (—CO—CH2-), sulfinylmethylene bonds (—S(=O)—CH2-), α-aza bonds (—NH—N(R)—CO—), wherein R is any alkyl (e.g., methyl), amine bonds (—CH2-NH—), sulfide bonds (—CH2-S—), ethylene bonds (—CH2-CH2-), hydroxyethylene bonds (—CH(OH)-CH2-), thioamide bonds (—CS—NH—), olefinic double bonds (—CH=CH—), fluorinated olefinic double bonds (—CF=CH—), retro amide bonds (—NH—CO—), peptide derivatives (—N(R)—CH2-CO—), wherein R is the "normal" side chain, naturally present on the carbon atom.

These modifications can occur at any of the bonds along the peptide chain and even at several (2-3) bonds at the same time.

Natural aromatic amino acids, Trp, Tyr and Phe, may be substituted by non-natural aromatic amino acids such as 1,2,3,4-tetrahydroisoquinoline-3-carboxylic acid (Tic), naphthylalanine, ring-methylated derivatives of Phe, halogenated derivatives of Phe or O-methyl-Tyr.

The peptides of some embodiments of the invention may also include one or more modified amino acids or one or more non-amino acid monomers (e.g. fatty acids, complex carbohydrates etc).

The term "amino acid" or "amino acids" is understood to include the 20 naturally occurring amino acids; those amino acids often modified post-translationally in vivo, including, for example, hydroxyproline, phosphoserine and phosphothreonine; and other unusual amino acids including, but not limited to, 2-aminoadipic acid, hydroxylysine, isodesmosine, nor-valine, nor-leucine and ornithine. Furthermore, the term "amino acid" includes both D- and L-amino acids.

Tables 1 and 2 below list naturally occurring amino acids (Table 1), and non-conventional or modified amino acids (e.g., synthetic, Table 2) which can be used with some embodiments of the invention.

TABLE 1

| Amino Acid | Three-Letter Abbreviation | One-letter Symbol |
|---|---|---|
| Alanine | Ala | A |
| Arginine | Arg | R |
| Asparagine | Asn | N |
| Aspartic acid | Asp | D |

TABLE 1-continued

| Amino Acid | Three-Letter Abbreviation | One-letter Symbol |
|---|---|---|
| Cysteine | Cys | C |
| Glutamine | Gln | Q |
| Glutamic Acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| Any amino acid as above | Xaa | X |

TABLE 2

| Non-conventional amino acid | Code | Non-conventional amino acid | Code |
|---|---|---|---|
| ornithine | Orn | hydroxyproline | Hyp |
| α-aminobutyric acid | Abu | aminonorbornyl-carboxylate | Norb |
| D-alanine | Dala | aminocyclopropane-carboxylate | Cpro |
| D-arginine | Darg | N-(3-guanidinopropyl)glycine | Narg |
| D-asparagine | Dasn | N-(carbamylmethyl)glycine | Nasn |
| D-aspartic acid | Dasp | N-(carboxymethyl)glycine | Nasp |
| D-cysteine | Dcys | N-(thiomethyl)glycine | Ncys |
| D-glutamine | Dgln | N-(2-carbamylethyl)glycine | Ngln |
| D-glutamic acid | Dglu | N-(2-carboxyethyl)glycine | Nglu |
| D-histidine | Dhis | N-(imidazolylethyl)glycine | Nhis |
| D-isoleucine | Dile | N-(1-methylpropyl)glycine | Nile |
| D-leucine | Dleu | N-(2-methylpropyl)glycine | Nleu |
| D-lysine | Dlys | N-(4-aminobutyl)glycine | Nlys |
| D-methionine | Dmet | N-(2-methylthioethyl)glycine | Nmet |
| D-ornithine | Dorn | N-(3-aminopropyl)glycine | Norn |
| D-phenylalanine | Dphe | N-benzylglycine | Nphe |
| D-proline | Dpro | N-(hydroxymethyl)glycine | Nser |
| D-serine | Dser | N-(1-hydroxyethyl)glycine | Nthr |
| D-threonine | Dthr | N-(3-indolylethyl) glycine | Nhtrp |
| D-tryptophan | Dtrp | N-(p-hydroxyphenyl)glycine | Ntyr |
| D-tyrosine | Dtyr | N-(1-methylethyl)glycine | Nval |
| D-valine | Dval | N-methylglycine | Nmgly |
| D-N-methylalanine | Dnmala | L-N-methylalanine | Nmala |
| D-N-methylarginine | Dnmarg | L-N-methylarginine | Nmarg |
| D-N-methylasparagine | Dnmasn | L-N-methylasparagine | Nmasn |
| D-N-methylasparatate | Dnmasp | L-N-methylaspartic acid | Nmasp |
| D-N-methylcysteine | Dnmcys | L-N-methylcysteine | Nmcys |
| D-N-methylglutamine | Dnmgln | L-N-methylglutamine | Nmgln |
| D-N-methylglutamate | Dnmglu | L-N-methylglutamic acid | Nmglu |
| D-N-methylhistidine | Dnmhis | L-N-methylhistidine | Nmhis |
| D-N-methylisoleucine | Dnmile | L-N-methylisolleucine | Nmile |

TABLE 2-continued

| Non-conventional amino acid | Code | Non-conventional amino acid | Code |
|---|---|---|---|
| D-N-methylleucine | Dnmleu | L-N-methylleucine | Nmleu |
| D-N-methyllysine | Dnmlys | L-N-methyllysine | Nmlys |
| D-N-methylmethionine | Dnmmet | L-N-methylmethionine | Nmmet |
| D-N-methylornithine | Dnmorn | L-N-methylornithine | Nmorn |
| D-N-methylphenylalanine | Dnmphe | L-N-methylphenylalanine | Nmphe |
| D-N-methylproline | Dnmpro | L-N-methylproline | Nmpro |
| D-N-methylserine | Dnmser | L-N-methylserine | Nmser |
| D-N-methylthreonine | Dnmthr | L-N-methylthreonine | Nmthr |
| D-N-methyltryptophan | Dnmtrp | L-N-methyltryptophan | Nmtrp |
| D-N-methyltyrosine | Dnmtyr | L-N-methyltyrosine | Nmtyr |
| D-N-methylvaline | Dnmval | L-N-methylvaline | Nmval |
| L-norleucine | Nle | L-N-methylnorleucine | Nmnle |
| L-norvaline | Nva | L-N-methylnorvaline | Nmnva |
| L-ethylglycine | Etg | L-N-methyl-ethylglycine | Nmetg |
| L-t-butylglycine | Tbug | L-N-methyl-t-butylglycine | Nmtbug |
| L-homophenylalanine | Hphe | L-N-methyl-homophenylalanine | Nmhphe |
| α-naphthylalanine | Anap | N-methyl-α-naphthylalanine | Nmanap |
| penicillamine | Pen | N-methylpenicillamine | Nmpen |
| γ-aminobutyric acid | Gabu | N-methyl-γ-aminobutyrate | Nmgabu |
| cyclohexylalanine | Chexa | N-methyl-cyclohexylalanine | Nmchexa |
| cyclopentylalanine | Cpen | N-methyl-cyclopentylalanine | Nmcpen |
| α-amino-α-methylbutyrate | Aabu | N-methyl-α-amino-α-methylbutyrate | Nmaabu |
| α-aminoisobutyric acid | Aib | N-methyl-α-aminoisobutyrate | Nmaib |
| D-α-methylarginine | Dmarg | L-α-methylarginine | Marg |
| D-α-methylasparagine | Dmasn | L-α-methylasparagine | Masn |
| D-α-methylaspartate | Dmasp | L-α-methylaspartate | Masp |
| D-α-methylcysteine | Dmcys | L-α-methylcysteine | Mcys |
| D-α-methylglutamine | Dmgln | L-α-methylglutamine | Mgln |
| D-α-methyl glutamic acid | Dmglu | L-α-methylglutamate | Mglu |
| D-α-methylhistidine | Dmhis | L-α-methylhistidine | Mhis |
| D-α-methylisoleucine | Dmile | L-α-methylisoleucine | Mile |
| D-α-methylleucine | Dmleu | L-α-methylleucine | Mleu |
| D-α-methyllysine | Dmlys | L-α-methyllysine | Mlys |
| D-α-methylmethionine | Dmmet | L-α-methylmethionine | Mmet |
| D-α-methylornithine | Dmorn | L-α-methylornithine | Morn |
| D-α-methylphenylalanine | Dmphe | L-α-methylphenylalanine | Mphe |
| D-α-methylproline | Dmpro | L-α-methylproline | Mpro |
| D-α-methylserine | Dmser | L-α-methylserine | Mser |
| D-α-methylthreonine | Dmthr | L-α-methylthreonine | Mthr |
| D-α-methyltryptophan | Dmtrp | L-α-methyltryptophan | Mtrp |
| D-α-methyltyrosine | Dmtyr | L-α-methyltyrosine | Mtyr |
| D-α-methylvaline | Dmval | L-α-methylvaline | Mval |
| N-cyclobutylglycine | Ncbut | L-α-methylnorvaline | Mnva |
| N-cycloheptylglycine | Nchep | L-α-methylethylglycine | Metg |
| N-cyclohexylglycine | Nchex | L-α-methyl-t-butylglycine | Mtbug |
| N-cyclodecylglycine | Ncdec | L-α-methyl-homophenylalanine | Mhphe |
| N-cyclododecylglycine | Ncdod | α-methyl-α-naphthylalanine | Manap |
| N-cyclooctylglycine | Ncoct | α-methylpenicillamine | Mpen |
| N-cyclopropylglycine | Ncpro | α-methyl-γ-aminobutyrate | Mgabu |
| N-cycloundecylglycine | Ncund | α-methyl-cyclohexylalanine | Mchexa |
| N-(2-aminoethyl)glycine | Naeg | α-methyl-cyclopentylalanine | Mcpen |
| N-(2,2-diphenylethyl)glycine | Nbhm | N-(N-(2,2-diphenylethyl) carbamylmethyl-glycine | Nnbhm |
| N-(3,3-diphenylpropyl)glycine | Nbhe | N-(N-(3,3-diphenylpropyl) carbamylmethyl-glycine | Nnbhe |
| 1-carboxy-1-(2,2-diphenylethylamino) cyclopropane | Nmbc | 1,2,3,4-tetrahydroisoquinoline-3-carboxylic acid | Tic |
| phosphoserine | pSer | phosphothreonine | pThr |
| phosphotyrosine | pTyr | O-methyl-tyrosine | |
| 2-aminoadipic acid | | hydroxylysine | |

The peptides of some embodiments of the invention are preferably utilized in a linear form, although it will be appreciated that in cases where cyclization does not severely interfere with peptide characteristics, cyclic forms of the peptide can also be utilized.

Since the present peptides are preferably utilized in therapeutics which require the peptides to be in soluble form, the peptides of some embodiments of the invention preferably include one or more non-natural or natural polar amino acids, including but not limited to serine and threonine which are capable of increasing peptide solubility due to their hydroxyl-containing side chain.

The amino acids of the peptides of the present invention may be substituted either conservatively or non-conservatively.

The term "conservative substitution" as used herein, refers to the replacement of an amino acid present in the native sequence in the peptide with a naturally or non-naturally occurring amino or a peptidomimetics having similar steric properties. Where the side-chain of the native amino acid to be replaced is either polar or hydrophobic, the conservative substitution should be with a naturally occurring amino acid, a non-naturally occurring amino acid or with a peptidomimetic moiety which is also polar or hydrophobic (in addition to having the same steric properties as the side-chain of the replaced amino acid).

As naturally occurring amino acids are typically grouped according to their properties, conservative substitutions by naturally occurring amino acids can be easily determined bearing in mind the fact that in accordance with the invention replacement of charged amino acids by sterically similar non-charged amino acids are considered as conservative substitutions.

For producing conservative substitutions by non-naturally occurring amino acids it is also possible to use amino acid analogs (synthetic amino acids) well known in the art. A peptidomimetic of the naturally occurring amino acid is well documented in the literature known to the skilled practitioner.

When affecting conservative substitutions the substituting amino acid should have the same or a similar functional group in the side chain as the original amino acid.

Conservative substitution tables providing functionally similar amino acids are well known in the art. Guidance concerning which amino acid changes are likely to be phenotypically silent can also be found in Bowie et al., 1990, Science 247: 1306 1310. Such conservatively modified variants are in addition to and do not exclude polymorphic variants, interspecies homologs, and alleles. Typical conservative substitutions include but are not limited to: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)). Amino acids can be substituted based upon properties associated with side chains, for example, amino acids with polar side chains may be substituted, for example, Serine (S) and Threonine (T); amino acids based on the electrical charge of a side chains, for example, Arginine (R) and Histidine (H); and amino acids that have hydrophobic side chains, for example, Valine (V) and Leucine (L). As indicated, changes are typically of a minor nature, such as conservative amino acid substitutions that do not significantly affect the folding or activity of the protein.

The phrase "non-conservative substitutions" as used herein refers to replacement of the amino acid as present in the parent sequence by another naturally or non-naturally occurring amino acid, having different electrochemical and/or steric properties. Thus, the side chain of the substituting amino acid can be significantly larger (or smaller) than the side chain of the native amino acid being substituted and/or can have functional groups with significantly different electronic properties than the amino acid being substituted. Examples of non-conservative substitutions of this type include the substitution of phenylalanine or cycohexylmethyl glycine for alanine, isoleucine for glycine, or —NH—CH [(—CH$_2$)$_5$—COOH]—CO— for aspartic acid. Those non-conservative substitutions which fall under the scope of the present invention are those which still constitute a peptide having anti-bacterial properties.

The N and C termini of the peptides of the present invention may be protected by function groups. Suitable functional groups are described in Green and Wuts, "Protecting Groups in Organic Synthesis", John Wiley and Sons, Chapters 5 and 7, 1991, the teachings of which are incorporated herein by reference. Preferred protecting groups are those that facilitate transport of the compound attached thereto into a cell, for example, by reducing the hydrophilicity and increasing the lipophilicity of the compounds.

According to specific embodiments, one or more of the amino acids may be modified by the addition of a functional group, for example (conceptually views as "chemically modified"). For example the side amino acid residues appearing in the native sequence may optionally be modified, although as described below alternatively other parts of the protein may optionally be modified, in addition to or in place of the side amino acid residues. The modification may optionally be performed during synthesis of the molecule if a chemical synthetic process is followed, for example by adding a chemically modified amino acid. However, chemical modification of an amino acid when it is already present in the molecule ("in situ" modification) is also possible. Modifications to the peptide or protein can be introduced by gene synthesis, site-directed (e.g., PCR based) or random mutagenesis (e.g., EMS) by exonuclease deletion, by chemical modification, or by fusion of polynucleotide sequences encoding a heterologous domain or binding protein, for example.

As used herein the term "chemical modification", when referring to a peptide, refers to a peptide where at least one of its amino acid residues is modified either by natural processes, such as processing or other post-translational modifications, or by chemical modification techniques which are well known in the art. Non-limiting exemplary types of modification include carboxymethylation, acetylation, acylation, phosphorylation, glycosylation, amidation, ADP-ribosylation, fatty acylation, addition of farnesyl group, an isofarnesyl group, a carbohydrate group, a fatty acid group, a linker for conjugation, functionalization, GPI anchor formation, covalent attachment of a lipid or lipid derivative, methylation, myristylation, pegylation, prenylation, phosphorylation, ubiquitination, or any similar process and known protecting/blocking groups. Ether bonds can optionally be used to join the serine or threonine hydroxyl to the hydroxyl of a sugar. Amide bonds can optionally be used to join the glutamate or aspartate carboxyl groups to an amino group on a sugar (Garg and Jeanloz, Advances in Carbohydrate Chemistry and Biochemistry, Vol. 43, Academic Press (1985); Kunz, Ang. Chem. Int. Ed. English 26:294-308 (1987)). Acetal and ketal bonds can also optionally be formed between amino acids and carbohydrates. Fatty acid acyl derivatives can optionally be made, for example, by acylation of a free amino group (e.g., lysine) (Toth et al., Peptides: Chemistry, Structure and Biology, Rivier and Marshal, eds., ESCOM Publ., Leiden, 1078-1079 (1990)).

According to specific embodiments, the modifications include the addition of a cycloalkane moiety to the peptide, as described in PCT Application No. WO 2006/050262, hereby incorporated by reference as if fully set forth herein. These moieties are designed for use with biomolecules and may optionally be used to impart various properties to proteins.

Furthermore, optionally any point on the peptide may be modified. For example, pegylation of a glycosylation moiety on a protein may optionally be performed, as described in PCT Application No. WO 2006/050247, hereby incorporated by reference as if fully set forth herein. One or more polyethylene glycol (PEG) groups may optionally be added to O-linked and/or N-linked glycosylation. The PEG group may optionally be branched or linear. Optionally any type of water-soluble polymer may be attached to a glycosylation site on a protein through a glycosyl linker.

By "PEGylated protein" is meant a protein, or a fragment thereof having biological activity, having a polyethylene glycol (PEG) moiety covalently bound to an amino acid residue of the protein.

By "polyethylene glycol" or "PEG" is meant a polyalkylene glycol compound or a derivative thereof, with or without coupling agents or derivatization with coupling or activating moieties (e.g., with thiol, triflate, tresylate, azirdine, oxirane, or preferably with a maleimide moiety). Compounds such as maleimido monomethoxy PEG are exemplary or activated PEG compounds of the invention. Other polyalkylene glycol compounds, such as polypropylene glycol, may be used in the present invention. Other appropriate polyalkylene glycol compounds include, but are not limited to, charged or neutral polymers of the following types: dextran, colominic acids or other carbohydrate based polymers, polymers of amino acids, and biotin derivatives.

According to specific embodiments, the peptide is modified to have an altered glycosylation pattern (i.e., altered from the original or native glycosylation pattern). As used herein, "altered" means having one or more carbohydrate moieties deleted, and/or having at least one glycosylation site added to the original protein.

Glycosylation of proteins is typically either N-linked or O-linked. N-linked refers to the attachment of the carbohydrate moiety to the side chain of an asparagine residue. The tripeptide sequences, asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-acetylgalactosamine, galactose, or xylose to a hydroxyamino acid, most commonly serine or threonine, although 5-hydroxyproline or 5-hydroxylysine may also be used.

Addition of glycosylation sites to a peptide is conveniently accomplished by altering the amino acid sequence of the peptide such that it contains one or more of the above-described tripeptide sequences (for N-linked glycosylation sites). The alteration may also be made by the addition of, or substitution by, one or more serine or threonine residues in the sequence of the original peptide (for O-linked glycosylation sites). The peptide's amino acid sequence may also be altered by introducing changes at the DNA level.

Another means of increasing the number of carbohydrate moieties on peptides is by chemical or enzymatic coupling of glycosides to the amino acid residues of the peptide. Depending on the coupling mode used, the sugars may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine. These methods are described e.g. in WO 87/05330, and in Aplin and Wriston, CRC Crit. Rev. Biochem., 22: 259-306 (1981).

Removal of any carbohydrate moieties present on a peptide may be accomplished chemically, enzymatically or by introducing changes at the DNA level. Chemical deglycosylation requires exposure of the peptide to trifluoromethanesulfonic acid, or an equivalent compound. This treatment results in the cleavage of most or all sugars except the linking sugar (N-acetylglucosamine or N-acetylgalactosamine), leaving the amino acid sequence intact.

Chemical deglycosylation is described by Hakimuddin et al., Arch. Biochem. Biophys., 259: 52 (1987); and Edge et al., Anal. Biochem., 118: 131 (1981). Enzymatic cleavage of carbohydrate moieties on peptides can be achieved by the use of a variety of endo- and exo-glycosidases as described by Thotakura et al., Meth. Enzymol., 138: 350 (1987).

According to specific embodiments, the peptide comprises a detectable tag. As used herein, in one embodiment the term "detectable tag" refers to any moiety that can be detected by a skilled practitioner using art known techniques. Detectable tags may be peptide sequences.

Optionally the detectable tag may be removable by chemical agents or by enzymatic means, such as proteolysis. Detectable tags of some embodiments of the present invention can be used for purification of the peptide. For example the term "detectable tag" includes chitin binding protein (CBP)-tag, maltose binding protein (MBP)-tag, glutathione-S-transferase (GST)-tag, poly(His)-tag, FLAG tag, Epitope tags, such as, V5-tag, c-myc-tag, and HA-tag, and fluorescence tags such as green fluorescent protein (GFP), red fluorescent protein (RFP), yellow fluorescent protein (YFP), blue fluorescent protein (BFP), and cyan fluorescent protein (CFP); as well as derivatives of these tags, or any tag known in the art. The term "detectable tag" also includes the term "detectable marker".

According to specific embodiment, the peptide comprises a detectable tag attached to its N-terminal (e.g. poly(His)-tag).

According to specific embodiments the peptide comprises a detectable tag attached to its C-terminal (e.g. poly(His)-tag).

According to specific embodiments, the N-terminal of the peptide does not comprise a detectable tag (e.g. poly(His)-tag).

According to specific embodiments, the C-terminal of the peptide does not comprise a detectable tag (e.g. poly(His)-tag).

According to specific embodiments the peptide is fused to a cleavable moiety. Thus, for example, to facilitate recovery, the expressed coding sequence can be engineered to encode the peptide of some embodiments of the present invention and fused cleavable moiety. In one embodiment, the peptide is designed such that it is readily isolated by affinity chromatography; e.g., by immobilization on a column specific for the cleavable moiety. In one embodiment, a cleavage site is engineered between the peptide and the cleavable moiety and the peptide can be released from the chromatographic column by treatment with an appropriate enzyme or agent that specifically cleaves the fusion protein at this site [e.g., see Booth et al., Immunol. Lett. 19:65-70 (1988); and Gardella et al., J. Biol. Chem. 265:15854-15859 (1990)].

According to specific embodiments, the peptide is an isolated peptide.

The peptides of some embodiments of the invention may be synthesized and purified by any techniques that are known to those skilled in the art of peptide synthesis, such as, but not limited to, solid phase and recombinant techniques.

For solid phase peptide synthesis, a summary of the many techniques may be found in J. M. Stewart and J. D. Young, Solid Phase Peptide Synthesis, W. H. Freeman Co. (San Francisco), 1963 and J. Meienhofer, Hormonal Proteins and Peptides, vol. 2, p. 46, Academic Press (New York), 1973. For classical solution synthesis see G. Schroder and K. Lupke, The Peptides, vol. 1, Academic Press (New York), 1965.

In general, these methods comprise the sequential addition of one or more amino acids or suitably protected amino acids to a growing peptide chain. Normally, either the amino or carboxyl group of the first amino acid is protected by a suitable protecting group. The protected or derivatized amino acid can then either be attached to an inert solid support or utilized in solution by adding the next amino acid in the sequence having the complimentary (amino or carboxyl) group suitably protected, under conditions suitable for forming the amide linkage. The protecting group is then removed from this newly added amino acid residue and the next amino acid (suitably protected) is then added, and so forth. After all the desired amino acids have been linked in the proper sequence, any remaining protecting groups (and any solid support) are removed sequentially or concurrently, to afford the final peptide compound. By simple modification of this general procedure, it is possible to add more than one amino acid at a time to a growing chain, for example, by coupling (under conditions which do not racemize chiral centers) a protected tripeptide with a properly protected dipeptide to form, after deprotection, a pentapeptide and so forth. Further description of peptide synthesis is disclosed in U.S. Pat. No. 6,472,505.

A preferred method of preparing the peptide compounds of some embodiments of the invention involves solid phase peptide synthesis.

Large scale peptide synthesis is described by Andersson Biopolymers 2000; 55(3):227-50.

According to specific embodiments, the peptide is synthesized using in vitro expression systems. Such in vitro synthesis methods are well known in the art and the components of the system are commercially available.

According to specific embodiments, the peptide is produced by recombinant DNA technology. A "recombinant" peptide, or protein refers to a peptide, or protein produced by recombinant DNA techniques; i.e., produced from cells transformed by an exogenous DNA construct encoding the desired peptide or protein.

Thus, according to another aspect of the present invention, there is provided an isolated polynucleotide comprising a nucleic acid sequence encoding any of the above described fusion proteins.

According to specific embodiments, the polynucleotide is least 70%, 75%, 80%, 81%, 82%, 83%, 84%, 85%, 86%, 87%, 88%, 88%, 90%, 91%, 92%, 93%, 94%, 95%, 96%, 97%, 98% or 99% homologous to the nucleic sequence as set forth in SEQ ID No. 55-66 or 68, each possibility represents a separate embodiment of the present invention.

According to specific embodiments, the polynucleotide is least 95%, 96%, 97%, 98% or 99% homologous to the nucleic sequence as set forth in SEQ ID No. 55-66 or 68.

According to specific embodiments, the polynucleotide comprises a nucleic acid sequence selected from the group consisting of SEQ ID NO: 55-66 and 68, each possibility represents a separate embodiment of the present invention.

According to specific embodiments, the polynucleotide consists of a nucleic acid sequence selected from the group consisting of SEQ ID NO: 55-66 and 68, each possibility represents a separate embodiment of the present invention.

According to specific embodiments, the polynucleotide comprises a nucleic acid sequence selected from the group consisting of SEQ ID NO: 55-61 and 68.

According to specific embodiments, the polynucleotide consists of a nucleic acid sequence selected from the group consisting of SEQ ID NO: 55-61 and 68.

According to specific embodiments, the polynucleotide comprises a nucleic acid sequence selected from the group consisting of SEQ ID NO: 55, 56 and 58.

According to specific embodiments, the polynucleotide consists of a nucleic acid sequence selected from the group consisting of SEQ ID NO: 55, 56 and 58.

According to another aspect of the present invention, there is provided an isolated polynucleotide comprising a nucleic acid sequence encoding any of the above described SIRPα amino acid sequence being 100-119 amino acids in length and having at least 95% identity to SEQ ID NOs: 24 and/or 26 or any of the above described 4-1BBL amino acid sequence being 185-202 amino acids in length and having at least 95% identity to an amino acid sequence selected from the group consisting of SEQ ID NOs: 22, 23, 27 and 28.

According to specific embodiments, the polynucleotide is least 70%, 75%, 80%, 81%, 82%, 83%, 84%, 85%, 86%, 87%, 88%, 88%, 90%, 91%, 92%, 93%, 94%, 95%, 96%, 97%, 98% or 99% homologous to the nucleic sequence as set forth in SEQ ID No. 33 or 34, each possibility represents a separate embodiment of the present invention.

According to specific embodiments, the polynucleotide is least 95%, 96%, 97%, 98% or 99% homologous to the nucleic sequence as set forth in SEQ ID No. 33 or 34.

According to specific embodiments, the polynucleotide comprises SEQ ID NO: 33 or 34.

According to specific embodiments, the polynucleotide consists of SEQ ID NO: 33 or 34.

According to specific embodiments, the polynucleotide is least 70%, 75%, 80%, 81%, 82%, 83%, 84%, 85%, 86%, 87%, 88%, 88%, 90%, 91%, 92%, 93%, 94%, 95%, 96%, 97%, 98% or 99% homologous to the nucleic sequence as set forth in SEQ ID NO: 39, 40, 41, 42, 73, 75, 77 or 79 each possibility represents a separate embodiment of the present invention.

According to specific embodiments, the polynucleotide is least 70%, 75%, 80%, 81%, 82%, 83%, 84%, 85%, 86%, 87%, 88%, 88%, 90%, 91%, 92%, 93%, 94%, 95%, 96%, 97%, 98% or 99% homologous to the nucleic sequence as set forth in SEQ ID NO: 39, 40, 41 or 42, each possibility represents a separate embodiment of the present invention.

According to specific embodiments, the polynucleotide is least 95%, 96%, 97%, 98% or 99% homologous to the nucleic sequence as set forth in SEQ ID NO: 39, 40, 41, 42, 73, 75, 77 or 79.

According to specific embodiments, the polynucleotide is least 95%, 96%, 97%, 98% or 99% homologous to the nucleic sequence as set forth in SEQ ID NO: 39, 40, 41 or 42.

According to specific embodiments, the polynucleotide comprises SEQ ID NO: 39, 40, 41, 42, 73, 75, 77 or 79.

According to specific embodiments, the polynucleotide comprises SEQ ID NO: 39, 40, 41 or 42.

According to specific embodiments, the polynucleotide consists of SEQ ID NO: 39, 40, 41, 42, 73, 75, 77 or 79.

According to specific embodiments, the polynucleotide consists of SEQ ID NO: 39, 40, 41 or 42.

As used herein the term "polynucleotide" refers to a single or double stranded nucleic acid sequence which is isolated and provided in the form of an RNA sequence, a complementary polynucleotide sequence (cDNA), a genomic polynucleotide sequence and/or a composite polynucleotide sequences (e.g., a combination of the above).

To express an exogenous polypeptide in mammalian cells, a polynucleotide sequence encoding the polypeptide is preferably ligated into a nucleic acid construct suitable for mammalian cell expression. Such a nucleic acid construct includes a promoter sequence for directing transcription of the polynucleotide sequence in the cell in a constitutive or inducible manner.

Hence, according to specific embodiments, there is provided nucleic acid construct comprising the polynucleotide and a regulatory element for directing expression of said polynucleotide in a host cell.

According to specific embodiments, the regulatory element is a heterologous regulatory element.

The nucleic acid construct (also referred to herein as an "expression vector") of some embodiments of the invention includes additional sequences which render this vector suitable for replication and integration in prokaryotes, eukaryotes, or preferably both (e.g., shuttle vectors). In addition, a typical cloning vector may also contain a transcription and translation initiation sequence, transcription and translation terminator and a polyadenylation signal. By way of example, such constructs will typically include a 5' LTR, a tRNA binding site, a packaging signal, an origin of second-strand DNA synthesis, and a 3' LTR or a portion thereof.

The nucleic acid construct of some embodiments of the invention typically includes a signal sequence for secretion of the peptide from a host cell in which it is placed. Preferably the signal sequence for this purpose is a mammalian signal sequence or the signal sequence of the polypeptide variants of some embodiments of the invention.

Eukaryotic promoters typically contain two types of recognition sequences, the TATA box and upstream promoter elements. The TATA box, located 25-30 base pairs upstream of the transcription initiation site, is thought to be involved in directing RNA polymerase to begin RNA synthesis. The other upstream promoter elements determine the rate at which transcription is initiated.

Preferably, the promoter utilized by the nucleic acid construct of some embodiments of the invention is active in the specific cell population transformed. Examples of cell type-specific and/or tissue-specific promoters include promoters such as albumin that is liver specific [Pinkert et al., (1987) Genes Dev. 1:268-277], lymphoid specific promoters [Calame et al., (1988) Adv. Immunol. 43:235-275]; in particular promoters of T-cell receptors [Winoto et al., (1989) EMBO J. 8:729-733] and immunoglobulins; [Banerji et al. (1983) Cell 33729-740], neuron-specific promoters such as the neurofilament promoter [Byrne et al. (1989) Proc. Natl. Acad. Sci. USA 86:5473-5477], pancreas-specific promoters [Edlunch et al. (1985) Science 230:912-916] or mammary gland-specific promoters such as the milk whey promoter (U.S. Pat. No. 4,873,316 and European Application Publication No. 264,166).

Enhancer elements can stimulate transcription up to 1,000 fold from linked homologous or heterologous promoters. Enhancers are active when placed downstream or upstream from the transcription initiation site. Many enhancer elements derived from viruses have a broad host range and are active in a variety of tissues. For example, the SV40 early gene enhancer is suitable for many cell types. Other enhancer/promoter combinations that are suitable for some embodiments of the invention include those derived from polyoma virus, human or murine cytomegalovirus (CMV), the long term repeat from various retroviruses such as murine leukemia virus, murine or Rous sarcoma virus and HIV. See, Enhancers and Eukaryotic Expression, Cold Spring Harbor Press, Cold Spring Harbor, N.Y. 1983, which is incorporated herein by reference.

In the construction of the expression vector, the promoter is preferably positioned approximately the same distance from the heterologous transcription start site as it is from the transcription start site in its natural setting. As is known in the art, however, some variation in this distance can be accommodated without loss of promoter function.

Polyadenylation sequences can also be added to the expression vector in order to increase the efficiency of SIRPα-4-1BBL, SIRPα or 4-1BBL mRNA translation. Two distinct sequence elements are required for accurate and efficient polyadenylation: GU or U rich sequences located downstream from the polyadenylation site and a highly conserved sequence of six nucleotides, AAUAAA, located 11-30 nucleotides upstream. Termination and polyadenylation signals that are suitable for some embodiments of the invention include those derived from SV40.

In addition to the elements already described, the expression vector of some embodiments of the invention may typically contain other specialized elements intended to increase the level of expression of cloned nucleic acids or to facilitate the identification of cells that carry the recombinant DNA. For example, a number of animal viruses contain DNA sequences that promote the extra chromosomal replication of the viral genome in permissive cell types. Plasmids bearing these viral replicons are replicated episomally as long as the appropriate factors are provided by genes either carried on the plasmid or with the genome of the host cell.

The vector may or may not include a eukaryotic replicon. If a eukaryotic replicon is present, then the vector is amplifiable in eukaryotic cells using the appropriate selectable marker. If the vector does not comprise a eukaryotic replicon, no episomal amplification is possible. Instead, the recombinant DNA integrates into the genome of the engineered cell, where the promoter directs expression of the desired nucleic acid.

The expression vector of some embodiments of the invention can further include additional polynucleotide sequences that allow, for example, the translation of several proteins from a single mRNA such as an internal ribosome entry site (IRES) and sequences for genomic integration of the promoter-chimeric polypeptide.

It will be appreciated that the individual elements comprised in the expression vector can be arranged in a variety of configurations. For example, enhancer elements, promoters and the like, and even the polynucleotide sequence(s) encoding a SIRPα-4-1BBL, a polypeptide comprising a SIRPα amino acid sequence or a polypeptide comprising a 4-1BBL amino acid sequence can be arranged in a "head-to-tail" configuration, may be present as an inverted complement, or in a complementary configuration, as an antiparallel strand. While such variety of configuration is more likely to occur with non-coding elements of the expression vector, alternative configurations of the coding sequence within the expression vector are also envisioned.

Examples for mammalian expression vectors include, but are not limited to, pcDNA3, pcDNA3.1(+/−), pGL3, pZeoSV2(+/−), pSecTag2, pDisplay, pEF/myc/cyto, pCMV/myc/cyto, pCR3.1, pSinRep5, DH26S, DHBB, pNMT1, pNMT41, pNMT81, which are available from Invitrogen, pCI which is available from Promega, pMbac, pPbac, pBK-RSV and pBK-CMV which are available from Strategene, pTRES which is available from Clontech, and their derivatives.

Expression vectors containing regulatory elements from eukaryotic viruses such as retroviruses can be also used. SV40 vectors include pSVT7 and pMT2. Vectors derived from bovine papilloma virus include pBV-1MTHA, and vectors derived from Epstein Bar virus include pHEBO, and p2O5. Other exemplary vectors include pMSG, pAV009/A+, pMTO10/A+, pMAMneo-5, baculovirus pDSVE, and any other vector allowing expression of proteins under the direction of the SV-40 early promoter, SV-40 later promoter, metallothionein promoter, murine mammary tumor virus promoter, Rous sarcoma virus promoter, polyhedrin promoter, or other promoters shown effective for expression in eukaryotic cells.

As described above, viruses are very specialized infectious agents that have evolved, in many cases, to elude host defense mechanisms. Typically, viruses infect and propagate in specific cell types. The targeting specificity of viral vectors utilizes its natural specificity to specifically target predetermined cell types and thereby introduce a recombinant gene into the infected cell. Thus, the type of vector used by some embodiments of the invention will depend on the cell type transformed. The ability to select suitable vectors according to the cell type transformed is well within the capabilities of the ordinary skilled artisan and as such no general description of selection consideration is provided herein. For example, bone marrow cells can be targeted using the human T cell leukemia virus type I (HTLV-I) and kidney cells may be targeted using the heterologous promoter present in the baculovirus Autographa californica nucleopolyhedrovirus (AcMNPV) as described in Liang C Y et al., 2004 (Arch Virol. 149: 51-60).

Recombinant viral vectors are useful for in vivo expression of SIRPα-4-1BBL, SIRPα or 4-1BBL since they offer advantages such as lateral infection and targeting specificity. Lateral infection is inherent in the life cycle of, for example, retrovirus and is the process by which a single infected cell produces many progeny virions that bud off and infect neighboring cells. The result is that a large area becomes rapidly infected, most of which was not initially infected by the original viral particles. This is in contrast to vertical-type of infection in which the infectious agent spreads only through daughter progeny. Viral vectors can also be produced that are unable to spread laterally. This characteristic can be useful if the desired purpose is to introduce a specified gene into only a localized number of targeted cells.

Various methods can be used to introduce the expression vector of some embodiments of the invention into cells. Such methods are generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor Mich. (1995), Vectors: A Survey of Molecular Cloning Vectors and Their Uses, Butterworths, Boston Mass. (1988) and Gilboa et at. [Biotechniques 4 (6): 504-512, 1986] and include, for example, stable or transient transfection, lipofection, electroporation and infection with recombinant viral vectors. In addition, see U.S. Pat. Nos. 5,464,764 and 5,487,992 for positive-negative selection methods.

Introduction of nucleic acids by viral infection offers several advantages over other methods such as lipofection and electroporation, since higher transfection efficiency can be obtained due to the infectious nature of viruses.

Currently preferred in vivo nucleic acid transfer techniques include transfection with viral or non-viral constructs, such as adenovirus, lentivirus, Herpes simplex I virus, or adeno-associated virus (AAV) and lipid-based systems. Useful lipids for lipid-mediated transfer of the gene are, for example, DOTMA, DOPE, and DC-Chol [Tonkinson et al., Cancer Investigation, 14(1): 54-65 (1996)]. The most preferred constructs for use in gene therapy are viruses, most preferably adenoviruses, AAV, lentiviruses, or retroviruses. A viral construct such as a retroviral construct includes at least one transcriptional promoter/enhancer or locus-defining element(s), or other elements that control gene expression by other means such as alternate splicing, nuclear RNA export, or post-translational modification of messenger. Such vector constructs also include a packaging signal, long terminal repeats (LTRs) or portions thereof, and positive and negative strand primer binding sites appropriate to the virus used, unless it is already present in the viral construct. In addition, such a construct typically includes a signal sequence for secretion of the peptide from a host cell in which it is placed. Preferably the signal sequence for this purpose is a mammalian signal sequence or the signal sequence of the polypeptide variants of some embodiments of the invention. Optionally, the construct may also include a signal that directs polyadenylation, as well as one or more restriction sites and a translation termination sequence. By way of example, such constructs will typically include a 5' LTR, a tRNA binding site, a packaging signal, an origin of second-strand DNA synthesis, and a 3' LTR or a portion thereof. Other vectors can be used that are non-viral, such as cationic lipids, polylysine, and dendrimers.

As mentioned, other than containing the necessary elements for the transcription and translation of the inserted coding sequence, the expression construct of some embodiments of the invention can also include sequences engineered to enhance stability, production, purification, yield or toxicity of the expressed peptide. For example, the expression of a fusion protein or a cleavable fusion protein comprising the SIRPα-4-1BBL protein or the polypeptide of some embodiments of the invention and a heterologous protein can be engineered. Such a fusion protein can be designed so that the fusion protein can be readily isolated by affinity chromatography; e.g., by immobilization on a column specific for the heterologous protein. Where a cleavage site is engineered between the SIRPα-4-1BBL protein or the polypeptide of some embodiments of the invention and the heterologous protein, the SIRPα-4-1BBL protein or the polypeptide can be released from the chromatographic column by treatment with an appropriate enzyme or agent that disrupts the cleavage site [e.g., see Booth et al. (1988) Immunol. Lett. 19:65-70; and Gardella et al., (1990) J. Biol. Chem. 265:15854-15859].

The present invention also contemplates cells comprising the composition described herein.

Thus, according to specific embodiments, there is provided a host cell comprising the SIRPα-4-1BBL fusion protein, the polypeptide comprising the SIRPα amino acid sequence and/or the polypeptide comprising the 4-1BBL amino acid sequence disclosed herein, the polynucleotide encoding same or the nucleic acid construct encoding same.

As mentioned hereinabove, a variety of prokaryotic or eukaryotic cells can be used as host-expression systems to express the polypeptides of some embodiments of the invention. These include, but are not limited to, microorganisms, such as bacteria transformed with a recombinant bacteriophage DNA, plasmid DNA or cosmid DNA expression vector containing the coding sequence; yeast transformed with recombinant yeast expression vectors containing the coding sequence; plant cell systems infected with recombinant virus expression vectors (e.g., cauliflower mosaic virus, CaMV; tobacco mosaic virus, TMV) or transformed with recombinant plasmid expression vectors, such as Ti plasmid, containing the coding sequence. Mammalian expression systems can also be used to express the polypeptides of some embodiments of the invention.

Examples of bacterial constructs include the pET series of *E. coli* expression vectors (Studier et al. (1990) Methods in Enzymol. 185:60-89).

Examples of eukaryotic cells which may be used along with the teachings of the invention include but are not limited to, mammalian cells, fungal cells, yeast cells, insect cells, algal cells or plant cells.

In yeast, a number of vectors containing constitutive or inducible promoters can be used, as disclosed in U.S. Pat. No. 5,932,447. Alternatively, vectors can be used which promote integration of foreign DNA sequences into the yeast chromosome.

In cases where plant expression vectors are used, the expression of the coding sequence can be driven by a number of promoters. For example, viral promoters such as the 35S RNA and 19S RNA promoters of CaMV [Brisson et al. (1984) Nature 310:511-514], or the coat protein promoter to TMV [Takamatsu et al. (1987) EMBO J. 6:307-311] can be used. Alternatively, plant promoters such as the small subunit of RUBISCO [Coruzzi et al. (1984) EMBO J. 3:1671-1680 and Brogli et al., (1984) Science 224:838-843] or heat shock promoters, e.g., soybean hsp17.5-E or hsp17.3-B [Gurley et al. (1986) Mol. Cell. Biol. 6:559-565] can be used. These constructs can be introduced into plant cells using Ti plasmid, Ri plasmid, plant viral vectors, direct DNA transformation, microinjection, electroporation and other techniques well known to the skilled artisan. See, for example, Weissbach & Weissbach, 1988, Methods for Plant Molecular Biology, Academic Press, NY, Section VIII, pp 421-463.

Other expression systems such as insects and mammalian host cell systems which are well known in the art can also be used by some embodiments of the invention.

According to specific embodiments the cell is a mammalian cell.

According to specific embodiment, the cell is a human cell.

According to a specific embodiment, the cell is a cell line.

According to another specific embodiment, the cell is a primary cell.

The cell may be derived from a suitable tissue including but not limited to blood, muscle, nerve, brain, heart, lung, liver, pancreas, spleen, thymus, esophagus, stomach, intestine, kidney, testis, ovary, hair, skin, bone, breast, uterus, bladder, spinal cord, or various kinds of body fluids. The cells may be derived from any developmental stage including embryo, fetal and adult stages, as well as developmental origin i.e., ectodermal, mesodermal, and endodermal origin.

Non limiting examples of mammalian cells include monkey kidney CV1 line transformed by SV40 (COS, e.g. COS-7, ATCC CRL 1651); human embryonic kidney line (HEK293 or HEK293 cells subcloned for growth in suspension culture, Graham et al., J. Gen Virol., 36:59 1977); baby hamster kidney cells (BHK, ATCC CCL 10); mouse sertoli cells (TM4, Mather, Biol. Reprod., 23:243-251 1980); monkey kidney cells (CV1 ATCC CCL 70); African green monkey kidney cells (VERO-76, ATCC CRL-1587); human cervical carcinoma cells (HeLa, ATCC CCL 2); NIH3T3, Jurkat, canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci., 383:44-68 1982); MRC 5 cells; FS4 cells; and a human hepatoma line (Hep G2), PER.C6, K562, and Chinese hamster ovary cells (CHO).

According to some embodiments of the invention, the mammalian cell is selected from the group consisting of a Chinese Hamster Ovary (CHO), HEK293, PER.C6, HT1080, NS0, Sp2/0, BHK, Namalwa, COS, HeLa and Vero cell.

According to some embodiments of the invention, the host cell comprises a Chinese Hamster Ovary (CHO), PER.C6 and 293 (e.g., Expi293F) cell.

According to another aspect of the present invention, there is provided a method of producing a SIRPα-4-1BBL fusion protein, a polypeptide comprising a SIRPα amino acid sequence or a polypeptide comprising a 4-1BBL amino acid sequence, the method comprising expressing in a host cell the polynucleotide or the nucleic acid construct described herein.

According to specific embodiments, the methods comprising isolating the fusion protein or the polypeptide.

According to specific embodiments, recovery of the recombinant polypeptide is effected following an appropriate time in culture. The phrase "recovering the recombinant polypeptide" refers to collecting the whole fermentation medium containing the polypeptide and need not imply additional steps of separation or purification. Notwithstanding the above, polypeptides of some embodiments of the invention can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, mix mode chromatography, metal affinity chromatography, Lectins affinity chromatography, chromatofocusing and differential solubilization.

According to specific embodiments, following synthesis and purification, the therapeutic efficacy of the peptide can be assayed either in vivo or in vitro. Such methods are known in the art and include for example cell viability, survival of transgenic mice, and expression of activation markers.

The compositions (e.g. the SRIPα-4-1BBL fusion protein, the polypeptide comprising a SIRPα amino acid sequence, the polypeptide comprising a 4-1BBL amino acid sequence disclosed herein, polynucleotide encoding same, nucleic acid construct encoding same and/or cells) of some embodiments of the invention can be administered to an organism per se, or in a pharmaceutical composition where it is mixed with suitable carriers or excipients.

Thus, the present invention, in some embodiments, features a pharmaceutical composition comprising a therapeutically effective amount of the compositions disclosed herein.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the composition (e.g. SIRPα-4-1BBL fusion protein, polypeptide comprising a SIRPα amino acid sequence, polypeptide comprising a 4-1BBL amino acid sequence, polynucleotide, nucleic acid construct and/or cells described herein) accountable for the biological effect.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). Depending on the route of administration, the active compound, i.e., a polypeptide, a polynucleotide, a nucleic acid construct and/or cell as described herein, may include one or more pharmaceutically acceptable salts. A "pharmaceutically acceptable salt" refers to a salt that retains the desired biological activity of the parent compound and does not impart any undesired toxicological effects (see e.g., Berge, S. M., et al. (1977) J. Pharm. Sci. 66: 1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A pharmaceutical composition according to at least some embodiments of the present invention also may include a pharmaceutically acceptable anti-oxidants. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like. A pharmaceutical composition according to at least some embodiments of the present invention also may include additives such as detergents and solubilizing agents (e.g., TWEEN 20 (polysorbate-20), TWEEN 80 (polysorbate-80)) and preservatives (e.g., Thimersol, benzyl alcohol) and bulking substances (e.g., lactose, mannitol).

Examples of suitable aqueous and nonaqueous carriers that may be employed in the pharmaceutical compositions according to at least some embodiments of the present invention include water, buffered saline of various buffer content (e.g., Tris-HCl, acetate, phosphate), pH and ionic strength, ethanol, polyols (such as glycerol, propylene glycol, polyethylene glycol, and the like), and suitable mixtures thereof, vegetable oils, such as olive oil, and injectable organic esters, such as ethyl oleate.

Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions according to at least some embodiments of the present invention is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin. Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. Generally, out of one hundred percent, this amount will range from about 0.01 percent to about ninety-nine percent of active ingredient, preferably from about 0.1 percent to about 70 percent, most preferably from about 1 percent to about 30 percent of active ingredient in combination with a pharmaceutically acceptable carrier.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms according to at least some embodiments of the present invention are dictated by and directly dependent on (a) the unique characteristics of the active compound and the particular therapeutic effect to be achieved, and (b) the limitations inherent in the art of compounding such an active compound for the treatment of sensitivity in individuals.

Techniques for formulation and administration of drugs may be found in "Remington's Pharmaceutical Sciences,"

Mack Publishing Co., Easton, PA, latest edition, which is incorporated herein by reference.

Pharmaceutical compositions of some embodiments of the invention may be manufactured by processes well known in the art, e.g., by means of conventional mixing, dissolving, granulating, dragee-making, levigating, emulsifying, encapsulating, entrapping or lyophilizing processes.

A composition of the present invention can be administered via one or more routes of administration using one or more of a variety of methods known in the art. As will be appreciated by the skilled artisan, the route and/or mode of administration will vary depending upon the desired results. Preferred routes of administration for therapeutic agents according to at least some embodiments of the present invention include intravascular delivery (e.g. injection or infusion), intravenous, intramuscular, intradermal, intraperitoneal, subcutaneous, spinal, oral, enteral, rectal, pulmonary (e.g. inhalation), nasal, topical (including transdermal, buccal and sublingual), intravesical, intravitreal, intraperitoneal, vaginal, brain delivery (e.g. intra-cerebroventricular, intracerebral, and convection enhanced diffusion), CNS delivery (e.g. intrathecal, perispinal, and intra-spinal) or parenteral (including subcutaneous, intramuscular, intraperitoneal, intravenous (IV) and intradermal), transdermal (either passively or using iontophoresis or electroporation), transmucosal (e.g., sublingual administration, nasal, vaginal, rectal, or sublingual), administration or administration via an implant, or other parenteral routes of administration, for example by injection or infusion, or other delivery routes and/or forms of administration known in the art. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion or using bioerodible inserts, and can be formulated in dosage forms appropriate for each route of administration. In a specific embodiment, a protein, a therapeutic agent or a pharmaceutical composition according to at least some embodiments of the present invention can be administered intraperitoneally or intravenously.

According to specific embodiments, the compositions disclosed herein are administered in an aqueous solution, by parenteral injection. The formulation may also be in the form of a suspension or emulsion. In general, pharmaceutical compositions for parenteral injection are provided including effective amounts of the compositions described herein, and optionally include pharmaceutically acceptable diluents, preservatives, solubilizers, emulsifiers, adjuvants and/or carriers. Such compositions optionally include one or more for the following: diluents, sterile water, buffered saline of various buffer content (e.g., Tris-HCl, acetate, phosphate), pH and ionic strength; and additives such as detergents and solubilizing agents (e.g., TWEEN 20 (polysorbate-20), TWEEN 80 (polysorbate-80)), anti-oxidants (e.g., water soluble antioxidants such as ascorbic acid, sodium metabisulfite, cysteine hydrochloride, sodium bisulfate, sodium metabisulfite, sodium sulfite; oil-soluble antioxidants, such as ascorbyl palmitate, butylated hydroxyanisole (BHA), butylated hydroxytoluene (BHT), lecithin, propyl gallate, alpha-tocopherol; and metal chelating agents, such as citric acid, ethylenediamine tetraacetic acid (EDTA), sorbitol, tartaric acid, phosphoric acid), and preservatives (e.g., Thimersol, benzyl alcohol) and bulking substances (e.g., lactose, mannitol). Examples of non-aqueous solvents or vehicles are ethanol, propylene glycol, polyethylene glycol, vegetable oils, such as olive oil and corn oil, gelatin, and injectable organic esters such as ethyl oleate. The formulations may be freeze dried (lyophilized) or vacuum dried and redissolved/resuspended immediately before use. The formulation may be sterilized by, for example, filtration through a bacteria retaining filter, by incorporating sterilizing agents into the compositions, by irradiating the compositions, or by heating the compositions.

Various compositions (e.g., polypeptides) disclosed herein can be applied topically. Topical administration does not work well for most peptide formulations, although it can be effective especially if applied to the lungs, nasal, oral (sublingual, buccal), vaginal, or rectal mucosa.

Compositions of the present invention can be delivered to the lungs while inhaling and traverse across the lung epithelial lining to the blood stream when delivered either as an aerosol or spray dried particles having an aerodynamic diameter of less than about 5 microns. A wide range of mechanical devices designed for pulmonary delivery of therapeutic products can be used, including but not limited to nebulizers, metered dose inhalers, and powder inhalers, all of which are familiar to those skilled in the art. Some specific examples of commercially available devices are the Ultravent nebulizer (Mallinckrodt Inc., St. Louis, Mo.); the Acorn II nebulizer (Marquest Medical Products, Englewood, Colo.); the Ventolin metered dose inhaler (Glaxo Inc., Research Triangle Park, N.C.); and the Spinhaler powder inhaler (Fisons Corp., Bedford, Mass.). Nektar, Alkermes and Mannkind all have inhalable insulin powder preparations approved or in clinical trials where the technology could be applied to the formulations described herein.

Formulations for administration to the mucosa will typically be spray dried drug particles, which may be incorporated into a tablet, gel, capsule, suspension or emulsion. Standard pharmaceutical excipients are available from any formulator. Oral formulations may be in the form of chewing gum, gel strips, tablets or lozenges.

Transdermal formulations may also be prepared. These will typically be ointments, lotions, sprays, or patches, all of which can be prepared using standard technology. Transdermal formulations will require the inclusion of penetration enhancers. Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

According to specific embodiments, the compositions disclosed herein are administered to a subject in a therapeutically effective amount. As used herein the term "effective amount" or "therapeutically effective amount" means a dosage sufficient to treat, inhibit, or alleviate one or more symptoms of the disorder being treated or to otherwise provide a desired pharmacologic and/or physiologic effect. The precise dosage will vary according to a variety of factors such as subject-dependent variables (e.g., age, immune system health, etc.), the disease, and the treatment being effected. For the polypeptide compositions disclosed herein, the polynucleotides and nucleic acids constructs encoding same and the cells described herein, as further studies are conducted, information will emerge regarding appropriate dosage levels for treatment of various conditions in various patients, and the ordinary skilled worker, considering the therapeutic context, age, and general health of the recipient, will be able to ascertain proper dosing. The selected dosage depends upon the desired therapeutic effect, on the route of administration, and on the duration of the treatment desired. For polypeptide compositions, generally dosage levels of 0.0001 to 100 mg/kg of body weight daily are administered to mammals and more usually 0.001 to 20 mg/kg. For example dosages can be 0.3 mg/kg body weight, 1 mg/kg body weight, 3 mg/kg body weight, 5 mg/kg body weight or 10 mg/kg body weight or within the range of 1-10 mg/kg. An exemplary treatment regime entails administration 5 times per week, 4 times per week, 3 times per week, 2 times per week, once per week, once every two weeks, once every three weeks, once every four weeks, once a month, once every 3 months or once every three to 6 months. Generally, for intravenous injection or infusion, dosage may be lower. Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms according to at least some embodiments of the present invention are dictated by and directly dependent on (a) the unique characteristics of the active compound and the particular therapeutic effect to be achieved, and (b) the limitations inherent in the art of compounding such an active compound for the treatment of sensitivity in individuals.

Optionally the polypeptide formulation may be administered in an amount between 0.0001 to 100 mg/kg weight of the patient/day, preferably between 0.001 to 20.0 mg/kg/day, according to any suitable timing regimen. A therapeutic composition according to at least some embodiments according to at least some embodiments of the present invention can be administered, for example, three times a day, twice a day, once a day, three times weekly, twice weekly or once weekly, once every two weeks or 3, 4, 5, 6, 7 or 8 weeks. Moreover, the composition can be administered over a short or long period of time (e.g., 1 week, 1 month, 1 year, 5 years).

Alternatively, the compositions disclosed herein can be administered as a sustained release formulation, in which case less frequent administration is required. Dosage and frequency vary depending on the half-life of the therapeutic agent in the patient. In general, human antibodies show the longest half-life, followed by humanized antibodies, chimeric antibodies, and nonhuman antibodies. The half-life for fusion proteins may vary widely. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

In certain embodiments, the polypeptide, polynucleotide, nucleic acid construct or cells compositions are administered locally, for example by injection directly into a site to be treated. Typically, the injection causes an increased localized concentration of the composition which is greater than that which can be achieved by systemic administration. The polypeptide compositions can be combined with a matrix as described above to assist in creating an increased localized concentration of the polypeptide compositions by reducing the passive diffusion of the polypeptides out of the site to be treated.

Pharmaceutical compositions of the present invention may be administered with medical devices known in the art. For example, in an optional embodiment, a pharmaceutical composition according to at least some embodiments of the present invention can be administered with a needles hypodermic injection device, such as the devices disclosed in U.S. Pat. Nos. 5,399,163; 5,383,851; 5,312,335; 5,064,413; 4,941,880; 4,790,824; or 4,596,556. Examples of well-known implants and modules useful in the present invention include: U.S. Pat. No. 4,487,603, which discloses an implantable micro-infusion pump for dispensing medication at a controlled rate; U.S. Pat. No. 4,486,194, which discloses a therapeutic device for administering medicaments through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. These patents are incorporated herein by reference. Many other such implants, delivery systems, and modules are known to those skilled in the art.

The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., Sustained and Controlled Release Drug Delivery Systems, J. R. Robinson, ed., Marcel Dekker, Inc., New York, 1978. Controlled release polymeric devices can be made for long term release systemically following implantation of a polymeric device (rod, cylinder, film, disk) or injection (microparticles). The matrix can be in the form of microparticles such as microspheres, where peptides are dispersed within a solid polymeric matrix or microcapsules, where the core is of a different material than the polymeric shell, and the peptide is dispersed or suspended in the core, which may be liquid or solid in nature. Unless specifically defined herein, microparticles, microspheres, and microcapsules are used interchangeably. Alternatively, the polymer may be cast as a thin slab or film, ranging from nanometers to four centimeters, a powder produced by grinding or other standard techniques, or even a gel such as a hydrogel.

Either non-biodegradable or biodegradable matrices can be used for delivery of the active agents disclosed herein, although biodegradable matrices are preferred. These may be natural or synthetic polymers, although synthetic polymers are preferred due to the better characterization of degradation and release profiles. The polymer is selected based on the period over which release is desired. In some cases linear release may be most useful, although in others a pulse release or "bulk release" may provide more effective results. The polymer may be in the form of a hydrogel (typically in absorbing up to about 90% by weight of water), and can optionally be crosslinked with multivalent ions or polymers.

The matrices can be formed by solvent evaporation, spray drying, solvent extraction and other methods known to those skilled in the art. Bioerodible microspheres can be prepared using any of the methods developed for making microspheres for drug delivery, for example, as described by Mathiowitz and Langer, J. Controlled Release, 5:13-22 (1987); Mathiowitz, et al., Reactive Polymers, 6:275-283 (1987); and Mathiowitz, et al., J. Appl Polymer ScL, 35:755-774 (1988).

The devices can be formulated for local release to treat the area of implantation or injection-which will typically deliver a dosage that is much less than the dosage for treatment of an entire body—or systemic delivery. These can be implanted or injected subcutaneously, into the muscle, fat, or swallowed. In certain embodiments, to ensure that the therapeutic compounds according to at least some embodiments of the present invention cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs, thus enhance targeted drug delivery (see, e.g., V. V. Ranade (1989) J. Clin. Pharmacol. 29:685). Exemplary targeting moieties include folate or biotin (see, e.g., U.S. Pat. No. 5,416,016 to Low et al.); mannosides (Umezawa et al., (1988) Biochem. Biophys. Res. Commun. 153:1038); antibodies (P. G. Bloeman et al. (1995) FEBS Lett. 357:140; M. Owais et al. (1995) Antimicrob. Agents Chemother. 39:180); surfactant protein A receptor (Briscoe et al. (1995) Am. J Physiol. 1233:134); p120 (Schreier et al. (1994) J. Biol. Chem. 269:9090); see also K. Keinanen; M. L. Laukkanen (1994) FEBS Lett. 346:123; J. J. Killion; I. J. Fidler (1994) Immunomethods 4:273.

Compositions of some embodiments of the invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as is further detailed above.

As used herein the term "about" refers to ±10%

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

When reference is made to particular sequence listings, such reference is to be understood to also encompass sequences that substantially correspond to its complementary sequence as including minor sequence variations, resulting from, e.g., sequencing errors, cloning errors, or other alterations resulting in base substitution, base deletion or base addition, provided that the frequency of such variations is less than 1 in 50 nucleotides, alternatively, less than 1 in 100 nucleotides, alternatively, less than 1 in 200 nucleotides, alternatively, less than 1 in 500 nucleotides, alternatively, less than 1 in 1000 nucleotides, alternatively, less than 1 in 5,000 nucleotides, alternatively, less than 1 in 10,000 nucleotides.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Maryland (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells-A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, C T (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, C A (1990); Marshak et al., "Strategies for Protein Purification and Characterization-A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Selection of SIRPα-4-1BBL Variants

A structural analysis of a SIRPα-4-1BBL fusion protein referred to herein as "DSP107" comprising an N-terminal signal peptide and a C-terminal his-tag (SEQ ID NO: 43, FIG. 1) was effected in order to optimize the following parameters:

Folding-proper folding to allow binding to targets, minimize potential di-sulfide scrambling;

Integrity-no exposed proteolytic sites;

Multimerization-explore potential multimerization of the two domains. Specifically, optimize trimerization of C-terminal domain formation;

High expression in mammalian expression system; and

Low immunogenicity.

Specifically, for the SIRPα domain (corresponding to amino acids 31-373 of UniProt ID P78324 EM domain, SEQ ID NO: 2):

1. A SIRPα comprehensive model was generated based on PDB structures: 2JJS, 2JJT, 2UV3, 2WNG, 4CMM, 4KJY, 6BIT. Since the C-terminal part of SIRPα is missing in these PDB structures (starting from VAL338, i.e. VSAHPKEQGSNTAAENTGSNERNIY, SEQ ID NO: 9) a modeling and homology-modeling techniques were applied to come up with a plausible predicted model.

2. Structural analysis-Structural analysis was performed in order to highlight potential elements within the fusion protein which may affect the desired profile. These analyses include:

Identification of hydrophobic segments which may cause protein aggregation and non-native oligomerization using electrostatic potential surface calculation with Delphi and CHARMM-based algorithms.

Homology modeling for the fusion proteins based on published x-ray structures.

Structure prediction for regions with no determined high-resolution structure (using structure prediction servers: robetta, TASSER and PEP-FOLD3).

Prediction of potential cleavage sites on the sequence of the fusion protein (or suggested variant) according to PROSPER server for proteolytic sites prediction.

3. A crude model for potential misfolded forms was generated to evaluate DSP107 docking of SIRPα expressed domain with 4-1BBL.

For 4-1BBL (corresponding to amino acids 50-254 of UniProt ID P41273 EM domain, SEQ ID NO: 3):

1. A 4-1BB-L extracellular (EC) domain model was generated based on PDB structure: 2X29. Since the N-terminal part of the 4-1BBL is missing and was not resolved in the X-ray, it seems that this segment (ACPWAVSGARASPGSAASPRLREGPELSPD, SEQ ID NO: 10) exposes hydrophobic residues to the solvent and attempts to predict its structure indicated an unstructured region. This might lower the stability of the fusion DSP107 and also might interfere with the proper orientation for trimerization via 4-1BBL.

2. The fusion protein was analyzed for proteolytic sites using the PROSPER server.

3. A loop within the 4-1BBL resolved domain was detected which is facing outwards toward the solvent, implying it could be a region which undergoes processing.

FIGS. 2A-3 and Table 3 below demonstrate the 3D models generated, the domains and segments identified, and the predicted proteolytic sites detected in the analysis of DSP107 fusion protein.

Taken together, the structural analysis indicated the following:
1. Removing an N-terminal segment of the 4-1BBL domain (ACPWAVSGARASPG, SEQ ID NO: 6/ACPWAV, SEQ ID NO: 7) is expected to lower flexibility and hydrophobicity of DSP107.
2. Removing the Ig-like C1 type1 and Ig-like C1 type2 will reduce the size of the protein while keeping its CD47 interacting domain active. Hence, the C-terminal of SIRPα should end with: TELSVRAKPS (SEQ ID NO: 8) linked to 4-1BBL.
3. In the N-terminal segment of the 4-1BBL domain (ACPWAVSGARASPG, SEQ ID NO: 6/ACPWAV, SEQ ID NO: 7) there is a free Cys residue which might prevent proper folding/rearrangement due to incorrect disulphide bonds.
4. 6-His tag at the N-terminal of SIRPα is expected to interact with the initial 3 Glutamic acids of SIRPα and result in masking of this region.
5. It seems that there are few cleavage sites on the flanking/unstructured regions.

Based on the structural analysis several SIRPα variants were designed having an amino acid sequence of SEQ ID NO: 24 or 26 which can be fused to 4-1BBL or any variant thereof.

In addition, based on the structural analysis several 4-1BBL variants were designed having an amino acid sequence of SEQ ID NO: 22, 23, 27, 28, 70, 72, 74 or 76 which can be fused to SIRPα or any variant thereof.

Moreover, to avoid the need of trimerization of the fusion protein to induce activity of the 4-1BBL moiety, 4-1BBL variants comprising 3 repeats of 4-1BBL amino acid sequence were designed, which can be fused to SIRPα or any variant thereof. An exemplary sequence of such a 4-1BBL variant comprises three repeats of SEQ ID NO: 23 having a (GGGGS)x2+GGGG (SEQ ID NO: 82) linker between the repeats has an amino acid sequence of SEQ ID NO: 78.

As an example for SIRPα-4-1BBL fusion comprising such a 3 repeats 4-1BBL amino acid sequence, predicted 3D models were generated using homology modeling followed by side chains and loop refinement. These models analysis predicted possible binding to the ligands and no interference between the different domains (FIGS. 37A-B).

TABLE 3

Predicted proteolytic sites in DSP107 SIRPα-4-1BBL fusion protein (SEQ ID NO: 5)

| Merops ID | Protease Name | Position | P4-P4' site (SEQ ID Nos) | N-fragment (kDa) | C-fragment (kDa) | Cleavage score |
|---|---|---|---|---|---|---|
| S01.131 | elastase-2 | 322 | TCQV\|EHDG (100\|101) | 37.79 | 28.76 | 0.93 |
| M10.004 | matrix metallopeptidase-9 | 330 | QPAV\|SKSH (102\|103) | 38.74 | 27.81 | 1.23 |
| S26.008 | thylakoidal processing peptidase | 337 | HDLK\|VSAH (104\|105) | 39.54 | 30.31 | 1.1 |
| S26.008 | thylakoidal processing peptidase | 342 | SAHP\|KEQG (106\|107) | 40.03 | 26.52 | 0.98 |
| S01.269 | glutamyl peptidase I | 352 | TAAE\|NTGS (108\|109) | 41.16 | 25.39 | 0.97 |
| M10.004 | matrix metallopeptidase-9 | 360 | NERN\|IYGA (110\|111) | 42.15 | 24.4 | 1.12 |
| M10.004 | matrix metallopeptidase-9 | 408 | MFAQ\|LVAQ (112\|113) | 47.77 | 18.79 | 0.98 |
| M10.005 | matrix metallopeptidase-3 | 412 | LVAQ\|NVLL (114\|115) | 48.18 | 18.38 | 1 |
| M10.004 | matrix metallopeptidase-9 | 413 | VAQN\|VLLI (116\|117) | 48.29 | 18.26 | 1.15 |
| A02.001 | HIV-1 retropepsin | 415 | QNVL\|LIDG (118\|119) | 48.5 | 18.05 | 1.31 |
| S01.133 | cathepsin G | 416 | NVLL\|IDGP (120\|121) | 48.62 | 17.94 | 1.08 |
| C01.036 | cathepsin K | 421 | DGPL\|SWYS (122\|123) | 49.23 | 17.33 | 1.03 |
| S01.133 | cathepsin G | 421 | DGPL\|SWYS (124\|125) | 49.23 | 17.33 | 1.11 |
| M10.003 | matrix metallopeptidase-2 | 422 | GPLS\|WYSD (126\|127) | 49.31 | 17.24 | 1 |
| S01.001 | chymotrypsin A (cattle-type) | 424 | LSWY\|SDPG (128/129) | 49.66 | 16.89 | 0.92 |
| S01.133 | cathepsin G | 424 | LSWY\|SDPG (130\|131) | 49.66 | 16.89 | 1.38 |

Following, several SIRPα-4-1BBL variants were designed. Their sequences including the rational for their selection and their 3D model are demonstrated in Table 4 hereinbelow and FIGS. 4-6 and 37A-B.

TABLE 4

Description of the designed SIRPα-4-1BBL variants

| Variant | Sequence | description | | comment |
|---|---|---|---|---|
| DSP107 | EEELQVIQPDKSVLVAAGETATLRCTATSLIPVGPIQWF RGAGPGRELIYNQKEGHFPRVTTVSDLTKRNNMDFSIRI GNITPADAGTYYCVKFRKGSPDDVEFKSGAGTELSVRA KPSAPVVSGPAARATPQHTVSFTCESHGFSPRDITLKWF KNGNELSDFQTNVDPVGESVSYSIHSTAKVVLTREDVH SQVICEVAHVTLQGDPLRGTANLSETIRVPPTLEVTQQP VRAENQVNVTCQVRKFYPQRLQLTWLENGNVSRTETA STVTENKDGTYNWMSWLLVNVSAHRDDVKLTCQVEH DGQPAVSKSHDLKVSAHPKEQGSNTAAENTGSNERNIY GACPWAVSGARASPGSAASPRLREGPELSPDDPAGLLD LRQGMFAQLVAQNVLLIDGPLSWYSDPGLAGVSLTGGL SYKEDTKELVVAKAGVYYVFFQLELRRVVAGEGSGSV SLALHLQPLRSAAGAAALALTVDLPPASSEARNSAFGFQ GRLLHLSAGQRLGVHLHTEARARHAWQLTQGATVLGL FRVTPEIPAGLPSPRSE (SEQ ID NO: 5) | SIRPα SEQ ID NO: 2 (343 amino acids), glycine linker, 4-1BBL SEQ ID NO: 3 (205 amino acids) | | |
| DSP107_var1 | EEELQVIQPDKSVLVAAGETATLRCTATSLIPVGPIQWF RGAGPGRELIYNQKEGHFPRVTTVSDLTKRNNMDFSIRI GNITPADAGTYYCVKFRKGSPDDVEFKSGAGTELSVRA KPSAPVVSGPAARATPQHTVSFTCESHGFSPRDITLKWF KNGNELSDFQTNVDPVGESVSYSIHSTAKVVLTREDVH SQVICEVAHVTLQGDPLRGTANLSETIRVPPTLEVTQQP VRAENQVNVTCQVRKFYPQRLQLTWLENGNVSRTETA STVTENKDGTYNWMSWLLVNVSAHRDDVKLTCQVEH DGQPAVSKSHDLKVSAHPKEQGSNTAAENTGSNERNIY GSGARASPGSAASPRLREGPELSPDDPAGLLDLRQGMF AQLVAQNVLLIDGPLSWYSDPGLAGVSLTGGLSYKEDT KELVVAKAGVYYVFFQLELRRVVAGEGSGSVSLALHL QPLRSAAGAAALALTVDLPPASSEARNSAFGFQGRLLH LSAGQRLGVHLHTEARARHAWQLTQGATVLGLFRVTP EIPAGLPSPRSE (SEQ ID NO: 11) | SIRPα SEQ ID NO: 2 (343 amino acids), glycine linker, 4-1BBL SEQ ID NO: 22 (199 amino acids) | Deletion of 6 amino acids from the N-terminal of 4-1BBL | Removing core hydrophobic segment |
| DSP107_var2 | EEELQVIQPDKSVLVAAGETATLRCTATSLIPVGPIQWF RGAGPGRELIYNQKEGHFPRVTTVSDLTKRNNMDFSIRI GNITPADAGTYYCVKFRKGSPDDVEFKSGAGTELSVRA KPSAPVVSGPAARATPQHTVSFTCESHGFSPRDITLKWF KNGNELSDFQTNVDPVGESVSYSIHSTAKVVLTREDVH SQVICEVAHVTLQGDPLRGTANLSETIRVPPTLEVTQQP VRAENQVNVTCQVRKFYPQRLQLTWLENGNVSRTETA STVTENKDGTYNWMSWLLVNVSAHRDDVKLTCQVEH DGQPAVSKSHDLKVSAHPKEQGSNTAAENTGSNERNIY GSAASPRLREGPELSPDDPAGLLDLRQGMFAQLVAQNV LLIDGPLSWYSDPGLAGVSLTGGLSYKEDTKELVVAKA GVYYVFFQLELRRVVAGEGSGSVSLALHLQPLRSAAGA AALALTVDLPPASSEARNSAFGFQGRLLHLSAGQRLGV HLHTEARARHAWQLTQGATVLGLFRVTPEIPAGLPSPRS E (SEQ ID NO: 13) | SIRPα SEQ ID NO: 2 (343 amino acids), glycine linker, 4-1BBL SEQ ID NO: 23 (191 amino acids) | Deletion of 14 amino acids from the N-terminal of 4-1BBL | Removing flanking (predicted to be less structured) and hydrophobic segment |
| DSP107_var3 | EEELQVIQPDKSVLVAAGETATLRCTATSLIPVGPIQWF RGAGPGRELIYNQKEGHFPRVTTVSDLTKRNNMDFSIRI GNITPADAGTYYCVKFRKGSPDDVEFKSGAGTELSVRA GACPWAVSGARASPGSAASPRLREGPELSPDDPAGLLD LRQGMFAQLVAQNVLLIDGPLSWYSDPGLAGVSLTGGL SYKEDTKELVVAKAGVYYVFFQLELRRVVAGEGSGSV SLALHLQPLRSAAGAAALALTVDLPPASSEARNSAFGFQ GRLLHLSAGQRLGVHLHTEARARHAWQLTQGATVLGL FRVTPEIPAGLPSPRSE (SEQ ID NO: 15) | SIRPα SEQ ID NO: 24 (116 amino acids), glycine linker, 4-1BBL SEQ ID NO: 3 (205 amino acids) | Deletion of SIRPα Ig-like C1-type 1 and 2 domains | Keeping only the SIRPα domain responsible for the interaction with CD47 |
| DSP107_var3.1 | EEELQVIQPDKSVLVAAGETATLRCTATSLIPVGPIQWF RGAGPGRELIYNQKEGHFPRVTTVSDLTKRNNMDFSIRI GNITPADAGTYYCVKFRKGSPDDVEFKSGAGTELSVRA GSGARASPGSAASPRLREGPELSPDDPAGLLDLRQGMF AQLVAQNVLLIDGPLSWYSDPGLAGVSLTGGLSYKEDT KELVVAKAGVYYVFFQLELRRVVAGEGSGSVSLALHL QPLRSAAGAAALALTVDLPPASSEARNSAFGFQGRLLH LSAGQRLGVHLHTEARARHAWQLTQGATVLGLFRVTP EIPAGLPSPRSE (SEQ ID NO: 16) | SIRPα SEQ ID NO: 24 (116 amino acids), glycine linker, 4-1BBL SEQ ID NO: 22 (199 amino acids) | Deletion of SIRPα Ig-like C1-type 1 and 2 domains + Deletion of 6 amino acids from the N-terminal of 4-1BBL | Keeping only the SIRPα domain + Removing core hydrophobic segment |
| DSP107_var4 | EEELQVIQPDKSVLVAAGETATLRCTATSLIPVGPIQWF RGAGPGRELIYNQKEGHFPRVTTVSDLTKRNNMDFSIRI GNITPADAGTYYCVKFRKGSPDDVEFKSGAGTELSVRA KPSAPVVSGPAARATPQHTVSFTCESHGFSPRDITLKWF KNGNELSDFQTNVDPVGESVSYSIHSTAKVVLTREDVH | SIRPα SEQ ID NO: 2 (343 amino acids), glycine linker, | Deletion of 8 amino acids from the N-terminal of 4-1BBL | Removing unstructured and core hydrophobic segment |

TABLE 4-continued

Description of the designed SIRPα-4-1BBL variants

| Variant | Sequence | description | | comment |
|---|---|---|---|---|
| | SQVICEVAHVTLQGDPLRGTANLSETIRVPPTLEVTQQP VRAENQVNVTCQVRKFYPQRLQLTWLENGNVSRTETA STVTENKDGTYNWMSWLLVNVSAHRDDVKLTCQVEH DGQPAVSKSHDLKVSAHPKEQGSNTAAENTGSNERNIY GARASPGSAASPRLREGPELSPDDPAGLLDLRQGMFAQ LVAQNVLLIDGPLSWYSDPGLAGVSLTGGLSYKEDTKE LVVAKAGVYYVFFQLELRRVVAGEGSGSVSLALHLQPL RSAAGAAALALTVDLPPASSEARNSAFGFQGRLLHLSA GQRLGVHLHTEARARHAWQLTQGATVLGLFRVTPEIPA GLPSPRSE (SEQ ID NO: 45) | 4-1BBL SEQ ID NO: 27 (197 aa) | | preceding the structured domain of 4-1BBL |
| DSP107_var5 | EEELQVIQPDKSVLVAAGETATLRCTATSLIPVGPIQWF RGAGPGRELIYNQKEGHFPRVTTVSDLTKRNNMDFSIRI GNITPADAGTYYCVKFRKGSPDDVEFKSGAGTELSVRA KPSAPVVSGPAARATPQHTVSFTCESHGFSPRDITLKWF KNGNELSDFQTNVDPVGESVSYSIHSTAKVVLTREDVH SQVICEVAHVTLQGDPLRGTANLSETIRVPPTLEVTQQP VRAENQVNVTCQVRKFYPQRLQLTWLENGNVSRTETA STVTENKDGTYNWMSWLLVNVSAHRDDVKLTCQVEH DGQPAVSKSHDLKVSAHPKEQGSNTAAENTGSNERNIY GLREGPELSPDDPAGLLDLRQGMFAQLVAQNVLLIDGP LSWYSDPGLAGVSLTGGLSYKEDTKELVVAKAGVYYV FFQLELRRVVAGEGSGSVSLALHLQPLRSAAGAAALAL TVDLPPASSEARNSAFGFQGRLLHLSAGQRLGVHLHTE ARARHAWQLTQGATVLGLFRVTPEIPAGLPSPRSE (SEQ ID NO: 46) | SIRPα SEQ ID NO: 2 (343 amino acids), glycine linker, 4-1BBL SEQ ID NO: 28 (185 aa) | Deletion of 20 amino acids from the N-terminal of 4-1BBL | Removing the long unstructured and hydrophobic segment preceding the structured domain of 4-1BBL |
| DSP107_var6 | EEELQVIQPDKSVLVAAGETATLRCTATSLIPVGPIQWF RGAGPGRELIYNQKEGHFPRVTTVSDLTKRNNMDFSIRI GNITPADAGTYYCVKFRKGSPDDVEFKSGAGTELSVRA GSAASPRLREGPELSPDDPAGLLDLRQGMFAQLVAQNV LLIDGPLSWYSDPGLAGVSLTGGLSYKEDTKELVVAKA GVYYVFFQLELRRVVAGEGSGSVSLALHLQPLRSAAGA AALALTVDLPPASSEARNSAFGFQGRLLHLSAGQRLGV HLHTEARARHAWQLTQGATVLGLFRVTPEIPAGLPSPRS E (SEQ ID NO: 47) | SIRPα SEQ ID NO: 24 (116 amino acids), glycine linker, 4-1BBL SEQ ID NO: 23 (191 amino acids) | Deletion of SIRPα Ig-like C1-type 1 and 2 domains + Deletion of 14 amino acids from the N-terminal of 4-1BBL | Keeping only the SIRPα domain + Removing flanking (predicted to be less structured) and hydrophobic segment of 4-1BBL |
| DSP107_var7 | EEELQVIQPDKSVLVAAGETATLRCTATSLIPVGPIQWF RGAGPGRELIYNQKEGHFPRVTTVSDLTKRNNMDFSIRI GNITPADAGTYYCVKFRKGSPDDVEFKSGAGTELSVRA GARASPGSAASPRLREGPELSPDDPAGLLDLRQGMFAQ LVAQNVLLIDGPLSWYSDPGLAGVSLTGGLSYKEDTKE LVVAKAGVYYVFFQLELRRVVAGEGSGSVSLALHLQPL RSAAGAAALALTVDLPPASSEARNSAFGFQGRLLHLSA GQRLGVHLHTEARARHAWQLTQGATVLGLFRVTPEIPA GLPSPRSE (SEQ ID NO: 48) | SIRPα SEQ ID NO: 24 (116 amino acids), glycine linker, 4-1BBL SEQ ID NO: 27 (197 aa) | Deletion of SIRPα Ig-like C1-type 1 and 2 domains + Deletion of 8 amino acids from the N-terminal of 4-1BBL | Keeping only the SIRPα domain + Removing unstructured and core hydrophobic segment preceding the structured domain of 4-1BBL |
| DSP107_var8 | EEELQVIQPDKSVLVAAGETATLRCTATSLIPVGPIQWF RGAGPGRELIYNQKEGHFPRVTTVSDLTKRNNMDFSIRI GNITPADAGTYYCVKFRKGSPDDVEFKSGAGTELSVRA GLREGPELSPDDPAGLLDLRQGMFAQLVAQNVLLIDGP LSWYSDPGLAGVSLTGGLSYKEDTKELVVAKAGVYYV FFQLELRRVVAGEGSGSVSLALHLQPLRSAAGAAALAL TVDLPPASSEARNSAFGFQGRLLHLSAGQRLGVHLHTE ARARHAWQLTQGATVLGLFRVTPEIPAGLPSPRSE (SEQ ID NO: 49) | SIRPα SEQ ID NO: 24 (116 amino acids), glycine linker, 4-1BBL SEQ ID NO: 28 (185 aa) | Deletion of SIRPα Ig-like C1-type 1 and 2 domains + Deletion of 20 amino acids from the N-terminal of 4-1BBL | Keeping only the SIRPα domain + Removing the long unstructured and hydrophobic segment preceding the structured domain of 4-1BBL |
| DSP107_var1_mut | EEEIQVIQPDKSVLVAAGETATLRCTITSLIPVGPIQWFR GAGPGRVLIYNQKEGHFPRVTTVSDLTKRNNMDFSIRIG NITPADAGTYYCIKFRKGSPDDVEFKSGAGTELSVRAKP SAPVVSGPAARATPQHTVSFTCESHGFSPRDITLKWFKN GNELSDFQTNVDPVGESVSYSIHSTAKVVLTREDVHSQ VICEVAHVTLQGDPLRGTANLSETIRVPPTLEVTQQPVR AENQVNVTCQVRKFYPQRLQLTWLENGNVSRTETAST VTENKDGTYNWMSWLLVNVSAHRDDVKLTCQVEHDG QPAVSKSHDLKVSAHPKEQGSNTAAENTGSNERNIYGS | SIRPα SEQ ID NO: 25 (343 amino acids), glycine linker, 4-1BBL SEQ ID NO: 22 (199 amino acids) | Deletion of 6 amino acids from the N-terminal of 4-1BBL + 4 stabilizing point mutations marked in bold | Removing core hydrophobic segment + incorporating stabilizing mutations |

TABLE 4-continued

Description of the designed SIRPα-4-1BBL variants

| Variant | Sequence | description | | comment |
|---|---|---|---|---|
| | GARASPGSAASPRLREGPELSPDDPAGLLDLRQGMFAQ<br>LVAQNVLLIDGPLSWYSDPGLAGVSLTGGLSYKEDTKE<br>LVVAKAGVYYVFFQLELRRVVAGEGSGSVSLALHLQPL<br>RSAAGAAALALTVDLPPASSEARNSAFGFQGRLLHLSA<br>GQRLGVHLHTEARARHAWQLTQGATVLGLFRVTPEIPA<br>GLPSPRSE (SEQ ID NO: 18) | | | |
| DSP107_var2_mut | EEEIQVIQPDKSVLVAAGETATLRCTITSLIPVGPIQWFR<br>GAGPGRVLIYNQKEGHFPRVTTVSDLTKRNNMDFSIRIG<br>NITPADAGTYYCIKFRKGSPDDVEFKSGAGTELSVRAKP<br>SAPVVSGPAARATPQHTVSFTCESHGFSPRDITLKWFKN<br>GNELSDFQTNVDPVGESVSYSIHSTAKVVLTREDVHSQ<br>VICEVAHVTLQGDPLRGTANLSETIRVPPTLEVTQQPVR<br>AENQVNVTCQVRKFYPQRLQLTWLENGNVSRTETAST<br>VTENKDGTYNWMSWLLVNVSAHRDDVKLTCQVEHDG<br>QPAVSKSHDLKVSAHPKEQGSNTAAENTGSNERNIYGS<br>AASPRLREGPELSPDDPAGLLDLRQGMFAQLVAQNVLL<br>IDGPLSWYSDPGLAGVSLTGGLSYKEDTKELVVAKAGV<br>YYVFFQLELRRVVAGEGSGSVSLALHLQPLRSAAGAAA<br>LALTVDLPPASSEARNSAFGFQGRLLHLSAGQRLGVHL<br>HTEARARHAWQLTQGATVLGLFRVTPEIPAGLPSPRSE<br>(SEQ ID NO: 19) | SIRPα SEQ ID<br>NO: 25 (343<br>amino acids),<br>glycine<br>linker,<br>4-1BBL SEQ<br>ID NO: 23<br>(191 amino<br>acids) | Deletion of<br>the N-terminal<br>segment from<br>4-1BBL 14<br>amino acids +<br>4 stabilizing<br>point<br>mutations<br>marked in bold | Removing<br>flanking<br>(predicted<br>to be less<br>structured)<br>and<br>hydrophobic<br>segment +<br>incorporating<br>stabilizing<br>mutations |
| DSP107_var3_mut | EEEIQVIQPDKSVLVAAGETATLRCTITSLIPVGPIQWFR<br>GAGPGRVLIYNQKEGHFPRVTTVSDLTKRNNMDFSIRIG<br>NITPADAGTYYCIKFRKGSPDDVEFKSGAGTELSVRAGA<br>CPWAVSGARASPGSAASPRLREGPELSPDDPAGLLDLRQ<br>GMFAQLVAQNVLLIDGPLSWYSDPGLAGVSLTGGLSYK<br>EDTKELVVAKAGVYYVFFQLELRRVVAGEGSGSVSLAL<br>HLQPLRSAAGAAALALTVDLPPASSEARNSAFGFQGRLL<br>HLSAGQRLGVHLHTEARARHAWQLTQGATVLGLFRVT<br>PEIPAGLPSPRSE (SEQ ID NO: 20) | SIRPα SEQ ID<br>NO: 26 (116<br>amino acids),<br>glycine<br>linker,<br>4-1BBL SEQ<br>ID NO: 3 (205<br>amino acids) | Deletion of<br>SIRPα Ig-like<br>C1-type 1 and<br>2 domains + 4<br>stabilizing<br>point<br>mutations<br>marked in bold | Keeping only<br>the SIRPα<br>domain<br>responsible<br>for the<br>interaction<br>with CD47 +<br>incorporating<br>stabilizing<br>mutations |
| DSP107_var3.1_mut | EEEIQVIQPDKSVLVAAGETATLRCTITSLIPVGPIQWFR<br>GAGPGRVLIYNQKEGHFPRVTTVSDLTKRNNMDFSIRIG<br>NITPADAGTYYCIKFRKGSPDDVEFKSGAGTELSVRASG<br>ARASPGSAASPRLREGPELSPDDPAGLLDLRQGMFAQL<br>VAQNVLLIDGPLSWYSDPGLAGVSLTGGLSYKEDTKEL<br>VVAKAGVYYVFFQLELRRVVAGEGSGSVSLALHLQPLR<br>SAAGAAALALTVDLPPASSEARNSAFGFQGRLLHLSAG<br>QRLGVHLHTEARARHAWQLTQGATVLGLFRVTPEIPAG<br>LPSPRSE (SEQ ID NO: 21) | SIRPα SEQ ID<br>NO: 26 (116<br>amino acids),<br>glycine<br>linker,<br>4-1BBL SEQ<br>ID NO: 22<br>(199 amino<br>acids) | Deletion of<br>SIRPα Ig-like<br>C1-type 1 and<br>2 domains + 4<br>stabilizing<br>point<br>mutations<br>marked in<br>bold +<br>Deletion of 6<br>amino acids<br>from the N-<br>terminal of 4-<br>1BBL | Keeping only<br>the SIRPα<br>domain<br>responsible<br>for the<br>interaction<br>with CD47 +<br>incorporating<br>stabilizing<br>mutations +<br>Removing core<br>hydrophobic<br>segment |
| DSP107_var2.1 | SAASPRLREGPELSPDDPAGLLDLRQGMFAQLVAQNVL<br>LIDGPLSWYSDPGLAGVSLTGGLSYKEDTKELVVAKAG<br>VYYVFFQLELRRVVAGEGSGSVSLALHLQPLRSAAGAA<br>ALALTVDLPPASSEARNSAFGFQGRLLHLSAGQRLGVH<br>LHTEARARHAWQLTQGATVLGLFRVTPEIPAGLPSPRSE<br>GEEELQVIQPDKSVLVAAGETATLRCTATSLIPVGPIQW<br>FRGAGPGRELIYNQKEGHFPRVTTVSDLTKRNNMDFSI<br>IGNITPADAGTYYCVKFRKGSPDDVEFKSGAGTELSVRA<br>KPSAPVVSGPAARATPQHTVSFTCESHGFSPRDITLKWF<br>KNGNELSDFQTNVDPVGESVSYSIHSTAKVVLTREDVH<br>SQVICEVAHVTLQGDPLRGTANLSETIRVPPTLEVTQQP<br>VRAENQVNVTCQVRKFYPQRLQLTWLENGNVSRTETA<br>STVTENKDGTYNWMSWLLVNVSAHRDDVKLTCQVEH<br>DGQPAVSKSHDLKVSAHPKEQGSNTAAENTGSNERNIY<br>(SEQ ID NO: 80) | 4-1BBL SEQ<br>ID NO: 23<br>(191 amino<br>acids),<br>glycine<br>linker, SIRPα<br>SEQ ID NO: 2<br>(343 amino<br>acids) | Deletion of 14<br>amino acids<br>from the N-<br>terminal of 4-<br>1BBL | Removing<br>flanking<br>(predicted<br>to be less<br>structured)<br>and<br>hydrophobic<br>segment |

Example 2

Manufacturing of SIRPα-4-1BBL Variants

For comparative functional analysis and production evaluation, several histidine-tagged SIRPα-4-1BBL fusion proteins were produced.

Production of the SIRPα-4-1BBL fusion protein referred to herein as "DSP107" comprising a C-terminal His tag (SEQ ID NO: 1) and three SIRPα-4-1BBL variants referred to herein as "DSP107_V1", "DSP107_V2" and "DSP107_V3.1" comprising a C-terminal His tag (SEQ ID NO: 12, 14 and 17, respectively], was effected in ExpiCHO cells.

Production of a "DSP107" comprising a N-terminal His tag (SEQ ID NO: 44), was effected in Expi293F cells.

Cells were transfected by a pcDNA3.4 expression vector cloned with coding sequence for the full fusion protein and the three variants. The sequences were cloned into the vector using EcoRI and HindIII restriction enzymes, with addition of Kozak sequence, artificial signal peptide (MGWSCHIL-FLVATATGVH, SEQ ID NO: 4) in the N-terminus, 6 His-tag in the N-terminus or in the C-terminus, and a stop codon in the C terminus (SEQ ID NO: 51-54 and 69). The proteins were collected from the supernatant of cell culture and purified by one-step purification by HisTrap™ FF Crude column.

Under these production conditions, the yield of the C-terminal his-tagged DSP107 (SEQ ID NO: 1) was approximately 67 mg per 1 liter of culture. In comparison, the yield of C-terminal his-tagged DSP107_V1 (SEQ ID NO: 12) and DSP107_V2 (SEQ ID NO: 14) was approximately 150 mg per 1 liter of culture; and the yield of C-terminal His tagged DSP107_V3.1 (SEQ ID NO: 17) was approximately 212 mg per 1 liter of culture. Yield was determined by BCA protein measurement of the final product.

Following, the His-tagged proteins were purified by size exclusion chromatography to collect the fraction of a purified trimer. 10 mg of His tagged DSP107_V1 and DSP107_V2 (SEQ ID NO: 12 and 14) were loaded on Superdex 200 column (60+100×1.6 cm) with PBS as mobile phase and at a flow rate of 1 ml/min. The major peak corresponding to protein trimers was collected.

Production of two variants of the SIRPα-4-1BBL fusion protein referred to herein as "DSP107_V1" and "DSP107_V2" (SEQ ID) NO: 11 and 13 respectively) was effected in CHO-K1 and in CHO-S cells (only DSP107-V2).

CHO-K1 cells were transfected by pGenHT1.0 expression vector cloned with coding sequences for the DSP107_V1 and DSP107_V2 variants. The sequences were cloned into the vector with addition of Kozak sequence and an artificial signal peptide (MGWSCIILFLVATATGVH, SEQ ID NO: 4) at the N-terminus. CHO-S cells were transfected by pMAXX1 expression vector cloned with the coding sequence for the DSP107_V2 variant. The sequence was cloned into the vector with addition of the 5' untranslated DNA sequence, Kozak sequence and a signal peptide of Rituximab Heavy chain (MGWSLILLFLVAVATRVLS, SEQ ID NO: 99). Transfected cells were selected as minipools and expression of DSP107 variants was evaluated in either batch or fed batch culture. The proteins were collected from the supernatant of the cell culture and evaluated by ELISA (FIG. 17) and SDS-PAGE (FIG. 18).

The yield of 5 days batch culture of CHO-K1 derived selected mini-pools was up to 75 mg/L for DSP107_V1 and up to 327 mg/L for DSP107_V2. The yield of 11 days fed batch of CHO-S derived selected mini-pools was up to 1200 mg/L.

Example 3

Determination of the Oligomeric State of the SIRPα-4-1BBL Variants

Materials—DSP107 comprising an N-terminal his-tag (SEQ ID NO: 44); and C-terminal his-tagged DSP107 (SEQ ID NO: 1), DSP107_V1 (SEQ ID NO: 12), DSP107_V2 (SEQ ID NO: 14) and DSP107_V3.1 (SEQ ID NO: 17), produced as described in Example 2 hereinabove. Spectra BR Protein molecular weight marker (Thermo Fisher Scientific, cat #26634), 4-20% polyacrylamide gel (BioRad, cat #556-8094), e-Stain peds (GenScript, cat #L02011), Laemmeli Loading buffer (BioRad, cat #161-0747).

Methods—

SDS-PAGE analysis-Two μg protein from each sample was mixed with loading buffer with or without β-mercaptoethanol (reduced and non-reduced conditions, respectively), heated for 5 minutes at 95° C. and separated on 4-20% gradient polyacrylamide gel electrophoresis SDS-PAGE. Proteins migration on the gel was visualized by staining with e-Stain peds and washing using the e-Stain machinery (GenScript), according to manufacturer instructions.

Mass Spectrometry (MS) analysis-5 μg of each protein sample were trypsinized either following IAA cys modification without reduction or following reductive dimethylation reduction and IAA cys modification. Samples were analyzed using the HFX mass spectrometer (Thermo) and identified by Discoverer software version 1.4 vs the human uniprot database and against decoy databases (in order to determine the false discovery rate—FDR) and vs the specific sequences using the Sequest search engine. In addition, massmatrix and starvoX software were used to detect s-s bond.

SEC-MALS analysis-Proteins were loaded on a Superdex 200 Increase column (GE Healthcare) and ran at a flow rate of 0.8 ml/min with 10 mM KPO4 pH 8.0+150 mM NaCl as mobile phase. Detection was performed by UV, MALS and RI using AKTA Explorer (GE)+MiniDawn TREOS+OPTI-LAB T-rex (WYATT).

Results—SDS-PAGE analysis of the produced SIRPα-4-1BBL variants demonstrated that N-terminal his-tagged DSP107 and C-terminal his-tagged DSP107 (SEQ ID NO: 44 and 1), as well as the C-terminal his-tagged DSP107_V1 and DSP107_V2, migrated in reducing conditions slightly slower than the 70 kDa-molecular weight marker (FIG. 7A). As expected, at similar conditions, the C-terminal his-tagged DSP107-V3.1 (SEQ ID NO: 17) migrated differently than the other variants appearing at similar location as the 40 kDa marker. Under non-reducing conditions, N-terminal his-tagged DSP107 and C-terminal his-tagged DSP107 (SEQ ID NO: 44 and 1), appeared mainly as high molecular weight proteins (~210 kDa) (FIG. 7B). Small fractions of these proteins, as well as C-terminal his-tagged DSP107_V1 and DSP107_V2 migrated similarly to their migration in reducing conditions (i.e. ~75 kDa). This might suggest that the DSP107 fusion protein contains S—S linked multimers. C-terminal his-tagged DSP107-V3.1 migrated similarly under reducing and non-reducing conditions, like C-terminal his-tagged DSP107-V1 and DSP107-V2, suggesting that the S—S predicted bond in the DSP107 protein is mediated by the free cysteine residue (Cys346) that was removed from the sequence of all three variants.

Mass Spectrometry (MS) analysis of reduced versus non-reduced N-terminal his-tagged DSP107 and C-terminal his-tagged DSP107 demonstrated that Cys346 was partially S—S bonded. This finding correlated with the presence of dimers in the non-reduced SDS-PAGE analysis of the N-terminal his-tagged DSP107 and C-terminal his-tagged DSP107 (SEQ ID NO: 44 and 1). On the other hand, Cys346 was removed from C-terminal his-tagged DSP_V1, DSP107_V2 and DSP107-V3.1, and accordingly, no high order oligomers are detected in the non-reduced SDS-PAGE analysis of the three variants.

SEC-MALS analysis of the produced SIRPα-4-1BBL proteins showed that all three His-tagged SIRPα-4-1BBL variants (SEQ ID NO: 12, 14 and 17) and the non-tagged DSP107_V2 (SEQ ID NO: 13) form trimers. The calculated mass of total protein was approximately 258 kDa for C-terminal his-tagged DSP107_V1 (SEQ ID NO: 12), 269 kDa for his tagged DSP107_V2 (SEQ ID NO: 14), 107 kDa for his tagged DSP107_V3.1 (SEQ ID NO: 17) and 210±20 kDa for DSP107_V2 (SEQ ID NO: 13) (FIG. 38).

Example 4

The SIRPα-4-1BBL Variants Contain Both Domains

Materials—N-terminal his-tagged DSP107 (SEQ ID NO: 44); and C-terminal his-tagged DSP107 (SEQ ID NO: 1), DSP107_V1 (SEQ ID NO: 12, DSP107_V2 (SEQ ID NO: 14) and DSP107_V3.1 (SEQ ID NO: 17), produced as described in Example 2 hereinabove. For the Western blot analysis: Spectra BR protein marker (Thermo Fisher Scientific, cat #26634), Laemmeli Loading buffer (BioRad, cat #161-0747), 4-20% polyacrylamide gel (BioRad, cat #556-8094), anti 4-1BBL (BioVision, 5369-100), anti SIRPα-biotinylated, (#LS-C370337, LsBio), secondary Goat Anti Rabbit IgG (H+L)-HRP Conjugate (R&D, cat #170-6515), Streptavidin Protein, HRP: (#21126, Thermoscientific), ECL Plus Western Blotting substrate (Pierce, cat #32132). For the sandwich ELISA: Anti 4-1BBL antibody (capture antibody from a matched pair; Abnova #H00008744-AP41), anti SIRPα-biotinylated antibody (LsBio #LS-C370337), Streptavidin Protein, HRP (#21126, Thermo Scientific), TMB substrate (1-Step™ Ultra TMB-ELISA Substrate Solution, Thermo Scientific #34028).

Methods—

Western blot analysis—Proteins (500 ng or 50 ng per lane) were treated at reducing or non-reducing conditions (in loading buffer containing β-mercaptoethanol and boiled for 5 minutes at 95° C., or in sample buffer without β-mercaptoethanol without heating, respectively) and separated on a 4-20% gradient SDS-PAGE gel. Proteins were transferred onto a PVDF membrane and incubated overnight with primary antibodies anti 4-1BBL (1:10000) or biotinylated anti-SIRPα (1:1000), followed by 1 hour incubation with a HRP-conjugated secondary antibody (1:10000) or streptavidin-HRP substrate (1:20000), respectively. Signals were detected following ECL development.

Sandwich ELISA—Plates are coated with anti 4-1BBL antibody (2.5 μg/ml in PBS) and blocked in blocking solution (PBS, 1% BSA, 0.005% Tween). The produced SIRPα-4-1BBL fusion proteins, serially diluted in blocking solution, were added to the coated plates and incubated for 2 hours, followed by incubation with detecting anti SIRPα-biotinylated antibody (1:100) and subsequent detection with streptavidin-HRP and TMB substrate, according to manufacturer recommendation. Plates were analyzed using a Plate reader (Thermo Scientific, Multiscan FC) at 450 nm, with reference at 620 nm.

Results-Separation of N-terminal his-tagged DSP107 (SEQ ID NO: 44), C-terminal his-tagged his tagged DSP107 (SEQ ID NO: 1) and the three C-terminal his-tagged DSP107 variants (DSP107_V1, DSP107_V2 and DSP107_V3.1 (SEQ ID NO: 12, 14 and 17) on an SDS-PAGE gel under non-reducing and reducing conditions, followed by immunoblotting with an anti-4-1BBL antibody (FIG. 8A-B) or anti SIRPα antibody (FIG. 8C), demonstrated that both the N-terminal side of the molecule and the C-terminal side of the molecule are present. In accordance with the SDS-PAGE analysis (Example 3 hereinabove), the western blot analysis demonstrated that the N-terminal his-tagged DSP107; and C-terminal his-tagged DSP107, DSP107_V1 and DSP107_V2 proteins migrated in reducing conditions as approximate size of 75 kDa, corresponding to the expected DSP107 monomer size. Additional bands of higher molecular weight were also detected with anti 4-1BBL antibody in the N-terminal his-tagged DSP107 and C-terminal his-tagged DSP107 fusion proteins, under non-reducing conditions, suggesting formation of an S—S linked multimer.

Following, a sandwich ELISA method was designed to detect the produced SIRPα-4-1BBL fusion proteins using a capture antibody which binds the 4-1BBL domain and a detecting antibody which binds the SIRPα domain. As shown in FIG. 9, N-terminal his-tagged DSP107 as well as C-terminal his-tagged DSP107_V1 and DSP107_V2 were detected and quantified in similar a dose response manner using the dual side ELISA, indicating that all tested fusion proteins comprise both the N-terminal domain and the C-terminal domain.

Example 5

The SIRPα-4-1BBL Variants Bind CD47 and 4-1BB

Binding Analysis of the SIRPα Moiety of SIRPα-4-1BBL Protein to CD47

The binding of the SIRPα domain of SIRPα-4-1BBL to human CD47 was evaluated using a CHO-K1 cell line that is overexpressing CD47 or a SUDHL4 human B cell lymphoma cell line that endogenously expresses CD47. CHO-K1 WT cells served as a negative control. The binding of the 4-1BBL domain of SIRPα-4-1BBL to human 4-1BB was evaluated using a human fibrosarcoma cell line HT1080 that is overexpressing 4-1BB (Wyzgol A. et al., J Immunol. 2009 183:1851-61). Wild-type HT1080 cell line served as a negative control. Cells were incubated with different concentrations of the produced SIRPα-4-1BBL fusion proteins followed by immuno-staining with a secondary anti 4-1BBL antibody to detect the binding to CD47. Alternatively, DSP107_V2 was biotinylated to measure the total binding capacity of the molecule. Specific binding was evaluated using an anti-CD47 blocking antibody or anti-4-1BB blocking antibody or combination of both antibodies. Binding was analyzed by flow cytometry (FACS).

Materials—C-terminal his-tagged DSP107 (SEQ ID NO: 1), DSP107_V1 (SEQ ID NO: 12, DSP107_V2 (SEQ ID NO: 14) and DSP107_V3.1 (SEQ ID NO: 17), and DSP107_V2 (SEQ ID NO: 13), produced as described in Example 2 hereinabove.

CHO-K1-WT and CHO-K1-CD47 cell lines (Bommel et al, 2017, Oncoimmunology 7(2): e1386361), SUDHL4 cells (ATCC CRL-2957), HT1080 cells (ATCC CCL-121), HT1080 cells overexpressing 4-1 BB (Wyzgol A. et al., J Immunol. 2009 183:1851-61), Fixable Viability Dye (BD Biosciences, cat #562247), Human Fc blocker, True stain FCX (Biolegend, cat #422302), EZ-Link NHS-PEG4-Biotin kit (Thermo Scientific, cat #A39259) and the following antibodies: anti 4-1BBL (Biolegend, cat #311506), anti-CD47 ("Inhibrix-like" produced by GenScript according to KAHR Medical instructions; Biolegend, cat #323124), anti-4-1BB (BD, cat #552532 Biolegend, cat #309810), isotype IgG1, k (Biolegend, cat #400112), APC streptavidin (SA) (Biolegend, cat #405207), CFSE (Thermo Fisher, cat #C34554), CytoLight Red (Incucyte, cat #4706).

Methods-Membrane expression of CD47 or 4-1BB was evaluated by flow cytometry using allophycocyanin (APC)-conjugated anti-CD47 and anti-4-1 BB antibodies, respectively, and the corresponding isotype controls. To determine binding of SIRPα-4-1BBL to CD47, cells were pre-incubated with human Fc blocker prior to incubation with different concentrations (0.01-50 μg/ml or 0.156-80 μg/mL, or 0.05-25 μg/mL, as indicated) of the produced SIRPα-4-1BBL proteins for 30 minutes or 1 hour on ice, followed by immuno-staining with antibodies against 4-1BBL, fixation and analysis by flow cytometry. To determine binding of SIRPα-4-1BBL to 4-1BB, the SIRPα-4-1BBL was biotinylated using the EZ-Link NHS-PEG4-Biotin kit, according to the manufacturer's protocol. Following, cells were washed and incubated for 1 hour at 37° C. with anti-CD47 blocking Ab, in order to prevent binding of the SIRPα arm to CD47 or binding was performed without blocking to demonstrate the total binding of the molecule (by its two ligands) to the cell. Following incubation, the biotinylated SIRPα-4-1BBL was added to the cells (serial dilutions: 0.05-50 μg/mL; 0.238-238 nM) and incubated for 20 minutes at 4° C. Following incubation, cells were washed, stained with a detection Ab, APC-Streptavidin (SA), and incubated for 30 minutes at 4° C., washed and analyzed by flow cytometry. CHO-K1-CD47 cells were stained with CFSE according to the manufacturer instructions, and HT1080 cells overexpressing cells were stained with Cyto-Light Red. The two stained cell lines were mixed at a 1:1 ratio (30 000 cells per cell line). In some experiments blocking antibody (αCD47, α41BB-10 μg/ml) was added and incubated for 30 minutes at 4° C. DSP107_V2 (seq ID:13) at 5 μg/ml was added and incubated for 30 minutes at RT. Cells were analyzed by using flow cytometry for the two dyes.

Results—High membrane expression of CD47 was observed on CHO-K1-K1 cells (FIGS. 19A-B and 20). All tested fusion proteins, bound to CD47 on CHO-K1-CD47 and DSP107_V2 (SEQ ID NO: 13) bound SUDHL4 cells and to 4-1BB and CD47 on HT1080 cells overexpressing 4-1BB in a dose dependent manner (FIGS. 10, 21A-B and 22A-F). The results show that the total binding of biotinylated DSP107_V2 to HT1080 4-1BB OX cells was higher compared to binding to HT1080 parental cells (FIGS. 22A-F). In addition, binding to HT1080 WT cells was totally abrogated following CD47 blockade with a specific blocking Ab; and binding to HT1080 4-1BB OX cells was only partially reduced. Similarly, only partial blocking to HT1080 4-1BB OX cells was induced by the anti-4-1BB Ab. Total abrogation of DSP107_V2 binding was achieved with dual-blocking of both CD47 and 4-1BB counterparts using both Abs (FIGS. 22A-F). The proteins did not bind CHO-K1-WT cells (FIG. 21A-B). Isotype control incubated with the highest concentration of protein did not show background staining.

Following, the simultaneous binding of DSP107_V2 (SEQ ID NO: 13) to CFSE-labeled HT1080 4-1BB OX cells and CytoLight Red-labelled CHO-K1 CD47 OX cells was evaluated. Following incubation, Doublet formation of co-stained complexes of DSP107_V2 with both CD47 and 4-1BB OX cells was observed (FIG. 23A), suggesting the approximation of adjacent cells through the immunogenic synapse. The mean results from three independent experiments comparing DSP107_V2 to medium control, demonstrated a significant increase in doublets, from ~10% to >30% (FIGS. 23B and 24). Importantly, the formation of doublets by DSP107_V2 was strongly inhibited upon co-incubation with either anti-CD47 or anti-4-1BB blocking Abs. This finding is in line with SIRPα-4-1BBL mode of action, binding to both CD47 and 4-1BB simultaneously.

Binding of SIRPα-4-1BBL to Human, Mouse and Cynomolgus Monkey CD47 and 4-1BB Counterparts The binding of the produced SIRPα-4-1BBL fusion proteins to CD47 and 4-1BB was determined by Surface Plasmon Resonance (SPR) assays.

Materials—N-terminal his-tagged DSP107 (SEQ ID NO: 44); and C-terminal his-tagged DSP107_V1 (SEQ ID NO: 12), DSP107_V2 (SEQ ID NO: 14) and DSP107_V2 (SEQ ID NO: 13), produced as described in Example 2 hereinabove.

Series S sensor chip CM5 (GE, cat. #BR100530), human Ab capture kit (GE, cat. #BR100839), human PDL1-hFc (R&D, cat. #156-B7-100), human CD47-hFc (R&D, cat #4670-CD-050), mouse CD47-hFc (R&D, cat. #1866-CD-050), cynomolgus CD47-hFc (ACROBiosystems, cat. #CD7-C5252), human 4-1BB-hFc (LsBio, cat #LS-G4041-100), mouse 4-1BB-hFc (R&D, cat. #937-4B-050), cynomolgus 4-1BB-hFc (R&D, cat. #9324-4B-100).

Methods—SPR assays were performed using a Biacore T100 biosensor (GE Healthcare). 25 μg/mL anti-human IgG (anti-Fc) antibody from the human Ab Capture Kit was coupled to all four flow-channels of the chip (Fc1-4), using a standard amine coupling protocol, as recommended by the manufacturer. Binding of CD47 and 4-1BB to the chip was performed in HBS-EP+ running buffer (10 mM HEPES pH 7.3, 150 mM NaCl, 3 mM EDTA, 0.0 5% Tween20): Human PDL1 (negative control) was loaded onto the reference channel Fc1 (10 μg/mL in the 1st experiment and 5 μg/mL in the 2nd experiment, for 10 seconds at 20 μl/min), while Fc2-4 were loaded with the human, mouse and cynomolgus CD47-hFc proteins (10 μg/mL in the 1st experiment and 5 μg/mL in the 2nd experiment, for 5 seconds at 20 μl/min). Following automated regeneration of the chip, it was re-loaded with the human PDL1-hFc on channel Fc1, and with the human, mouse and cynomolgus 4-1BB-hFc proteins (10, 5 and 7.5 μg/mL in the 1st experiment; 5, 2.5 and 3.75 μg/mL in the 2nd experiment, respectively, for 5 sec at 20 μL/min) on channels Fc2-4. The chip was fully charged with all counterparts (average immobilized amount of ligand was 150RU). Following, the N-terminal his-tagged DSP107 (SEQ ID NO: 44), C-terminal his-tagged DSP107_V1 (SEQ ID NO: 12) and DSP107_V2 (SEQ ID NO: 14) were passed over all four channels. This process was iteratively repeated with various concentrations of the SIRPα-4-1BBL fusion proteins (500-0.1 2 nM, in serial 1:2 dilutions), at flow rate of 50 μL/min (association time: 120 sec; dissociation time: 300 sec for CD47 proteins and 600 sec for 4-1BB proteins). 3M MgCl2 solution was injected (45 sec at 20 μl/min) at the end of each cycle, to regenerate the active surface by dislodging the captured molecules. The binding parameters were evaluated using Kinetic 1:1 Binding model in BiaEvaluation software v. 3.0.2 (GE Healthcare).

Results—The kinetic analysis demonstrated that N-terminal his-tagged DSP107 and the two C-terminal his-tagged SIRPα-4-1BBL variants DSP107_V1 and DSP107_V2, have similar and high affinities to the human and cynomolgus CD47, and lower affinity to the murine CD47 (Table 5A hereinbelow). Kinetic analysis of DSP107_V2 (SEQ ID NO: 13) showed similar and high affinities to the human and cynomolgus CD47, and no affinity to the murine CD47 (Tables 5B-C). All four SIRPα-4-1BBL fusion proteins tested show similar and high affinities to human and cynomolgus 4-1BB, and do not bind murine 4-1BB. None of the SIRPα-4-1BBL fusion proteins tested bound the human PDL1 negative control.

TABLE 5A kinetic SPR analysis of N-terminal his-tagged DSP107 (SEQ ID NO: 44); and C-terminal his-tagged DSP107_V1 (SEQ ID NO: 12) and DSP107_V2 (SEQ ID NO: 14)

| Exp. # | SIRPα-4-1BBL variant | Counterpart | ka (1/(M·sec)) | kd (1/sec) | KD (M) |
|---|---|---|---|---|---|
| 1 | N-terminal his-tagged DSP107 | hPDL1 | 0 | 0 | 0 |
|   | C-terminal his-tagged DSP107-V2 |  | 0 | 0 | 0 |
| 2 | C-terminal his-tagged DSP107-V2 |  | 0 | 0 | 0 |
|   | C-terminal his-tagged DSP107-V1 |  | 0 | 0 | 0 |
| 1 | N-terminal his-tagged DSP107 | hCD47 | 1.81E+06 | 3.07E-03 | 1.70E-09 |
|   | C-terminal his-tagged DSP107-V2 |  | 9.02E+05 | 1.46E-03 | 1.61E-09 |
| 2 | C-terminal his-tagged DSP107-V2 |  | 5.29E+05 | 7.88E-04 | 1.49E-09 |
|   | C-terminal his-tagged DSP107-V1 |  | 7.91E+05 | 1.82E-03 | 2.30E-09 |
| 1 | N-terminal his-tagged DSP107 | mCD47 | 4.12E+04 | 9.26E-04 | 2.25E-08 |
|   | C-terminal his-tagged DSP107-V2 |  | 1.34E+05 | 8.19E-04 | 6.12E-09 |
| 2 | C-terminal his-tagged DSP107-V2 |  | 7.30E+04 | 8.41E-04 | 1.15E-08 |
|   | C-terminal his-tagged DSP107-V1 |  | 2.69E+04 | 3.97E-04 | 1.48E-08 |
| 1 | N-terminal his-tagged DSP107 | cCD47 | 1.73E+06 | 3.39E-03 | 1.96E-09 |
|   | C-terminal his-tagged DSP107-V2 |  | 7.87E+05 | 1.49E-03 | 1.89E-09 |
| 2 | C-terminal his-tagged DSP107-V2 |  | 6.13E+05 | 8.71E-04 | 1.42E-09 |
|   | C-terminal his-tagged DSP107-V1 |  | 6.54E+05 | 2.11E-03 | 3.23E-09 |
| 1 | N-terminal his-tagged DSP107 | h4-1BB | 2.36E+05 | 1.64E-04 | 6.96E-10 |
|   | C-terminal his-tagged DSP107-V2 |  | 1.49E+05 | 1.46E-04 | 9.80E-10 |
| 2 | C-terminal his-tagged DSP107-V2 |  | 4.84E+05 | 1.47E-04 | 3.05E-10 |
|   | C-terminal his-tagged DSP107-V1 |  | 6.34E+05 | 1.56E-04 | 2.47E-10 |
| 1 | N-terminal his-tagged DSP107 | m4-1BB | 0 | 0 | 0 |
|   | C-terminal his-tagged DSP107-V2 |  | 0 | 0 | 0 |
| 2 | C-terminal his-tagged DSP107-V2 |  | 0 | 0 | 0 |
|   | C-terminal his-tagged DSP107-V1 |  | 0 | 0 | 0 |
| 1 | N-terminal his-tagged DSP107 | c4-1BB | 5.11E+05 | 1.59E-04 | 3.11E-10 |
|   | C-terminal his-tagged DSP107-V2 |  | 3.22E+05 | 1.29E-04 | 4.02E-10 |
| 2 | C-terminal his-tagged DSP107-V2 |  | 7.99E+05 | 1.39E-04 | 1.74E-10 |
|   | C-terminal his-tagged DSP107-V1 |  | 1.07E+06 | 1.27E-04 | 1.19E-10 |

TABLE 5B kinetic SPR analysis of DSP107_V2 (SEQ ID NO: 13)

| Repeat number | Target receptor | ka (1/(M · sec)) | kd (1/sec) | KD (M) |
|---|---|---|---|---|
| 1 | hPD-L1 | N.D. | N.D. | N.D. |
| 2 |  | N.D. | N.D. | N.D. |
| 3 |  | N.D. | N.D. | N.D. |
| 1 | hCD47 | 9.09E+06 | 1.08E−02 | 1.18E−09 |
| 2 |  | 8.55E+06 | 9.72E−03 | 1.14E−09 |
| 3 |  | 8.36E+06 | 9.84E−03 | 1.18E−09 |
| 1 | mCD47 | N.D. | N.D. | N.D. |
| 2 |  | N.D. | N.D. | N.D. |
| 3 |  | N.D. | N.D. | N.D. |
| 1 | cCD47 | 1.03E+07 | 1.88E−02 | 1.82E−09 |
| 2 |  | 8.65E+06 | 1.46E−02 | 1.68E−09 |
| 3 |  | 8.70E+06 | 1.51E−02 | 1.74E−09 |
| 1 | h4-1BB | 2.90E+05 | 1.92E−04 | 6.62E−10 |
| 2 |  | 3.02E+05 | 1.81E−04 | 5.99E−10 |
| 3 |  | 2.81E+05 | 2.34B−04 | 8.34E−10 |
| 1 | m4-1BB | N.D. | N.D. | N.D. |
| 2 |  | N.D. | N.D. | N.D. |
| 3 |  | N.D. | N.D. | N.D. |
| 1 | c4-1BB | 5.88E+05 | 1.78E−04 | 3.02E−10 |
| 2 |  | 5.81E+05 | 1.75E−04 | 3.01E−10 |
| 3 |  | 5.35E+05 | 2.20E−04 | 4.11E−10 |

*N.D = not detected

TABLE 5C

Average affinity constants of DSP_V2 (SEQ ID NO: 13) to human, mouse and cynomolgus CD47 and 4-1BB

| Counterpart | KD (RM) | | |
|---|---|---|---|
|  | Mouse | Monkey | Human |
| CD47 | 0 | 1.75 nM | 1.17 nM |
| 4-1BB | 0 | 33.8 nM | 70 nM |

Example 6

Activation of 4-1Bb by the SIRPα-+1BBL Variants

The activation effect of the 4-1BB receptor by the produced SIRPα-4-1BBL fusion proteins is tested by using HT1080 cells that are overexpressing the 4-1BB receptor. Specifically, the HT1080-4-1BB cell line is overexpressing 4-1BB and is known to secrete IL8 upon binding of 4-1BBL (Wyzgol et al., 2009, *J Immunol.* 183(3):1851-61). Hence, binding of 4-1BBL to the 4-1BB receptor on the surface of these cells, is expected to result in activating a signaling pathway followed by secretion of IL8. To this end, the cells are incubated in the presence of different concentrations of the His-tagged SIRPα-4-1BBL and IL8 secretion to the culture media is determined by ELISA.

Materials—N-terminal his-tagged DSP107 (SEQ ID NO: 44); and C-terminal his-tagged DSP107 (SEQ ID NO: 1), DSP107_V1 (SEQ ID NO: 12, DSP107_V2 (SEQ ID NO: 14) and DSP107_V3.1 (SEQ ID NO: 17), and DSP107_V2 (SEQ ID NO: 13), produced as described in Example 2 hereinabove.

HT1080-4-1BB cells (Wyzgol, et al, 2009, The Journal of Immunology), recombinant human His-tagged CD47 protein (ACRO Biosystem, cat #CD7-H5227), recombinant human His-tagged 4-1BBL protein (Cell Signaling, cat #8460LF), IL8 ELISA kit (cat #D8000C, R&D), DMEM (cat #01-055-1A, Biological industries), FBS (cat #10270106, Rhenium), AIM V (serum free medium) (ThermoScientific), anti-CD47 Ab (Invitrogen, cat #16-0479-85, clone B6H12).

Methods—Single culture assay: flat bottom, 96-wells plates were coated with 5 μg/mL recombinant human His-tagged CD47 protein. Following a washing step, SIRPα-4-1BBL fusion protein was added (0-5 μg/mL) and incubated for 1 hour at 37° C. WT HT1080 cell or HT1018-4-1BB cells were added to the wells (10,000 cells/well) and incubated for 24 hours at 37° C. in serum free medium. Following incubation, IL8 concentration in the supernatant was determined by IL-8 ELISA kit according to the manufacturer's protocol. Plates were analyzed using a Plate reader (Thermo Scientific, Multiscan FC) at 450 nm, with reference at 540 nm. The effect of SIRPα-4-1BBL was also compared to that of its individual soluble components, human SIRPα, human 4-1BBL, or the combination of both. To determine binding specificity, an anti-CD47 blocking antibody competitor was added to the cultures 1 hour prior to addition of the SIRPα-4-1BBL fusion protein, to block its binding via the SIRPα arm.

Co-culture assay: CHO-K1 WT or CHO-K1-CD47 cells were seeded in flat bottom 96-wells plates (10,000 cells/well) and incubated overnight at 37° C. The following day, the supernatant was discarded, SIRPα-4-1BBL fusion protein was added (0-10 μg/mL) and incubated for 1 hour at 37° C., followed by a washing step. HT1080 WT or HT1080-4-1BB cells were then added (10,000 cells/well) and incubated for 24 hours at 37° C. Following incubation, IL8 concentration in the supernatant was determined by IL-8 ELISA kit according to the manufacturer's protocol. Plates were analyzed using a Plate reader (Thermo Scientific, Multiscan FC) at 450 nm, with reference at 540 nm.

Results—In the single-culture assay, DSP107-V2 (SEQ ID NO: 13) induced IL-8 secretion from HT1080-4-1BB cells in the presence of plate-bound CD47, while in the absence of CD47, a significantly lower activation effect was evident (FIG. 25A, p<0.003; ~3 fold decrease). The activity of both plate-bound and soluble DSP107_V2 was totally abrogated by anti-CD47 antibody. Blockage of the soluble DSP107_V2 might be attributed to abrogation of its low binding to endogenous CD47, expressed on HT1080 cells.

Further, DSP107_V2 activated 4-1BB signaling more effectively (~3 fold increase) than soluble 4-1BBL or the combination of soluble SIRPα and 4-1BBL (FIG. 25B). As expected, soluble SIRPα had no effect due to no interaction with the 4-1BB receptor.

In addition, IL-8 secretion from HT1080-4-1BB cells following treatment with DSP107_V2 was significantly enhanced (p<0.0032) (~3.5 fold) in the presence of CHO-K1-CD47 cells, as compared to CHO-K1 WT cells. IL-8 secretion was totally blocked by anti-CD47 antibody, further suggesting that cross-presentation is necessary to transmit the co-stimulatory signal by the 4-1BBL arm through the 4-1BB receptor (FIG. 26).

Example 7

Activation of T Cells by the SIRPα-4-1BBL Variants

The activation of a T cell requires two signals: ligation of the T-Cell Receptor (TCR) with the Major Histocompatibility Complex (MHC)/peptide complex on the Antigen Presenting Cell (APC) and cross-linking of co-stimulatory receptors on the T cell with the corresponding ligands on the APC. 4-1BB is a T cell co-stimulatory receptor which upon ligation to 4-1BBL promotes expansion, survival, differentiation and cytokine expression of both CD8+ and CD4+ T cells.

Numerous methods are known in the art to determine activation of T cells, including but not limited to:

Expression of activation markers on the surface of the T cells (for example: CD25, CD69, CD62L, CD137, CD107a, PD1 etc.). Expression of activation markers is tested by staining the cells with specific antibodies and flow cytometry analysis (FACS).

Secretion of inflammatory cytokines (for example: IL2, IL6, IL8, INF gamma etc.). Secretion of inflammatory cytokine is tested by ELISA.

Proliferation, measured by pre-staining of T cells with CFSE (carboxyfluorescein succinimidyl ester) and determining deviation of cells by CFSE dilution that is determined by FACS.

Killing of a target cell e.g. cancer cells that is measured by pre-labeling the cancer cells using e.g. Calcine-AM reagent and measuring Calcine release into the culture medium using luminescence plate reader.

To this end, the effect of the produced SIRPα-4-1BBL fusion proteins on proliferation of human Peripheral Blood Mononuclear Cells (PBMCs) was evaluated as follows:

Materials—N-terminal his-tagged DSP107 (SEQ ID NO: 44); C-terminal his-tagged DSP107_V1 (SEQ ID NO: 12) and DSP107_V2 (SEQ ID NO: 14), produced as described in Example 2 hereinabove.

Ficoll-Paque (cat #17-1440-03, GE Healthcare), RPMI 1640 (cat #01-100-1A, Biological industries), FBS (cat #12657-029, Gibco), L-Glutamine (cat #25030-024, Gibco), Pen Strep (cat #15140-122, Gibco), Leaf purified Anti-human CD3 (cat #BLG-317315, BioLegend), Recombinant human IL-2 (cat #589106, Biolegend), anti-4-1BB antibody (cat #BLG-106109), anti-IgG antibody (cat #BLG-402012).

Methods—Human PBMCs were isolated from healthy donor peripheral blood using Ficoll-Paque method (Grienvic et al. 2016, Biopreserv Biobank. 14(5):410-415). Following, the cells were cultured for 7 days with addition of different concentrations of the various His-tagged SIRPα-4-1BBL proteins, in the presence of sub-optimal concentrations of anti-CD3 (30 ng/ml) or IL-2 (1000 U/ml) or anti-CD3 plus IL-2. Proliferation of PBMCs was determined by The IncuCyte® S3 Live-Cell Analysis System (IncuCyte) according to the manufacturer's protocol. Cells were tested for 4-1BB surface expression at day 0 and day 3 of the experiment by flow cytometry.

Results—Incubation of PBMCs with N-terminal his-tagged DSP107, C-terminal his-tagged DSP107_V1 and C-terminal his-tagged DSP107_V2 increased cells confluency, which indicates higher proliferation rates, of cells stimulated with anti-CD3 antibody, with or without the addition of IL-2 (FIG. 11). An optimum induction was obtained at a concentration of 0.01 μg/ml of all tested SIRPα-4-1BBL fusion proteins. Thus, binding of N-terminal his-tagged C-terminal his-tagged DSP107, C-terminal his-tagged DSP107_V1 and C-terminal his-tagged DSP107_V2 enabled 4-1BBL/4-1BB-mediated co-stimulation and induction of T cells proliferation. These results are in correlation with induced 4-1BB expression, following stimulation with anti CD3 with or without IL-2 (FIG. 12).

In a following set up, the effect of DSP107_V2 (SEQ ID NO: 13) on human PBMC and T cells proliferation was evaluated as follows:

Materials—DSP107_V2 (SEQ ID NO: 13), produced as described in Example 2 hereinabove.

Ficoll-Paque (cat #17-1440-03, GE Healthcare), RPMI 1640 (cat #01-100-1A, Biological industries), FBS (cat #12657-029, Gibco), L-Glutamine (cat #25030-024, Gibco), Pen Strep (cat #15140-122, Gibco), Recombinant human IL-2 (cat #589106, Biolegend), anti-CD3/CD28 activating Dynabeads, EasySep Direct Human T-cell Isolation kit (STEMCELL Technologies), Cell Proliferation Dye (CPD, e-Biosciences, cat #65-0842-85), His tagged-CD47 recombinant protein (ACRO Biosystem, cat #CD7-H5227).

Methods—Human PBMCs were isolated from healthy donor peripheral blood using Ficoll-Paque method (Grienvic et al. 2016, Biopreserv Biobank. 14(5):410-415). Following, for Incucyte analysis, 96-wells, flat-bottom plates were coated with Poly-L-Ornithine (0.01%, 50 μL, incubated for 1 hour at 37° C.) to allow PBMC cell adherence. PBMCs were seeded (50,000/well) in the presence of rhIL-2 (1000 U/mL) and DSP107_V2 (0.33 μg/mL). Plates were incubated for 5 days at 37° C. in the IncuCyte machine. Phase screening images were taken every 3 hours and cell density was analyzed using IncuCyte Live Cell Analysis System (Sartorius). For flow cytometry analysis, T-cells were isolated from PBMCs by negative selection magnetic beads (EasySep Direct Human T-cell Isolation kit, STEMCELL Technologies) and stained with Cell Proliferation Dye (CPD), according to manufacturer's instructions. Stained T-cells were cultured for 3 or 5 days in 96-wells plates, or following pre-coating of the plates with His tagged-CD47 recombinant protein (2 μg/mL, for 3 hours at 37° C.), in the presence of sub-optimal concentrations of human anti-CD3/CD28 Dynabeads T-cell activator (1:10 bead per T-cell) and DSP107_V2 (0.3-3 μg/mL). Following, CD3+ T cells were analyzed by flow cytometry for CPD levels.

Results—DSP107_V2 (SEQ ID NO: 13) augmented the proliferation of freshly isolated human PBMCs induced by IL-2, as determined by phase images analysis captured by the Incucyte software. Specifically, cell density dramatically increased following 5 days of incubation of PBMCs with IL-2 (1000 U/mL) and 1.6 nM (0.33 μg/mL) DSP107_V2, as compared to PBMCs treated with IL-2 only. Representative images are shown in FIG. 28. Similarly, DSP107_V2 (SEQ ID NO: 13) significantly enhanced proliferation by 16-35%, p<0.0025) of CPD-stained T-cells induced by a sub-optimal level of anti-CD3/CD28 Dynabeads in the presence of plate-bound CD47, as determined by flow cytometry (FIG. 29).

The effect of the produced SIRPα-4-1BBL fusion proteins on expression of T cells activation markers was evaluated as follows:

Materials—DSP107_V2 (SEQ ID NO: 13), produced as described in Example 2 hereinabove.

Ficoll-Paque (cat #17-1440-03, GE Healthcare), RPMI 1640 (cat #01-100-1A, Biological industries), FBS (cat #12657-029, Gibco), L-Glutamine (cat #25030-024, Gibco), Pen Strep (cat #15140-122, Gibco), Leaf purified Anti-human CD3 (cat #BLG-317315, BioLegend), anti-4-1BB antibody (cat #BLG-106109), PE anti-CD25 antibody (Biolegend, cat #302606), FITC Anti-human CD3 Ab (Biolegend, cat #317310).

Methods—Human PBMCs were isolated from peripheral blood of healthy donors using standard Ficoll gradient method, according to manufacture instructions. 96-wells plates were pre-coated with anti-human CD3 antibody (0.5 μg/mL), by incubation for three hours at 37° C. PBMCs from three donors were cultured in the anti-CD3 pre-coated plates (100,000 cells/well) with different concentrations of DSP107_V2 (SEQ ID NO: 13, 0-5 μg/mL), for 48 hours at 37° C., 5% $CO_2$. Following incubation, gated $CD3^+$ T cells were analyzed by flow cytometry for expression of the activation markers CD25 and 4-1BB.

Results—expression of the CD25 and 4-1BB activation markers was induced on T cells by anti-CD3, and was significantly enhanced by DSP107_V2 (SEQ ID NO: 13) in a dose dependent manner, in all three tested donors (FIG. 27, 0.0012<p<0.041 for 4-1BB expression; 0.0039<p<0.047 for CD25 expression).

The effect of the produced SIRPα-4-1BBL fusion proteins on T-cell mediated killing of target cancer cells was evaluated as follows:

Materials and Methods—For Incucyte analysis, four ATCC cancer cell lines, SNU423, SNU387 and SNU423 hepatocellular carcinoma (HCC) and Ovcar8 ovarian cancer cell line, were transduced with IncuCyte NucLight Red Lentivirus Reagent (EF1α, Puro; 3TU/Cell) suitable for transducing cells with a non-perturbing nuclear restricted red fluorescent label. Puromycin selection (2 µg/mL) was applied to achieve stable cell lines. Nuc-red fluorescence and CD47 expression on the surface of the cancer cell lines were validated by flow cytometry prior to the assay (data not shown). T-cells were isolated from peripheral blood samples of two healthy donors using negative selection magnetic beads. Isolated T-cells were co-cultured with the different cancer cell lines at an Effector to Tumor ratio (E:T) of 5:1 and activated with a sub-optimal concentration of anti-CD3/CD28 dynabeads (1:10 beads per cells) and DSP107_V2 (SEQ ID NO: 13), produced as described in Example 2 hereinabove (0.11, 0.33 and 1 µg/mL). IncuCyte green fluorescence Caspase 3/7 substrate reagent was added to the co-culture to mark apoptotic cells. Cells were incubated for 5 days in the Incucyte machine. Phase, green and red fluorescent images were recorded every 1.5 hours, and the overlapping green and red fluorescence ("yellow") signals were quantified as apoptotic cancer cell signals.

For flow cytometry analysis of apoptotic CFSE-labelled tumor cells, PBMCs were isolated from the peripheral blood of a healthy donor and expanded using anti-CD3 and IL-2 for 11 days. Mesothelioma cancer cell lines MSTO and H2052 (ATCC) were stained with CFSE according to protocol. Expanded PBMCs and stained cancer cells were co-cultured at several E:T ratios, in the presence of 0.1 µg/mL or 1 ng/ml of DSP107_V2 (SEQ ID NO: 13), produced as described in Example 2 hereinabove. Live CFSE labeled cancer cells were analyzed by flow cytometry following detachment with trypsin.

Results—DSP107_V2 enhanced the killing of hepatocellular, ovarian and mesothelioma cancer cell lines, mediated by T-cells (FIGS. 30A-C and 31A-B).

Specifically, Incucyte analysis demonstrated that co-culture of hepatocellular and ovarian cancer cell lines in the presence of T cells, activated with a sub-optimal concentration of anti-CD3/CD28 Dynabeads, resulted in killing of the cancer cells; and addition of DSP107_V2 enhanced the T-cell mediated killing of SNU387, SNU423 and Ovcar8 cells by 49%, 27% and 23% respectively (FIGS. 30A-C). No killing was observed following incubation of these cancer cell lines with DSP107_V2 alone (FIGS. 30A-C), supporting no direct cytotoxic effect on cancer cell lines in the absence of T-cells.

Flow cytometry analysis demonstrated that co-culture of CFSE-labeled mesothelioma cancer cell lines with T-cells, at various E:T ratios, resulted in cancer cell killing that was enhanced in the presence of DSP107_V2 (up to 52% cell death was induced by DSP107_V2, as compared to no death in the absence of DSP107_V2, at E:T ratios 1:1-1:5, FIGS. 31A-B). Similarly to hepatocellular and ovarian cancer cell lines, no killing of CFSE-labeled mesothelioma cancer cell lines was observed following incubation with DSP107_V2, in the absence of T-cells.

Example 8

The Effect of the SIRPα-4-1BBL Variants on Blocking CD47 Binding

The SIRPα part of SIRPα-4-1BBL is designed to block the "don't eat me signal" by blocking the interaction of endogenous SIRPα expressed on antigen presenting cells (APCs) with CD47 expressed on tumor cells.

To this end, the effect of the produced SIRPα-4-1BBL fusion proteins as blockers to this interaction was evaluated.

Materials—N-terminal his-tagged DSP107 (SEQ ID NO: 44); C-terminal his-tagged DSP107 (SEQ ID NO: 1), DSP107_V1 (SEQ ID NO: 12, DSP107_V2 (SEQ ID NO: 14) and DSP107_V3.1 (SEQ ID NO: 17), and DSP107_V2 (SEQ ID NO: 13), produced as described in Example 2 hereinabove.

Recombinant human CD47 (Acrobiosystems, CD7-H5227), anti hCD47 neutralizing ab (Novus, AF4670), Biotinylated SIRPα (Acrobiosystems, CDA-H82F2).

Methods—ELISA plates were coated overnight with recombinant human CD47. The plates were washed and incubated for 1 hour with different concentrations of the produced SIRPα-4-1BBL fusion proteins or a positive control anti CD47 antibody. Following, a biotinylated SIRPα was added; and following 1 hour incubation the plates were washed and blotted with Streptavidin-HRP and TMB substrate according to a standard ELISA protocol (FIG. 13A). Plates were analyzed using a Plate reader (Thermo Scientific, Multiscan FC) at 450 nm, with reference at 620 nm.

Results—All tested SIRPα-4-1BBL fusion proteins efficiently blocked the interaction of SIRPα with CD47, similarly to the positive control blocking antibody (FIG. 13B). EC50 values were in the range of 0.075-0.238 µg/ml (FIG. 13C).

Example 9

The Effect of the SIRPα-4-1BBL Variants on Macrophages and Polymorphonuclear Cells As mentioned, the SIRPα part of the SIRPα-4-1BBL fusion protein is designed to block the "don't eat me" signal induced by CD47 expressing tumor cells, towards the endogenous SIRPα expressed on APCs such as macrophages and granulocytes, by competing and blocking the interaction of CD47 on tumor cells with the endogenous SIRPα. This blockage of the "don't eat me" signal induces tumor cells phagocytosis.

To this end, the effect of the produced SIRPα-4-1BBL fusion proteins on phagocytosis of tumor cells by human macrophages or polymorphonuclear cells (PMNs) was evaluated using a flow cytometry-based assay or fluorescent microscopy.

Materials—N-terminal his-tagged DSP107 (SEQ ID NO: 1); C-terminal his-tagged DSP107_V1 (SEQ ID NO: 12, DSP107_V2 (SEQ ID NO: 14) and DSP107_V3.1 (SEQ ID NO: 17); and DSP107_V2 (SEQ ID NO: 13) produced as described in Example 2 hereinabove.

Human cancer cell lines Ramos (Lymphoma), DLD-1 (colon carcinoma), Daudi, SUDHLS, SUDHL4, U2932, SUDHL2, SUDHL6, SUDHL10, DUDHL4 and OCI-LY3 (Lymphomas).

Methods—Polymorphonuclear cells (PMNs) and PBMCs were isolated from blood samples of healthy volunteers by density gradient centrifugation, followed by ammonium chloride lysis of erythrocytes.

For the PMNs assay, Ramos and DLD-1 cancer cells were labelled with Vybrant DiD and mixed with isolated PMNs at an effector-to-target ratio of 1:1. Mixed cultures were treated for 2 hours with the produced SIRPα-4-1BBL fusion protein, alone or in combination with therapeutic antibodies rituximab (RTX; anti-CD20) or cetuximab (CTX; anti-EGFR); or for 18 hours with the produced SIRPα-4-1BBL fusion proteins only. Following, phagocytosis of cancer cells by PMNs was analyzed by flow cytometry.

For the macrophages assay, monocytes were further enriched from the isolated PBMCs by MACS sorting using CD14 magnetic MicroBeads (Miltenyi Biotec). Monocytes were differentiated into macrophages (MO) in RPMI 1640 culture medium+10% FCS supplemented with GM-CSF (50 ng/ml) and M-CSF (50 ng/ml) for 7 days. To generate type 1 macrophages (M1), MO cells were primed by LPS and IFN-γ for additional 24 hours. Alternatively, to generate type 2 macrophages (M2) MO cells were incubated with 100 ng/ml IL-4 for 24 hours. SUDHL5, SUDHL4, OCI-LY3, SUDHL2, SUDHL6, SUDHL10, SC-1, Ramos and Daudi cancer cells were labelled with V450 cytoplasmic dye and mixed with the isolated and in vitro-differentiated type I macrophages (M1) at effector-to-target ratio of 1:1 or 1:5. Mixed cultures were treated with the produced SIRPα-4-1BBL fusion proteins for 2-2.5 hours, alone or in combination with RTX, Trastuzumab or CTX. Following incubation, tumor cells that were not engulfed were washed out and the macrophages were stained with anti-CD11b AF 594 Ab. Phagocytosis of cancer cells by macrophages was analyzed by fluorescent microscopy. In other experiments, phagocytosis was evaluated by Incucyte as follows: Tumor cells from various lymphoma cell lines were pre-stained with CFSE and macrophages were pre-stained with IncuCyte Cytolight red cytoplasmic dye according to the manufacturer's protocol. Stained tumor cells and macrophages were co-cultured at a 1:5 macrophage to tumor cell ratio, and phase red and green images were taken by Incucyte. Phagocytosis was quantified as the proportion of macrophages positive for tumor cell engulfment ("yellow" signal) out of the total macrophages (red signal).

Results—All tested His-tagged SIRPα-4-1BBL fusion proteins enhanced PMNs-mediated phagocytosis of Ramos and DLD1 cancer cells following 2 hours of incubation in combination with the therapeutic antibodies Rituximab (RTX) or Cetuximab (CTX) (FIG. 14A). Further enhancement of PMN mediated phagocytosis of Ramos and DLD1 cancer cells was demonstrated following 18 hours of incubation (FIG. 14B).

In addition, all tested His-tagged SIRPα-4-1BBL fusion proteins augmented macrophages-mediated phagocytosis of SUDHL4, SUDHL5 and Oci-Ly3 lymphoma cell lines following 2 hours of incubation, which was further enhanced when combined with Rituximab (RTX) (FIG. 15). In addition, C-terminal his-tagged DSP107_V2 (SEQ ID NO: 14) augmented macrophages mediated phagocytosis of SUDHL4 following 2 hours of incubation, in a dose depended manner (FIG. 16).

Further, Rituximab-induced phagocytosis of tumor cells by M1 macrophages was enhanced following incubation with 2.5 μg/ml DSP107_V2 (SEQ ID NO: 13) (FIG. 32A). DSP107_V2 also increased the number of Ramos cells engulfed by each macrophage (-32B).

A wide panel of lymphoma cell lines were then tested using the Incucyte imaging system. M1 macrophage-mediated phagocytosis of cancer cell lines was observed following incubation of the M1 macrophages with the cancer cells and 2.1 μg/ml DSP107_V2 as a single agent (FIG. 32C). An additive phagocytic effect was also observed when DSP107_V2 was used in combination with rituximab, compared to the effect induced by rituximab as a single agent (FIG. 32D).

Interestingly, DSP107_V2 (SEQ ID NO: 13) also enhanced the phagocytosis induced by M0 and M2 macrophages, both as a single agent and in combination with rituximab, however to a less extend then that observed for M1 macrophages (data not shown). In similar experiments with DLD-1 colon carcinoma cells, significantly more DLD-I cells were phagocytosed by macrophages with DSP107_V2 single agent treatment (2.1 μg/mL) compared to medium control (FIG. 32E). Further, a combination therapy of DSP107_V2 and trastuzumab (an anti-Her2 antibody) clearly demonstrated augmentation of tumor cell phagocytosis compared to trastuzumab treatment as a single agent (FIG. 32E).

Example 10

The Effect of the SIRPα-4-1BBL Variants on Granulocyte Cells

Materials and methods-Leukocytes were isolated from peripheral blood of healthy donors using standard procedure. Tumor cells were pre-stained with CFSE (Thermo Fisher) or Vybrant DiD Cell-Labeling Solution (Thermo Fisher) according to the manufacturer's protocol. Isolated leukocytes and stained tumor cells were mixed at a 1:1 leukocyte to tumor cell ratio, and incubated in the presence of DSP107_V2 (SEQ ID NO: 13), with or without therapeutic antibody rituximab (1 μg/mL). Uptake of tumor cells by granulocytes was subsequently evaluated by flow cytometry, quantifying the Vybrant DiD-positive granulocyte population. To evaluate phagocytosis of carcinoma cell lines, DLD-1 colon carcinoma cells were stained with CFSE and co-cultured with macrophages at a macrophage:tumor cell ratio of 1:5 for 2 hours, in the presence of either DSP107_V2 (SEQ ID NO: 13), or trastuzumab (anti Human Epidermal Growth Factor Receptor 2 (HER2) Ab; 0.1 μg/mL), or a combination of DSP107_V2 and trastuzumab. After incubation, cells were detached from the plate using Trypsin/EDTA solution, macrophages were stained using CD11b-APC Ab and samples were analyzed by FACS. The effect of DSP107_V2 (SEQ ID NO: 13) on the uptake of tumor cells by granulocytes was also compared to His-tagged SIRPα or soluble 4-1BBL or combination of both.

Results—The effect of DSP107_V2 and the combination of soluble His-tagged SIRPα plus soluble 4-1BBL, on granulocyte-mediated tumor cell phagocytosis was further evaluated on multiple lymphoma cell lines. Phagocytosis following incubation with DSP107_V2 or the combination of its soluble components was tested as a single agent and compared to culture medium. Tumor cell phagocytosis was also tested with rituximab as a single agent and in combination with DSP107_V2 or the combination of its soluble components. Following 2.5 hours of incubation with 2.1 μg/ml DSP107_V2, granulocyte-mediated phagocytosis of lymphoma cells was stimulated by DSP107_V2 but not by the combination of soluble SIRPα and soluble 4-1BBL (FIG. 33B). Rituximab also demonstrated a strong single agent stimulation of granulocyte-mediated tumor cell phagocytosis. This effect was enhanced in combination with DSP107_V2 but not in combination with the mixture of soluble SIRPα and soluble 4-1BBL (FIGS. 33B-F).

Example 11

The In-Vivo Anti-Tumor Effect of the SIRPα-4-1BBL Variants

Four different in-vivo mouse models are used for testing the efficacy of the produced SIRPα-4-1BBL fusion proteins in treating cancer:

1. Nude-SCID mice inoculated with human tumor cells. In this model, the SIRPα-4-1BBL fusion protein interacts with mouse and human CD47 (expressed on the tumor cells) and the effect of the fusion protein on mouse macrophages activity is tested.
2. NSG mice inoculated with human stem cells and human tumor cells. In this model, the SIRPα-4-1BBL fusion protein interacts with mouse and human CD47 (expressed on the tumor and the immune cells) and with 4-1BB on human T cells. The effect of the fusion protein on mouse and human macrophages, as well as human T cells, is tested.
3. C57BL/6-human-4-1BB knock-in mice inoculated with MC38 mouse colon carcinoma or other cancer cell line or with cancer cell line overexpressing the human CD47. In this model, the mouse 4-1BB extracellular domain is replaced by that of a human 4-1BB. Hence, the SIRPα-4-1BBL fusion protein can interact with the human 4-1BB expressed on mouse T cells. The fusion protein interacts with mouse and human CD47 on the tumor cells. The effect of the fusion protein on mouse macrophages, as well as mouse T cells, is tested.
4. Syngeneic mouse tumor models that express mouse CD47. In these models, the SIRPα-4-1BBL fusion protein interacts with mouse CD47 on the tumor cells. The effect of the fusion protein on mouse macrophages is tested.

Methods—

In all four models, mice are inoculated with tumor cells intravenously (IV), intraperitoneally (IP), subcutaneously (SC) or orthotopically. Once the tumor is palpable (~80 mm$^3$), mice are treated IV, IP, SC or orthotopically, with different doses and different regimens of the SIRPα-4-1BBL fusion proteins; e.g. N-terminal his-tagged (SEQ ID NO: 44), C-terminal his-tagged DSP107 (SEQ ID NO: 1), C-terminal his-tagged DSP107_V1 (SEQ ID NO: 12), C-terminal his-tagged DSP107_V2 (SEQ ID NO: 14) and C-terminal his-tagged DSP107_V3.1 (SEQ ID NO: 17), produced as described in Example 1 hereinabove.

Mice are followed for weights and clinical signs. Tumors are measured few times a week by caliper, tumor volume is calculated according to the following equation: V=length× width$^2$/2. Mice Weight is measured routinely. Tumor growth and survival are monitored through the whole experiment.

Infiltration of immune cells into the tumor is tested by resecting the tumor or draining lymph nodes, digestion and immune phenotyping using specific antibodies staining and flow cytometry analysis. Additionally, or alternatively, infiltration of immune cells or necrotic grade of tumors is determined by resecting the tumors, paraffin embedding and sectioning for immunohistochemistry staining with specific antibodies.

At sacrificing, mice organs are harvested and embedded into paraffin blocks for H&E and IHC staining.

Blood samples are taken from mice at different time points, according to common procedures, for the following tests: PK analysis, cytokines measurements in plasma, FACS profiling of blood cells sub-populations in circulation, hematology testing, serum chemistry testing, anti-drug-antibody (ADA) analysis and neutralizing antibodies analysis (NAB).

Example 12

The In-Vivo Anti-Tumor Effect of the SIRPα-4-1BBL Variants, Using a Human 4-1BB Knock in Mouse Model In order to test the effect of the SIRPα-4-1BBL variants fusion proteins in mice, a human 4-1BB (h4-1BB) knock-in mice (C57BL/6 background) was utilized. Human CD47-expressing MC38 (hCD47 MC38) cells were selected as the tumor model. Of note, it has been shown that SIRPα in C57BL/6 mice does not interact with human CD47 [Yamauchi, T., et al., (2013) Blood, 121(8): p. 1316-25] and therefore no phagocytosis of hCD47 MC38 cells by native phagocytes could occur in this model. In addition, the binding of DSP107 to murine WT MC38 colon carcinoma cells was compared to that of human DLD1 colon carcinoma cells using flow cytometric analysis (FIG. 34). Based on the low binding of DSP107 to murine MC38, hCD47 MC38 cells were selected for the in vivo efficacy study. Consequently, the SIRPα arm of the SIRPα-4-1BBL variants fusion proteins was expected to target the tumor cells expressing human CD47, but not to have any effect on promoting tumor cell phagocytosis in this model.

Materials and methods—Female h4-1BB knock-in C57BL/6 mice, 8-9 weeks old (Crown Bioscience) were inoculated subcutaneously with 1×10$^6$ hCD47 MC38 cells (Crown Bioscience). Treatment was initiated once tumors reached a size of 60-100 mm$^3$. Following random assignment, six animals per group received intraperitoneal (IP) injections of either DSP107_V2 (SEQ ID NO: 13; 250 μg/injection; 12.5 mg/kg), administered once daily on days 0, 1, 2, 3 and 4, or anti-murine PD-L1 Ab (clone 10F.9G2, Bioxcell; 60 μg/injection), administered IP biweekly for 3 weeks, or a combination of DSP107_V2 (SEQ ID NO: 13) and anti-murine PD-L1 Ab. Control mice were injected with 200 μl of Phosphate-Buffered Saline (PBS). DSP107_V2 was administrated only during the first week of the experiment to avoid potential development of mouse-anti-human antibodies. Tumor volume was determined three times a week using a caliper, and the individual volumes were calculated by the formula: V=([width]2×length)/2. Mice were sacrificed individually once tumors reached a volume of 3000 mm$^3$.

Results-Treatment with anti PD-L1 or DSP107_V2 (SEQ ID NO: 13) as a single agent inhibited tumor growth (50.4% and 29.5%, respectively, FIG. 35A). The percentage of Tumor Growth Inhibition (TGI) was further enhanced when PD-L1 or DSP107_V2 were combined (83%, p=0.02 compared to vehicle-treated control). In addition, based on Mental cox analysis, combined treatment with DSP107_V2 and anti PD-L1 resulted in a statistically significant improvement in survival compared to vehicle-treated, control mice (p=0.01; 35B).

Example 13

The In-Vivo Anti-DLBCL Effect of the SIRPα-4-1BBL Variants, Using an NSG Mouse Model The effect of SIRPα-4-1BBL variants fusion proteins in the treatment of human DLBCL tumors in-vivo in the context of human immune system was evaluated using NSG mice, inoculated with SUDHL6 human DLBCL cells and with human PBMCs. These mice were further treated with a SIRPα-4-1BBL variants fusion protein as a single agent. Mice were followed for tumor growth.

Materials and methods—14 weeks old, female, NSG mice were inoculated S.C. with 1×10$^6$ SUDHL6 cells on day 0. On day 7, mice were randomly assorted to the following two groups:
1. Five mice—PBMCs
2. Six mice—PBMCs+DSP107_V2 (SEQ ID NO: 13)

PBMCs were isolated from peripheral blood of healthy donor using the standard Ficoll gradient method according to manufacturer's instructions. On day 7 the mice were inoculated I.V. with isolated PBMCs 1×10$^6$ cells per mouse. Frozen PBMCs from the same donors were used to re-inject the mice on day 13 (1×10$^6$ cells per mouse). The mice from the DSP107_V2 group were treated with 250 μg/mouse DSP107_V2 (SEQ ID NO: 13) I.P. day on, day off, for 2 weeks starting on day 7. Mice were followed for any clinical signs. Tumors were measured by micro caliper. Tumor volume was calculated by the following equation: Length× Length×Width/2. Mice were sacrificed on day 22, tumors were removed and weighted.

Results—Treatment with PBMCs and DSP107_V2 inhibited tumor growth by about 3.7 fold compared to control group, injected with PBMCs only, by day 20 (FIG. 36A). Treatment with PBMCs+DSP107_V2 significantly reduced tumor weight as determined following mice sacrifice at day 22 (FIG. 36B). Importantly, none of the treatments affected mice weight, suggesting no major side effect on mice health (data not shown).

TABLE 6

Average tumor volumes on days 13, 15 and 20

| Day | Mice | PBMCs | PBMCs + DSP107_V2 (SEQ ID NO: 13) |
|---|---|---|---|
| 13 | 1 | 216.00 | 352.00 |
|  | 2 | 261.36 | 236.25 |
|  | 3 | 0.00 | 196.02 |
|  | 4 | 174.60 | 100.00 |
|  | 5 | 264.60 | 109.35 |
|  | 6 |  | 154.80 |
|  | AVG | 183.31 | 191.40 |
| 15 | 1 | 274.63 | 104.10 |
|  | 2 | 283.08 | 100.00 |
|  | 3 | 290.23 | 329.60 |
|  | 4 | 281.75 | 198.83 |
|  | 5 | 322.40 | 255.79 |
|  | 6 |  | 299.57 |
|  | AVG | 290.42 | 214.65 |
| 20 | 1 | 959.62 | 895.40 |
|  | 2 | 1266.23 | 336.68 |
|  | 3 | 751.06 | 11.70 |
|  | 4 | 1231.22 | 9.40 |
|  | 5 | 1666.00 | 450.51 |
|  | 6 |  | 478.33 |
|  | AVG | 1174.83 | 363.67 |

*Tumors were measured by micro caliper on days 13, 15 and 20. Tumor volumes were calculated, and group average was calculated accordingly.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A SIRPα-4-1BBL fusion protein as set forth in SEQ ID NO: 13.

2. A polynucleotide encoding the SIRPα-4-1BBL fusion protein of claim 1.

3. A nucleic acid construct comprising the polynucleotide of claim 2, and a regulatory element for directing expression of said polynucleotide in a host cell.

4. A host cell comprising the SIRPα-4-1BBL fusion protein of claim 1.

5. A method of producing the SIRPα-4-1BBL fusion protein of claim 1, the method comprising expressing in a host cell the polynucleotide of claim 2.

6. The method of claim 5, comprising isolating the fusion protein or the polypeptide.

7. A method of treating a disease comprising cells that overexpress CD47 comprising administering to a subject in need thereof the SIRPα-4-1BBL fusion protein of claim 1.

8. An article of manufacture comprising the SIRPα-4-1BBL fusion protein of claim 1; and a therapeutic antibody.

9. The method of claim 7, wherein said disease comprises cancer.

10. A method of activating immune cells in vitro, the method comprising contacting the immune cells with the SIRPα-4-1BBL fusion protein of claim 1.

* * * * *

SEQUENCE LISTING

```
<160> NUMBER OF SEQ ID NOS: 131

<210> SEQ ID NO 1
<211> LENGTH: 555
<212> TYPE: PRT
<213> ORGANISM: Artificial sequence
<220> FEATURE:
<223> OTHER INFORMATION: ORIGINAL SIRPa-4-1BBL with C-terminal His Tag

<400> SEQUENCE: 1

Glu Glu Glu Leu Gln Val Ile Gln Pro Asp Lys Ser Val Leu Val Ala
1               5                   10                  15

Ala Gly Glu Thr Ala Thr Leu Arg Cys Thr Ala Thr Ser Leu Ile Pro
            20                  25                  30

Val Gly Pro Ile Gln Trp Phe Arg Gly Ala Gly Pro Gly Arg Glu Leu
        35                  40                  45

Ile Tyr Asn Gln Lys Glu Gly His Phe Pro Arg Val Thr Thr Val Ser
    50                  55                  60
```

```
Asp Leu Thr Lys Arg Asn Asn Met Asp Phe Ser Ile Arg Ile Gly Asn
 65                  70                  75                  80

Ile Thr Pro Ala Asp Ala Gly Thr Tyr Tyr Cys Val Lys Phe Arg Lys
                 85                  90                  95

Gly Ser Pro Asp Asp Val Glu Phe Lys Ser Gly Ala Gly Thr Glu Leu
                100                 105                 110

Ser Val Arg Ala Lys Pro Ser Ala Pro Val Val Ser Gly Pro Ala Ala
            115                 120                 125

Arg Ala Thr Pro Gln His Thr Val Ser Phe Thr Cys Glu Ser His Gly
            130                 135                 140

Phe Ser Pro Arg Asp Ile Thr Leu Lys Trp Phe Lys Asn Gly Asn Glu
145                 150                 155                 160

Leu Ser Asp Phe Gln Thr Asn Val Asp Pro Val Gly Glu Ser Val Ser
                165                 170                 175

Tyr Ser Ile His Ser Thr Ala Lys Val Val Leu Thr Arg Glu Asp Val
                180                 185                 190

His Ser Gln Val Ile Cys Glu Val Ala His Val Thr Leu Gln Gly Asp
            195                 200                 205

Pro Leu Arg Gly Thr Ala Asn Leu Ser Glu Thr Ile Arg Val Pro Pro
            210                 215                 220

Thr Leu Glu Val Thr Gln Gln Pro Val Arg Ala Glu Asn Gln Val Asn
225                 230                 235                 240

Val Thr Cys Gln Val Arg Lys Phe Tyr Pro Gln Arg Leu Gln Leu Thr
                245                 250                 255

Trp Leu Glu Asn Gly Asn Val Ser Arg Thr Glu Thr Ala Ser Thr Val
                260                 265                 270

Thr Glu Asn Lys Asp Gly Thr Tyr Asn Trp Met Ser Trp Leu Leu Val
            275                 280                 285

Asn Val Ser Ala His Arg Asp Asp Val Lys Leu Thr Cys Gln Val Glu
            290                 295                 300

His Asp Gly Gln Pro Ala Val Ser Lys Ser His Asp Leu Lys Val Ser
305                 310                 315                 320

Ala His Pro Lys Glu Gln Gly Ser Asn Thr Ala Ala Glu Asn Thr Gly
                325                 330                 335

Ser Asn Glu Arg Asn Ile Tyr Gly Ala Cys Pro Trp Ala Val Ser Gly
            340                 345                 350

Ala Arg Ala Ser Pro Gly Ser Ala Ala Ser Pro Arg Leu Arg Glu Gly
            355                 360                 365

Pro Glu Leu Ser Pro Asp Asp Pro Ala Gly Leu Leu Asp Leu Arg Gln
            370                 375                 380

Gly Met Phe Ala Gln Leu Val Ala Gln Asn Val Leu Leu Ile Asp Gly
385                 390                 395                 400

Pro Leu Ser Trp Tyr Ser Asp Pro Gly Leu Ala Gly Val Ser Leu Thr
                405                 410                 415

Gly Gly Leu Ser Tyr Lys Glu Asp Thr Lys Glu Leu Val Val Ala Lys
            420                 425                 430

Ala Gly Val Tyr Tyr Val Phe Phe Gln Leu Glu Leu Arg Arg Val Val
            435                 440                 445

Ala Gly Glu Gly Ser Gly Ser Val Ser Leu Ala Leu His Leu Gln Pro
            450                 455                 460

Leu Arg Ser Ala Ala Gly Ala Ala Ala Leu Ala Leu Thr Val Asp Leu
465                 470                 475                 480
```

```
Pro Pro Ala Ser Ser Glu Ala Arg Asn Ser Ala Phe Gly Phe Gln Gly
            485                 490                 495

Arg Leu Leu His Leu Ser Ala Gly Gln Arg Leu Gly Val His Leu His
        500                 505                 510

Thr Glu Ala Arg Ala Arg His Ala Trp Gln Leu Thr Gln Gly Ala Thr
        515                 520                 525

Val Leu Gly Leu Phe Arg Val Thr Pro Glu Ile Pro Ala Gly Leu Pro
        530                 535                 540

Ser Pro Arg Ser Glu His His His His His His
545             550                 555

<210> SEQ ID NO 2
<211> LENGTH: 343
<212> TYPE: PRT
<213> ORGANISM: Artificial sequence
<220> FEATURE:
<223> OTHER INFORMATION: ORIGINAL SIRPa DOMAIN

<400> SEQUENCE: 2

Glu Glu Glu Leu Gln Val Ile Gln Pro Asp Lys Ser Val Leu Val Ala
1               5                   10                  15

Ala Gly Glu Thr Ala Thr Leu Arg Cys Thr Ala Thr Ser Leu Ile Pro
            20                  25                  30

Val Gly Pro Ile Gln Trp Phe Arg Gly Ala Gly Pro Gly Arg Glu Leu
        35                  40                  45

Ile Tyr Asn Gln Lys Glu Gly His Phe Pro Arg Val Thr Thr Val Ser
    50                  55                  60

Asp Leu Thr Lys Arg Asn Asn Met Asp Phe Ser Ile Arg Ile Gly Asn
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Ala Pro Val Val Ser Gly Pro Ala Ala
        115                 120                 125

Arg Ala Thr Pro Gln His Thr Val Ser Phe Thr Cys Glu Ser His Gly
    130                 135                 140

Phe Ser Pro Arg Asp Ile Thr Leu Lys Trp Phe Lys Asn Gly Asn Glu
145                 150                 155                 160

Leu Ser Asp Phe Gln Thr Asn Val Asp Pro Val Gly Glu Ser Val Ser
                165                 170                 175

Tyr Ser Ile His Ser Thr Ala Lys Val Val Leu Thr Arg Glu Asp Val
            180                 185                 190

His Ser Gln Val Ile Cys Glu Val Ala His Val Thr Leu Gln Gly Asp
        195                 200                 205

Pro Leu Arg Gly Thr Ala Asn Leu Ser Glu Thr Ile Arg Val Pro Pro
    210                 215                 220

Thr Leu Glu Val Thr Gln Gln Pro Val Arg Ala Glu Asn Gln Val Asn
225                 230                 235                 240

Val Thr Cys Gln Val Arg Lys Phe Tyr Pro Gln Arg Leu Gln Leu Thr
                245                 250                 255

Trp Leu Glu Asn Gly Asn Val Ser Arg Thr Glu Thr Ala Ser Thr Val
            260                 265                 270

Thr Glu Asn Lys Asp Gly Thr Tyr Asn Trp Met Ser Trp Leu Leu Val
        275                 280                 285
```

```
Asn Val Ser Ala His Arg Asp Asp Val Lys Leu Thr Cys Gln Val Glu
        290                 295                 300
His Asp Gly Gln Pro Ala Val Ser Lys Ser His Asp Leu Lys Val Ser
305                 310                 315                 320
Ala His Pro Lys Glu Gln Gly Ser Asn Thr Ala Ala Glu Asn Thr Gly
                325                 330                 335
Ser Asn Glu Arg Asn Ile Tyr
            340
```

<210> SEQ ID NO 3
<211> LENGTH: 205
<212> TYPE: PRT
<213> ORGANISM: Artificial sequence
<220> FEATURE:
<223> OTHER INFORMATION: ORIGINAL 4-1BBL DOMAIN

<400> SEQUENCE: 3

```
Ala Cys Pro Trp Ala Val Ser Gly Ala Arg Ala Ser Pro Gly Ser Ala
1               5                   10                  15
Ala Ser Pro Arg Leu Arg Glu Gly Pro Glu Leu Ser Pro Asp Asp Pro
            20                  25                  30
Ala Gly Leu Leu Asp Leu Arg Gln Gly Met Phe Ala Gln Leu Val Ala
        35                  40                  45
Gln Asn Val Leu Leu Ile Asp Gly Pro Leu Ser Trp Tyr Ser Asp Pro
    50                  55                  60
Gly Leu Ala Gly Val Ser Leu Thr Gly Gly Leu Ser Tyr Lys Glu Asp
65                  70                  75                  80
Thr Lys Glu Leu Val Val Ala Lys Ala Gly Val Tyr Tyr Val Phe Phe
                85                  90                  95
Gln Leu Glu Leu Arg Arg Val Val Ala Gly Glu Gly Ser Gly Ser Val
            100                 105                 110
Ser Leu Ala Leu His Leu Gln Pro Leu Arg Ser Ala Ala Gly Ala Ala
        115                 120                 125
Ala Leu Ala Leu Thr Val Asp Leu Pro Pro Ala Ser Ser Glu Ala Arg
    130                 135                 140
Asn Ser Ala Phe Gly Phe Gln Gly Arg Leu Leu His Leu Ser Ala Gly
145                 150                 155                 160
Gln Arg Leu Gly Val His Leu His Thr Glu Ala Arg Ala Arg His Ala
                165                 170                 175
Trp Gln Leu Thr Gln Gly Ala Thr Val Leu Gly Leu Phe Arg Val Thr
            180                 185                 190
Pro Glu Ile Pro Ala Gly Leu Pro Ser Pro Arg Ser Glu
        195                 200                 205
```

<210> SEQ ID NO 4
<211> LENGTH: 19
<212> TYPE: PRT
<213> ORGANISM: Artificial sequence
<220> FEATURE:
<223> OTHER INFORMATION: SIGNAL PEPTIDE

<400> SEQUENCE: 4

```
Met Gly Trp Ser Cys Ile Ile Leu Phe Leu Val Ala Thr Ala Thr Gly
1               5                   10                  15
Val His Ser
```

<210> SEQ ID NO 5
<211> LENGTH: 549

```
<212> TYPE: PRT
<213> ORGANISM: Artificial sequence
<220> FEATURE:
<223> OTHER INFORMATION: ORIGINAL SIRPa-4-1BBL without His Tag

<400> SEQUENCE: 5
```

| | | | | | | | | | | | | | | |
|---|---|---|---|---|---|---|---|---|---|---|---|---|---|---|
| Glu | Glu | Glu | Leu | Gln | Val | Ile | Gln | Pro | Asp | Lys | Ser | Val | Leu | Val | Ala |
| 1 | | | | 5 | | | | | 10 | | | | | 15 | |

Ala Gly Glu Thr Ala Thr Leu Arg Cys Thr Ala Thr Ser Leu Ile Pro
            20                  25                  30

Val Gly Pro Ile Gln Trp Phe Arg Gly Ala Gly Pro Gly Arg Glu Leu
            35                  40                  45

Ile Tyr Asn Gln Lys Glu Gly His Phe Pro Arg Val Thr Thr Val Ser
 50                  55                  60

Asp Leu Thr Lys Arg Asn Asn Met Asp Phe Ser Ile Arg Ile Gly Asn
 65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Ala Pro Val Val Ser Gly Pro Ala Ala
            115                 120                 125

Arg Ala Thr Pro Gln His Thr Val Ser Phe Thr Cys Glu Ser His Gly
130                 135                 140

Phe Ser Pro Arg Asp Ile Thr Leu Lys Trp Phe Lys Asn Gly Asn Glu
145                 150                 155                 160

Leu Ser Asp Phe Gln Thr Asn Val Asp Pro Val Gly Glu Ser Val Ser
                165                 170                 175

Tyr Ser Ile His Ser Thr Ala Lys Val Val Leu Thr Arg Glu Asp Val
            180                 185                 190

His Ser Gln Val Ile Cys Glu Val Ala His Val Thr Leu Gln Gly Asp
            195                 200                 205

Pro Leu Arg Gly Thr Ala Asn Leu Ser Glu Thr Ile Arg Val Pro Pro
210                 215                 220

Thr Leu Glu Val Thr Gln Gln Pro Val Arg Ala Glu Asn Gln Val Asn
225                 230                 235                 240

Val Thr Cys Gln Val Arg Lys Phe Tyr Pro Gln Arg Leu Gln Leu Thr
                245                 250                 255

Trp Leu Glu Asn Gly Asn Val Ser Arg Thr Glu Thr Ala Ser Thr Val
                260                 265                 270

Thr Glu Asn Lys Asp Gly Thr Tyr Asn Trp Met Ser Trp Leu Leu Val
            275                 280                 285

Asn Val Ser Ala His Arg Asp Asp Val Lys Leu Thr Cys Gln Val Glu
290                 295                 300

His Asp Gly Gln Pro Ala Val Ser Lys Ser His Asp Leu Lys Val Ser
305                 310                 315                 320

Ala His Pro Lys Glu Gln Gly Ser Asn Thr Ala Ala Glu Asn Thr Gly
                325                 330                 335

Ser Asn Glu Arg Asn Ile Tyr Gly Ala Cys Pro Trp Ala Val Ser Gly
            340                 345                 350

Ala Arg Ala Ser Pro Gly Ser Ala Ala Ser Pro Arg Leu Arg Glu Gly
            355                 360                 365

Pro Glu Leu Ser Pro Asp Asp Pro Ala Gly Leu Leu Asp Leu Arg Gln
            370                 375                 380

```
Gly Met Phe Ala Gln Leu Val Ala Gln Asn Val Leu Ile Asp Gly
385                 390                 395                 400

Pro Leu Ser Trp Tyr Ser Asp Pro Gly Leu Ala Gly Val Ser Leu Thr
            405                 410                 415

Gly Gly Leu Ser Tyr Lys Glu Asp Thr Lys Glu Leu Val Val Ala Lys
            420                 425                 430

Ala Gly Val Tyr Tyr Val Phe Phe Gln Leu Glu Leu Arg Arg Val Val
            435                 440                 445

Ala Gly Glu Gly Ser Gly Ser Val Ser Leu Ala Leu His Leu Gln Pro
        450                 455                 460

Leu Arg Ser Ala Ala Gly Ala Ala Ala Leu Ala Leu Thr Val Asp Leu
465                 470                 475                 480

Pro Pro Ala Ser Ser Glu Ala Arg Asn Ser Ala Phe Gly Phe Gln Gly
                485                 490                 495

Arg Leu Leu His Leu Ser Ala Gly Gln Arg Leu Gly Val His Leu His
                500                 505                 510

Thr Glu Ala Arg Ala Arg His Ala Trp Gln Leu Thr Gln Gly Ala Thr
            515                 520                 525

Val Leu Gly Leu Phe Arg Val Thr Pro Glu Ile Pro Ala Gly Leu Pro
530                 535                 540

Ser Pro Arg Ser Glu
545
```

```
<210> SEQ ID NO 6
<211> LENGTH: 14
<212> TYPE: PRT
<213> ORGANISM: Artificial sequence
<220> FEATURE:
<223> OTHER INFORMATION: partial sequence of the n-terminal of 4-1BBL
      domain

<400> SEQUENCE: 6

Ala Cys Pro Trp Ala Val Ser Gly Ala Arg Ala Ser Pro Gly
1               5                   10

<210> SEQ ID NO 7
<211> LENGTH: 6
<212> TYPE: PRT
<213> ORGANISM: Artificial sequence
<220> FEATURE:
<223> OTHER INFORMATION: partial sequence of the n-terminal of 4-1BBL
      domain

<400> SEQUENCE: 7

Ala Cys Pro Trp Ala Val
1               5

<210> SEQ ID NO 8
<211> LENGTH: 10
<212> TYPE: PRT
<213> ORGANISM: Artificial sequence
<220> FEATURE:
<223> OTHER INFORMATION: partial sequence of the C-terminal of SIRP-
      alpha

<400> SEQUENCE: 8

Thr Glu Leu Ser Val Arg Ala Lys Pro Ser
1               5                   10

<210> SEQ ID NO 9
<211> LENGTH: 25
<212> TYPE: PRT
```

-continued

```
<213> ORGANISM: Artificial sequence
<220> FEATURE:
<223> OTHER INFORMATION: partial sequence of SIRP-alpha

<400> SEQUENCE: 9

Val Ser Ala His Pro Lys Glu Gln Gly Ser Asn Thr Ala Ala Glu Asn
1               5                   10                  15

Thr Gly Ser Asn Glu Arg Asn Ile Tyr
            20                  25

<210> SEQ ID NO 10
<211> LENGTH: 30
<212> TYPE: PRT
<213> ORGANISM: Artificial sequence
<220> FEATURE:
<223> OTHER INFORMATION: partial sequence of the 4-1BB-L

<400> SEQUENCE: 10

Ala Cys Pro Trp Ala Val Ser Gly Ala Arg Ala Ser Pro Gly Ser Ala
1               5                   10                  15

Ala Ser Pro Arg Leu Arg Glu Gly Pro Glu Leu Ser Pro Asp
            20                  25                  30

<210> SEQ ID NO 11
<211> LENGTH: 543
<212> TYPE: PRT
<213> ORGANISM: Artificial sequence
<220> FEATURE:
<223> OTHER INFORMATION: DSP107_var1 without His Tag

<400> SEQUENCE: 11

Glu Glu Glu Leu Gln Val Ile Gln Pro Asp Lys Ser Val Leu Val Ala
1               5                   10                  15

Ala Gly Glu Thr Ala Thr Leu Arg Cys Thr Ala Thr Ser Leu Ile Pro
            20                  25                  30

Val Gly Pro Ile Gln Trp Phe Arg Gly Ala Gly Pro Gly Arg Glu Leu
        35                  40                  45

Ile Tyr Asn Gln Lys Glu Gly His Phe Pro Arg Val Thr Thr Val Ser
    50                  55                  60

Asp Leu Thr Lys Arg Asn Asn Met Asp Phe Ser Ile Arg Ile Gly Asn
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Ala Pro Val Val Ser Gly Pro Ala Ala
        115                 120                 125

Arg Ala Thr Pro Gln His Thr Val Ser Phe Thr Cys Glu Ser His Gly
    130                 135                 140

Phe Ser Pro Arg Asp Ile Thr Leu Lys Trp Phe Lys Asn Gly Asn Glu
145                 150                 155                 160

Leu Ser Asp Phe Gln Thr Asn Val Asp Pro Val Gly Glu Ser Val Ser
                165                 170                 175

Tyr Ser Ile His Ser Thr Ala Lys Val Val Leu Thr Arg Glu Asp Val
            180                 185                 190

His Ser Gln Val Ile Cys Glu Val Ala His Val Thr Leu Gln Gly Asp
        195                 200                 205

Pro Leu Arg Gly Thr Ala Asn Leu Ser Glu Thr Ile Arg Val Pro Pro
    210                 215                 220
```

Thr Leu Glu Val Thr Gln Gln Pro Val Arg Ala Glu Asn Gln Val Asn
225                 230                 235                 240

Val Thr Cys Gln Val Arg Lys Phe Tyr Pro Gln Arg Leu Gln Leu Thr
                245                 250                 255

Trp Leu Glu Asn Gly Asn Val Ser Arg Thr Glu Thr Ala Ser Thr Val
                260                 265                 270

Thr Glu Asn Lys Asp Gly Thr Tyr Asn Trp Met Ser Trp Leu Leu Val
            275                 280                 285

Asn Val Ser Ala His Arg Asp Asp Val Lys Leu Thr Cys Gln Val Glu
        290                 295                 300

His Asp Gly Gln Pro Ala Val Ser Lys Ser His Asp Leu Lys Val Ser
305                 310                 315                 320

Ala His Pro Lys Glu Gln Gly Ser Asn Thr Ala Ala Glu Asn Thr Gly
                325                 330                 335

Ser Asn Glu Arg Asn Ile Tyr Gly Ser Gly Ala Arg Ala Ser Pro Gly
                340                 345                 350

Ser Ala Ala Ser Pro Arg Leu Arg Glu Gly Pro Glu Leu Ser Pro Asp
            355                 360                 365

Asp Pro Ala Gly Leu Leu Asp Leu Arg Gln Gly Met Phe Ala Gln Leu
        370                 375                 380

Val Ala Gln Asn Val Leu Leu Ile Asp Gly Pro Leu Ser Trp Tyr Ser
385                 390                 395                 400

Asp Pro Gly Leu Ala Gly Val Ser Leu Thr Gly Gly Leu Ser Tyr Lys
                405                 410                 415

Glu Asp Thr Lys Glu Leu Val Val Lys Ala Gly Val Tyr Tyr Val
                420                 425                 430

Phe Phe Gln Leu Glu Leu Arg Arg Val Val Ala Gly Glu Gly Ser Gly
            435                 440                 445

Ser Val Ser Leu Ala Leu His Leu Gln Pro Leu Arg Ser Ala Ala Gly
450                 455                 460

Ala Ala Ala Leu Ala Leu Thr Val Asp Leu Pro Pro Ala Ser Ser Glu
465                 470                 475                 480

Ala Arg Asn Ser Ala Phe Gly Phe Gln Gly Arg Leu Leu His Leu Ser
                485                 490                 495

Ala Gly Gln Arg Leu Gly Val His Leu His Thr Glu Ala Arg Ala Arg
            500                 505                 510

His Ala Trp Gln Leu Thr Gln Gly Ala Thr Val Leu Gly Leu Phe Arg
        515                 520                 525

Val Thr Pro Glu Ile Pro Ala Gly Leu Pro Ser Pro Arg Ser Glu
530                 535                 540

<210> SEQ ID NO 12
<211> LENGTH: 549
<212> TYPE: PRT
<213> ORGANISM: Artificial sequence
<220> FEATURE:
<223> OTHER INFORMATION: DSP107_var1 with His Tag

<400> SEQUENCE: 12

Glu Glu Glu Leu Gln Val Ile Gln Pro Asp Lys Ser Val Leu Val Ala
1               5                   10                  15

Ala Gly Glu Thr Ala Thr Leu Arg Cys Thr Ala Thr Ser Leu Ile Pro
                20                  25                  30

Val Gly Pro Ile Gln Trp Phe Arg Gly Ala Gly Pro Gly Arg Glu Leu
            35                  40                  45

```
Ile Tyr Asn Gln Lys Glu Gly His Phe Pro Arg Val Thr Val Ser
 50                  55                  60

Asp Leu Thr Lys Arg Asn Asn Met Asp Phe Ser Ile Arg Ile Gly Asn
 65                  70                  75                  80

Ile Thr Pro Ala Asp Ala Gly Thr Tyr Tyr Cys Val Lys Phe Arg Lys
                 85                  90                  95

Gly Ser Pro Asp Asp Val Glu Phe Lys Ser Gly Ala Gly Thr Glu Leu
                100                 105                 110

Ser Val Arg Ala Lys Pro Ser Ala Pro Val Val Ser Gly Pro Ala Ala
            115                 120                 125

Arg Ala Thr Pro Gln His Thr Val Ser Phe Thr Cys Glu Ser His Gly
130                 135                 140

Phe Ser Pro Arg Asp Ile Thr Leu Lys Trp Phe Lys Asn Gly Asn Glu
145                 150                 155                 160

Leu Ser Asp Phe Gln Thr Asn Val Asp Pro Val Gly Glu Ser Val Ser
                165                 170                 175

Tyr Ser Ile His Ser Thr Ala Lys Val Val Leu Thr Arg Glu Asp Val
                180                 185                 190

His Ser Gln Val Ile Cys Glu Val Ala His Val Thr Leu Gln Gly Asp
            195                 200                 205

Pro Leu Arg Gly Thr Ala Asn Leu Ser Glu Thr Ile Arg Val Pro Pro
210                 215                 220

Thr Leu Glu Val Thr Gln Gln Pro Val Arg Ala Glu Asn Gln Val Asn
225                 230                 235                 240

Val Thr Cys Gln Val Arg Lys Phe Tyr Pro Gln Arg Leu Gln Leu Thr
                245                 250                 255

Trp Leu Glu Asn Gly Asn Val Ser Arg Thr Glu Thr Ala Ser Thr Val
                260                 265                 270

Thr Glu Asn Lys Asp Gly Thr Tyr Asn Trp Met Ser Trp Leu Leu Val
            275                 280                 285

Asn Val Ser Ala His Arg Asp Asp Val Lys Leu Thr Cys Gln Val Glu
290                 295                 300

His Asp Gly Gln Pro Ala Val Ser Lys Ser His Asp Leu Lys Val Ser
305                 310                 315                 320

Ala His Pro Lys Glu Gln Gly Ser Asn Thr Ala Ala Glu Asn Thr Gly
                325                 330                 335

Ser Asn Glu Arg Asn Ile Tyr Gly Ser Gly Ala Arg Ala Ser Pro Gly
                340                 345                 350

Ser Ala Ala Ser Pro Arg Leu Arg Glu Gly Pro Glu Leu Ser Pro Asp
            355                 360                 365

Asp Pro Ala Gly Leu Leu Asp Leu Arg Gln Gly Met Phe Ala Gln Leu
370                 375                 380

Val Ala Gln Asn Val Leu Leu Ile Asp Gly Pro Leu Ser Trp Tyr Ser
385                 390                 395                 400

Asp Pro Gly Leu Ala Gly Val Ser Leu Thr Gly Leu Ser Tyr Lys
                405                 410                 415

Glu Asp Thr Lys Glu Leu Val Val Ala Lys Ala Gly Val Tyr Tyr Val
            420                 425                 430

Phe Phe Gln Leu Glu Leu Arg Arg Val Val Ala Gly Glu Gly Ser Gly
                435                 440                 445

Ser Val Ser Leu Ala Leu His Leu Gln Pro Leu Arg Ser Ala Ala Gly
450                 455                 460
```

```
Ala Ala Ala Leu Ala Leu Thr Val Asp Leu Pro Ala Ser Ser Glu
465                 470                 475                 480

Ala Arg Asn Ser Ala Phe Gly Phe Gln Gly Arg Leu Leu His Leu Ser
                485                 490                 495

Ala Gly Gln Arg Leu Gly Val His Leu His Thr Glu Ala Arg Ala Arg
                500                 505                 510

His Ala Trp Gln Leu Thr Gln Gly Ala Thr Val Leu Gly Leu Phe Arg
                515                 520                 525

Val Thr Pro Glu Ile Pro Ala Gly Leu Pro Ser Pro Arg Ser Glu His
                530                 535                 540

His His His His His
545
```

<210> SEQ ID NO 13
<211> LENGTH: 535
<212> TYPE: PRT
<213> ORGANISM: Artificial sequence
<220> FEATURE:
<223> OTHER INFORMATION: DSP107_var2 without His Tag

<400> SEQUENCE: 13

```
Glu Glu Glu Leu Gln Val Ile Gln Pro Asp Lys Ser Val Leu Val Ala
1               5                   10                  15

Ala Gly Glu Thr Ala Thr Leu Arg Cys Thr Ala Thr Ser Leu Ile Pro
                20                  25                  30

Val Gly Pro Ile Gln Trp Phe Arg Gly Ala Gly Pro Gly Arg Glu Leu
                35                  40                  45

Ile Tyr Asn Gln Lys Glu Gly His Phe Pro Arg Val Thr Thr Val Ser
50                  55                  60

Asp Leu Thr Lys Arg Asn Asn Met Asp Phe Ser Ile Arg Ile Gly Asn
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
                100                 105                 110

Ser Val Arg Ala Lys Pro Ser Ala Pro Val Val Ser Gly Pro Ala Ala
                115                 120                 125

Arg Ala Thr Pro Gln His Thr Val Ser Phe Thr Cys Glu Ser His Gly
130                 135                 140

Phe Ser Pro Arg Asp Ile Thr Leu Lys Trp Phe Lys Asn Gly Asn Glu
145                 150                 155                 160

Leu Ser Asp Phe Gln Thr Asn Val Asp Pro Val Gly Glu Ser Val Ser
                165                 170                 175

Tyr Ser Ile His Ser Thr Ala Lys Val Val Leu Thr Arg Glu Asp Val
                180                 185                 190

His Ser Gln Val Ile Cys Glu Val Ala His Val Thr Leu Gln Gly Asp
                195                 200                 205

Pro Leu Arg Gly Thr Ala Asn Leu Ser Glu Thr Ile Arg Val Pro Pro
                210                 215                 220

Thr Leu Glu Val Thr Gln Gln Pro Val Arg Ala Glu Asn Gln Val Asn
225                 230                 235                 240

Val Thr Cys Gln Val Arg Lys Phe Tyr Pro Gln Arg Leu Gln Leu Thr
                245                 250                 255

Trp Leu Glu Asn Gly Asn Val Ser Arg Thr Glu Thr Ala Ser Thr Val
                260                 265                 270
```

Thr Glu Asn Lys Asp Gly Thr Tyr Asn Trp Met Ser Trp Leu Leu Val
          275                 280                 285

Asn Val Ser Ala His Arg Asp Asp Val Lys Leu Thr Cys Gln Val Glu
290                 295                 300

His Asp Gly Gln Pro Ala Val Ser Lys Ser His Asp Leu Lys Val Ser
305                 310                 315                 320

Ala His Pro Lys Glu Gln Gly Ser Asn Thr Ala Ala Glu Asn Thr Gly
              325                 330                 335

Ser Asn Glu Arg Asn Ile Tyr Gly Ser Ala Ala Ser Pro Arg Leu Arg
              340                 345                 350

Glu Gly Pro Glu Leu Ser Pro Asp Asp Pro Ala Gly Leu Leu Asp Leu
          355                 360                 365

Arg Gln Gly Met Phe Ala Gln Leu Val Ala Gln Asn Val Leu Leu Ile
          370                 375                 380

Asp Gly Pro Leu Ser Trp Tyr Ser Asp Pro Gly Leu Ala Gly Val Ser
385                 390                 395                 400

Leu Thr Gly Gly Leu Ser Tyr Lys Glu Asp Thr Lys Glu Leu Val Val
              405                 410                 415

Ala Lys Ala Gly Val Tyr Tyr Val Phe Phe Gln Leu Glu Leu Arg Arg
              420                 425                 430

Val Val Ala Gly Glu Gly Ser Gly Ser Val Ser Leu Ala Leu His Leu
          435                 440                 445

Gln Pro Leu Arg Ser Ala Ala Gly Ala Ala Ala Leu Ala Leu Thr Val
          450                 455                 460

Asp Leu Pro Pro Ala Ser Ser Glu Ala Arg Asn Ser Ala Phe Gly Phe
465                 470                 475                 480

Gln Gly Arg Leu Leu His Leu Ser Ala Gly Gln Arg Leu Gly Val His
              485                 490                 495

Leu His Thr Glu Ala Arg Ala Arg His Ala Trp Gln Leu Thr Gln Gly
              500                 505                 510

Ala Thr Val Leu Gly Leu Phe Arg Val Thr Pro Glu Ile Pro Ala Gly
          515                 520                 525

Leu Pro Ser Pro Arg Ser Glu
          530                 535

<210> SEQ ID NO 14
<211> LENGTH: 541
<212> TYPE: PRT
<213> ORGANISM: Artificial sequence
<220> FEATURE:
<223> OTHER INFORMATION: DSP107_var2 with His Tag

<400> SEQUENCE: 14

Glu Glu Glu Leu Gln Val Ile Gln Pro Asp Lys Ser Val Leu Val Ala
1               5                   10                  15

Ala Gly Glu Thr Ala Thr Leu Arg Cys Thr Ala Thr Ser Leu Ile Pro
              20                  25                  30

Val Gly Pro Ile Gln Trp Phe Arg Gly Ala Gly Pro Gly Arg Glu Leu
          35                  40                  45

Ile Tyr Asn Gln Lys Glu Gly His Phe Pro Arg Val Thr Thr Val Ser
  50                  55                  60

Asp Leu Thr Lys Arg Asn Asn Met Asp Phe Ser Ile Arg Ile Gly Asn
65                  70                  75                  80

Ile Thr Pro Ala Asp Ala Gly Thr Tyr Tyr Cys Val Lys Phe Arg Lys
              85                  90                  95

-continued

```
Gly Ser Pro Asp Asp Val Glu Phe Lys Ser Gly Ala Gly Thr Glu Leu
            100                 105                 110

Ser Val Arg Ala Lys Pro Ser Ala Pro Val Val Ser Gly Pro Ala Ala
        115                 120                 125

Arg Ala Thr Pro Gln His Thr Val Ser Phe Thr Cys Glu Ser His Gly
    130                 135                 140

Phe Ser Pro Arg Asp Ile Thr Leu Lys Trp Phe Lys Asn Gly Asn Glu
145                 150                 155                 160

Leu Ser Asp Phe Gln Thr Asn Val Asp Pro Val Gly Glu Ser Val Ser
                165                 170                 175

Tyr Ser Ile His Ser Thr Ala Lys Val Val Leu Thr Arg Glu Asp Val
            180                 185                 190

His Ser Gln Val Ile Cys Glu Val Ala His Val Thr Leu Gln Gly Asp
        195                 200                 205

Pro Leu Arg Gly Thr Ala Asn Leu Ser Glu Thr Ile Arg Val Pro Pro
    210                 215                 220

Thr Leu Glu Val Thr Gln Gln Pro Val Arg Ala Glu Asn Gln Val Asn
225                 230                 235                 240

Val Thr Cys Gln Val Arg Lys Phe Tyr Pro Gln Arg Leu Gln Leu Thr
                245                 250                 255

Trp Leu Glu Asn Gly Asn Val Ser Arg Thr Glu Thr Ala Ser Thr Val
            260                 265                 270

Thr Glu Asn Lys Asp Gly Thr Tyr Asn Trp Met Ser Trp Leu Leu Val
        275                 280                 285

Asn Val Ser Ala His Arg Asp Asp Val Lys Leu Thr Cys Gln Val Glu
    290                 295                 300

His Asp Gly Gln Pro Ala Val Ser Lys Ser His Asp Leu Lys Val Ser
305                 310                 315                 320

Ala His Pro Lys Glu Gln Gly Ser Asn Thr Ala Ala Glu Asn Thr Gly
                325                 330                 335

Ser Asn Glu Arg Asn Ile Tyr Gly Ser Ala Ala Ser Pro Arg Leu Arg
            340                 345                 350

Glu Gly Pro Glu Leu Ser Pro Asp Asp Pro Ala Gly Leu Leu Asp Leu
        355                 360                 365

Arg Gln Gly Met Phe Ala Gln Leu Val Ala Gln Asn Val Leu Leu Ile
    370                 375                 380

Asp Gly Pro Leu Ser Trp Tyr Ser Asp Pro Gly Leu Ala Gly Val Ser
385                 390                 395                 400

Leu Thr Gly Gly Leu Ser Tyr Lys Glu Asp Thr Lys Glu Leu Val Val
                405                 410                 415

Ala Lys Ala Gly Val Tyr Tyr Val Phe Phe Gln Leu Glu Leu Arg Arg
            420                 425                 430

Val Val Ala Gly Glu Gly Ser Gly Ser Val Ser Leu Ala Leu His Leu
        435                 440                 445

Gln Pro Leu Arg Ser Ala Ala Gly Ala Ala Ala Leu Ala Leu Thr Val
    450                 455                 460

Asp Leu Pro Pro Ala Ser Ser Glu Ala Arg Asn Ser Ala Phe Gly Phe
465                 470                 475                 480

Gln Gly Arg Leu Leu His Leu Ser Ala Gly Gln Arg Leu Gly Val His
                485                 490                 495

Leu His Thr Glu Ala Arg Ala Arg His Ala Trp Gln Leu Thr Gln Gly
            500                 505                 510

Ala Thr Val Leu Gly Leu Phe Arg Val Thr Pro Glu Ile Pro Ala Gly
```

```
                515                 520                 525
Leu Pro Ser Pro Arg Ser Glu His His His His His
    530                 535                 540

<210> SEQ ID NO 15
<211> LENGTH: 322
<212> TYPE: PRT
<213> ORGANISM: Artificial sequence
<220> FEATURE:
<223> OTHER INFORMATION: DSP107_var3 without His Tag

<400> SEQUENCE: 15

Glu Glu Glu Leu Gln Val Ile Gln Pro Asp Lys Ser Val Leu Val Ala
1               5                   10                  15

Ala Gly Glu Thr Ala Thr Leu Arg Cys Thr Ala Thr Ser Leu Ile Pro
            20                  25                  30

Val Gly Pro Ile Gln Trp Phe Arg Gly Ala Gly Pro Gly Arg Glu Leu
        35                  40                  45

Ile Tyr Asn Gln Lys Glu Gly His Phe Pro Arg Val Thr Thr Val Ser
    50                  55                  60

Asp Leu Thr Lys Arg Asn Asn Met Asp Phe Ser Ile Arg Ile Gly Asn
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Gly Ala Cys Pro Trp Ala Val Ser Gly Ala Arg Ala
        115                 120                 125

Ser Pro Gly Ser Ala Ala Ser Pro Arg Leu Arg Glu Gly Pro Glu Leu
    130                 135                 140

Ser Pro Asp Asp Pro Ala Gly Leu Leu Asp Leu Arg Gln Gly Met Phe
145                 150                 155                 160

Ala Gln Leu Val Ala Gln Asn Val Leu Leu Ile Asp Gly Pro Leu Ser
                165                 170                 175

Trp Tyr Ser Asp Pro Gly Leu Ala Gly Val Ser Leu Thr Gly Gly Leu
            180                 185                 190

Ser Tyr Lys Glu Asp Thr Lys Glu Leu Val Val Ala Lys Ala Gly Val
        195                 200                 205

Tyr Tyr Val Phe Phe Gln Leu Glu Leu Arg Arg Val Val Ala Gly Glu
    210                 215                 220

Gly Ser Gly Ser Val Ser Leu Ala Leu His Leu Gln Pro Leu Arg Ser
225                 230                 235                 240

Ala Ala Gly Ala Ala Ala Leu Ala Leu Thr Val Asp Leu Pro Pro Ala
                245                 250                 255

Ser Ser Glu Ala Arg Asn Ser Ala Phe Gly Phe Gln Gly Arg Leu Leu
            260                 265                 270

His Leu Ser Ala Gly Gln Arg Leu Gly Val His Leu His Thr Glu Ala
        275                 280                 285

Arg Ala Arg His Ala Trp Gln Leu Thr Gln Gly Ala Thr Val Leu Gly
    290                 295                 300

Leu Phe Arg Val Thr Pro Glu Ile Pro Ala Gly Leu Pro Ser Pro Arg
305                 310                 315                 320

Ser Glu

<210> SEQ ID NO 16
```

```
<211> LENGTH: 316
<212> TYPE: PRT
<213> ORGANISM: Artificial sequence
<220> FEATURE:
<223> OTHER INFORMATION: DSP107_var3.1 without His Tag

<400> SEQUENCE: 16

Glu Glu Glu Leu Gln Val Ile Gln Pro Asp Lys Ser Val Leu Val Ala
1               5                   10                  15

Ala Gly Glu Thr Ala Thr Leu Arg Cys Thr Ala Thr Ser Leu Ile Pro
            20                  25                  30

Val Gly Pro Ile Gln Trp Phe Arg Gly Ala Gly Pro Gly Arg Glu Leu
        35                  40                  45

Ile Tyr Asn Gln Lys Glu Gly His Phe Pro Arg Val Thr Thr Val Ser
    50                  55                  60

Asp Leu Thr Lys Arg Asn Asn Met Asp Phe Ser Ile Arg Ile Gly Asn
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Gly Ser Gly Ala Arg Ala Ser Pro Gly Ser Ala Ala
        115                 120                 125

Ser Pro Arg Leu Arg Glu Gly Pro Glu Leu Ser Pro Asp Asp Pro Ala
    130                 135                 140

Gly Leu Leu Asp Leu Arg Gln Gly Met Phe Ala Gln Leu Val Ala Gln
145                 150                 155                 160

Asn Val Leu Leu Ile Asp Gly Pro Leu Ser Trp Tyr Ser Asp Pro Gly
                165                 170                 175

Leu Ala Gly Val Ser Leu Thr Gly Gly Leu Ser Tyr Lys Glu Asp Thr
            180                 185                 190

Lys Glu Leu Val Val Ala Lys Ala Gly Val Tyr Tyr Val Phe Phe Gln
        195                 200                 205

Leu Glu Leu Arg Arg Val Val Ala Gly Glu Gly Ser Gly Ser Val Ser
    210                 215                 220

Leu Ala Leu His Leu Gln Pro Leu Arg Ser Ala Ala Gly Ala Ala Ala
225                 230                 235                 240

Leu Ala Leu Thr Val Asp Leu Pro Pro Ala Ser Ser Glu Ala Arg Asn
                245                 250                 255

Ser Ala Phe Gly Phe Gln Gly Arg Leu Leu His Leu Ser Ala Gly Gln
            260                 265                 270

Arg Leu Gly Val His Leu His Thr Glu Ala Arg Ala Arg His Ala Trp
        275                 280                 285

Gln Leu Thr Gln Gly Ala Thr Val Leu Gly Leu Phe Arg Val Thr Pro
    290                 295                 300

Glu Ile Pro Ala Gly Leu Pro Ser Pro Arg Ser Glu
305                 310                 315

<210> SEQ ID NO 17
<211> LENGTH: 322
<212> TYPE: PRT
<213> ORGANISM: Artificial sequence
<220> FEATURE:
<223> OTHER INFORMATION: DSP107_var3.1 with His Tag

<400> SEQUENCE: 17

Glu Glu Glu Leu Gln Val Ile Gln Pro Asp Lys Ser Val Leu Val Ala
```

```
               1               5                  10                 15
           Ala Gly Glu Thr Ala Thr Leu Arg Cys Thr Ala Thr Ser Leu Ile Pro
                          20                 25                 30

Val Gly Pro Ile Gln Trp Phe Arg Gly Ala Gly Pro Gly Arg Glu Leu
                          35                 40                 45

Ile Tyr Asn Gln Lys Glu Gly His Phe Pro Arg Val Thr Thr Val Ser
            50                 55                 60

Asp Leu Thr Lys Arg Asn Asn Met Asp Phe Ser Ile Arg Ile Gly Asn
            65                 70                 75                 80

Ile Thr Pro Ala Asp Ala Gly Thr Tyr Tyr Cys Val Lys Phe Arg Lys
                          85                 90                 95

Gly Ser Pro Asp Asp Val Glu Phe Lys Ser Gly Ala Gly Thr Glu Leu
                         100                105                110

Ser Val Arg Ala Gly Ser Gly Ala Arg Ala Ser Pro Gly Ser Ala Ala
                         115                120                125

Ser Pro Arg Leu Arg Glu Gly Pro Glu Leu Ser Pro Asp Asp Pro Ala
                         130                135                140

Gly Leu Leu Asp Leu Arg Gln Gly Met Phe Ala Gln Leu Val Ala Gln
           145                150                155                160

Asn Val Leu Leu Ile Asp Gly Pro Leu Ser Trp Tyr Ser Asp Pro Gly
                         165                170                175

Leu Ala Gly Val Ser Leu Thr Gly Gly Leu Ser Tyr Lys Glu Asp Thr
                         180                185                190

Lys Glu Leu Val Val Ala Lys Ala Gly Val Tyr Tyr Val Phe Phe Gln
                         195                200                205

Leu Glu Leu Arg Arg Val Val Ala Gly Glu Gly Ser Gly Ser Val Ser
                         210                215                220

Leu Ala Leu His Leu Gln Pro Leu Arg Ser Ala Gly Ala Ala Ala
           225                230                235                240

Leu Ala Leu Thr Val Asp Leu Pro Pro Ala Ser Ser Glu Ala Arg Asn
                         245                250                255

Ser Ala Phe Gly Phe Gln Gly Arg Leu Leu His Leu Ser Ala Gly Gln
                         260                265                270

Arg Leu Gly Val His Leu His Thr Glu Ala Arg Ala Arg His Ala Trp
                         275                280                285

Gln Leu Thr Gln Gly Ala Thr Val Leu Gly Leu Phe Arg Val Thr Pro
                         290                295                300

Glu Ile Pro Ala Gly Leu Pro Ser Pro Arg Ser Glu His His His His
           305                310                315                320

His His

<210> SEQ ID NO 18
           <211> LENGTH: 543
           <212> TYPE: PRT
           <213> ORGANISM: Artificial sequence
           <220> FEATURE:
           <223> OTHER INFORMATION: DSP107_Var1Mut without His Tag

<400> SEQUENCE: 18

Glu Glu Glu Ile Gln Val Ile Gln Pro Asp Lys Ser Val Leu Val Ala
            1              5                  10                 15

Ala Gly Glu Thr Ala Thr Leu Arg Cys Thr Ile Thr Ser Leu Ile Pro
                          20                 25                 30

Val Gly Pro Ile Gln Trp Phe Arg Gly Ala Gly Pro Gly Arg Val Leu
                          35                 40                 45
```

```
Ile Tyr Asn Gln Lys Glu Gly His Phe Pro Arg Val Thr Val Ser
 50                  55                  60

Asp Leu Thr Lys Arg Asn Asn Met Asp Phe Ser Ile Arg Ile Gly Asn
 65                      70                  75                  80

Ile Thr Pro Ala Asp Ala Gly Thr Tyr Tyr Cys Ile Lys Phe Arg Lys
                     85                  90                  95

Gly Ser Pro Asp Asp Val Glu Phe Lys Ser Gly Ala Gly Thr Glu Leu
                100                 105                 110

Ser Val Arg Ala Lys Pro Ser Ala Pro Val Val Ser Gly Pro Ala Ala
            115                 120                 125

Arg Ala Thr Pro Gln His Thr Val Ser Phe Thr Cys Glu Ser His Gly
130                 135                 140

Phe Ser Pro Arg Asp Ile Thr Leu Lys Trp Phe Lys Asn Gly Asn Glu
145                 150                 155                 160

Leu Ser Asp Phe Gln Thr Asn Val Asp Pro Val Gly Glu Ser Val Ser
                165                 170                 175

Tyr Ser Ile His Ser Thr Ala Lys Val Val Leu Thr Arg Glu Asp Val
                180                 185                 190

His Ser Gln Val Ile Cys Glu Val Ala His Val Thr Leu Gln Gly Asp
            195                 200                 205

Pro Leu Arg Gly Thr Ala Asn Leu Ser Glu Thr Ile Arg Val Pro Pro
210                 215                 220

Thr Leu Glu Val Thr Gln Gln Pro Val Arg Ala Glu Asn Gln Val Asn
225                 230                 235                 240

Val Thr Cys Gln Val Arg Lys Phe Tyr Pro Gln Arg Leu Gln Leu Thr
                245                 250                 255

Trp Leu Glu Asn Gly Asn Val Ser Arg Thr Glu Thr Ala Ser Thr Val
                260                 265                 270

Thr Glu Asn Lys Asp Gly Thr Tyr Asn Trp Met Ser Trp Leu Leu Val
                275                 280                 285

Asn Val Ser Ala His Arg Asp Asp Val Lys Leu Thr Cys Gln Val Glu
290                 295                 300

His Asp Gly Gln Pro Ala Val Ser Lys Ser His Asp Leu Lys Val Ser
305                 310                 315                 320

Ala His Pro Lys Glu Gln Gly Ser Asn Thr Ala Ala Glu Asn Thr Gly
                325                 330                 335

Ser Asn Glu Arg Asn Ile Tyr Gly Ser Gly Ala Arg Ala Ser Pro Gly
                340                 345                 350

Ser Ala Ala Ser Pro Arg Leu Arg Glu Gly Pro Glu Leu Ser Pro Asp
            355                 360                 365

Asp Pro Ala Gly Leu Leu Asp Leu Arg Gln Gly Met Phe Ala Gln Leu
370                 375                 380

Val Ala Gln Asn Val Leu Leu Ile Asp Gly Pro Leu Ser Trp Tyr Ser
385                 390                 395                 400

Asp Pro Gly Leu Ala Gly Val Ser Leu Thr Gly Gly Leu Ser Tyr Lys
                405                 410                 415

Glu Asp Thr Lys Glu Leu Val Val Ala Lys Ala Gly Val Tyr Tyr Val
                420                 425                 430

Phe Phe Gln Leu Glu Leu Arg Arg Val Val Ala Gly Glu Gly Ser Gly
                435                 440                 445

Ser Val Ser Leu Ala Leu His Leu Gln Pro Leu Arg Ser Ala Ala Gly
450                 455                 460
```

```
Ala Ala Ala Leu Ala Leu Thr Val Asp Leu Pro Pro Ala Ser Ser Glu
465                 470                 475                 480

Ala Arg Asn Ser Ala Phe Gly Phe Gln Gly Arg Leu Leu His Leu Ser
            485                 490                 495

Ala Gly Gln Arg Leu Gly Val His Leu His Thr Glu Ala Arg Ala Arg
        500                 505                 510

His Ala Trp Gln Leu Thr Gln Gly Ala Thr Val Leu Gly Leu Phe Arg
        515                 520                 525

Val Thr Pro Glu Ile Pro Ala Gly Leu Pro Ser Pro Arg Ser Glu
    530                 535                 540

<210> SEQ ID NO 19
<211> LENGTH: 535
<212> TYPE: PRT
<213> ORGANISM: Artificial sequence
<220> FEATURE:
<223> OTHER INFORMATION: DSP107_Var2Mut without His Tag

<400> SEQUENCE: 19

Glu Glu Glu Ile Gln Val Ile Gln Pro Asp Lys Ser Val Leu Val Ala
1               5                   10                  15

Ala Gly Glu Thr Ala Thr Leu Arg Cys Thr Ile Thr Ser Leu Ile Pro
            20                  25                  30

Val Gly Pro Ile Gln Trp Phe Arg Gly Ala Gly Pro Gly Arg Val Leu
        35                  40                  45

Ile Tyr Asn Gln Lys Glu Gly His Phe Pro Arg Val Thr Thr Val Ser
    50                  55                  60

Asp Leu Thr Lys Arg Asn Asn Met Asp Phe Ser Ile Arg Ile Gly Asn
65                  70                  75                  80

Ile Thr Pro Ala Asp Ala Gly Thr Tyr Tyr Cys Ile Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Ala Pro Val Val Ser Gly Pro Ala Ala
        115                 120                 125

Arg Ala Thr Pro Gln His Thr Val Ser Phe Thr Cys Glu Ser His Gly
    130                 135                 140

Phe Ser Pro Arg Asp Ile Thr Leu Lys Trp Phe Lys Asn Gly Asn Glu
145                 150                 155                 160

Leu Ser Asp Phe Gln Thr Asn Val Asp Pro Val Gly Glu Ser Val Ser
                165                 170                 175

Tyr Ser Ile His Ser Thr Ala Lys Val Val Leu Thr Arg Glu Asp Val
            180                 185                 190

His Ser Gln Val Ile Cys Glu Val Ala His Val Thr Leu Gln Gly Asp
        195                 200                 205

Pro Leu Arg Gly Thr Ala Asn Leu Ser Glu Thr Ile Arg Val Pro Pro
    210                 215                 220

Thr Leu Glu Val Thr Gln Gln Pro Val Arg Ala Glu Asn Gln Val Asn
225                 230                 235                 240

Val Thr Cys Gln Val Arg Lys Phe Tyr Pro Gln Arg Leu Gln Leu Thr
                245                 250                 255

Trp Leu Glu Asn Gly Asn Val Ser Arg Thr Glu Thr Ala Ser Thr Val
            260                 265                 270

Thr Glu Asn Lys Asp Gly Thr Tyr Asn Trp Met Ser Trp Leu Leu Val
    275                 280                 285
```

```
Asn Val Ser Ala His Arg Asp Asp Val Lys Leu Thr Cys Gln Val Glu
    290                 295                 300

His Asp Gly Gln Pro Ala Val Ser Lys Ser His Asp Leu Lys Val Ser
305                 310                 315                 320

Ala His Pro Lys Glu Gln Gly Ser Asn Thr Ala Ala Glu Asn Thr Gly
                325                 330                 335

Ser Asn Glu Arg Asn Ile Tyr Gly Ser Ala Ala Ser Pro Arg Leu Arg
            340                 345                 350

Glu Gly Pro Glu Leu Ser Pro Asp Asp Pro Ala Gly Leu Leu Asp Leu
        355                 360                 365

Arg Gln Gly Met Phe Ala Gln Leu Val Ala Gln Asn Val Leu Leu Ile
370                 375                 380

Asp Gly Pro Leu Ser Trp Tyr Ser Asp Pro Gly Leu Ala Gly Val Ser
385                 390                 395                 400

Leu Thr Gly Gly Leu Ser Tyr Lys Glu Asp Thr Lys Glu Leu Val Val
                405                 410                 415

Ala Lys Ala Gly Val Tyr Tyr Val Phe Phe Gln Leu Glu Leu Arg Arg
            420                 425                 430

Val Val Ala Gly Glu Gly Ser Gly Ser Val Ser Leu Ala Leu His Leu
        435                 440                 445

Gln Pro Leu Arg Ser Ala Ala Gly Ala Ala Leu Ala Leu Thr Val
450                 455                 460

Asp Leu Pro Pro Ala Ser Ser Glu Ala Arg Asn Ser Ala Phe Gly Phe
465                 470                 475                 480

Gln Gly Arg Leu Leu His Leu Ser Ala Gly Gln Arg Leu Gly Val His
                485                 490                 495

Leu His Thr Glu Ala Arg Ala Arg His Ala Trp Gln Leu Thr Gln Gly
            500                 505                 510

Ala Thr Val Leu Gly Leu Phe Arg Val Thr Pro Glu Ile Pro Ala Gly
        515                 520                 525

Leu Pro Ser Pro Arg Ser Glu
530                 535

<210> SEQ ID NO 20
<211> LENGTH: 322
<212> TYPE: PRT
<213> ORGANISM: Artificial sequence
<220> FEATURE:
<223> OTHER INFORMATION: DSP107_Var3Mut without His Tag

<400> SEQUENCE: 20

Glu Glu Glu Ile Gln Val Ile Gln Pro Asp Lys Ser Val Leu Val Ala
1               5                   10                  15

Ala Gly Glu Thr Ala Thr Leu Arg Cys Thr Ile Thr Ser Leu Ile Pro
            20                  25                  30

Val Gly Pro Ile Gln Trp Phe Arg Gly Ala Gly Pro Gly Arg Val Leu
        35                  40                  45

Ile Tyr Asn Gln Lys Glu Gly His Phe Pro Arg Val Thr Thr Val Ser
    50                  55                  60

Asp Leu Thr Lys Arg Asn Asn Met Asp Phe Ser Ile Arg Ile Gly Asn
65              70                  75                  80

Ile Thr Pro Ala Asp Ala Gly Thr Tyr Tyr Cys Ile Lys Phe Arg Lys
                85                  90                  95

Gly Ser Pro Asp Asp Val Glu Phe Lys Ser Gly Ala Gly Thr Glu Leu
            100                 105                 110
```

-continued

```
Ser Val Arg Ala Gly Ala Cys Pro Trp Ala Val Ser Gly Ala Arg Ala
            115                 120                 125
Ser Pro Gly Ser Ala Ala Ser Pro Arg Leu Arg Glu Gly Pro Glu Leu
        130                 135                 140
Ser Pro Asp Asp Pro Ala Gly Leu Leu Asp Leu Arg Gln Gly Met Phe
145                 150                 155                 160
Ala Gln Leu Val Ala Gln Asn Val Leu Ile Asp Gly Pro Leu Ser
                165                 170                 175
Trp Tyr Ser Asp Pro Gly Leu Ala Gly Val Ser Leu Thr Gly Gly Leu
            180                 185                 190
Ser Tyr Lys Glu Asp Thr Lys Glu Leu Val Val Ala Lys Ala Gly Val
        195                 200                 205
Tyr Tyr Val Phe Phe Gln Leu Glu Leu Arg Arg Val Val Ala Gly Glu
    210                 215                 220
Gly Ser Gly Ser Val Ser Leu Ala Leu His Leu Gln Pro Leu Arg Ser
225                 230                 235                 240
Ala Ala Gly Ala Ala Ala Leu Ala Leu Thr Val Asp Leu Pro Pro Ala
                245                 250                 255
Ser Ser Glu Ala Arg Asn Ser Ala Phe Gly Phe Gln Gly Arg Leu Leu
            260                 265                 270
His Leu Ser Ala Gly Gln Arg Leu Gly Val His Leu His Thr Glu Ala
        275                 280                 285
Arg Ala Arg His Ala Trp Gln Leu Thr Gln Gly Ala Thr Val Leu Gly
    290                 295                 300
Leu Phe Arg Val Thr Pro Glu Ile Pro Ala Gly Leu Pro Ser Pro Arg
305                 310                 315                 320
Ser Glu
```

<210> SEQ ID NO 21
<211> LENGTH: 315
<212> TYPE: PRT
<213> ORGANISM: Artificial sequence
<220> FEATURE:
<223> OTHER INFORMATION: DSP170_Var3.1Mut without His tag

<400> SEQUENCE: 21

```
Glu Glu Glu Ile Gln Val Ile Gln Pro Asp Lys Ser Val Leu Val Ala
1               5                   10                  15
Ala Gly Glu Thr Ala Thr Leu Arg Cys Thr Ile Thr Ser Leu Ile Pro
                20                  25                  30
Val Gly Pro Ile Gln Trp Phe Arg Gly Ala Gly Pro Gly Arg Val Leu
            35                  40                  45
Ile Tyr Asn Gln Lys Glu Gly His Phe Pro Arg Val Thr Thr Val Ser
        50                  55                  60
Asp Leu Thr Lys Arg Asn Asn Met Asp Phe Ser Ile Arg Ile Gly Asn
65                  70                  75                  80
Ile Thr Pro Ala Asp Ala Gly Thr Tyr Tyr Cys Ile Lys Phe Arg Lys
                85                  90                  95
Gly Ser Pro Asp Asp Val Glu Phe Lys Ser Gly Ala Gly Thr Glu Leu
            100                 105                 110
Ser Val Arg Ala Ser Gly Ala Arg Ala Ser Pro Gly Ser Ala Ala Ser
        115                 120                 125
Pro Arg Leu Arg Glu Gly Pro Glu Leu Ser Pro Asp Asp Pro Ala Gly
    130                 135                 140
Leu Leu Asp Leu Arg Gln Gly Met Phe Ala Gln Leu Val Ala Gln Asn
```

```
                145                 150                 155                 160
Val Leu Leu Ile Asp Gly Pro Leu Ser Trp Tyr Ser Asp Pro Gly Leu
                    165                 170                 175

Ala Gly Val Ser Leu Thr Gly Gly Leu Ser Tyr Lys Glu Asp Thr Lys
                    180                 185                 190

Glu Leu Val Val Ala Lys Ala Gly Val Tyr Tyr Val Phe Gln Leu
                    195                 200                 205

Glu Leu Arg Arg Val Val Ala Gly Glu Gly Ser Gly Ser Val Ser Leu
                    210                 215                 220

Ala Leu His Leu Gln Pro Leu Arg Ser Ala Ala Gly Ala Ala Ala Leu
225                 230                 235                 240

Ala Leu Thr Val Asp Leu Pro Pro Ala Ser Ser Glu Ala Arg Asn Ser
                    245                 250                 255

Ala Phe Gly Phe Gln Gly Arg Leu Leu His Leu Ser Ala Gly Gln Arg
                    260                 265                 270

Leu Gly Val His Leu His Thr Glu Ala Arg Ala Arg His Ala Trp Gln
                    275                 280                 285

Leu Thr Gln Gly Ala Thr Val Leu Gly Leu Phe Arg Val Thr Pro Glu
                    290                 295                 300

Ile Pro Ala Gly Leu Pro Ser Pro Arg Ser Glu
305                 310                 315

<210> SEQ ID NO 22
<211> LENGTH: 199
<212> TYPE: PRT
<213> ORGANISM: Artificial sequence
<220> FEATURE:
<223> OTHER INFORMATION: 199 amino acid sequence of 4-1BBL segment

<400> SEQUENCE: 22

Ser Gly Ala Arg Ala Ser Pro Gly Ser Ala Ala Ser Pro Arg Leu Arg
1               5                   10                  15

Glu Gly Pro Glu Leu Ser Pro Asp Asp Pro Ala Gly Leu Leu Asp Leu
                    20                  25                  30

Arg Gln Gly Met Phe Ala Gln Leu Val Ala Gln Asn Val Leu Leu Ile
                    35                  40                  45

Asp Gly Pro Leu Ser Trp Tyr Ser Asp Pro Gly Leu Ala Gly Val Ser
            50                  55                  60

Leu Thr Gly Gly Leu Ser Tyr Lys Glu Asp Thr Lys Glu Leu Val Val
65                  70                  75                  80

Ala Lys Ala Gly Val Tyr Tyr Val Phe Phe Gln Leu Glu Leu Arg Arg
                    85                  90                  95

Val Val Ala Gly Glu Gly Ser Gly Ser Val Ser Leu Ala Leu His Leu
                    100                 105                 110

Gln Pro Leu Arg Ser Ala Ala Gly Ala Ala Ala Leu Ala Leu Thr Val
            115                 120                 125

Asp Leu Pro Pro Ala Ser Ser Glu Ala Arg Asn Ser Ala Phe Gly Phe
            130                 135                 140

Gln Gly Arg Leu Leu His Leu Ser Ala Gly Gln Arg Leu Gly Val His
145                 150                 155                 160

Leu His Thr Glu Ala Arg Ala Arg His Ala Trp Gln Leu Thr Gln Gly
                    165                 170                 175

Ala Thr Val Leu Gly Leu Phe Arg Val Thr Pro Glu Ile Pro Ala Gly
                    180                 185                 190

Leu Pro Ser Pro Arg Ser Glu
```

```
                195

<210> SEQ ID NO 23
<211> LENGTH: 191
<212> TYPE: PRT
<213> ORGANISM: Artificial sequence
<220> FEATURE:
<223> OTHER INFORMATION: 191 amino acid sequence of 4-1BBL segment

<400> SEQUENCE: 23

Ser Ala Ala Ser Pro Arg Leu Arg Glu Gly Pro Glu Leu Ser Pro Asp
1               5                   10                  15

Asp Pro Ala Gly Leu Leu Asp Leu Arg Gln Gly Met Phe Ala Gln Leu
            20                  25                  30

Val Ala Gln Asn Val Leu Leu Ile Asp Gly Pro Leu Ser Trp Tyr Ser
        35                  40                  45

Asp Pro Gly Leu Ala Gly Val Ser Leu Thr Gly Gly Leu Ser Tyr Lys
    50                  55                  60

Glu Asp Thr Lys Glu Leu Val Val Ala Lys Ala Gly Val Tyr Tyr Val
65                  70                  75                  80

Phe Phe Gln Leu Glu Leu Arg Arg Val Val Ala Gly Glu Gly Ser Gly
                85                  90                  95

Ser Val Ser Leu Ala Leu His Leu Gln Pro Leu Arg Ser Ala Ala Gly
            100                 105                 110

Ala Ala Ala Leu Ala Leu Thr Val Asp Leu Pro Pro Ala Ser Ser Glu
        115                 120                 125

Ala Arg Asn Ser Ala Phe Gly Phe Gln Gly Arg Leu Leu His Leu Ser
    130                 135                 140

Ala Gly Gln Arg Leu Gly Val His Leu His Thr Glu Ala Arg Ala Arg
145                 150                 155                 160

His Ala Trp Gln Leu Thr Gln Gly Ala Thr Val Leu Gly Leu Phe Arg
                165                 170                 175

Val Thr Pro Glu Ile Pro Ala Gly Leu Pro Ser Pro Arg Ser Glu
            180                 185                 190

<210> SEQ ID NO 24
<211> LENGTH: 116
<212> TYPE: PRT
<213> ORGANISM: Artificial sequence
<220> FEATURE:
<223> OTHER INFORMATION: 116 amino acid sequence of SIRPa segment

<400> SEQUENCE: 24

Glu Glu Glu Leu Gln Val Ile Gln Pro Asp Lys Ser Val Leu Val Ala
1               5                   10                  15

Ala Gly Glu Thr Ala Thr Leu Arg Cys Thr Ala Thr Ser Leu Ile Pro
            20                  25                  30

Val Gly Pro Ile Gln Trp Phe Arg Gly Ala Gly Pro Gly Arg Glu Leu
        35                  40                  45

Ile Tyr Asn Gln Lys Glu Gly His Phe Pro Arg Val Thr Thr Val Ser
    50                  55                  60

Asp Leu Thr Lys Arg Asn Asn Met Asp Phe Ser Ile Arg Ile Gly Asn
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110
```

Ser Val Arg Ala
        115

<210> SEQ ID NO 25
<211> LENGTH: 343
<212> TYPE: PRT
<213> ORGANISM: Artificial sequence
<220> FEATURE:
<223> OTHER INFORMATION: 343 amino acids sequence of SIRPa with 4 point
      mutations

<400> SEQUENCE: 25

Glu Glu Glu Ile Gln Val Ile Gln Pro Asp Lys Ser Val Leu Val Ala
1               5                   10                  15

Ala Gly Glu Thr Ala Thr Leu Arg Cys Thr Ile Thr Ser Leu Ile Pro
            20                  25                  30

Val Gly Pro Ile Gln Trp Phe Arg Gly Ala Gly Pro Gly Arg Val Leu
        35                  40                  45

Ile Tyr Asn Gln Lys Glu Gly His Phe Pro Arg Val Thr Thr Val Ser
    50                  55                  60

Asp Leu Thr Lys Arg Asn Asn Met Asp Phe Ser Ile Arg Ile Gly Asn
65                  70                  75                  80

Ile Thr Pro Ala Asp Ala Gly Thr Tyr Tyr Cys Ile Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Ala Pro Val Val Ser Gly Pro Ala Ala
        115                 120                 125

Arg Ala Thr Pro Gln His Thr Val Ser Phe Thr Cys Glu Ser His Gly
    130                 135                 140

Phe Ser Pro Arg Asp Ile Thr Leu Lys Trp Phe Lys Asn Gly Asn Glu
145                 150                 155                 160

Leu Ser Asp Phe Gln Thr Asn Val Asp Pro Val Gly Glu Ser Val Ser
                165                 170                 175

Tyr Ser Ile His Ser Thr Ala Lys Val Val Leu Thr Arg Glu Asp Val
            180                 185                 190

His Ser Gln Val Ile Cys Glu Val Ala His Val Thr Leu Gln Gly Asp
        195                 200                 205

Pro Leu Arg Gly Thr Ala Asn Leu Ser Glu Thr Ile Arg Val Pro Pro
    210                 215                 220

Thr Leu Glu Val Thr Gln Gln Pro Val Arg Ala Glu Asn Gln Val Asn
225                 230                 235                 240

Val Thr Cys Gln Val Arg Lys Phe Tyr Pro Gln Arg Leu Gln Leu Thr
                245                 250                 255

Trp Leu Glu Asn Gly Asn Val Ser Arg Thr Glu Thr Ala Ser Thr Val
            260                 265                 270

Thr Glu Asn Lys Asp Gly Thr Tyr Asn Trp Met Ser Trp Leu Leu Val
        275                 280                 285

Asn Val Ser Ala His Arg Asp Asp Val Lys Leu Thr Cys Gln Val Glu
    290                 295                 300

His Asp Gly Gln Pro Ala Val Ser Lys Ser His Asp Leu Lys Val Ser
305                 310                 315                 320

Ala His Pro Lys Glu Gln Gly Ser Asn Thr Ala Ala Glu Asn Thr Gly
                325                 330                 335

Ser Asn Glu Arg Asn Ile Tyr
            340

```
<210> SEQ ID NO 26
<211> LENGTH: 116
<212> TYPE: PRT
<213> ORGANISM: Artificial sequence
<220> FEATURE:
<223> OTHER INFORMATION: 116 amino acids sequence of SIRPa with 4 point
      mutations

<400> SEQUENCE: 26

Glu Glu Glu Ile Gln Val Ile Gln Pro Asp Lys Ser Val Leu Val Ala
1               5                   10                  15

Ala Gly Glu Thr Ala Thr Leu Arg Cys Thr Ile Thr Ser Leu Ile Pro
            20                  25                  30

Val Gly Pro Ile Gln Trp Phe Arg Gly Ala Gly Pro Gly Arg Val Leu
        35                  40                  45

Ile Tyr Asn Gln Lys Glu Gly His Phe Pro Arg Val Thr Thr Val Ser
    50                  55                  60

Asp Leu Thr Lys Arg Asn Asn Met Asp Phe Ser Ile Arg Ile Gly Asn
65                  70                  75                  80

Ile Thr Pro Ala Asp Ala Gly Thr Tyr Tyr Cys Ile Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala
            115

<210> SEQ ID NO 27
<211> LENGTH: 197
<212> TYPE: PRT
<213> ORGANISM: Artificial sequence
<220> FEATURE:
<223> OTHER INFORMATION: 197 amino acid sequence of 4-1BBL segment

<400> SEQUENCE: 27

Ala Arg Ala Ser Pro Gly Ser Ala Ala Ser Pro Arg Leu Arg Glu Gly
1               5                   10                  15

Pro Glu Leu Ser Pro Asp Asp Pro Ala Gly Leu Leu Asp Leu Arg Gln
            20                  25                  30

Gly Met Phe Ala Gln Leu Val Ala Gln Asn Val Leu Leu Ile Asp Gly
        35                  40                  45

Pro Leu Ser Trp Tyr Ser Asp Pro Gly Leu Ala Gly Val Ser Leu Thr
    50                  55                  60

Gly Gly Leu Ser Tyr Lys Glu Asp Thr Lys Glu Leu Val Val Ala Lys
65                  70                  75                  80

Ala Gly Val Tyr Tyr Val Phe Phe Gln Leu Glu Leu Arg Arg Val Val
                85                  90                  95

Ala Gly Glu Gly Ser Gly Ser Val Ser Leu Ala Leu His Leu Gln Pro
            100                 105                 110

Leu Arg Ser Ala Ala Gly Ala Ala Ala Leu Ala Leu Thr Val Asp Leu
            115                 120                 125

Pro Pro Ala Ser Ser Glu Ala Arg Asn Ser Ala Phe Gly Phe Gln Gly
            130                 135                 140

Arg Leu Leu His Leu Ser Ala Gly Gln Arg Leu Gly Val His Leu His
145                 150                 155                 160

Thr Glu Ala Arg Ala Arg His Ala Trp Gln Leu Thr Gln Gly Ala Thr
                165                 170                 175
```

```
Val Leu Gly Leu Phe Arg Val Thr Pro Glu Ile Pro Ala Gly Leu Pro
            180                 185                 190

Ser Pro Arg Ser Glu
        195

<210> SEQ ID NO 28
<211> LENGTH: 185
<212> TYPE: PRT
<213> ORGANISM: Artificial sequence
<220> FEATURE:
<223> OTHER INFORMATION: 185 amino acid sequence of 4-1BBL segment

<400> SEQUENCE: 28

Leu Arg Glu Gly Pro Glu Leu Ser Pro Asp Asp Pro Ala Gly Leu Leu
1               5                   10                  15

Asp Leu Arg Gln Gly Met Phe Ala Gln Leu Val Ala Gln Asn Val Leu
            20                  25                  30

Leu Ile Asp Gly Pro Leu Ser Trp Tyr Ser Asp Pro Gly Leu Ala Gly
        35                  40                  45

Val Ser Leu Thr Gly Gly Leu Ser Tyr Lys Glu Asp Thr Lys Glu Leu
    50                  55                  60

Val Val Ala Lys Ala Gly Val Tyr Tyr Val Phe Phe Gln Leu Glu Leu
65                  70                  75                  80

Arg Arg Val Val Ala Gly Glu Gly Ser Gly Ser Val Ser Leu Ala Leu
                85                  90                  95

His Leu Gln Pro Leu Arg Ser Ala Ala Gly Ala Ala Ala Leu Ala Leu
            100                 105                 110

Thr Val Asp Leu Pro Pro Ala Ser Ser Glu Ala Arg Asn Ser Ala Phe
        115                 120                 125

Gly Phe Gln Gly Arg Leu Leu His Leu Ser Ala Gly Gln Arg Leu Gly
130                 135                 140

Val His Leu His Thr Glu Ala Arg Ala Arg His Ala Trp Gln Leu Thr
145                 150                 155                 160

Gln Gly Ala Thr Val Leu Gly Leu Phe Arg Val Thr Pro Glu Ile Pro
                165                 170                 175

Ala Gly Leu Pro Ser Pro Arg Ser Glu
            180                 185

<210> SEQ ID NO 29
<211> LENGTH: 504
<212> TYPE: PRT
<213> ORGANISM: Artificial sequence
<220> FEATURE:
<223> OTHER INFORMATION: amino acid sequence of full length SIRP

<400> SEQUENCE: 29

Met Glu Pro Ala Gly Pro Ala Pro Gly Arg Leu Gly Pro Leu Leu Cys
1               5                   10                  15

Leu Leu Leu Ala Ala Ser Cys Ala Trp Ser Gly Val Ala Gly Glu Glu
            20                  25                  30

Glu Leu Gln Val Ile Gln Pro Asp Lys Ser Val Leu Val Ala Ala Gly
        35                  40                  45

Glu Thr Ala Thr Leu Arg Cys Thr Ala Thr Ser Leu Ile Pro Val Gly
    50                  55                  60

Pro Ile Gln Trp Phe Arg Gly Ala Gly Pro Gly Arg Glu Leu Ile Tyr
65                  70                  75                  80

Asn Gln Lys Glu Gly His Phe Pro Arg Val Thr Thr Val Ser Asp Leu
                85                  90                  95
```

```
Thr Lys Arg Asn Asn Met Asp Phe Ser Ile Arg Ile Gly Asn Ile Thr
            100                 105                 110

Pro Ala Asp Ala Gly Thr Tyr Tyr Cys Val Lys Phe Arg Lys Gly Ser
        115                 120                 125

Pro Asp Asp Val Glu Phe Lys Ser Gly Ala Gly Thr Glu Leu Ser Val
        130                 135                 140

Arg Ala Lys Pro Ser Ala Pro Val Val Ser Gly Pro Ala Ala Arg Ala
145                 150                 155                 160

Thr Pro Gln His Thr Val Ser Phe Thr Cys Glu Ser His Gly Phe Ser
                165                 170                 175

Pro Arg Asp Ile Thr Leu Lys Trp Phe Lys Asn Gly Asn Glu Leu Ser
            180                 185                 190

Asp Phe Gln Thr Asn Val Asp Pro Val Gly Glu Ser Val Ser Tyr Ser
        195                 200                 205

Ile His Ser Thr Ala Lys Val Val Leu Thr Arg Glu Asp Val His Ser
210                 215                 220

Gln Val Ile Cys Glu Val Ala His Val Thr Leu Gln Gly Asp Pro Leu
225                 230                 235                 240

Arg Gly Thr Ala Asn Leu Ser Glu Thr Ile Arg Val Pro Pro Thr Leu
                245                 250                 255

Glu Val Thr Gln Gln Pro Val Arg Ala Glu Asn Gln Val Asn Val Thr
            260                 265                 270

Cys Gln Val Arg Lys Phe Tyr Pro Gln Arg Leu Gln Leu Thr Trp Leu
        275                 280                 285

Glu Asn Gly Asn Val Ser Arg Thr Glu Thr Ala Ser Thr Val Thr Glu
        290                 295                 300

Asn Lys Asp Gly Thr Tyr Asn Trp Met Ser Trp Leu Leu Val Asn Val
305                 310                 315                 320

Ser Ala His Arg Asp Asp Val Lys Leu Thr Cys Gln Val Glu His Asp
                325                 330                 335

Gly Gln Pro Ala Val Ser Lys Ser His Asp Leu Lys Val Ser Ala His
            340                 345                 350

Pro Lys Glu Gln Gly Ser Asn Thr Ala Ala Glu Asn Thr Gly Ser Asn
        355                 360                 365

Glu Arg Asn Ile Tyr Ile Val Val Gly Val Val Cys Thr Leu Leu Val
370                 375                 380

Ala Leu Leu Met Ala Ala Leu Tyr Leu Val Arg Ile Arg Gln Lys Lys
385                 390                 395                 400

Ala Gln Gly Ser Thr Ser Ser Thr Arg Leu His Glu Pro Glu Lys Asn
                405                 410                 415

Ala Arg Glu Ile Thr Gln Asp Thr Asn Asp Ile Thr Tyr Ala Asp Leu
            420                 425                 430

Asn Leu Pro Lys Gly Lys Lys Pro Ala Pro Gln Ala Ala Glu Pro Asn
        435                 440                 445

Asn His Thr Glu Tyr Ala Ser Ile Gln Thr Ser Pro Gln Pro Ala Ser
        450                 455                 460

Glu Asp Thr Leu Thr Tyr Ala Asp Leu Asp Met Val His Leu Asn Arg
465                 470                 475                 480

Thr Pro Lys Gln Pro Ala Pro Lys Pro Glu Pro Ser Phe Ser Glu Tyr
                485                 490                 495

Ala Ser Val Gln Val Pro Arg Lys
            500
```

<210> SEQ ID NO 30
<211> LENGTH: 1512
<212> TYPE: DNA
<213> ORGANISM: Artificial sequence
<220> FEATURE:
<223> OTHER INFORMATION: nucleic acid sequence of full length SIRP

<400> SEQUENCE: 30

```
atggagcccg ccggcccggc ccccggccgc ctcgggccgc tgctctgcct gctgctcgcc      60
gcgtcctgcg cctggtcagg agtggcgggt gaggaggagc tgcaggtgat tcagcctgac     120
aagtccgtat cagttgcagc tggagagtcg gccattctgc actgcactgt gacctccctg     180
atccctgtgg ggcccatcca gtggttcaga ggagctggac cagcccggga attaatctac     240
aatcaaaaag aaggccactt ccccccgggta caactgtttt cagagtccac aaagagagaa     300
aacatggact tttccatcag catcagtaac atcaccccag cagatgccgg cacctactac     360
tgtgtgaagt tccggaaagg agccctgac  acggagttta agtctggagc aggcactgag      420
ctgtctgtgc gtgccaaacc ctctgccccc gtggtatcgg ccctgcggc gagggccaca      480
cctcagcaca cagtgagctt cacctgcgag tcccacggct ctcacccag  agacatcacc      540
ctgaaatggt tcaaaaatgg gaatgagctc tcagacttcc agaccaacgt ggaccccgta      600
ggagagagcg tgtcctacag catccacagc acagccaagg tggtgctgac ccgcgaggac      660
gttcactctc aagtcatctg cgaggtggcc cacgtcacct gcagggggga ccctcttcgt      720
gggactgcca acttgtctga gaccatccga gttccaccca ccttggaggt tactcaacag      780
cccgtgaggg cagagaacca ggtgaatgtc acctgccagg tgaggaagtt ctaccccag       840
agactacagc tgacctggtt ggagaatgga aacgtgtccc ggacagaaac ggcctcaacc      900
gttacagaga caaggatgg  tacctacaac tggatgagct ggctcctggt gaatgtatct      960
gcccacaggg atgatgtgaa gctcacctgc caggtggagc atgacgggca gccagcggtc     1020
agcaaaagcc atgacctgaa ggtctcagcc caccccaagg agcagggctc aaataccgcc     1080
gctgagaaca ctggatctaa tgaacggaac atctatattg tggtgggtgt ggtgtgcacc     1140
ttgctggtgg ccctactgat ggcggccctc tacctcgtcc gaatcagaca gaagaaagcc     1200
cagggctcca cttcttctac aaggttgcat gagcccgaga gaatgccag  agaaataaca      1260
caggacacaa atgatatcac atatgcagac ctgaacctgc caaggggaa  gaagcctgct      1320
ccccaggctg cggagcccaa caaccacacg gagtatgcca gcattcagac cagcccgcag     1380
cccgcgtcgg aggacaccct cacctatgct gacctggaca tggtccacct caaccggacc     1440
cccaagcagc cggcccccaa gcctgagccg tccttctcag agtacgccag cgtccaggtc     1500
ccgaggaagt ga                                                         1512
```

<210> SEQ ID NO 31
<211> LENGTH: 1029
<212> TYPE: DNA
<213> ORGANISM: Artificial sequence
<220> FEATURE:
<223> OTHER INFORMATION: nucleic acid sequence encoding SEQ ID NO: 2

<400> SEQUENCE: 31

```
gaggaggagc tgcaggtgat tcagcctgac aagtccgtat cagttgcagc tggagagtcg      60
gccattctgc actgcactgt gacctccctg atccctgtgg ggcccatcca gtggttcaga     120
ggagctggac cagcccggga attaatctac aatcaaaaag aaggccactt ccccccgggta    180
acaactgtttt cagagtccac aaagagagaa aacatggact tttccatcag catcagtaac    240
```

```
atcacccag cagatgccgg cacctactac tgtgtgaagt tccggaaagg gagccctgac    300
acggagttta agtctggagc aggcactgag ctgtctgtgc gtgccaaacc ctctgccccc    360
gtggtatcgg gccctgcggc gagggccaca cctcagcaca cagtgagctt cacctgcgag    420
tcccacggct tctcacccag agacatcacc ctgaaatggt tcaaaaatgg aatgagctc    480 tcagacttcc agaccaacgt ggaccccgta ggagagagcg tgtcctacag catccacagc    540
acagccaagg tggtgctgac ccgcgaggac gttcactctc aagtcatctg cgaggtggcc    600
cacgtcacct tgcaggggga ccctcttcgt gggactgcca acttgtctga gaccatccga    660
gttccaccca ccttggaggt tactcaacag cccgtgaggg cagagaacca ggtgaatgtc    720
acctgccagg tgaggaagtt ctaccccag agactacagc tgacctggtt ggagaatgga    780
aacgtgtccc ggacagaaac ggcctcaacc gttacagaga acaaggatgg tacctacaac    840
tggatgagct ggctcctggt gaatgtatct gcccacaggg atgatgtgaa gctcacctgc    900
caggtggagc atgacgggca gccagcggtc agcaaaagcc atgacctgaa ggtctcagcc    960
cacccgaagg agcagggctc aaataccgcc gctgagaaca ctggatctaa tgaacggaac   1020
atctatatt                                                         1029
```

<210> SEQ ID NO 32
<211> LENGTH: 227
<212> TYPE: PRT
<213> ORGANISM: Artificial sequence
<220> FEATURE:
<223> OTHER INFORMATION: THE DELETED PART OF SEQ ID NO: 2 FOR GENERATION
      OF THE 116 AA VARIANT

<400> SEQUENCE: 32

```
Lys Pro Ser Ala Pro Val Val Ser Gly Pro Ala Ala Arg Ala Thr Pro
1               5                  10                  15

Gln His Thr Val Ser Phe Thr Cys Glu Ser His Gly Phe Ser Pro Arg
            20                  25                  30

Asp Ile Thr Leu Lys Trp Phe Lys Asn Gly Asn Glu Leu Ser Asp Phe
        35                  40                  45

Gln Thr Asn Val Asp Pro Val Gly Glu Ser Val Ser Tyr Ser Ile His
    50                  55                  60

Ser Thr Ala Lys Val Val Leu Thr Arg Glu Asp Val His Ser Gln Val
65                  70                  75                  80

Ile Cys Glu Val Ala His Val Thr Leu Gln Gly Asp Pro Leu Arg Gly
                85                  90                  95

Thr Ala Asn Leu Ser Glu Thr Ile Arg Val Pro Pro Thr Leu Glu Val
            100                 105                 110

Thr Gln Gln Pro Val Arg Ala Glu Asn Gln Val Asn Val Thr Cys Gln
        115                 120                 125

Val Arg Lys Phe Tyr Pro Gln Arg Leu Gln Leu Thr Trp Leu Glu Asn
    130                 135                 140

Gly Asn Val Ser Arg Thr Glu Thr Ala Ser Thr Val Thr Glu Asn Lys
145                 150                 155                 160

Asp Gly Thr Tyr Asn Trp Met Ser Trp Leu Leu Val Asn Val Ser Ala
                165                 170                 175

His Arg Asp Asp Val Lys Leu Thr Cys Gln Val Glu His Asp Gly Gln
            180                 185                 190

Pro Ala Val Ser Lys Ser His Asp Leu Lys Val Ser Ala His Pro Lys
        195                 200                 205
```

Glu Gln Gly Ser Asn Thr Ala Ala Glu Asn Thr Gly Ser Asn Glu Arg
    210                 215                 220

Asn Ile Tyr
225

<210> SEQ ID NO 33
<211> LENGTH: 348
<212> TYPE: DNA
<213> ORGANISM: Artificial sequence
<220> FEATURE:
<223> OTHER INFORMATION: nucleic acid sequence encoding SEQ ID NO: 24

<400> SEQUENCE: 33
gaagaggaac tgcaagtgat ccagcctgac aagtccgtgc tggtggctgc tggcgaaacc      60
gccacactga gatgtaccgc cacctctctg atccctgtgg gccctatcca gtggtttaga     120
ggcgctggac ctggcagaga gctgatctac aaccagaaag agggccactt tcctagagtg     180
accaccgtgt ccgacctgac caagcggaac aacatggact ctccatccg gatcggcaac     240 atcaccctg ctgatgccgg cacctactac tgcgtgaagt tccggaaggg ctcccctgac     300
gacgtcgagt ttaaatccgg cgctggcacc gaactgtccg tgcgagct                 348

<210> SEQ ID NO 34
<211> LENGTH: 348
<212> TYPE: DNA
<213> ORGANISM: Artificial sequence
<220> FEATURE:
<223> OTHER INFORMATION: nucleic acid sequence encoding SEQ ID NO: 26

<400> SEQUENCE: 34
gaagaggaaa tccaagtgat ccagcctgac aagtccgtgc tggtggctgc tggcgaaacc      60
gccacactga gatgtaccat cacctctctg atccctgtgg gccctatcca gtggtttaga     120
ggcgctggac ctggcagagt gctgatctac aaccagaaag agggccactt tcctagagtg     180
accaccgtgt ccgacctgac caagcggaac aacatggact ctccatccg gatcggcaac     240 atcaccctg ctgatgccgg cacctactac tgcatcaagt tccggaaggg ctcccctgac     300
gacgtcgagt ttaaatccgg cgctggcacc gaactgtccg tgcgagct                 348

<210> SEQ ID NO 35
<211> LENGTH: 1029
<212> TYPE: DNA
<213> ORGANISM: Artificial sequence
<220> FEATURE:
<223> OTHER INFORMATION: nucleic acid sequence encoding SEQ ID NO: 25

<400> SEQUENCE: 35
gaagaggaaa tccaagtgat ccagcctgac aagtccgtgc tggtggctgc tggcgaaacc      60
gccacactga gatgtaccat cacctctctg atccctgtgg gccctatcca gtggtttaga     120
ggcgctggac ctggcagagt gctgatctac aaccagaaag agggccactt tcctagagtg     180
accaccgtgt ccgacctgac caagcggaac aacatggact ctccatccg gatcggcaac     240 atcaccctg ctgatgccgg cacctactac tgcatcaagt tccggaaggg ctcccctgac     300
gacgtcgagt ttaaatccgg cgctggcacc gaactgtccg tgcgagctaa accttctgct     360
cccgtggtgt ctgcccctgc cgctagagct acacctcagc acaccgtgtc ttttacctgc     420
gagtcccacg gcttcagccc tagagacatc accctgaagt ggttcaagaa cggcaacgag     480
ctgtccgact ccagaccaa cgtggaccct gtggagagt ccgtgtccta ctccatccac     540
tctaccgcca aggtggtgct gacccgagag gacgtgcaca gccaagtgat ctgtgaagtg     600

```
gcccacgtga ccctccaggg cgatcctttg agaggcaccg ccaacctgtc cgagacaatc      660
agagtgcctc ctacactgga agtgacccag cagcctgtgc gggccgagaa tcaagtgaac      720
gtgacctgcc aagtgcggaa gttctaccct cagagactgc agctgacctg gctggaaaac      780
ggcaatgtgt ccagaaccga dacagcctcc accgtgaccg agaacaagga tggcacctac      840
aattggatgt cctggctgct cgtgaacgtg tccgctcaca gagatgacgt gaagctgaca      900
tgccaggtgg aacacgatgg ccagcctgcc gtgtctaagt cccacgacct gaaagtgtct      960
gctcacccca agagcaggg ctccaatacc gccgctgaga caccggctc caacgagaga      1020 aacatctac                                                              1029
```

<210> SEQ ID NO 36
<211> LENGTH: 254
<212> TYPE: PRT
<213> ORGANISM: Artificial sequence
<220> FEATURE:
<223> OTHER INFORMATION: amino acid sequence of full length 4-1BBL

<400> SEQUENCE: 36

```
Met Glu Tyr Ala Ser Asp Ala Ser Leu Asp Pro Glu Ala Pro Trp Pro
1               5                   10                  15

Pro Ala Pro Arg Ala Arg Ala Cys Arg Val Leu Pro Trp Ala Leu Val
                20                  25                  30

Ala Gly Leu Leu Leu Leu Leu Leu Ala Ala Ala Cys Ala Val Phe
            35                  40                  45

Leu Ala Cys Pro Trp Ala Val Ser Gly Ala Arg Ala Ser Pro Gly Ser
50                  55                  60

Ala Ala Ser Pro Arg Leu Arg Glu Gly Pro Glu Leu Ser Pro Asp Asp
65                  70                  75                  80

Pro Ala Gly Leu Leu Asp Leu Arg Gln Gly Met Phe Ala Gln Leu Val
                85                  90                  95

Ala Gln Asn Val Leu Leu Ile Asp Gly Pro Leu Ser Trp Tyr Ser Asp
                100                 105                 110

Pro Gly Leu Ala Gly Val Ser Leu Thr Gly Gly Leu Ser Tyr Lys Glu
            115                 120                 125

Asp Thr Lys Glu Leu Val Val Ala Lys Ala Gly Val Tyr Tyr Val Phe
        130                 135                 140

Phe Gln Leu Glu Leu Arg Arg Val Val Ala Gly Glu Gly Ser Gly Ser
145                 150                 155                 160

Val Ser Leu Ala Leu His Leu Gln Pro Leu Arg Ser Ala Ala Gly Ala
                165                 170                 175

Ala Ala Leu Ala Leu Thr Val Asp Leu Pro Pro Ala Ser Ser Glu Ala
                180                 185                 190

Arg Asn Ser Ala Phe Gly Phe Gln Gly Arg Leu Leu His Leu Ser Ala
            195                 200                 205

Gly Gln Arg Leu Gly Val His Leu His Thr Glu Ala Arg Ala Arg His
        210                 215                 220

Ala Trp Gln Leu Thr Gln Gly Ala Thr Val Leu Gly Leu Phe Arg Val
225                 230                 235                 240

Thr Pro Glu Ile Pro Ala Gly Leu Pro Ser Pro Arg Ser Glu
                245                 250
```

<210> SEQ ID NO 37
<211> LENGTH: 765
<212> TYPE: DNA

```
<213> ORGANISM: Artificial sequence
<220> FEATURE:
<223> OTHER INFORMATION: nucleic acid sequence of full length 4-1BBL

<400> SEQUENCE: 37
atggaatacg cctctgacgc ttcactggac cccgaagccc cgtggcctcc cgcgccccgc    60
gctcgcgcct gccgcgtact gccttgggcc ctggtcgcgg ggctgctgct gctgctgctg   120
ctcgctgccg cctgcgccgt cttcctcgcc tgcccctggg ccgtgtccgg ggctcgcgcc   180
tcgcccggct ccgcggccag cccgagactc cgcgagggtc ccgagctttc gcccgacgat   240
cccgccggcc tcttggacct gcggcagggc atgtttgcgc agctggtggc ccaaaatgtt   300
ctgctgatcg atgggcccct gagctggtac agtgacccag gcctggcagg cgtgtccctg   360
acggggggcc tgagctacaa agaggacacg aaggagctgg tggtggccaa ggctggagtc   420
tactatgtct tctttcaact agagctgcgg cgcgtggtgg ccggcgaggg ctcaggctcc   480
gtttcacttg cgctgcacct gcagccactg cgctctgctg ctggggccgc cgccctggct   540
ttgaccgtgg acctgccacc cgcctcctcc gaggctcgga actcggcctt cggtttccag   600
ggccgcttgc tgcacctgag tgccggccag cgcctgggcg tccatcttca cactgaggcc   660
agggcacgcg atgcctggca gcttacccag ggcgccacag tcttgggact cttccgggtg   720
acccccgaaa tcccagccgg actcccttca ccgaggtcgg aataa               765

<210> SEQ ID NO 38
<211> LENGTH: 615
<212> TYPE: DNA
<213> ORGANISM: Artificial sequence
<220> FEATURE:
<223> OTHER INFORMATION: nucleic acid sequence encoding SEQ ID NO: 3

<400> SEQUENCE: 38
gcctgcccct gggccgtgtc cggggctcgc gcctcgcccg gctccgcggc cagcccgaga    60
ctccgcgagg gtcccgagct ttcgcccgac gatcccgccg gcctcttgga cctgcggcag   120
ggcatgtttg cgcagctggt ggcccaaaat gttctgctga tcgatgggcc cctgagctgg   180
tacagtgacc caggcctggc aggcgtgtcc ctgacggggg gcctgagcta caaagaggac   240
acgaaggagc tggtggtggc caaggctgga gtctactatg tcttctttca actagagctg   300
cggcgcgtgg tggccggcga gggctcaggc tccgtttcac ttgcgctgca cctgcagcca   360
ctgcgctctg ctgctggggc cgccgccctg gctttgaccg tggacctgcc accgcctcc   420
tccgaggctc ggaactcggc cttcggtttc cagggccgct tgctgcacct gagtgccggc   480
cagcgcctgg gcgtccatct tcacactgag gccagggcac gccatgcctg gcagcttacc   540
cagggcgcca cagtcttggg actcttccgg gtgaccccccg aaatcccagc cggactccct   600
tcaccgaggt cggaa                                                   615

<210> SEQ ID NO 39
<211> LENGTH: 624
<212> TYPE: DNA
<213> ORGANISM: Artificial sequence
<220> FEATURE:
<223> OTHER INFORMATION: nucleic acid sequence encoding SEQ ID NO: 22

<400> SEQUENCE: 39
atctacggcg cctgtccttg ggctgtgtct ggcgctagag catctcctgg ctctgctgcc    60
tctcctagac tgagagaggg acctgagctg tctcctgatg atcctgctgg cctgctggat   120
ctgagacagg gcatgtttgc tcagctggtg gcccagaacg tgctgctgat tgatggccct   180
```

```
ctgtcctggt actctgatcc tggattggct ggcgtgtccc tgactggcgg cctgtcttac    240
aaagaggaca ccaaagaact ggtggtggcc aaggccggcg tgtactacgt gttctttcag    300
ctggaactgc ggagagtggt ggccggcgaa ggatctggat ctgtgtctct ggcactgcat    360
ctgcagcccc tgagatctgc tgcaggcgct gctgctctgg ctctgacagt tgatctgcct    420
cctgcctcct ccgaggccag aaactccgcc tttggcttcc aaggcagact gctgcatctg    480
tctgccggcc agagactggg agtccatctg catacagagg ctagagccag gcacgcctgg    540
cagttgacac aaggtgctac agtgctgggc ctgttcagag tgaccccaga gattccagcc    600
ggcctgcctt ctccaagatc cgag                                            624
```

<210> SEQ ID NO 40
<211> LENGTH: 573
<212> TYPE: DNA
<213> ORGANISM: Artificial sequence
<220> FEATURE:
<223> OTHER INFORMATION: nucleic acid sequence encoding SEQ ID NO: 23

<400> SEQUENCE: 40

```
tctgctgcct ctcctagact gagagaggga cctgagctgt ctcctgatga tcctgctggc     60
ctgctggatc tgagacaggg catgtttgct cagctggtgg cccagaacgt gctgctgatt    120
gatggccctc tgtcctggta ctctgatcct ggattggctg gcgtgtccct gactggcggc    180
ctgtcttaca aagaggacac caaagaactg gtggtggcca aggccggcgt gtactacgtg    240
ttctttcagc tggaactgcg gagagtggtg gccggcgaag gatctggatc tgtgtctctg    300
gcactgcatc tgcagcccct gagatctgct gcaggcgctg ctgctctggc tctgacagtt    360
gatctgcctc ctgcctcctc cgaggccaga aactccgcct ttggcttcca aggcagactg    420
ctgcatctgt ctgccggcca gagactggga gtccatctgc atacagaggc tagagccagg    480
cacgcctggc agttgacaca aggtgctaca gtgctgggcc tgttcagagt gaccccagag    540
attccagccg gcctgccttc tccaagatcc gag                                 573
```

<210> SEQ ID NO 41
<211> LENGTH: 591
<212> TYPE: DNA
<213> ORGANISM: Artificial sequence
<220> FEATURE:
<223> OTHER INFORMATION: nucleic acid sequence encoding SEQ ID NO: 27

<400> SEQUENCE: 41

```
gctagagcat ctcctggctc tgctgcctct cctagactga gagggacc tgagctgtct      60 cctgatgatc ctgctggcct gctggatctg agacagggca tgtttgctca gctggtggcc   120
cagaacgtgc tgctgattga tggccctctg tcctggtact ctgatcctgg attggctggc   180
gtgtccctga ctggcggcct gtcttacaaa gaggacacca agaactggt ggtggccaag    240 gccggcgtgt actacgtgtt ctttcagctg gaactgcgga gagtggtggc cggcgaagga   300
tctggatctg tgtctctggc actgcatctg cagcccctga gatctgctgc aggcgctgct   360
gctctggctc tgacagttga tctgcctcct gcctcctccg aggccagaaa ctccgccttt   420
ggcttccaag gcagactgct gcatctgtct gccggcaga gactgggagt ccatctgcat    480
acagaggcta gagccaggca cgcctggcag ttgacacaag gtgctacagt gctgggcctg   540
ttcagagtga ccccagagat tccagccggc ctgccttctc caagatccga g             591
```

<210> SEQ ID NO 42

<211> LENGTH: 555
<212> TYPE: DNA
<213> ORGANISM: Artificial sequence
<220> FEATURE:
<223> OTHER INFORMATION: nucleic acid sequence encoding SEQ ID NO: 28

<400> SEQUENCE: 42

```
ctgagagagg gacctgagct gtctcctgat gatcctgctg gcctgctgga tctgagacag      60
ggcatgtttg ctcagctggt ggcccagaac gtgctgctga ttgatggccc tctgtcctgg     120
tactctgatc ctggattggc tggcgtgtcc ctgactggcg gcctgtctta caaagaggac     180
accaaagaac tggtggtggc caaggccggc gtgtactacg tgttctttca gctggaactg     240
cggagagtgg tggccggcga aggatctgga tctgtgtctc tggcactgca tctgcagccc     300
ctgagatctg ctgcaggcgc tgctgctctg gctctgacag ttgatctgcc tcctgcctcc     360
tccgaggcca gaaactccgc ctttggcttc aaggcagac tgctgcatct gtctgccggc     420
cagagactgg gagtccatct gcatacagag gctagagcca ggcacgcctg gcagttgaca     480
caaggtgcta cagtgctggg cctgttcaga gtgaccccag agattccagc cggcctgcct     540
tctccaagat ccgag                                                      555
```

<210> SEQ ID NO 43
<211> LENGTH: 574
<212> TYPE: PRT
<213> ORGANISM: Artificial sequence
<220> FEATURE:
<223> OTHER INFORMATION: ORIGINAL SIRPa-4-1BBL with signal peptide and C-term His Tag

<400> SEQUENCE: 43

```
Met Gly Trp Ser Cys Ile Ile Leu Phe Leu Val Ala Thr Ala Thr Gly
1               5                   10                  15

Val His Ser Glu Glu Glu Leu Gln Val Ile Gln Pro Asp Lys Ser Val
            20                  25                  30

Leu Val Ala Ala Gly Glu Thr Ala Thr Leu Arg Cys Thr Ala Thr Ser
        35                  40                  45

Leu Ile Pro Val Gly Pro Ile Gln Trp Phe Arg Gly Ala Gly Pro Gly
    50                  55                  60

Arg Glu Leu Ile Tyr Asn Gln Lys Glu Gly His Phe Pro Arg Val Thr
65                  70                  75                  80

Thr Val Ser Asp Leu Thr Lys Arg Asn Asn Met Asp Phe Ser Ile Arg
                85                  90                  95

Ile Gly Asn Ile Thr Pro Ala Asp Ala Gly Thr Tyr Tyr Cys Val Lys
            100                 105                 110

Phe Arg Lys Gly Ser Pro Asp Asp Val Glu Phe Lys Ser Gly Ala Gly
        115                 120                 125

Thr Glu Leu Ser Val Arg Ala Lys Pro Ser Ala Pro Val Val Ser Gly
    130                 135                 140

Pro Ala Ala Arg Ala Thr Pro Gln His Thr Val Ser Phe Thr Cys Glu
145                 150                 155                 160

Ser His Gly Phe Ser Pro Arg Asp Ile Thr Leu Lys Trp Phe Lys Asn
                165                 170                 175

Gly Asn Glu Leu Ser Asp Phe Gln Thr Asn Val Asp Pro Val Gly Glu
            180                 185                 190

Ser Val Ser Tyr Ser Ile His Ser Thr Ala Lys Val Val Leu Thr Arg
        195                 200                 205

Glu Asp Val His Ser Gln Val Ile Cys Glu Val Ala His Val Thr Leu
```

```
                  210                 215                 220
Gln Gly Asp Pro Leu Arg Gly Thr Ala Asn Leu Ser Glu Thr Ile Arg
225                 230                 235                 240

Val Pro Pro Thr Leu Glu Val Thr Gln Gln Pro Val Arg Ala Glu Asn
                245                 250                 255

Gln Val Asn Val Thr Cys Gln Val Arg Lys Phe Tyr Pro Gln Arg Leu
                260                 265                 270

Gln Leu Thr Trp Leu Glu Asn Gly Asn Val Ser Arg Thr Glu Thr Ala
                275                 280                 285

Ser Thr Val Thr Glu Asn Lys Asp Gly Thr Tyr Asn Trp Met Ser Trp
                290                 295                 300

Leu Leu Val Asn Val Ser Ala His Arg Asp Asp Val Lys Leu Thr Cys
305                 310                 315                 320

Gln Val Glu His Asp Gly Gln Pro Ala Val Ser Lys Ser His Asp Leu
                325                 330                 335

Lys Val Ser Ala His Pro Lys Glu Gln Gly Ser Asn Thr Ala Ala Glu
                340                 345                 350

Asn Thr Gly Ser Asn Glu Arg Asn Ile Tyr Gly Ala Cys Pro Trp Ala
                355                 360                 365

Val Ser Gly Ala Arg Ala Ser Pro Gly Ser Ala Ala Ser Pro Arg Leu
                370                 375                 380

Arg Glu Gly Pro Glu Leu Ser Pro Asp Asp Pro Ala Gly Leu Leu Asp
385                 390                 395                 400

Leu Arg Gln Gly Met Phe Ala Gln Leu Val Ala Gln Asn Val Leu Leu
                405                 410                 415

Ile Asp Gly Pro Leu Ser Trp Tyr Ser Asp Pro Gly Leu Ala Gly Val
                420                 425                 430

Ser Leu Thr Gly Gly Leu Ser Tyr Lys Glu Asp Thr Lys Glu Leu Val
                435                 440                 445

Val Ala Lys Ala Gly Val Tyr Tyr Val Phe Phe Gln Leu Glu Leu Arg
                450                 455                 460

Arg Val Val Ala Gly Glu Gly Ser Gly Ser Val Ser Leu Ala Leu His
465                 470                 475                 480

Leu Gln Pro Leu Arg Ser Ala Gly Ala Ala Leu Ala Leu Thr
                485                 490                 495

Val Asp Leu Pro Pro Ala Ser Ser Glu Ala Arg Asn Ser Ala Phe Gly
                500                 505                 510

Phe Gln Gly Arg Leu Leu His Leu Ser Ala Gly Gln Arg Leu Gly Val
                515                 520                 525

His Leu His Thr Glu Ala Arg Ala Arg His Ala Trp Gln Leu Thr Gln
                530                 535                 540

Gly Ala Thr Val Leu Gly Leu Phe Arg Val Thr Pro Glu Ile Pro Ala
545                 550                 555                 560

Gly Leu Pro Ser Pro Arg Ser Glu His His His His His
                565                 570
```

<210> SEQ ID NO 44
<211> LENGTH: 555
<212> TYPE: PRT
<213> ORGANISM: Artificial sequence
<220> FEATURE:
<223> OTHER INFORMATION: ORIGINAL SIRPa-4-1BBL with signal peptide and
      N-terminal His Tag

<400> SEQUENCE: 44

```
His His His His His Glu Glu Glu Leu Gln Val Ile Gln Pro Asp
1               5                   10                  15

Lys Ser Val Leu Val Ala Ala Gly Glu Thr Ala Thr Leu Arg Cys Thr
                20                  25                  30

Ala Thr Ser Leu Ile Pro Val Gly Pro Ile Gln Trp Phe Arg Gly Ala
            35                  40                  45

Gly Pro Gly Arg Glu Leu Ile Tyr Asn Gln Lys Glu Gly His Phe Pro
        50                  55                  60

Arg Val Thr Thr Val Ser Asp Leu Thr Lys Arg Asn Asn Met Asp Phe
65                  70                  75                  80

Ser Ile Arg Ile Gly Asn Ile Thr Pro Ala Asp Ala Gly Thr Tyr Tyr
                85                  90                  95

Cys Val Lys Phe Arg Lys Gly Ser Pro Asp Asp Val Glu Phe Lys Ser
            100                 105                 110

Gly Ala Gly Thr Glu Leu Ser Val Arg Ala Lys Pro Ser Ala Pro Val
        115                 120                 125

Val Ser Gly Pro Ala Ala Arg Ala Thr Pro Gln His Thr Val Ser Phe
    130                 135                 140

Thr Cys Glu Ser His Gly Phe Ser Pro Arg Asp Ile Thr Leu Lys Trp
145                 150                 155                 160

Phe Lys Asn Gly Asn Glu Leu Ser Asp Phe Gln Thr Asn Val Asp Pro
                165                 170                 175

Val Gly Glu Ser Val Ser Tyr Ser Ile His Ser Thr Ala Lys Val Val
            180                 185                 190

Leu Thr Arg Glu Asp Val His Ser Gln Val Ile Cys Glu Val Ala His
        195                 200                 205

Val Thr Leu Gln Gly Asp Pro Leu Arg Gly Thr Ala Asn Leu Ser Glu
    210                 215                 220

Thr Ile Arg Val Pro Pro Thr Leu Glu Val Thr Gln Gln Pro Val Arg
225                 230                 235                 240

Ala Glu Asn Gln Val Asn Val Thr Cys Gln Val Arg Lys Phe Tyr Pro
                245                 250                 255

Gln Arg Leu Gln Leu Thr Trp Leu Glu Asn Gly Asn Val Ser Arg Thr
            260                 265                 270

Glu Thr Ala Ser Thr Val Thr Glu Asn Lys Asp Gly Thr Tyr Asn Trp
        275                 280                 285

Met Ser Trp Leu Leu Val Asn Val Ser Ala His Arg Asp Asp Val Lys
    290                 295                 300

Leu Thr Cys Gln Val Glu His Asp Gly Gln Pro Ala Val Ser Lys Ser
305                 310                 315                 320

His Asp Leu Lys Val Ser Ala His Pro Lys Glu Gln Gly Ser Asn Thr
                325                 330                 335

Ala Ala Glu Asn Thr Gly Ser Asn Glu Arg Asn Ile Tyr Gly Ala Cys
            340                 345                 350

Pro Trp Ala Val Ser Gly Ala Arg Ala Ser Pro Gly Ser Ala Ala Ser
        355                 360                 365

Pro Arg Leu Arg Glu Gly Pro Glu Leu Ser Pro Asp Asp Pro Ala Gly
    370                 375                 380

Leu Leu Asp Leu Arg Gln Gly Met Phe Ala Gln Leu Val Ala Gln Asn
385                 390                 395                 400

Val Leu Leu Ile Asp Gly Pro Leu Ser Trp Tyr Ser Asp Pro Gly Leu
                405                 410                 415

Ala Gly Val Ser Leu Thr Gly Gly Leu Ser Tyr Lys Glu Asp Thr Lys
```

```
                    420                 425                 430
Glu Leu Val Val Ala Lys Ala Gly Val Tyr Tyr Val Phe Phe Gln Leu
                435                 440                 445
Glu Leu Arg Arg Val Val Ala Gly Glu Gly Ser Gly Ser Val Ser Leu
            450                 455                 460
Ala Leu His Leu Gln Pro Leu Arg Ser Ala Ala Gly Ala Ala Ala Leu
465                 470                 475                 480
Ala Leu Thr Val Asp Leu Pro Pro Ala Ser Ser Glu Ala Arg Asn Ser
                485                 490                 495
Ala Phe Gly Phe Gln Gly Arg Leu Leu His Leu Ser Ala Gly Gln Arg
            500                 505                 510
Leu Gly Val His Leu His Thr Glu Ala Arg Ala Arg His Ala Trp Gln
        515                 520                 525
Leu Thr Gln Gly Ala Thr Val Leu Gly Leu Phe Arg Val Thr Pro Glu
        530                 535                 540
Ile Pro Ala Gly Leu Pro Ser Pro Arg Ser Glu
545                 550                 555

<210> SEQ ID NO 45
<211> LENGTH: 541
<212> TYPE: PRT
<213> ORGANISM: Artificial sequence
<220> FEATURE:
<223> OTHER INFORMATION: DSP107 Var. 4 [SIRP SEQ ID NO: 2 (343 amino
      acids), glycine linker, 4-1BBL SEQ ID NO: 27 (197 aa)]

<400> SEQUENCE: 45

Glu Glu Glu Leu Gln Val Ile Gln Pro Asp Lys Ser Val Leu Val Ala
1               5                   10                  15
Ala Gly Glu Thr Ala Thr Leu Arg Cys Thr Ala Thr Ser Leu Ile Pro
            20                  25                  30
Val Gly Pro Ile Gln Trp Phe Arg Gly Ala Gly Pro Gly Arg Glu Leu
        35                  40                  45
Ile Tyr Asn Gln Lys Glu Gly His Phe Pro Arg Val Thr Thr Val Ser
    50                  55                  60
Asp Leu Thr Lys Arg Asn Asn Met Asp Phe Ser Ile Arg Ile Gly Asn
65                  70                  75                  80
Ile Thr Pro Ala Asp Ala Gly Thr Tyr Tyr Cys Val Lys Phe Arg Lys
                85                  90                  95
Gly Ser Pro Asp Asp Val Glu Phe Lys Ser Gly Ala Gly Thr Glu Leu
            100                 105                 110
Ser Val Arg Ala Lys Pro Ser Ala Pro Val Val Ser Gly Pro Ala Ala
        115                 120                 125
Arg Ala Thr Pro Gln His Thr Val Ser Phe Thr Cys Glu Ser His Gly
    130                 135                 140
Phe Ser Pro Arg Asp Ile Thr Leu Lys Trp Phe Lys Asn Gly Asn Glu
145                 150                 155                 160
Leu Ser Asp Phe Gln Thr Asn Val Asp Pro Val Gly Glu Ser Val Ser
                165                 170                 175
Tyr Ser Ile His Ser Thr Ala Lys Val Val Leu Thr Arg Glu Asp Val
            180                 185                 190
His Ser Gln Val Ile Cys Glu Val Ala His Val Thr Leu Gln Gly Asp
        195                 200                 205
Pro Leu Arg Gly Thr Ala Asn Leu Ser Glu Thr Ile Arg Val Pro Pro
    210                 215                 220
```

-continued

Thr Leu Glu Val Thr Gln Gln Pro Val Arg Ala Glu Asn Gln Val Asn
225                 230                 235                 240

Val Thr Cys Gln Val Arg Lys Phe Tyr Pro Gln Arg Leu Gln Leu Thr
            245                 250                 255

Trp Leu Glu Asn Gly Asn Val Ser Arg Thr Glu Thr Ala Ser Thr Val
        260                 265                 270

Thr Glu Asn Lys Asp Gly Thr Tyr Asn Trp Met Ser Trp Leu Leu Val
    275                 280                 285

Asn Val Ser Ala His Arg Asp Asp Val Lys Leu Thr Cys Gln Val Glu
290                 295                 300

His Asp Gly Gln Pro Ala Val Ser Lys Ser His Asp Leu Lys Val Ser
305                 310                 315                 320

Ala His Pro Lys Glu Gln Gly Ser Asn Thr Ala Ala Glu Asn Thr Gly
            325                 330                 335

Ser Asn Glu Arg Asn Ile Tyr Gly Ala Arg Ala Ser Pro Gly Ser Ala
        340                 345                 350

Ala Ser Pro Arg Leu Arg Glu Gly Pro Glu Leu Ser Pro Asp Asp Pro
    355                 360                 365

Ala Gly Leu Leu Asp Leu Arg Gln Gly Met Phe Ala Gln Leu Val Ala
370                 375                 380

Gln Asn Val Leu Leu Ile Asp Gly Pro Leu Ser Trp Tyr Ser Asp Pro
385                 390                 395                 400

Gly Leu Ala Gly Val Ser Leu Thr Gly Gly Leu Ser Tyr Lys Glu Asp
            405                 410                 415

Thr Lys Glu Leu Val Val Ala Lys Ala Gly Val Tyr Tyr Val Phe Phe
        420                 425                 430

Gln Leu Glu Leu Arg Arg Val Val Ala Gly Glu Gly Ser Gly Ser Val
    435                 440                 445

Ser Leu Ala Leu His Leu Gln Pro Leu Arg Ser Ala Ala Gly Ala Ala
450                 455                 460

Ala Leu Ala Leu Thr Val Asp Leu Pro Pro Ala Ser Ser Glu Ala Arg
465                 470                 475                 480

Asn Ser Ala Phe Gly Phe Gln Gly Arg Leu Leu His Leu Ser Ala Gly
            485                 490                 495

Gln Arg Leu Gly Val His Leu His Thr Glu Ala Arg Ala Arg His Ala
        500                 505                 510

Trp Gln Leu Thr Gln Gly Ala Thr Val Leu Gly Leu Phe Arg Val Thr
    515                 520                 525

Pro Glu Ile Pro Ala Gly Leu Pro Ser Pro Arg Ser Glu
530                 535                 540

<210> SEQ ID NO 46
<211> LENGTH: 529
<212> TYPE: PRT
<213> ORGANISM: Artificial sequence
<220> FEATURE:
<223> OTHER INFORMATION: DSP107 Var. 5: SIRP SEQ ID NO: 2 (343 amino
      acids), glycine linker, 4-1BBL SEQ ID NO: 28 (185 aa)

<400> SEQUENCE: 46

Glu Glu Glu Leu Gln Val Ile Gln Pro Asp Lys Ser Val Leu Val Ala
1               5                   10                  15

Ala Gly Glu Thr Ala Thr Leu Arg Cys Thr Ala Thr Ser Leu Ile Pro
            20                  25                  30

Val Gly Pro Ile Gln Trp Phe Arg Gly Ala Gly Pro Gly Arg Glu Leu
        35                  40                  45

```
Ile Tyr Asn Gln Lys Glu Gly His Phe Pro Arg Val Thr Val Ser
 50                  55                  60

Asp Leu Thr Lys Arg Asn Asn Met Asp Phe Ser Ile Arg Ile Gly Asn
 65                  70                  75                  80

Ile Thr Pro Ala Asp Ala Gly Thr Tyr Tyr Cys Val Lys Phe Arg Lys
                 85                  90                  95

Gly Ser Pro Asp Asp Val Glu Phe Lys Ser Gly Ala Gly Thr Glu Leu
            100                 105                 110

Ser Val Arg Ala Lys Pro Ser Ala Pro Val Val Ser Gly Pro Ala Ala
            115                 120                 125

Arg Ala Thr Pro Gln His Thr Val Ser Phe Thr Cys Glu Ser His Gly
130                 135                 140

Phe Ser Pro Arg Asp Ile Thr Leu Lys Trp Phe Lys Asn Gly Asn Glu
145                 150                 155                 160

Leu Ser Asp Phe Gln Thr Asn Val Asp Pro Val Gly Glu Ser Val Ser
                165                 170                 175

Tyr Ser Ile His Ser Thr Ala Lys Val Val Leu Thr Arg Glu Asp Val
                180                 185                 190

His Ser Gln Val Ile Cys Glu Val Ala His Val Thr Leu Gln Gly Asp
            195                 200                 205

Pro Leu Arg Gly Thr Ala Asn Leu Ser Glu Thr Ile Arg Val Pro Pro
210                 215                 220

Thr Leu Glu Val Thr Gln Gln Pro Val Arg Ala Glu Asn Gln Val Asn
225                 230                 235                 240

Val Thr Cys Gln Val Arg Lys Phe Tyr Pro Gln Arg Leu Gln Leu Thr
                245                 250                 255

Trp Leu Glu Asn Gly Asn Val Ser Arg Thr Glu Thr Ala Ser Thr Val
            260                 265                 270

Thr Glu Asn Lys Asp Gly Thr Tyr Asn Trp Met Ser Trp Leu Leu Val
275                 280                 285

Asn Val Ser Ala His Arg Asp Asp Val Lys Leu Thr Cys Gln Val Glu
290                 295                 300

His Asp Gly Gln Pro Ala Val Ser Lys Ser His Asp Leu Lys Val Ser
305                 310                 315                 320

Ala His Pro Lys Glu Gln Gly Ser Asn Thr Ala Ala Glu Asn Thr Gly
                325                 330                 335

Ser Asn Glu Arg Asn Ile Tyr Gly Leu Arg Glu Gly Pro Glu Leu Ser
            340                 345                 350

Pro Asp Pro Ala Gly Leu Leu Asp Leu Arg Gln Gly Met Phe Ala
            355                 360                 365

Gln Leu Val Ala Gln Asn Val Leu Leu Ile Asp Gly Pro Leu Ser Trp
370                 375                 380

Tyr Ser Asp Pro Gly Leu Ala Gly Val Ser Leu Thr Gly Gly Leu Ser
385                 390                 395                 400

Tyr Lys Glu Asp Thr Lys Glu Leu Val Val Ala Lys Ala Gly Val Tyr
                405                 410                 415

Tyr Val Phe Phe Gln Leu Glu Leu Arg Arg Val Val Ala Gly Glu Gly
            420                 425                 430

Ser Gly Ser Val Ser Leu Ala Leu His Leu Gln Pro Leu Arg Ser Ala
            435                 440                 445

Ala Gly Ala Ala Ala Leu Ala Leu Thr Val Asp Leu Pro Pro Ala Ser
450                 455                 460
```

Ser Glu Ala Arg Asn Ser Ala Phe Gly Phe Gln Gly Arg Leu Leu His
465                 470                 475                 480

Leu Ser Ala Gly Gln Arg Leu Gly Val His Leu His Thr Glu Ala Arg
            485                 490                 495

Ala Arg His Ala Trp Gln Leu Thr Gln Gly Ala Thr Val Leu Gly Leu
        500                 505                 510

Phe Arg Val Thr Pro Glu Ile Pro Ala Gly Leu Pro Ser Pro Arg Ser
            515                 520                 525

Glu

<210> SEQ ID NO 47
<211> LENGTH: 308
<212> TYPE: PRT
<213> ORGANISM: Artificial sequence
<220> FEATURE:
<223> OTHER INFORMATION: DSP107 Var 6: SIRP SEQ ID NO: 24 (116 amino
      acids), glycine linker, 4-1BBL SEQ ID NO: 23 (191 amino acids):]

<400> SEQUENCE: 47

Glu Glu Glu Leu Gln Val Ile Gln Pro Asp Lys Ser Val Leu Val Ala
1               5                   10                  15

Ala Gly Glu Thr Ala Thr Leu Arg Cys Thr Ala Thr Ser Leu Ile Pro
            20                  25                  30

Val Gly Pro Ile Gln Trp Phe Arg Gly Ala Gly Pro Gly Arg Glu Leu
        35                  40                  45

Ile Tyr Asn Gln Lys Glu Gly His Phe Pro Arg Val Thr Thr Val Ser
    50                  55                  60

Asp Leu Thr Lys Arg Asn Asn Met Asp Phe Ser Ile Arg Ile Gly Asn
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Gly Ser Ala Ala Ser Pro Arg Leu Arg Glu Gly Pro
        115                 120                 125

Glu Leu Ser Pro Asp Asp Pro Ala Gly Leu Leu Asp Leu Arg Gln Gly
    130                 135                 140

Met Phe Ala Gln Leu Val Ala Gln Asn Val Leu Leu Ile Asp Gly Pro
145                 150                 155                 160

Leu Ser Trp Tyr Ser Asp Pro Gly Leu Ala Gly Val Ser Leu Thr Gly
                165                 170                 175

Gly Leu Ser Tyr Lys Glu Asp Thr Lys Glu Leu Val Val Ala Lys Ala
            180                 185                 190

Gly Val Tyr Tyr Val Phe Phe Gln Leu Glu Leu Arg Arg Val Val Ala
        195                 200                 205

Gly Glu Gly Ser Gly Ser Val Ser Leu Ala Leu His Leu Gln Pro Leu
    210                 215                 220

Arg Ser Ala Ala Gly Ala Ala Ala Leu Ala Leu Thr Val Asp Leu Pro
225                 230                 235                 240

Pro Ala Ser Ser Glu Ala Arg Asn Ser Ala Phe Gly Phe Gln Gly Arg
                245                 250                 255

Leu Leu His Leu Ser Ala Gly Gln Arg Leu Gly Val His Leu His Thr
            260                 265                 270

Glu Ala Arg Ala Arg His Ala Trp Gln Leu Thr Gln Gly Ala Thr Val
        275                 280                 285

```
Leu Gly Leu Phe Arg Val Thr Pro Glu Ile Pro Ala Gly Leu Pro Ser
    290                 295                 300

Pro Arg Ser Glu
305
```

<210> SEQ ID NO 48
<211> LENGTH: 314
<212> TYPE: PRT
<213> ORGANISM: Artificial sequence
<220> FEATURE:
<223> OTHER INFORMATION: Var 7: SIRP SEQ ID NO: 24 (116 amino acids),
      glycine linker, 4-1BBL SEQ ID NO: 27 (197 aa)

<400> SEQUENCE: 48

```
Glu Glu Glu Leu Gln Val Ile Gln Pro Asp Lys Ser Val Leu Val Ala
1               5                   10                  15

Ala Gly Glu Thr Ala Thr Leu Arg Cys Thr Ala Thr Ser Leu Ile Pro
            20                  25                  30

Val Gly Pro Ile Gln Trp Phe Arg Gly Ala Gly Pro Gly Arg Glu Leu
        35                  40                  45

Ile Tyr Asn Gln Lys Glu Gly His Phe Pro Arg Val Thr Thr Val Ser
50                  55                  60

Asp Leu Thr Lys Arg Asn Asn Met Asp Phe Ser Ile Arg Ile Gly Asn
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Gly Ala Arg Ala Ser Pro Gly Ser Ala Ala Ser Pro
        115                 120                 125

Arg Leu Arg Glu Gly Pro Glu Leu Ser Pro Asp Asp Pro Ala Gly Leu
130                 135                 140

Leu Asp Leu Arg Gln Gly Met Phe Ala Gln Leu Val Ala Gln Asn Val
145                 150                 155                 160

Leu Leu Ile Asp Gly Pro Leu Ser Trp Tyr Ser Asp Pro Gly Leu Ala
                165                 170                 175

Gly Val Ser Leu Thr Gly Gly Leu Ser Tyr Lys Glu Asp Thr Lys Glu
            180                 185                 190

Leu Val Val Ala Lys Ala Gly Val Tyr Tyr Val Phe Phe Gln Leu Glu
        195                 200                 205

Leu Arg Arg Val Val Ala Gly Glu Gly Ser Gly Ser Val Ser Leu Ala
210                 215                 220

Leu His Leu Gln Pro Leu Arg Ser Ala Ala Gly Ala Ala Ala Leu Ala
225                 230                 235                 240

Leu Thr Val Asp Leu Pro Pro Ala Ser Ser Glu Ala Arg Asn Ser Ala
                245                 250                 255

Phe Gly Phe Gln Gly Arg Leu Leu His Leu Ser Ala Gly Gln Arg Leu
            260                 265                 270

Gly Val His Leu His Thr Glu Ala Arg Ala Arg His Ala Trp Gln Leu
        275                 280                 285

Thr Gln Gly Ala Thr Val Leu Gly Leu Phe Arg Val Thr Pro Glu Ile
    290                 295                 300

Pro Ala Gly Leu Pro Ser Pro Arg Ser Glu
305                 310
```

<210> SEQ ID NO 49

<211> LENGTH: 302
<212> TYPE: PRT
<213> ORGANISM: Artificial sequence
<220> FEATURE:
<223> OTHER INFORMATION: DSP107 Var 8: SIRP SEQ ID NO: 24 (116 amino acids), glycine linker, 4-1BBL SEQ ID NO: 28 (185 aa)

<400> SEQUENCE: 49

```
Glu Glu Glu Leu Gln Val Ile Gln Pro Asp Lys Ser Val Leu Val Ala
1               5                   10                  15

Ala Gly Glu Thr Ala Thr Leu Arg Cys Thr Ala Thr Ser Leu Ile Pro
            20                  25                  30

Val Gly Pro Ile Gln Trp Phe Arg Gly Ala Gly Pro Gly Arg Glu Leu
        35                  40                  45

Ile Tyr Asn Gln Lys Glu Gly His Phe Pro Arg Val Thr Thr Val Ser
    50                  55                  60

Asp Leu Thr Lys Arg Asn Asn Met Asp Phe Ser Ile Arg Ile Gly Asn
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Gly Leu Arg Glu Gly Pro Glu Leu Ser Pro Asp Asp
        115                 120                 125

Pro Ala Gly Leu Leu Asp Leu Arg Gln Gly Met Phe Ala Gln Leu Val
    130                 135                 140

Ala Gln Asn Val Leu Leu Ile Asp Gly Pro Leu Ser Trp Tyr Ser Asp
145                 150                 155                 160

Pro Gly Leu Ala Gly Val Ser Leu Thr Gly Gly Leu Ser Tyr Lys Glu
                165                 170                 175

Asp Thr Lys Glu Leu Val Val Ala Lys Ala Gly Val Tyr Tyr Val Phe
            180                 185                 190

Phe Gln Leu Glu Leu Arg Arg Val Val Ala Gly Glu Gly Ser Gly Ser
        195                 200                 205

Val Ser Leu Ala Leu His Leu Gln Pro Leu Arg Ser Ala Ala Gly Ala
    210                 215                 220

Ala Ala Leu Ala Leu Thr Val Asp Leu Pro Pro Ala Ser Ser Glu Ala
225                 230                 235                 240

Arg Asn Ser Ala Phe Gly Phe Gln Gly Arg Leu Leu His Leu Ser Ala
                245                 250                 255

Gly Gln Arg Leu Gly Val His Leu His Thr Glu Ala Arg Ala Arg His
            260                 265                 270

Ala Trp Gln Leu Thr Gln Gly Ala Thr Val Leu Gly Leu Phe Arg Val
        275                 280                 285

Thr Pro Glu Ile Pro Ala Gly Leu Pro Ser Pro Arg Ser Glu
    290                 295                 300
```

<210> SEQ ID NO 50
<211> LENGTH: 1722
<212> TYPE: DNA
<213> ORGANISM: Artificial sequence
<220> FEATURE:
<223> OTHER INFORMATION: nucleic acid sequence encoding SEQ ID NO: 44

<400> SEQUENCE: 50

```
atgggctggt cctgcatcat cctgtttctg gtggctaccg ctaccggcgt gcactcccac      60
caccaccatc accacgaaga ggaactgcaa gtgatccagc ctgacaagtc cgtgctggtg     120
```

-continued

```
gctgctggcg aaaccgccac actgagatgt accgccacct ctctgatccc tgtgggccct      180
atccagtggt ttagaggcgc tggacctggc agagagctga tctacaacca gaaagagggc      240
cactttccta gagtgaccac cgtgtccgac ctgaccaagc ggaacaacat ggacttctcc      300
atccggatcg caacatcac ccctgctgat gccggcacct actactgcgt gaagttccgg       360
aagggctccc ctgacgacgt cgagtttaaa tccggcgctg caccgaact gtccgtgcga       420 gctaaacctt ctgctcccgt ggtgtctggc cctgccgcta gagctacacc tcagcacacc      480
gtgtctttta cctgcgagtc ccacggcttc agccctagag acatcaccct gaagtggttc      540
aagaacggca cgagctgtc cgacttccag accaacgtgg accctgtggg agagtccgtg       600
tcctactcca tccactctac cgccaaggtg gtgctgaccc gagaggacgt gcacagccaa      660
gtgatctgtg aagtggccca cgtgaccctc cagggcgatc tttgagagg caccgccaac      720 ctgtccgaga caatcagagt gcctcctaca ctggaagtga cccagcagcc tgtgcgggcc      780
gagaatcaag tgaacgtgac ctgccaagtg cggaagttct accctcagag actgcagctg      840
acctggctgg aaaacggcaa tgtgtccaga accgagacag cctccaccgt gaccgagaac      900
aaggatggca cctacaattg gatgtcctgg ctgctcgtga acgtgtccgc tcacagagat      960
gacgtgaagc tgacatgcca ggtggaacac gatggccagc tgccgtgtc taagtcccac      1020 gacctgaaag tgtctgctca ccccaaagag cagggctcca ataccgccgc tgagaacacc      1080
ggctccaacg agagaaacat ctacggcgcc tgtccttggg ctgtgtctgg cgctagagca     1140
tctcctggct ctgctgcctc tcctagactg agagagggac ctgagctgtc tcctgatgat     1200
cctgctggcc tgctggatct gagacagggc atgtttgctc agctggtggc ccagaacgtg     1260
ctgctgattg atggccctct gtcctggtac tctgatcctg gattgctgg cgtgtccctg      1320 actggcggcc tgtcttacaa agaggacacc aaagaactgg tggtggccaa ggccggcgtg     1380
tactacgtgt tctttcagct ggaactgcgg agagtggtgg ccggcgaagg atctggatct     1440
gtgtctctgg cactgcatct gcagccctg agatctgctg caggcgctgc tgctctggct      1500
ctgacagttg atctgcctcc tgcctcctcc gaggccagaa actccgcctt tggcttccaa     1560
ggcagactgc tgcatctgtc tgccggccag agactgggag tccatctgca tacagaggct     1620
agagccaggc acgcctggca gttgacacaa ggtgctacag tgctgggcct gttcagagtg     1680
accccagaga ttccagccgg cctgccttct ccaagatccg ag                        1722
```

<210> SEQ ID NO 51
<211> LENGTH: 1749
<212> TYPE: DNA
<213> ORGANISM: Artificial sequence
<220> FEATURE:
<223> OTHER INFORMATION: Cloned sequence of the C-terminal his-tagged (CH)-DSP-107

<400> SEQUENCE: 51

```
gaattcccgc cgccaccatg ggctggtcct gcatcatcct gtttctggtg gctaccgcta       60
ccggcgtgca ctccgaagag gaactgcaag tgatccagcc tgacaagtcc gtgctggtgg      120
ctgctggcga aaccgccaca ctgagatgta ccgccacctc tctgatccct gtgggcccta     180
tccagtggtt tagaggcgct ggacctggca gagagctgat ctacaaccag aaagagggcc    240
actttcctag agtgaccacc gtgtccgacc tgaccaagcg gaacaacatg gacttctcca    300
tccggatcgc aacatcacc cctgctgatg ccggcaccta ctactgcgtg aagttccgga     360
agggctcccc tgacgacgtc gagtttaaat ccggcgctgg caccgaactg tccgtgcgag    420
```

```
ctaaaccttc tgctcccgtg gtgtctggcc ctgccgctag agctacacct cagcacaccg    480
tgtcttttac ctgcgagtcc cacggcttca gccctagaga catcaccctg aagtggttca    540
agaacggcaa cgagctgtcc gacttccaga ccaacgtgga ccctgtggga gagtccgtgt    600
cctactccat ccactctacc gccaaggtgg tgctgacccg agaggacgtg cacagccaag    660
tgatctgtga agtggcccac gtgaccctcc agggcgatcc tttgagaggc accgccaacc    720
tgtccgagac aatcagagtg cctcctacac tggaagtgac ccagcagcct gtgcgggccg    780
agaatcaagt gaacgtgacc tgccaagtgc ggaagttcta ccctcagaga ctgcagctga    840
cctggctgga aaacggcaat gtgtccgaaa ccgagacagc ctccaccgtg accgagaaca    900
aggatggcac ctacaattgg atgtcctggc tgctcgtgaa cgtgtccgct cacagagatg    960
acgtgaagct gacatgccag gtggaacacg atggccagcc tgccgtgtct aagtcccacg   1020
acctgaaagt gtctgctcac cccaaagagc agggctccaa taccgccgct gagaacaccg   1080
gctccaacga gagaaacatc tacgcgcct gtccttgggc tgtgtctggc gctagagcat   1140
ctcctggctc tgctgcctct cctagactga gagagggacc tgagctgtct cctgatgatc   1200
ctgctggcct gctggatctg agacagggca tgtttgctca gctggtggcc cagaacgtgc   1260
tgctgattga tggccctctg tcctggtact ctgatcctgg attggctggc gtgtccctga   1320
ctggcggcct gtcttacaaa gaggacacca agaactggt ggtggccaag gccggcgtgt   1380
actacgtgtt ctttcagctg gaactgcgga gagtggtggc cggcgaagga tctggatctg   1440
tgtctctggc actgcatctg cagccccctga gatctgctgc aggcgctgct gctctggctc   1500
tgacagttga tctgcctcct gcctcctccg aggccagaaa ctccgccttt ggcttccaag   1560
gcagactgct gcatctgtct gccggccaga gactgggagt ccatctgcat acagaggcta   1620
gagccaggca cgcctggcag ttgacacaag gtgctacagt gctgggcctg ttcagagtga   1680
ccccagagat ccagccggc ctgccttctc caagatccga gcaccaccac catcaccact   1740
gataagctt                                                          1749

<210> SEQ ID NO 52
<211> LENGTH: 1731
<212> TYPE: DNA
<213> ORGANISM: Artificial sequence
<220> FEATURE:
<223> OTHER INFORMATION: Cloned sequence of the C-terminal his-tagged
      (CH)-V1 DSP-107

<400> SEQUENCE: 52
gaattcccgc cgccaccatg gctggtcct gcatcatcct gtttctggtg ctaccgcta     60 ccggcgtgca ctccgaagag gaactgcaag tgatccagcc tgacaagtcc gtgctggtgg    120
ctgctggcga aaccgccaca ctgagatgta ccgccacctc tctgatccct gtgggcccta    180
tccagtggtt tagaggcgct ggacctggca gagagctgat ctacaaccag aaagagggcc    240
actttcctag agtgaccacc gtgtccgacc tgaccaagcg gaacaacatg gacttctcca    300
tccggatcgg caacatcacc cctgctgatg ccggcaccta ctactgcgtg aagttccgga    360
agggctcccc tgacgacgtc gagtttaaat ccggcgctgg caccgaactg tccgtgcgag    420
ctaaaccttc tgctcccgtg gtgtctggcc ctgccgctag agctacacct cagcacaccg    480
tgtcttttac ctgcgagtcc cacggcttca gccctagaga catcaccctg aagtggttca    540
agaacggcaa cgagctgtcc gacttccaga ccaacgtgga ccctgtggga gagtccgtgt    600
cctactccat ccactctacc gccaaggtgg tgctgacccg agaggacgtg cacagccaag    660
```

```
tgatctgtga agtggcccac gtgaccctcc agggcgatcc tttgagaggc accgccaacc    720
tgtccgagac aatcagagtg cctcctacac tggaagtgac ccagcagcct gtgcgggccg    780
agaatcaagt gaacgtgacc tgccaagtgc ggaagttcta ccctcagaga ctgcagctga    840
cctggctgga aaacggcaat gtgtccagaa ccgagacagc ctccaccgtg accgagaaca    900
aggatggcac ctacaattgg atgtcctggc tgctcgtgaa cgtgtccgct cacagagatg    960
acgtgaagct gacatgccag gtggaacacg atggccagcc tgccgtgtct aagtcccacg   1020
acctgaaagt gtctgctcac cccaaagagc agggctccaa taccgccgct gagaacaccg   1080
gctccaacga gagaaacatc tacgctctg gcgctagggc ctctcctgga tctgctgctt    1140
ctcccagact gagagagggc cctgagctgt ctcctgatga tcctgctgga ctgctggatc   1200
tgagacaggg catgtttgct cagctggtgg cccagaacgt gctgctgatt gatgcccctc   1260
tgtcctggta ctctgatcct ggattggctg gcgtgtccct gactggcggc ctgtcttaca   1320
aagaggacac caaagaactg gtggtggcca aggccggcgt gtactacgtg ttctttcagc   1380
tggaactgcg gagagtggtg gccggcgaag atctggatc tgtgtctctg gctctgcatc    1440
tgcagcccct gagatctgca gcaggcgctg cagctctggc actgacagtt gatctgcctc   1500
ctgcctcctc cgaggccaga aactccgcct ttggcttcca aggcagactg ctgcacctgt   1560
ctgctggaca gagactggga gtgcacctcc acacagaggc cagagctaga catgcctggc   1620
agttgacaca gggcgctaca gtgctgggcc tgttcagagt gacacctgag attccagccg   1680
gcctgccttc tccaagatcc gagcaccacc accatcacca ctgataagct t             1731

<210> SEQ ID NO 53
<211> LENGTH: 1707
<212> TYPE: DNA
<213> ORGANISM: Artificial sequence
<220> FEATURE:
<223> OTHER INFORMATION: Cloned sequence of the C-terminal his-tagged
      (CH)-V2 DSP-107

<400> SEQUENCE: 53
gaattcccgc cgccaccatg gctggtcct gcatcatcct gtttctggtg gctaccgcta     60
ccggcgtgca ctccgaagag gaactgcaag tgatccagcc tgacaagtcc gtgctggtgg   120
ctgctggcga accgccaca ctgagatgta ccgccacctc tctgatccct gtgggcccta    180
tccagtggtt tagaggcgct ggacctggca gagagctgat ctacaaccag aaagagggcc   240
actttcctag agtgaccacc gtgtccgacc tgaccaagcg gaacaacatg gacttctcca   300
tccggatcgg caacatcacc cctgctgatg ccggcaccta ctactgcgtg aagttccgga   360
agggctcccc tgacgacgtc gagtttaaat ccggcgctgg caccgaactg tccgtgcgag   420
ctaaaccttc tgctcccgtg gtgtctggcc ctgccgctag agctacacct cagcacaccg   480 tgtctttac ctgcgagtcc cacggcttca gccctagaga catcccctg aagtggttca    540 agaacggcaa cgagctgtcc gacttccaga ccaacgtgga ccctgtggga gagtccgtgt   600
cctactccat ccactctacc gccaaggtgg tgctgacccg agaggacgtg cacagccaag   660
tgatctgtga agtggcccac gtgaccctcc agggcgatcc tttgagaggc accgccaacc   720
tgtccgagac aatcagagtg cctcctacac tggaagtgac ccagcagcct gtgcgggccg   780
agaatcaagt gaacgtgacc tgccaagtgc ggaagttcta ccctcagaga ctgcagctga   840
cctggctgga aaacggcaat gtgtccagaa ccgagacagc ctccaccgtg accgagaaca   900
aggatggcac ctacaattgg atgtcctggc tgctcgtgaa cgtgtccgct cacagagatg   960
```

-continued

```
acgtgaagct gacatgccag gtggaacacg atggccagcc tgccgtgtct aagtcccacg    1020
acctgaaagt gtctgctcac cccaaagagc agggctccaa taccgccgct gagaacaccg    1080
gctccaacga gagaaacatc tacggctctg ccgcctctcc tagactgaga gagggacctg    1140
agctgtctcc tgatgatcct gctggcctgc tggatctgag acagggcatg tttgctcagc    1200
tggtggccca gaacgtgctg ctgattgatg ccctctgtc ctggtactct gatcctggat    1260
tggctggcgt gtccctgact ggcggcctgt cttacaaaga ggacaccaaa gaactggtgg    1320
tggccaaggc cggcgtgtac tacgtgttct ttcagctgga actgcggaga gtggtggccg    1380
gcgaaggatc tggatctgtg tctctggctc tgcatctgca gcccctgaga tctgctgcag    1440
gcgctgctgc tctggcactg acagttgatc tgcctcctgc ctcctccgag gccagaaact    1500
ccgcctttgg cttccaaggc agactgctgc atctgtctgc cggccagaga ctgggagtcc    1560
atctgcatac agaggccaga gctagacacg cttggcagtt gacacagggc gctacagtgc    1620
tgggcctgtt cagagtgaca cctgagatcc cagccggcct gccttctcca agatctgagc    1680
accaccacca tcaccactga taagctt                                        1707
```

<210> SEQ ID NO 54
<211> LENGTH: 1047
<212> TYPE: DNA
<213> ORGANISM: Artificial sequence
<220> FEATURE:
<223> OTHER INFORMATION: Cloned sequence of the C-terminal his-tagged
      (CH)-V3.1 DSP-107

<400> SEQUENCE: 54

```
gaattcccgc cgccaccatg ggctggtcct gcatcatcct gtttctggtg gctaccgcta     60
ccggcgtgca ctccgaagag gaactgcaag tgatccagcc tgacaagtcc gtgctggtgg    120
ctgctggcga aaccgccaca ctgagatgta ccgccacctc tctgatccct gtgggcccta    180
tccagtggtt tagaggcgct ggacctggca gagagctgat ctacaaccag aaagagggcc    240
actttcctag agtgaccacc gtgtccgacc tgaccaagcg gaacaacatg gacttctcca    300
tccggatcgg caacatcacc cctgctgatg ccggcaccta ctactgcgtg aagttccgga    360
agggctcccc tgacgacgtc gagttttaaat ccggcgctgg caccgagctg tccgtcagag    420
cttctggtgc tagagcctct cctggctctg ccgcttctcc tagactgaga gagggacctg    480
agctgtctcc tgatgatcct gctggcctgc tggatctgag acagggcatg tttgctcagc    540
tggtggccca gaacgtgctg ctgattgatg ccctctgtc ctggtactct gatcctggat    600
tggctggcgt gtccctgact ggcggcctgt cttacaaaga ggacaccaaa gaactggtgg    660
tggccaaggc cggcgtgtac tacgtgttct ttcagctgga actgcggaga gtggtggccg    720
gcgaaggatc tggatctgtg tctctggcac tgcatctgca gcctctgaga tctgctgcag    780
gcgctgctgc tctggctctg acagttgatc tgcctcctgc ctcctccgag gccagaaact    840
ccgcctttgg cttccaaggc agactgctgc atctgtctgc cggccagaga ctgggagtcc    900
atctgcatac agaggccaga gctagacacg cttggcagtt gacacagggc gctacagtgc    960
tgggcctgtt cagagtgaca cctgagatcc cagccggcct gccttctcca agatctgagc   1020
accaccacca tcaccactga taagctt                                       1047
```

<210> SEQ ID NO 55
<211> LENGTH: 1629
<212> TYPE: DNA
<213> ORGANISM: Artificial sequence
<220> FEATURE:
<223> OTHER INFORMATION: nucleic acid sequence encoding SEQ ID NO: 11
      (DSP107_var1 without His Tag

<400> SEQUENCE: 55
gaagaggaac tgcaagtgat ccagcctgac aagtccgtgc tggtggctgc tggcgaaacc      60
gccacactga gatgtaccgc cacctctctg atccctgtgg gccctatcca gtggtttaga     120
ggcgctggac ctggcagaga gctgatctac aaccagaaag agggccactt tcctagagtg     180
accaccgtgt ccgacctgac caagcggaac aacatggact tctccatccg gatcggcaac     240
atcacccctg ctgatgccgg cacctactac tgcgtgaagt tccggaaggg ctcccctgac     300
gacgtcgagt ttaaatccgg cgctggcacc gaactgtccg tgcgagctaa accttctgct     360
cccgtggtgt ctggccctgc cgctagagct cacctcagc acaccgtgtc ttttacctgc     420
gagtcccacg gcttcagccc tagagacatc accctgaagt ggttcaagaa cggcaacgag     480
ctgtccgact ccagaccaa cgtgaccct gtgggagagt ccgtgtccta ctccatccac     540
tctaccgcca aggtggtgct gacccgagag gacgtgcaca gccaagtgat ctgtgaagtg     600
gcccacgtga ccctccaggg cgatcctttg agaggcaccg ccaacctgtc cgagacaatc     660
agagtgcctc ctacactgga agtgacccag cagcctgtgc gggccgagaa tcaagtgaac     720
gtgacctgcc aagtgcggaa gttctaccct cagagactgc agctgacctg gctggaaaac     780
ggcaatgtgt ccgaaccga cagcctcc accgtgaccg agaacaagga tggcacctac     840
aattggatgt cctggctgct cgtgaacgtg tccgctcaca gagatgacgt gaagctgaca     900
tgccaggtgg aacacgatgg ccagcctgcc gtgtctaagt cccacgacct gaaagtgtct     960
gctcaccca aagagcaggg ctccaatacc gccgctgaga caccggctc aacgagaga    1020
aacatctacg ctctggcgc tagggcctct cctggatctg ctgcttctcc cagactgaga    1080
gagggccctg agctgtctcc tgatgatcct gctggactgc tggatctgag acagggcatg    1140
tttgctcagc tggtggccca gaacgtgctg ctgattgatg cccctctgtc ctggtactct    1200
gatcctggat tggctggcgt gtccctgact ggcggcctgt cttacaaaga ggacaccaaa    1260
gaactggtgg tggccaaggc cggcgtgtac tacgtgttct ttcagctgga actgcggaga    1320
gtggtggccg gcgaaggatc tggatctgtg tctctggctc tgcatctgca gcccctgaga    1380
tctgcagcag gcgctgcagc tctggcactg acagttgatc tgcctcctgc ctcctccgag    1440
gccagaaaact ccgcctttgg cttccaaggc agactgctgc acctgtctgc tggacagaga    1500
ctgggagtgc acctccacac agaggccaga gctagacatg cctggcagtt gacacagggc    1560
gctacagtgc tgggcctgtt cagagtgaca cctgagattc agccggcct gccttctcca    1620
agatccgag                                                            1629

<210> SEQ ID NO 56
<211> LENGTH: 1605
<212> TYPE: DNA
<213> ORGANISM: Artificial sequence
<220> FEATURE:
<223> OTHER INFORMATION: nucleic acid sequence encoding SEQ ID NO: 13
      (DSP107_var2 without His Tag)

<400> SEQUENCE: 56
gaagaggaac tgcaagtgat ccagcctgac aagtccgtgc tggtggctgc tggcgaaacc      60
gccacactga gatgtaccgc cacctctctg atccctgtgg gccctatcca gtggtttaga     120
ggcgctggac ctggcagaga gctgatctac aaccagaaag agggccactt tcctagagtg     180

```
accaccgtgt ccgacctgac caagcggaac aacatggact tctccatccg gatcggcaac    240
atcacccctg ctgatgccgg cacctactac tgcgtgaagt tccggaaggg ctcccctgac    300
gacgtcgagt ttaaatccgg cgctggcacc gaactgtccg tgcgagctaa accttctgct    360
cccgtggtgt ctggccctgc cgctagagct acacctcagc acaccgtgtc ttttacctgc    420
gagtcccacg gcttcagccc tagagacatc accctgaagt ggttcaagaa cggcaacgag    480
ctgtccgact ccagaccaa cgtggaccct gtgggagagt ccgtgtccta ctccatccac    540
tctaccgcca aggtggtgct gacccgagag gacgtgcaca gccaagtgat ctgtgaagtg    600
gcccacgtga ccctccaggg cgatcctttg agaggcaccg ccaacctgtc cgagacaatc    660
agagtgcctc ctacactgga agtgacccag cagcctgtgc gggccgagaa tcaagtgaac    720
gtgacctgcc aagtgcggaa gttctaccct cagagactgc agctgacctg gctgaaaaac    780
ggcaatgtgt ccagaaccga gacagcctcc accgtgaccg agaacaagga tggcacctac    840
aattggatgt cctggctgct cgtgaacgtg tccgctcaca gagatgacgt gaagctgaca    900
tgccaggtgg aacacgatgg ccagcctgcc gtgtctaagt cccacgacct gaaagtgtct    960
gctcacccca agagcagggg ctccaatacc gccgctgaga caccggctc caacgagaga    1020 aacatctacg ctctgccgc ctctcctaga ctgagagagg acctgagct gtctcctgat    1080 gatcctgctg gcctgctgga tctgagacag ggcatgtttg ctcagctggt ggcccagaac    1140
gtgctgctga ttgatggccc tctgtcctgg tactctgatc ctggattggc tggcgtgtcc    1200
ctgactggcg gcctgtctta caagaggac accaagaac tggtggtggc caaggccggc    1260
gtgtactacg tgttctttca gctggaactg cggagagtgg tggccggcga aggatctgga    1320
tctgtgtctc tggctctgca tctgcagccc ctgagatctg ctgcaggcgc tgctgctctg    1380
gcactgacag ttgatctgcc tcctgcctcc tccgaggcca gaaactccgc ctttggcttc    1440
caaggcagac tgctgcatct gtctgccggc cagagactgg gagtccatct gcatacagag    1500
gccagagcta gacacgcttg gcagttgaca cagggcgcta cagtgctggg cctgttcaga    1560
gtgacacctg agatcccagc cggcctgcct tctccaagat ctgag                   1605
```

<210> SEQ ID NO 57
<211> LENGTH: 966
<212> TYPE: DNA
<213> ORGANISM: Artificial sequence
<220> FEATURE:
<223> OTHER INFORMATION: nucleic acid sequence encoding SEQ ID NO: 15
      (DSP107_var3 without His Tag)

<400> SEQUENCE: 57

```
gaagaggaac tgcaagtgat ccagcctgac aagtccgtgc tggtggctgc tggcgaaacc     60
gccacactga gatgtaccgc cacctctctg atccctgtgg gccctatcca gtggtttaga    120
ggcgctggac ctggcagaga gctgatctac aaccagaaag agggccactt cctagagtg    180 accaccgtgt ccgacctgac caagcggaac aacatggact tctccatccg gatcggcaac    240
atcacccctg ctgatgccgg cacctactac tgcgtgaagt tccggaaggg ctcccctgac    300
gacgtcgagt ttaaatccgg cgctggcacc gaactgtccg tgcgagctgg cgcctgtcct    360
tgggctgtgt ctggcgctag agcatctcct ggctctgctg cctctcctag actgagagag    420
ggacctgagc tgtctcctga tgatcctgct ggcctgctgg atctgagaca gggcatgttt    480
gctcagctgg tggcccagaa cgtgctgctg attgatggcc ctctgtcctg gtactctgat    540
cctggattgg ctggcgtgtc cctgactggc ggcctgtctt acaagaggga caccaagaa    600
```

```
ctggtggtgg ccaaggccgg cgtgtactac gtgttctttc agctggaact gcggagagtg      660
gtggccggcg aaggatctgg atctgtgtct ctggcactgc atctgcagcc cctgagatct      720
gctgcaggcg ctgctgctct ggctctgaca gttgatctgc ctcctgcctc ctccgaggcc      780
agaaactccg cctttggctt ccaaggcaga ctgctgcatc tgtctgccgg ccagagactg      840
ggagtccatc tgcatacaga ggctagagcc aggcacgcct ggcagttgac acaaggtgct      900
acagtgctgg gcctgttcag agtgacccca gagattccag ccggcctgcc ttctccaaga      960
tccgag                                                                 966

<210> SEQ ID NO 58
<211> LENGTH: 945
<212> TYPE: DNA
<213> ORGANISM: Artificial sequence
<220> FEATURE:
<223> OTHER INFORMATION: nucleic acid sequence encoding SEQ ID NO: 16:
      (DSP107_var3.1 without His Tag)

<400> SEQUENCE: 58
gaagaggaac tgcaagtgat ccagcctgac aagtccgtgc tggtggctgc tggcgaaacc       60
gccacactga gatgtaccgc cacctctctg atccctgtgg ccctatcca gtggtttaga      120 ggcgctggac ctggcagaga gctgatctac aaccagaaag agggccactt cctagagtg      180 accaccgtgt ccgacctgac caagcggaac aacatggact ctccatccg gatcggcaac      240 atcaccctg ctgatgccgg cacctactac tgcgtgaagt tccggaaggg ctcccctgac      300
gacgtcgagt ttaaatccgg cgctggcacc gagctgtccg tcagagcttc tggtgctaga      360
gcctctcctg gctctgccgc ttctcctaga ctgagagagg acctgagct gtctcctgat      420 gatcctgctg gcctgctgga tctgagacag ggcatgtttg ctcagctggt ggcccagaac      480
gtgctgctga ttgatggccc tctgtcctgg tactctgatc ctggattggc tggcgtgtcc      540
ctgactggcg gcctgtctta caaagaggac accaagaac tggtggtggc caaggccggc      600
gtgtactacg tgttctttca gctggaactg cggagagtgg tggccggcga aggatctgga      660
tctgtgtctc tggcactgca tctgcagcct ctgagatctg ctgcaggcgc tgctgctctg      720
gctctgacag ttgatctgcc tcctgcctcc tccgaggcca gaaactccgc ctttggcttc      780
caaggcagac tgctgcatct gtctgccggc cagagactgg gagtccatct gcatacagag      840
gccagagcta gacacgcttg gcagttgaca cagggcgcta cagtgctggg cctgttcaga      900
gtgacacctg agatcccagc cggcctgcct tctccaagat ctgag                     945

<210> SEQ ID NO 59
<211> LENGTH: 1629
<212> TYPE: DNA
<213> ORGANISM: Artificial sequence
<220> FEATURE:
<223> OTHER INFORMATION: nucleic acid sequence encoding SEQ ID NO: 18
      (DSP107_Var1Mut without His Tag)

<400> SEQUENCE: 59
gaagaggaaa tccaagtgat ccagcctgac aagtccgtgc tggtggctgc tggcgaaacc       60
gccacactga gatgtaccat cacctctctg atccctgtgg ccctatcca gtggtttaga      120 ggcgctggac ctggcagaat gctgatctac aaccagaaag agggccactt cctagagtg      180 accaccgtgt ccgacctgac caagcggaac aacatcgact ctccatccg gatcggcaac      240 atcaccctg ctgatgccgg cacctactac tgcgtgaagt tccggaaggg ctcccctgac      300
gacgtcgagt ttaaatccgg cgctggcacc gaactgtccg tgcgagctaa accttctgct      360
```

```
cccgtggtgt ctggccctgc cgctagagct acacctcagc acaccgtgtc ttttacctgc    420
gagtcccacg gcttcagccc tagagacatc accctgaagt ggttcaagaa cggcaacgag    480
ctgtccgact ccagaccaa cgtggaccct gtgggagagt ccgtgtccta ctccatccac     540
tctaccgcca aggtggtgct gacccgagag gacgtgcaca gccaagtgat ctgtgaagtg    600
gcccacgtga ccctccaggg cgatcctttg agaggcaccg ccaacctgtc cgagacaatc    660
agagtgcctc ctacactgga agtgacccag cagcctgtgc gggccgagaa tcaagtgaac    720
gtgacctgcc aagtgcggaa gttctaccct cagagactgc agctgacctg gctggaaaac    780
ggcaatgtgt ccagaaccga gacagcctcc accgtgaccg agaacaagga tggcacctac    840
aattggatgt cctggctgct cgtgaacgtg tccgctcaca gagatgacgt gaagctgaca    900
tgccaggtgg aacacgatgg ccagcctgcc gtgtctaagt cccacgacct gaaagtgtct    960
gctcacccca agagcagggg ctccaatacc gccgctgaga acaccggctc caacgagaga   1020
aacatctacg gctctggcgc tagggcctct cctggatctg ctgcttctcc cagactgaga   1080
gagggccctg agctgtctcc tgatgatcct gctggactgc tggatctgag acagggcatg   1140
tttgctcagc tggtggccca gaacgtgctg ctgattgatg gccctctgtc ctggtactct   1200
gatcctggat tggctggcgt gtccctgact ggcggcctgt cttacaaaga ggacaccaaa   1260
gaactggtgg tggccaaggc cggcgtgtac tacgtgttct ttcagctgga actgcggaga   1320
gtggtggccg gcgaaggatc tggatctgtg tctctggctc tgcatctgca gcccctgaga   1380
tctgcagcag gcgctgcagc tctggcactg acagttgatc tgcctcctgc ctcctccgag   1440
gccagaaact ccgcctttgg cttccaaggc agactgctgc acctgtctgc tggacagaga   1500 ctggagtgc acctccacac agaggccaga gctagacatg cctggcagtt gacacagggc   1560
gctacagtgc tgggcctgtt cagagtgaca cctgagattc agccggcct gccttctcca    1620 agatccgag                                                           1629
```

<210> SEQ ID NO 60
<211> LENGTH: 1605
<212> TYPE: DNA
<213> ORGANISM: Artificial sequence
<220> FEATURE:
<223> OTHER INFORMATION: nucleic acid sequence encoding SEQ ID NO: 19: (DSP107_Var2Mut without His Tag)

<400> SEQUENCE: 60

```
gaagaggaaa tccaagtgat ccagcctgac aagtccgtgc tggtggctgc tggcgaaacc     60
gccacactga gatgtaccat cacctctctg atccctgtgg gccctatcca gtggttaga    120 ggcgctggac ctggcagaat gctgatctac aaccagaaag agggccactt tcctagagtg    180
accaccgtgt ccgacctgac caagcggaac aacatcgact tctccatccg gatcggcaac    240
atcacccctg ctgatgccgg cacctactac tgcgtgaagt tccggaaggg ctcccctgac    300
gacgtcgagt ttaaatccgg cgctggcacc gaactgtccg tgcagctaa accttctgct    360 cccgtggtgt ctggccctgc cgctagagct acacctcagc acaccgtgtc ttttacctgc    420
gagtcccacg gcttcagccc tagagacatc accctgaagt ggttcaagaa cggcaacgag    480
ctgtccgact ccagaccaa cgtggaccct gtgggagagt ccgtgtccta ctccatccac     540
tctaccgcca aggtggtgct gacccgagag gacgtgcaca gccaagtgat ctgtgaagtg    600
gcccacgtga ccctccaggg cgatcctttg agaggcaccg ccaacctgtc cgagacaatc    660
agagtgcctc ctacactgga agtgacccag cagcctgtgc gggccgagaa tcaagtgaac    720
```

```
gtgacctgcc aagtgcggaa gttctaccct cagagactgc agctgacctg gctggaaaac    780
ggcaatgtgt ccagaaccga gacagcctcc accgtgaccg agaacaagga tggcacctac    840
aattggatgt cctggctgct cgtgaacgtg tccgctcaca gagatgacgt gaagctgaca    900
tgccaggtgg aacacgatgg ccagcctgcc gtgtctaagt cccacgacct gaaagtgtct    960
gctcacccca agagcagggc tccaatacc gccgctgaga acaccggctc aacgagaga     1020
aacatctacg gctctgccgc ctctcctaga ctgagagagg gacctgagct gtctcctgat   1080
gatcctgctg gcctgctgga tctgagacag ggcatgtttg ctcagctggt ggcccagaac   1140
gtgctgctga ttgatggccc tctgtcctgg tactctgatc ctggattggc tggcgtgtcc   1200
ctgactggcg gcctgtctta caagaggac accaaagaac tggtggtggc caaggccggc   1260
gtgtactacg tgttctttca gctggaactg cggagagtgg tggccggcga aggatctgga   1320
tctgtgtctc tggctctgca tctgcagccc ctgagatctg ctgcaggcgc tgctgctctg   1380
gcactgacag ttgatctgcc tcctgcctcc tccgaggcca gaaactccgc ctttggcttc   1440
caaggcagac tgctgcatct gtctgccggc cagagactgg gagtccatct gcatacagag   1500
gccagagcta gacacgcttg gcagttgaca cagggcgcta cagtgctggg cctgttcaga   1560
gtgacacctg agatcccagc cggcctgcct tctccaagat ctgag                   1605
```

<210> SEQ ID NO 61
<211> LENGTH: 966
<212> TYPE: DNA
<213> ORGANISM: Artificial sequence
<220> FEATURE:
<223> OTHER INFORMATION: nucleic acid sequence encoding SEQ ID NO: 20
      (DSP107_Var3Mut without His Tag)

<400> SEQUENCE: 61

```
gaagaggaaa tccaagtgat ccagcctgac aagtccgtgc tggtggctgc tggcgaaacc     60
gccacactga gatgtaccat cacctctctg atccctgtgg cccctatcca gtggtttaga   120
ggcgctggac ctggcagagt gctgatctac aaccagaaag agggccactt tcctagagtg   180
accaccgtgt ccgacctgac caagcggaac aacatggact ctccatccg gatcggcaac   240
atcacccctg ctgatgccgg cacctactac tgcatcaagt tccggaaggg ctcccctgac   300
gacgtcgagt ttaaatccgg cgctggcacc gaactgtccg tgcagctgg cgcctgtcct   360
tgggctgtgt ctggcgctag agcatctcct ggctctgctg cctctcctag actgagagag   420
ggacctgagc tgtctcctga tgatcctgct ggcctgctgg atctgagaca gggcatgttt   480
gctcagctgg tggcccagaa cgtgctgctg attgatggcc ctctgtcctg gtactctgat   540
cctggattgg ctggcgtgtc cctgactggc ggcctgtctt acaaagagga caccaaagaa   600
ctggtggtgg ccaaggccgg cgtgtactac gtgttctttc agctggaact gcggagagtg   660
gtggccggcg aaggatctgg atctgtgtct ctggcactgc atctgcagcc cctgagatct   720
gctgcaggcg ctgctgctct ggctctgaca gttgatctgc ctcctgcctc ctccgaggcc   780
agaaactccg cctttggctt ccaaggcaga ctgctgcatc tgtctgccgg ccagagactg   840
ggagtccatc tgcatacaga ggctagagcc aggcacgcct ggcagttgac acaaggtgct   900
acagtgctgg gcctgttcag agtgaccca gagattccag ccggcctgcc ttctccaaga   960
tccgag                                                              966
```

<210> SEQ ID NO 62
<211> LENGTH: 1623

<212> TYPE: DNA
<213> ORGANISM: Artificial sequence
<220> FEATURE:
<223> OTHER INFORMATION: nucleic acid sequence encoding SEQ ID NO: 45
      (Var 4)

<400> SEQUENCE: 62

```
gaagaggaac tgcaagtgat ccagcctgac aagtccgtgc tggtggctgc tggcgaaacc       60
gccacactga gatgtaccgc cacctctctg atccctgtgg ccctatcca gtggtttaga      120
ggcgctggac ctggcagaga gctgatctac aaccagaaag agggccactt tcctagagtg      180
accaccgtgt ccgacctgac caagcggaac aacatggact ctccatccg gatcggcaac      240
atcacccctg ctgatgccgg cacctactac tgcgtgaagt tccggaaggg ctcccctgac      300
gacgtcgagt ttaaatccgg cgctggcacc gaactgtccg tgcgagctaa accttctgct      360
cccgtggtgt ctggccctgc cgctagagct acacctcagc acaccgtgtc ttttacctgc      420
gagtcccacg gcttcagccc tagagacatc accctgaagt ggttcaagaa cggcaacgag      480
ctgtccgact tccagaccaa cgtggaccct gtgggagagt ccgtgtccta ctccatccac      540
tctaccgcca aggtggtgct gacccgagag gacgtgcaca gccaagtgat ctgtgaagtg      600
gcccacgtga ccctccaggg cgatcctttg agaggcaccg ccaacctgtc cgagacaatc      660
agagtgcctc ctacactgga agtgacccag cagcctgtgc gggccgagaa tcaagtgaac      720
gtgacctgcc aagtgcggaa gttctaccct cagagactgc agctgacctg gctggaaaac      780
ggcaatgtgt ccagaaccga cagcctcc accgtgaccg agaacaagga tggcacctac      840
aattggatgt cctggctgct cgtgaacgtg tccgctcaca gagatgacgt gaagctgaca      900
tgccaggtgg aacacgatgg ccagcctgcc gtgtctaagt cccacgacct gaaagtgtct      960
gctcacccca agagcaggg ctccaatacc gccgctgaga cacccggctc caacgagaga     1020
aacatctacg gagctagagc atctcctggc tctgctgcct ctcctagact gagagaggga     1080
cctgagctgt ctcctgatga tcctgctggc ctgctggatc tgagacaggg catgtttgct     1140
cagctggtgg cccagaacgt gctgctgatt gatggccctc tgtcctggta ctctgatcct     1200
ggattggctg gcgtgtccct gactggcggc ctgtcttaca agaggacac caaagaactg     1260
gtggtggcca aggccggcgt gtactacgtg ttctttcagc tggaactgcg gagagtggtg     1320
gccggcgaag gatctggatc tgtgtctctg gcactgcatc tgcagcccct gagatctgct     1380
gcaggcgctg ctgctctggc tctgacagtt gatctgcctc ctgcctcctc cgaggccaga     1440
aactccgcct ttggcttcca aggcagactg ctgcatctgt ctgccggcca gagactggga     1500
gtccatctgc atacagaggc tagagccagg cacgcctggc agttgacaca aggtgctaca     1560
gtgctgggcc tgttcagagt gacccagag attccagccg gcctgccttc tccaagatcc     1620
gag                                                                  1623
```

<210> SEQ ID NO 63
<211> LENGTH: 1587
<212> TYPE: DNA
<213> ORGANISM: Artificial sequence
<220> FEATURE:
<223> OTHER INFORMATION: nucleic acid sequence encoding SEQ ID NO: 46
      (Var 5)

<400> SEQUENCE: 63

```
gaagaggaac tgcaagtgat ccagcctgac aagtccgtgc tggtggctgc tggcgaaacc       60
gccacactga gatgtaccgc cacctctctg atccctgtgg gcctatcca gtggtttaga      120
```

```
ggcgctggac ctggcagaga gctgatctac aaccagaaag agggccactt tcctagagtg    180
accaccgtgt ccgacctgac caagcggaac aacatggact tctccatccg gatcggcaac    240
atcacccctg ctgatgccgg cacctactac tgcgtgaagt tccggaaggg ctcccctgac    300
gacgtcgagt ttaaatccgg cgctggcacc gaactgtccg tgcgagctaa accttctgct    360
cccgtggtgt ctggccctgc cgctagagct acacctcagc acaccgtgtc ttttacctgc    420
gagtccacg gcttcagccc tagagacatc accctgaagt ggttcaagaa cggcaacgag    480
ctgtccgact tccagaccaa cgtggaccct gtgggagagt ccgtgtccta ctccatccac    540
tctaccgcca aggtggtgct gacccgagag acgtgcaca gccaagtgat ctgtgaagtg    600
gcccacgtga ccctccaggg cgatcctttg agaggcaccg ccaacctgtc cgagacaatc    660
agagtgcctc ctacactgga agtgacccag cagcctgtgc gggccgagaa tcaagtgaac    720
gtgacctgcc aagtgcggaa gttctaccct cagagactgc agctgacctg gctggaaaac    780
ggcaatgtgt ccagaaccga cagcctcc accgtgaccg agaacaagga tggcaccta    840
aattggatgt cctggctgct cgtgaacgtg tccgctcaca gagatgacgt gaagctgaca    900
tgccaggtgg aacacgatgg ccagcctgcc gtgtctaagt cccacgacct gaaagtgtct    960
gctcacccca agagcagggg ctccaatacc gccgctgaga caccggctc caacgagaga   1020
aacatctacg gactgagaga gggacctgag ctgtctcctg atgatcctgc tggcctgctg   1080
gatctgagac agggcatgtt tgctcagctg gtggcccaga cgtgctgct gattgatggc   1140
cctctgtcct ggtactctga tcctggattg gctggcgtgt ccctgactgg cggcctgtct   1200
tacaaagagg acaccaaaga actggtggtg gccaaggccg cgtgtacta cgtgttcttt   1260
cagctggaac tgcggagagt ggtggccggc gaaggatctg gatctgtgtc tctggcactg   1320
catctgcagc cctgagatc tgctgcaggc gctgctgctc tggctctgac agttgatctg   1380
cctcctgcct cctccgaggc cagaaactcc gcctttggct tccaaggcag actgctgcat   1440
ctgtctgccg gccagagact gggagtccat ctgcatacag aggctagagc caggcacgcc   1500
tggcagttga cacaaggtgc tacagtgctg ggcctgttca gagtgacccc agagattcca   1560
gccggcctgc cttctccaag atccgag                                        1587

<210> SEQ ID NO 64
<211> LENGTH: 924
<212> TYPE: DNA
<213> ORGANISM: Artificial sequence
<220> FEATURE:
<223> OTHER INFORMATION: nucleic acid sequence encoding SEQ ID NO: 47
      (Var 6)

<400> SEQUENCE: 64
gaagaggaac tgcaagtgat ccagcctgac aagtccgtgc tggtggctgc tggcgaaacc     60
gccacactga gatgtaccgc cacctctctg atccctgtgg gccctatcca gtggtttaga    120
ggcgctggac ctggcagaga gctgatctac aaccagaaag agggccactt tcctagagtg    180
accaccgtgt ccgacctgac caagcggaac aacatggact tctccatccg gatcggcaac    240
atcacccctg ctgatgccgg cacctactac tgcgtgaagt tccggaaggg ctcccctgac    300
gacgtcgagt ttaaatccgg cgctggcacc gaactgtccg tgcgagctgg atctgctgcc    360
tctcctagac tgagagaggg acctgagctg tctcctgatg atcctgctgg cctgctggat    420
ctgagacagg gcatgtttgc tcagctggtg gcccagaacg tgctgctgat tgatggccct    480
ctgtcctggt actctgatcc tggattggct ggcgtgtccc tgactggcgg cctgtcttac    540
```

```
aaagaggaca ccaaagaact ggtggtggcc aaggccggcg tgtactacgt gttctttcag      600
ctggaactgc ggagagtggt ggccggcgaa ggatctggat ctgtgtctct ggcactgcat      660
ctgcagcccc tgagatctgc tgcaggcgct gctgctctgg ctctgacagt tgatctgcct      720
cctgcctcct ccgaggccag aaactccgcc tttggcttcc aaggcagact gctgcatctg      780
tctgccggcc agagactggg agtccatctg catacagagg ctagagccag gcacgcctgg      840
cagttgacac aaggtgctac agtgctgggc ctgttcagag tgaccccaga gattccagcc      900
ggcctgcctt ctccaagatc cgag                                            924

<210> SEQ ID NO 65
<211> LENGTH: 942
<212> TYPE: DNA
<213> ORGANISM: Artificial sequence
<220> FEATURE:
<223> OTHER INFORMATION: nucleic acid sequence encoding SEQ ID NO: 48
      (Var 7)

<400> SEQUENCE: 65
gaagaggaac tgcaagtgat ccagcctgac aagtccgtgc tggtggctgc tggcgaaacc       60
gccacactga gatgtaccgc cacctctctg atccctgtgg gccctatcca gtggtttaga      120
ggcgctggac ctggcagaga gctgatctac aaccagaaag agggccactt tcctagagtg      180
accaccgtgt ccgacctgac caagcggaac aacatggact ctccatccg gatcggcaac       240 atcacccctg ctgatgccgg cacctactac tgcgtgaagt tccggaaggg ctcccctgac      300
gacgtcgagt ttaaatccgg cgctggcacc gaactgtccg tgcgagctgg agctagagca      360
tctcctggct ctgctgcctc tcctagactg agagagggac ctgagctgtc tcctgatgat      420
cctgctggcc tgctggatct gagacagggc atgtttgctc agctggtggc ccagaacgtg      480
ctgctgattg atggccctct gtcctggtac tctgatcctg gattggctgg cgtgtccctg      540
actggcggcc tgtcttacaa agaggacacc aaagaactgg tggtggccaa ggccggcgtg      600
tactacgtgt tctttcagct ggaactgcgg agagtggtgg ccggcgaagg atctggatct      660
gtgtctctgg cactgcatct gcagcccctg agatctgctg caggcgctgc tgctctggct      720
ctgacagttg atctgcctcc tgcctcctcc gaggccagaa actccgcctt tggcttccaa      780
ggcagactgc tgcatctgtc tgccggccag agactgggag tccatctgca tacagaggct      840
agagccaggc acgcctggca gttgacacaa ggtgctacag tgctgggcct gttcagagtg      900
accccagaga ttccagccgg cctgccttct ccaagatccg ag                         942

<210> SEQ ID NO 66
<211> LENGTH: 906
<212> TYPE: DNA
<213> ORGANISM: Artificial sequence
<220> FEATURE:
<223> OTHER INFORMATION: nucleic acid sequence encoding SEQ ID NO: 49
      (Var 8)

<400> SEQUENCE: 66
gaagaggaac tgcaagtgat ccagcctgac aagtccgtgc tggtggctgc tggcgaaacc       60
gccacactga gatgtaccgc cacctctctg atccctgtgg gccctatcca gtggtttaga      120
ggcgctggac ctggcagaga gctgatctac aaccagaaag agggccactt tcctagagtg      180
accaccgtgt ccgacctgac caagcggaac aacatggact ctccatccg gatcggcaac       240 atcacccctg ctgatgccgg cacctactac tgcgtgaagt tccggaaggg ctcccctgac      300
gacgtcgagt ttaaatccgg cgctggcacc gaactgtccg tgcgagctgg actgagagag      360
```

```
ggacctgagc tgtctcctga tgatcctgct ggcctgctgg atctgagaca gggcatgttt      420
gctcagctgg tggcccagaa cgtgctgctg attgatggcc tctgtcctg gtactctgat       480 cctggattgg ctggcgtgtc cctgactggc ggcctgtctt acaaagagga caccaaagaa      540
ctggtggtgg ccaaggccgg cgtgtactac gtgttctttc agctggaact gcggagagtg      600
gtggccggcg aaggatctgg atctgtgtct ctggcactgc atctgcagcc cctgagatct      660 gctgcaggc ctgctgctct ggctctgaca gttgatctgc ctcctgcctc ctccgaggcc       720
agaaactccg cctttggctt ccaaggcaga ctgctgcatc tgtctgccgg ccagagactg      780
ggagtccatc tgcatacaga ggctagagcc aggcacgcct ggcagttgac acaaggtgct      840
acagtgctgg gcctgttcag agtgacccca gagattccag ccggcctgcc ttctccaaga     900
tccgag                                                                906
```

<210> SEQ ID NO 67
<211> LENGTH: 1029
<212> TYPE: DNA
<213> ORGANISM: Artificial sequence
<220> FEATURE:
<223> OTHER INFORMATION: alternative nucleic acid sequence encoding SEQ
      ID NO: 2 (original SIRP fragment)

<400> SEQUENCE: 67

```
gaagaggaac tgcaagtgat ccagcctgac aagtccgtgc tggtggctgc tggcgaaacc      60
gccacactga gatgtaccgc cacctctctg atccctgtgg ccctatcca gtggtttaga      120 ggcgctggac ctggcagaga gctgatctac aaccagaaag agggccactt tcctagagtg     180
accaccgtgt ccgacctgac caagcggaac aacatggact ctccatccg gatcggcaac      240 atcaccctg ctgatgccgg cacctactac tgcgtgaagt tccggaaggg ctcccctgac      300
gacgtcgagt ttaaatccgg cgctggcacc gaactgtccg tgcgagctaa accttctgct     360
cccgtggtgt ctggccctgc cgctagagct acacctcagc acaccgtgtc ttttacctgc     420
gagtcccacg gcttcagccc tagagacatc accctgaagt ggttcaagaa cggcaacgag    480
ctgtccgact ccagaccaa cgtggaccct gtgggagagt ccgtgtccta ctccatccac     540
tctaccgcca aggtggtgct gacccgagag gacgtgcaca gccaagtgat ctgtgaagtg    600
gcccacgtga ccctccaggg cgatcctttg agaggcaccg ccaacctgtc cgagacaatc    660
agagtgcctc ctacactgga agtgacccag cagcctgtgc gggccgagaa tcaagtgaac    720
gtgacctgcc aagtgcggaa gttctacccct cagagactgc agctgacctg gctgaaaaac   780
ggcaatgtgt ccagaaccga cagcctcc accgtgaccg agaacaagga tggcacctac     840
aattggatgt cctggctgct cgtgaacgtg tccgctcaca gagatgacgt gaagctgaca    900
tgccaggtgg aacacgatgg ccagcctgcc gtgtctaagt cccacgacct gaaagtgtct    960 gctcaccca agagcaggg ctccaatacc gccgctgaga cacgggctc caacgagaga     1020 aacatctac                                                             1029
```

<210> SEQ ID NO 68
<211> LENGTH: 945
<212> TYPE: DNA
<213> ORGANISM: Artificial sequence
<220> FEATURE:
<223> OTHER INFORMATION: nucleic acid SEQUENCE FOR SEQ ID NO: 21

<400> SEQUENCE: 68

```
gaagaggaaa tccaagtgat ccagcctgac aagtccgtgc tggtggctgc tggcgaaacc      60
```

```
gccacactga gatgtaccat cacctctctg atccctgtgg gccctatcca gtggtttaga    120
ggcgctggac ctggcagagt gctgatctac aaccagaaag agggccactt tcctagagtg    180
accaccgtgt ccgacctgac caagcggaac aacatggact tctccatccg gatcggcaac    240
atcacccctg ctgatgccgg cacctactac tgcatcaagt tccggaaggg ctcccctgac    300
gacgtcgagt ttaaatccgg cgctggcacc gagctgtccg tcagagcttc tggtgctaga    360
gcctctcctg gctctgccgc ttctcctaga ctgagagagg gacctgagct gtctcctgat    420
gatcctgctg gcctgctgga tctgagacag ggcatgtttg ctcagctggt ggcccagaac    480
gtgctgctga ttgatggccc tctgtcctgg tactctgatc ctggattggc tggcgtgtcc    540
ctgactggcg gcctgtctta caaagaggac accaaagaac tggtggtggc caaggccggc    600
gtgtactacg tgttctttca gctggaactg cggagagtgg tggccggcga aggatctgga    660
tctgtgtctc tggcactgca tctgcagcct ctgagatctg ctgcaggcgc tgctgctctg    720
gctctgacag ttgatctgcc tcctgcctcc tccgaggcca gaaactccgc ctttggcttc    780
caaggcagac tgctgcatct gtctgccggc cagagactgg gagtccatct gcatacagag    840
gccagagcta gacacgcttg gcagttgaca cagggcgcta cagtgctggg cctgttcaga    900
gtgacacctg agatcccagc cggcctgcct tctccaagat ctgag                   945
```

<210> SEQ ID NO 69
<211> LENGTH: 1749
<212> TYPE: DNA
<213> ORGANISM: Artificial sequence
<220> FEATURE:
<223> OTHER INFORMATION: Cloned sequence of the N-terminal his-tagged
      (NH)-DSP-107

<400> SEQUENCE: 69

```
gaattcccgc cgccaccatg ggctggtcct gcatcattct gtttctggtg gccacagcca     60
ccggcgtgca ctctcaccat catcaccacc atgaagagga actgcaagtg atccagcctg    120
acaagagcgt gctggtggct gctggcgaaa cagccacact gagatgtacc gccacctctc    180
tgatccctgt gggccctatc cagtggttta gaggcgctgg acctggcaga gagctgatct    240
acaaccagaa agagggacac ttccccagag tgaccaccgt gtccgacctg accaagcgga    300
acaacatgga cttcagcatc cggatcggca acatcacccc tgccgatgcc ggcacctact    360
actgcgtgaa gttcagaaag ggcagccccg acgacgtcga gtttaaaagc ggagccggca    420
cagagctgag cgtgcgggct aaaccttctg ctcctgtggt gtctgaccct gccgctagag    480
ctacacctca gcaccgtg tcttttacct gcgagagcca cggcttcagc cccagagata    540
tcaccctgaa gtggttcaag aacggcaacg agctgtccga cttccagacc aacgtggacc    600
ctgtgggaga gagcgtgtcc tacagcatcc acagcacagc caaggtggtg ctgacccggg    660
aagatgtgca ctcccaagtg atttgcgagg tggcccacgt taccctgcaa ggcgatcctc    720
tgagaggcac cgccaatctg agcgagacaa tccgggtgcc acctacactg aagtgaccc    780 agcagcctgt gcgggccgag aatcaagtga acgtgacctg ccaagtgcgg aagttctacc    840
ctcagagact gcagctgacc tggctggaaa acggcaatgt gtccagaacc gagacagcca    900
gcaccgtgac cgagaacaag gatggcacct acaattggat gagctggctg ctcgtgaatg    960
tgtctgccca ccgggacgat gtgaagctga catgccaggt ggaacacgat ggccagcctg   1020
ccgtgtctaa gagccacgac ctgaaggtgt ccgctcatcc caaagagcag gctctaata   1080 ctgccgccga gaacaccggc agcaacgaga gaaatatcta cggcgcttgt ccttgggccg   1140
```

```
tttctggcgc tagagcctct cctggatctg ccgcttctcc cagactgaga gagggacctg    1200
agctgagccc tgatgatcct gctggactgc tggatctgag acagggcatg tttgcccagc    1260
tggtggccca gaatgtgctg ctgattgatg ccctctgtc ctggtacagc gatcctggac     1320
ttgctggcgt tagcctgact ggcggcctga gctacaaaga ggacaccaaa gaactggtgg    1380
tggccaaggc cggcgtgtac tacgtgttct ttcagctgga actgcggaga gtggtggccg    1440
gcgaaggatc tggatctgtg tctctggctc tgcatctgca gcctctgaga tctgctgctg    1500
gtgctgctgc tctggccctg acagttgatc tgcctcctgc ctctagcgag gccagaaact    1560
ccgcctttgg cttccaaggc agactgctgc acctgagcgc tggacagaga ctgggagtcc    1620
atctgcacac agaagccaga gctagacacg cctggcagct gacacaaggc gctacagtgc    1680
tgggcctgtt cagagtgacc cctgagattc agccggcct gccatctcct agatctgagt     1740
gataagctt                                                             1749
```

<210> SEQ ID NO 70
<211> LENGTH: 184
<212> TYPE: PRT
<213> ORGANISM: Artificial sequence
<220> FEATURE:
<223> OTHER INFORMATION: 4-1BBL -21-0  184 aa

<400> SEQUENCE: 70

```
Arg Glu Gly Pro Glu Leu Ser Pro Asp Asp Pro Ala Gly Leu Leu Asp
1               5                   10                  15

Leu Arg Gln Gly Met Phe Ala Gln Leu Val Ala Gln Asn Val Leu Leu
            20                  25                  30

Ile Asp Gly Pro Leu Ser Trp Tyr Ser Asp Pro Gly Leu Ala Gly Val
        35                  40                  45

Ser Leu Thr Gly Gly Leu Ser Tyr Lys Glu Asp Thr Lys Glu Leu Val
    50                  55                  60

Val Ala Lys Ala Gly Val Tyr Tyr Val Phe Phe Gln Leu Glu Leu Arg
65                  70                  75                  80

Arg Val Val Ala Gly Glu Gly Ser Gly Ser Val Ser Leu Ala Leu His
                85                  90                  95

Leu Gln Pro Leu Arg Ser Ala Ala Gly Ala Ala Leu Ala Leu Thr
            100                 105                 110

Val Asp Leu Pro Pro Ala Ser Ser Glu Ala Arg Asn Ser Ala Phe Gly
        115                 120                 125

Phe Gln Gly Arg Leu Leu His Leu Ser Ala Gly Gln Arg Leu Gly Val
    130                 135                 140

His Leu His Thr Glu Ala Arg Ala Arg His Ala Trp Gln Leu Thr Gln
145                 150                 155                 160

Gly Ala Thr Val Leu Gly Leu Phe Arg Val Thr Pro Glu Ile Pro Ala
                165                 170                 175

Gly Leu Pro Ser Pro Arg Ser Glu
            180
```

<210> SEQ ID NO 71
<211> LENGTH: 552
<212> TYPE: DNA
<213> ORGANISM: Artificial sequence
<220> FEATURE:
<223> OTHER INFORMATION: na sequence encoding SEQ ID NO: 70

<400> SEQUENCE: 71

```
agagagggcc ctgagctgtc tcctgatgat cctgctggac tgctggacct gagacagggc    60
atgtttgctc agctggtggc ccagaacgtg ctgctgattg atggccctct gtcctggtac   120
tctgatcctg gattggctgg cgtgtccctg actggcggcc tgtcttacaa agaggacacc   180
aaagaactgg tggtcgccaa ggccggcgtg tactacgtgt tctttcagct ggaactgcgg   240
agagtggtgg ctggcgaagg atctggatct gtgtctctgg ccctgcatct gcagcctctg   300
agaagtgctg caggcgctgc tgcactggct ctgacagttg atctgcctcc tgcctcctcc   360
gaggccagaa actccgcctt tggcttccaa ggcagactgc tgcatctgtc tgccggacag   420
agactgggag tgcacctcca tacagaggcc agagctagac acgcttggca gttgacacag   480
ggcgctacag tgctgggcct gtttagagtg acacctgaga tcccagccgg cctgccatct   540
ccaagatctg aa                                                        552
```

<210> SEQ ID NO 72
<211> LENGTH: 182
<212> TYPE: PRT
<213> ORGANISM: Artificial sequence
<220> FEATURE:
<223> OTHER INFORMATION: 4-1BBL -23-0 182 aa

<400> SEQUENCE: 72

```
Gly Pro Glu Leu Ser Pro Asp Asp Pro Ala Gly Leu Leu Asp Leu Arg
1               5                   10                  15

Gln Gly Met Phe Ala Gln Leu Val Ala Gln Asn Val Leu Leu Ile Asp
                20                  25                  30

Gly Pro Leu Ser Trp Tyr Ser Asp Pro Gly Leu Ala Gly Val Ser Leu
            35                  40                  45

Thr Gly Gly Leu Ser Tyr Lys Glu Asp Thr Lys Glu Leu Val Val Ala
        50                  55                  60

Lys Ala Gly Val Tyr Tyr Val Phe Phe Gln Leu Glu Leu Arg Arg Val
65                  70                  75                  80

Val Ala Gly Glu Gly Ser Gly Ser Val Ser Leu Ala Leu His Leu Gln
                85                  90                  95

Pro Leu Arg Ser Ala Ala Gly Ala Ala Ala Leu Ala Leu Thr Val Asp
            100                 105                 110

Leu Pro Pro Ala Ser Ser Glu Ala Arg Asn Ser Ala Phe Gly Phe Gln
        115                 120                 125

Gly Arg Leu Leu His Leu Ser Ala Gly Gln Arg Leu Gly Val His Leu
    130                 135                 140

His Thr Glu Ala Arg Ala Arg His Ala Trp Gln Leu Thr Gln Gly Ala
145                 150                 155                 160

Thr Val Leu Gly Leu Phe Arg Val Thr Pro Glu Ile Pro Ala Gly Leu
                165                 170                 175

Pro Ser Pro Arg Ser Glu
            180
```

<210> SEQ ID NO 73
<211> LENGTH: 546
<212> TYPE: DNA
<213> ORGANISM: Artificial sequence
<220> FEATURE:
<223> OTHER INFORMATION: na sequence encoding SEQ ID NO: 72

<400> SEQUENCE: 73

```
ggccctgagc tgtctcctga tgatcctgct ggactgctgg acctgagaca gggcatgttt    60
gctcagctgg tggcccagaa cgtgctgctg attgatggcc ctctgtcctg gtactctgat   120
```

```
cctggattgg ctggcgtgtc cctgactggc ggcctgtctt acaaagagga caccaaagaa      180
ctggtggtcg ccaaggccgg cgtgtactac gtgttctttc agctggaact gcggagagtg      240
gtggctggcg aaggatctgg atctgtgtct ctggccctgc atctgcagcc tctgagaagt      300
gctgcaggcg ctgctgcact ggctctgaca gttgatctgc ctcctgcctc ctccgaggcc      360
agaaactccg cctttggctt ccaaggcaga ctgctgcatc tgtctgccgg acagagactg      420
ggagtgcacc tccatacaga ggccagagct agacacgctt ggcagttgac acagggcgct      480
acagtgctgg gcctgtttag agtgacacct gagatcccag ccggcctgcc atctccaaga      540
tctgaa                                                                546
```

```
<210> SEQ ID NO 74
<211> LENGTH: 183
<212> TYPE: PRT
<213> ORGANISM: Artificial sequence
<220> FEATURE:
<223> OTHER INFORMATION: 4-1BBL -14-8 183 aa

<400> SEQUENCE: 74
```

Ser Ala Ala Ser Pro Arg Leu Arg Glu Gly Pro Glu Leu Ser Pro Asp
1               5                   10                  15

Asp Pro Ala Gly Leu Leu Asp Leu Arg Gln Gly Met Phe Ala Gln Leu
            20                  25                  30

Val Ala Gln Asn Val Leu Leu Ile Asp Gly Pro Leu Ser Trp Tyr Ser
        35                  40                  45

Asp Pro Gly Leu Ala Gly Val Ser Leu Thr Gly Gly Leu Ser Tyr Lys
    50                  55                  60

Glu Asp Thr Lys Glu Leu Val Val Ala Lys Ala Gly Val Tyr Tyr Val
65                  70                  75                  80

Phe Phe Gln Leu Glu Leu Arg Arg Val Val Ala Gly Glu Gly Ser Gly
                85                  90                  95

Ser Val Ser Leu Ala Leu His Leu Gln Pro Leu Arg Ser Ala Ala Gly
            100                 105                 110

Ala Ala Ala Leu Ala Leu Thr Val Asp Leu Pro Pro Ala Ser Ser Glu
        115                 120                 125

Ala Arg Asn Ser Ala Phe Gly Phe Gln Gly Arg Leu Leu His Leu Ser
    130                 135                 140

Ala Gly Gln Arg Leu Gly Val His Leu His Thr Glu Ala Arg Ala Arg
145                 150                 155                 160

His Ala Trp Gln Leu Thr Gln Gly Ala Thr Val Leu Gly Leu Phe Arg
                165                 170                 175

Val Thr Pro Glu Ile Pro Ala
            180

```
<210> SEQ ID NO 75
<211> LENGTH: 551
<212> TYPE: DNA
<213> ORGANISM: Artificial sequence
<220> FEATURE:
<223> OTHER INFORMATION: na sequence encoding SEQ ID NO: 74 551 bp

<400> SEQUENCE: 75
gatctgccgc ttctcctaga ctgagagagg gccctgagct gtctcctgat gatcctgctg       60
gactgctgga cctgagacag ggcatgtttg ctcagctggt ggcccagaac gtgctgctga      120
ttgatggccc tctgtcctgg tactctgatc ctggattggc tggcgtgtcc ctgactggcg      180
```

```
gcctgtctta caaagaggac accaaagaac tggtggtcgc caaggccggc gtgtactacg    240
tgttctttca gctggaactg cggagagtgg tggctggcga aggatctgga tctgtgtctc    300
tggccctgca tctgcagcct ctgagaagtg ctgcaggcgc tgctgcactg gctctgacag    360
ttgatctgcc tcctgcctcc tccgaggcca gaaactccgc ctttggcttc caaggcagac    420
tgctgcatct gtctgccgga cagagactgg gagtgcacct ccatacagag gccagagcta    480
gacacgcttg gcagttgaca cagggcgcta cagtgctggg cctgtttaga gtgacacctg    540
agatcccagc c                                                         551
```

<210> SEQ ID NO 76
<211> LENGTH: 176
<212> TYPE: PRT
<213> ORGANISM: Artificial sequence
<220> FEATURE:
<223> OTHER INFORMATION: 4-1BBL -21-8  176 aa

<400> SEQUENCE: 76

```
Arg Glu Gly Pro Glu Leu Ser Pro Asp Asp Pro Ala Gly Leu Leu Asp
1               5                  10                  15

Leu Arg Gln Gly Met Phe Ala Gln Leu Val Ala Gln Asn Val Leu Leu
            20                  25                  30

Ile Asp Gly Pro Leu Ser Trp Tyr Ser Asp Pro Gly Leu Ala Gly Val
        35                  40                  45

Ser Leu Thr Gly Gly Leu Ser Tyr Lys Glu Asp Thr Lys Glu Leu Val
    50                  55                  60

Val Ala Lys Ala Gly Val Tyr Tyr Val Phe Phe Gln Leu Glu Leu Arg
65                  70                  75                  80

Arg Val Val Ala Gly Glu Gly Ser Gly Ser Val Ser Leu Ala Leu His
                85                  90                  95

Leu Gln Pro Leu Arg Ser Ala Ala Gly Ala Ala Ala Leu Ala Leu Thr
            100                 105                 110

Val Asp Leu Pro Pro Ala Ser Ser Glu Ala Arg Asn Ser Ala Phe Gly
        115                 120                 125

Phe Gln Gly Arg Leu Leu His Leu Ser Ala Gly Gln Arg Leu Gly Val
    130                 135                 140

His Leu His Thr Glu Ala Arg Ala Arg His Ala Trp Gln Leu Thr Gln
145                 150                 155                 160

Gly Ala Thr Val Leu Gly Leu Phe Arg Val Thr Pro Glu Ile Pro Ala
                165                 170                 175
```

<210> SEQ ID NO 77
<211> LENGTH: 528
<212> TYPE: DNA
<213> ORGANISM: Artificial sequence
<220> FEATURE:
<223> OTHER INFORMATION: na sequence encoding SEQ ID NO: 76 528 bp

<400> SEQUENCE: 77

```
agagagggcc ctgagctgtc tcctgatgat cctgctggac tgctggacct gagacagggc    60
atgtttgctc agctggtggc ccagaacgtg ctgctgattg atggccctct gtcctggtac    120
tctgatcctg gattggctgg cgtgtccctg actggcggcc tgtcttacaa agaggacacc    180
aaagaactgg tggtcgccaa ggccggcgtg tactacgtgt tctttcagct ggaactgcgg    240
agagtggtgg ctggcgaagg atctggatct gtgtctctgg ccctgcatct gcagcctctg    300
agaagtgctg caggcgctgc tgcactggct ctgacagttg atctgcctcc tgcctcctcc    360
```

| | | |
|---|---|---|
| gaggccagaa actccgcctt tggcttccaa ggcagactgc tgcatctgtc tgccggacag | | 420 |
| agactgggag tgcacctcca tacagaggcc agagctagac acgcttggca gttgacacag | | 480 |
| ggcgctacag tgctgggcct gtttagagtg acacctgaga tcccagcc | | 528 |

<210> SEQ ID NO 78
<211> LENGTH: 601
<212> TYPE: PRT
<213> ORGANISM: Artificial sequence
<220> FEATURE:
<223> OTHER INFORMATION: sc3x4-1BBL -14-0  601 aa

<400> SEQUENCE: 78

Ser Ala Ala Ser Pro Arg Leu Arg Glu Gly Pro Glu Leu Ser Pro Asp
1               5                   10                  15

Asp Pro Ala Gly Leu Leu Asp Leu Arg Gln Gly Met Phe Ala Gln Leu
            20                  25                  30

Val Ala Gln Asn Val Leu Leu Ile Asp Gly Pro Leu Ser Trp Tyr Ser
        35                  40                  45

Asp Pro Gly Leu Ala Gly Val Ser Leu Thr Gly Gly Leu Ser Tyr Lys
    50                  55                  60

Glu Asp Thr Lys Glu Leu Val Val Ala Lys Ala Gly Val Tyr Tyr Val
65                  70                  75                  80

Phe Phe Gln Leu Glu Leu Arg Arg Val Val Ala Gly Glu Gly Ser Gly
                85                  90                  95

Ser Val Ser Leu Ala Leu His Leu Gln Pro Leu Arg Ser Ala Ala Gly
            100                 105                 110

Ala Ala Leu Ala Leu Thr Val Asp Leu Pro Pro Ala Ser Ser Glu
            115                 120                 125

Ala Arg Asn Ser Ala Phe Gly Phe Gln Gly Arg Leu Leu His Leu Ser
    130                 135                 140

Ala Gly Gln Arg Leu Gly Val His Leu His Thr Glu Ala Arg Ala Arg
145                 150                 155                 160

His Ala Trp Gln Leu Thr Gln Gly Ala Thr Val Leu Gly Leu Phe Arg
                165                 170                 175

Val Thr Pro Glu Ile Pro Ala Gly Leu Pro Ser Pro Arg Ser Glu Gly
            180                 185                 190

Gly Gly Gly Ser Gly Gly Gly Ser Gly Gly Gly Ser Ala Ala
        195                 200                 205

Ser Pro Arg Leu Arg Glu Gly Pro Glu Leu Ser Pro Asp Asp Pro Ala
    210                 215                 220

Gly Leu Leu Asp Leu Arg Gln Gly Met Phe Ala Gln Leu Val Ala Gln
225                 230                 235                 240

Asn Val Leu Leu Ile Asp Gly Pro Leu Ser Trp Tyr Ser Asp Pro Gly
                245                 250                 255

Leu Ala Gly Val Ser Leu Thr Gly Gly Leu Ser Tyr Lys Glu Asp Thr
            260                 265                 270

Lys Glu Leu Val Val Ala Lys Ala Gly Val Tyr Tyr Val Phe Phe Gln
        275                 280                 285

Leu Glu Leu Arg Arg Val Val Ala Gly Glu Gly Ser Gly Ser Val Ser
    290                 295                 300

Leu Ala Leu His Leu Gln Pro Leu Arg Ser Ala Ala Gly Ala Ala Ala
305                 310                 315                 320

Leu Ala Leu Thr Val Asp Leu Pro Pro Ala Ser Ser Glu Ala Arg Asn
                325                 330                 335

Ser Ala Phe Gly Phe Gln Gly Arg Leu Leu His Leu Ser Ala Gly Gln
                340                 345                 350

Arg Leu Gly Val His Leu His Thr Glu Ala Arg Ala Arg His Ala Trp
            355                 360                 365

Gln Leu Thr Gln Gly Ala Thr Val Leu Gly Leu Phe Arg Val Thr Pro
        370                 375                 380

Glu Ile Pro Ala Gly Leu Pro Ser Pro Arg Ser Gly Gly Gly Gly
385                 390                 395                 400

Ser Gly Gly Gly Ser Gly Gly Gly Ser Ala Ala Ser Pro Arg
                405                 410                 415

Leu Arg Glu Gly Pro Glu Leu Ser Pro Asp Pro Ala Gly Leu Leu
            420                 425                 430

Asp Leu Arg Gln Gly Met Phe Ala Gln Leu Val Ala Gln Asn Val Leu
        435                 440                 445

Leu Ile Asp Gly Pro Leu Ser Trp Tyr Ser Asp Pro Gly Leu Ala Gly
        450                 455                 460

Val Ser Leu Thr Gly Gly Leu Ser Tyr Lys Glu Asp Thr Lys Glu Leu
465                 470                 475                 480

Val Val Ala Lys Ala Gly Val Tyr Tyr Val Phe Phe Gln Leu Glu Leu
                485                 490                 495

Arg Arg Val Val Ala Gly Glu Gly Ser Gly Ser Val Ser Leu Ala Leu
            500                 505                 510

His Leu Gln Pro Leu Arg Ser Ala Gly Ala Ala Leu Ala Leu
        515                 520                 525

Thr Val Asp Leu Pro Pro Ala Ser Ser Glu Ala Arg Asn Ser Ala Phe
        530                 535                 540

Gly Phe Gln Gly Arg Leu Leu His Leu Ser Ala Gly Gln Arg Leu Gly
545                 550                 555                 560

Val His Leu His Thr Glu Ala Arg Ala Arg His Ala Trp Gln Leu Thr
                565                 570                 575

Gln Gly Ala Thr Val Leu Gly Leu Phe Arg Val Thr Pro Glu Ile Pro
            580                 585                 590

Ala Gly Leu Pro Ser Pro Arg Ser Glu
        595                 600

<210> SEQ ID NO 79
<211> LENGTH: 1803
<212> TYPE: DNA
<213> ORGANISM: Artificial sequence
<220> FEATURE:
<223> OTHER INFORMATION: na sequence encoding SEQ ID NO: 78

<400> SEQUENCE: 79

```
tctgccgcca gccctaggct gcgcgaggga cccgagctga gcccagacga tcccgccggc    60
ctgctggacc tgaggcaggg aatgttcgca cagctggtgg cccagaacgt gctgctgatc   120
gacggccctc tgtcctggta ctctgatcca ggcctggccg gcgtgtccct gacaggaggc   180
ctgtcttata aggaggatac caaggagctg gtggtggcaa aggcaggcgt gtactacgtg   240
ttcttccagc tggagctgag gagagtggtg gcaggagagg gcagcggctc cgtgtctctg   300
gccctgcacc tccagcctct gcggagcgcc gccggcgccg ccgccctggc cctgaccgtg   360
gatctgcctc cagccagctc cgaggccagg aatagcgcct tcggctttca gggccgcctg   420
ctgcacctgt ccgccggcca gcggctggga gtgcacctgc acacagaggc cagagccgg   480 cacgcatggc agctgacaca gggagcaacc gtgctgggcc tgttccgcgt gacccctgag   540
```

-continued

| | |
|---|---|
| atcccagccg gcctgccaag cccccggtcc gagggcggcg gcggctctgg cggaggaggc | 600 |
| agcggaggcg gcggctctgc cgccagcccc aggctgcgcg agggacccga gctgtcccca | 660 |
| gacgatcctg ccggcctgct ggacctgcgc cagggaatgt ttgcccagct ggtggctcaa | 720 |
| aacgtgctgt taatcgacgg ccctctgagc tggtactctg atcctggcct ggccggcgtg | 780 |
| agcctgaccg gcggcctgtc ctacaaagag gatactaaag agctggtggt cgccaaagcc | 840 |
| ggcgtgtact acgtgttctt ccaactggag ctgaggaggg tcgtcgccgg cgaaggcagc | 900 |
| ggctccgtgt ctctggccct gcacctccag ccgctgagga gcgccgccgg cgccgccgcc | 960 |
| ctggccctga cggtggacct gccacctgcc tctagcgagg caagaaattc tgccttcggc | 1020 |
| ttccagggca ggctgctgca cctgagcgcc ggccagcgcc tgggcgtcca cctgcatacc | 1080 |
| gaagccagag cccggcatgc ctggcagctg acccagggcg ccaccgtgct gggcctgttc | 1140 |
| agagtgaccc cagagatccc cgccggcctg cctagcccaa ggtccgaagg cggcggcggc | 1200 |
| tccggcggcg gaggctctgg aggagggggc tctgccgcca gcccaaggct gcgcgaggga | 1260 |
| cccgagctgt cgcctgacga tccagccggc ctgctggacc tgcgtcaggg catgttcgcc | 1320 |
| cagctggtgg ctcagaacgt gctgttaatc gacggcccac tgtcttggta ttctgatccc | 1380 |
| ggcctggccg gcgtgtctct gacaggaggc ctgagctaca agaggatac aaagagctg | 1440 |
| gtggtcgcta agctggcgt gtactacgtg ttcttccaac tggagctgcg cagggtcgtc | 1500 |
| gccggcgagg cagcggctc cgtgtctctg gccctgcacc tccagccatt acggagcgcc | 1560 |
| gccggcgccg ccgccctggc cctgactgtg gacctgccac cagcctcctc tgaggcacgg | 1620 |
| aacagcgcct tcggcttcca aggcagactg ctgcacctgt ctgccggcca gaggctgggc | 1680 |
| gtccacctgc acaccgaagc cagagcccgg cacgcctggc agctgactca gggcgctacc | 1740 |
| gtgctgggcc tgttccgcgt aaccccagag atccctgccg gcctgcccag ccctcggtcc | 1800 |
| gag | 1803 |

<210> SEQ ID NO 80
<211> LENGTH: 535
<212> TYPE: PRT
<213> ORGANISM: Artificial sequence
<220> FEATURE:
<223> OTHER INFORMATION: DSP107_Var2

<400> SEQUENCE: 80

```
Ser Ala Ala Ser Pro Arg Leu Arg Glu Gly Pro Glu Leu Ser Pro Asp
1               5                   10                  15

Asp Pro Ala Gly Leu Leu Asp Leu Arg Gln Gly Met Phe Ala Gln Leu
            20                  25                  30

Val Ala Gln Asn Val Leu Leu Ile Asp Gly Pro Leu Ser Trp Tyr Ser
        35                  40                  45

Asp Pro Gly Leu Ala Gly Val Ser Leu Thr Gly Gly Leu Ser Tyr Lys
    50                  55                  60

Glu Asp Thr Lys Glu Leu Val Val Ala Lys Ala Gly Val Tyr Tyr Val
65                  70                  75                  80

Phe Phe Gln Leu Glu Leu Arg Arg Val Val Ala Gly Glu Gly Ser Gly
                85                  90                  95

Ser Val Ser Leu Ala Leu His Leu Gln Pro Leu Arg Ser Ala Ala Gly
            100                 105                 110

Ala Ala Ala Leu Ala Leu Thr Val Asp Leu Pro Pro Ala Ser Ser Glu
        115                 120                 125

Ala Arg Asn Ser Ala Phe Gly Phe Gln Gly Arg Leu Leu His Leu Ser
```

```
            130                 135                 140
Ala Gly Gln Arg Leu Gly Val His Leu His Thr Glu Ala Arg Ala Arg
145                 150                 155                 160

His Ala Trp Gln Leu Thr Gln Gly Ala Thr Val Leu Gly Leu Phe Arg
                165                 170                 175

Val Thr Pro Glu Ile Pro Ala Gly Leu Pro Ser Pro Arg Ser Glu Gly
                180                 185                 190

Glu Glu Glu Leu Gln Val Ile Gln Pro Asp Lys Ser Val Leu Val Ala
                195                 200                 205

Ala Gly Glu Thr Ala Thr Leu Arg Cys Thr Ala Thr Ser Leu Ile Pro
210                 215                 220

Val Gly Pro Ile Gln Trp Phe Arg Gly Ala Gly Pro Gly Arg Glu Leu
225                 230                 235                 240

Ile Tyr Asn Gln Lys Glu Gly His Phe Pro Arg Val Thr Thr Val Ser
                245                 250                 255

Asp Leu Thr Lys Arg Asn Asn Met Asp Phe Ser Ile Arg Ile Gly Asn
                260                 265                 270

Ile Thr Pro Ala Asp Ala Gly Thr Tyr Tyr Cys Val Lys Phe Arg Lys
                275                 280                 285

Gly Ser Pro Asp Asp Val Glu Phe Lys Ser Gly Ala Gly Thr Glu Leu
290                 295                 300

Ser Val Arg Ala Lys Pro Ser Ala Pro Val Val Ser Gly Pro Ala Ala
305                 310                 315                 320

Arg Ala Thr Pro Gln His Thr Val Ser Phe Thr Cys Glu Ser His Gly
                325                 330                 335

Phe Ser Pro Arg Asp Ile Thr Leu Lys Trp Phe Lys Asn Gly Asn Glu
                340                 345                 350

Leu Ser Asp Phe Gln Thr Asn Val Asp Pro Val Gly Glu Ser Val Ser
                355                 360                 365

Tyr Ser Ile His Ser Thr Ala Lys Val Val Leu Thr Arg Glu Asp Val
                370                 375                 380

His Ser Gln Val Ile Cys Glu Val Ala His Val Thr Leu Gln Gly Asp
385                 390                 395                 400

Pro Leu Arg Gly Thr Ala Asn Leu Ser Glu Thr Ile Arg Val Pro Pro
                405                 410                 415

Thr Leu Glu Val Thr Gln Gln Pro Val Arg Ala Glu Asn Gln Val Asn
                420                 425                 430

Val Thr Cys Gln Val Arg Lys Phe Tyr Pro Gln Arg Leu Gln Leu Thr
                435                 440                 445

Trp Leu Glu Asn Gly Asn Val Ser Arg Thr Glu Thr Ala Ser Thr Val
450                 455                 460

Thr Glu Asn Lys Asp Gly Thr Tyr Asn Trp Met Ser Trp Leu Leu Val
465                 470                 475                 480

Asn Val Ser Ala His Arg Asp Asp Val Lys Leu Thr Cys Gln Val Glu
                485                 490                 495

His Asp Gly Gln Pro Ala Val Ser Lys Ser His Asp Leu Lys Val Ser
                500                 505                 510

Ala His Pro Lys Glu Gln Gly Ser Asn Thr Ala Ala Glu Asn Thr Gly
                515                 520                 525

Ser Asn Glu Arg Asn Ile Tyr
530                 535

<210> SEQ ID NO 81
```

```
<211> LENGTH: 699
<212> TYPE: DNA
<213> ORGANISM: Artificial sequence
<220> FEATURE:
<223> OTHER INFORMATION: NA sequence of SEQ ID NO: 80

<400> SEQUENCE: 81
tctgctgcct ctcctagact gagagaggga cctgagctgt ctcctgatga tcctgctggc     60
ctgctggatc tgagacaggg catgtttgct cagctggtgg cccagaacgt gctgctgatt    120
gatggccctc tgtcctggta ctctgatcct ggattggctg gcgtgtccct gactggcggc    180
ctgtcttaca aagaggacac caaagaactg gtggtggcca aggccggcgt gtactacgtg    240
ttctttcagc tggaactgcg gagagtggtg gccggcgaag gatctggatc tgtgtctctg    300
gcactgcatc tgcagcccct gagatctgct gcaggcgctg ctgctctggc tctgacagtt    360
gatctgcctc ctgcctcctc cgaggccaga aactccgcct ttggcttcca aggcagactg    420
ctgcatctgt ctgccggcca gagactggga gtccatctgc atacagaggc tagagccagg    480
cacgcctggc agttgacaca aggtgctaca gtgctgggcc tgttcagagt gaccccagag    540
attccagccg gcctgccttc tccaagatcc gagggcgaag aggaactgca agtgatccag    600
cctgacaagt ccgtgctggt ggctgctggc gaaaccgcca cactgagatg taccgccacc    660
tctctgatcc ctgtgggccc tatccagtgg tttagaggc                           699

<210> SEQ ID NO 82
<211> LENGTH: 14
<212> TYPE: PRT
<213> ORGANISM: Artificial sequence
<220> FEATURE:
<223> OTHER INFORMATION: polypeptide linker

<400> SEQUENCE: 82

Gly Gly Gly Gly Ser Gly Gly Gly Gly Ser Gly Gly Gly Gly
1               5                   10

<210> SEQ ID NO 83
<211> LENGTH: 9
<212> TYPE: PRT
<213> ORGANISM: Artificial sequence
<220> FEATURE:
<223> OTHER INFORMATION: polypeptide linker

<400> SEQUENCE: 83

Gly Gly Gly Gly Ser Gly Gly Gly Gly
1               5

<210> SEQ ID NO 84
<211> LENGTH: 5
<212> TYPE: PRT
<213> ORGANISM: Artificial sequence
<220> FEATURE:
<223> OTHER INFORMATION: polypeptide linker
<220> FEATURE:
<221> NAME/KEY: REPEAT
<222> LOCATION: (1)..(5)
<223> OTHER INFORMATION: may repeat 1-4 times

<400> SEQUENCE: 84

Gly Gly Gly Gly Ser
1               5

<210> SEQ ID NO 85
<211> LENGTH: 5
<212> TYPE: PRT
```

```
<213> ORGANISM: Artificial sequence
<220> FEATURE:
<223> OTHER INFORMATION: polypeptide linker

<400> SEQUENCE: 85

Gly Gly Gly Gly Ser
1               5

<210> SEQ ID NO 86
<211> LENGTH: 10
<212> TYPE: PRT
<213> ORGANISM: Artificial sequence
<220> FEATURE:
<223> OTHER INFORMATION: polypeptide linker

<400> SEQUENCE: 86

Gly Gly Gly Gly Ser Gly Gly Gly Gly Ser
1               5                   10

<210> SEQ ID NO 87
<211> LENGTH: 5
<212> TYPE: PRT
<213> ORGANISM: Artificial sequence
<220> FEATURE:
<223> OTHER INFORMATION: polypeptide linker
<220> FEATURE:
<221> NAME/KEY: REPEAT
<222> LOCATION: (1)..(5)
<223> OTHER INFORMATION: may repeat 1-3 times

<400> SEQUENCE: 87

Glu Ala Ala Ala Lys
1               5

<210> SEQ ID NO 88
<211> LENGTH: 7
<212> TYPE: PRT
<213> ORGANISM: Artificial sequence
<220> FEATURE:
<223> OTHER INFORMATION: polypeptide linker
<220> FEATURE:
<221> NAME/KEY: REPEAT
<222> LOCATION: (2)..(6)
<223> OTHER INFORMATION: repeat 2-5 times

<400> SEQUENCE: 88

Ala Glu Ala Ala Ala Lys Ala
1               5

<210> SEQ ID NO 89
<211> LENGTH: 12
<212> TYPE: PRT
<213> ORGANISM: Artificial sequence
<220> FEATURE:
<223> OTHER INFORMATION: polypeptide linker

<400> SEQUENCE: 89

Ala Glu Ala Ala Ala Lys Glu Ala Ala Ala Lys Ala
1               5                   10

<210> SEQ ID NO 90
<211> LENGTH: 46
<212> TYPE: PRT
<213> ORGANISM: Artificial sequence
<220> FEATURE:
<223> OTHER INFORMATION: polypeptide linker

<400> SEQUENCE: 90
```

```
Ala Glu Ala Ala Ala Lys Glu Ala Ala Lys Glu Ala Ala Lys
1               5                  10                  15

Glu Ala Ala Ala Lys Ala Leu Glu Ala Glu Ala Ala Lys Glu Ala
            20                  25                  30

Ala Ala Lys Glu Ala Ala Ala Lys Glu Ala Ala Ala Lys Ala
        35                  40                  45
```

<210> SEQ ID NO 91
<211> LENGTH: 5
<212> TYPE: PRT
<213> ORGANISM: Artificial sequence
<220> FEATURE:
<223> OTHER INFORMATION: polypeptide linker

<400> SEQUENCE: 91

```
Pro Ala Pro Ala Pro
1               5
```

<210> SEQ ID NO 92
<211> LENGTH: 18
<212> TYPE: PRT
<213> ORGANISM: Artificial sequence
<220> FEATURE:
<223> OTHER INFORMATION: polypeptide linker

<400> SEQUENCE: 92

```
Lys Glu Ser Gly Ser Val Ser Ser Glu Gln Leu Ala Gln Phe Arg Ser
1               5                  10                  15

Leu Asp
```

<210> SEQ ID NO 93
<211> LENGTH: 14
<212> TYPE: PRT
<213> ORGANISM: Artificial sequence
<220> FEATURE:
<223> OTHER INFORMATION: polypeptide linker

<400> SEQUENCE: 93

```
Glu Gly Lys Ser Ser Gly Ser Gly Ser Glu Ser Lys Ser Thr
1               5                  10
```

<210> SEQ ID NO 94
<211> LENGTH: 12
<212> TYPE: PRT
<213> ORGANISM: Artificial sequence
<220> FEATURE:
<223> OTHER INFORMATION: polypeptide linker

<400> SEQUENCE: 94

```
Gly Ser Ala Gly Ser Ala Ala Gly Ser Gly Glu Phe
1               5                  10
```

<210> SEQ ID NO 95
<211> LENGTH: 229
<212> TYPE: PRT
<213> ORGANISM: Artificial sequence
<220> FEATURE:
<223> OTHER INFORMATION: polypeptide linker

<400> SEQUENCE: 95

```
Glu Ser Lys Tyr Gly Pro Pro Cys Pro Pro Cys Pro Ala Pro Glu Phe
1               5                  10                  15

Glu Gly Gly Pro Ser Val Phe Leu Phe Pro Pro Lys Pro Lys Asp Thr
            20                  25                  30
```

Leu Met Ile Ser Arg Thr Pro Glu Val Thr Cys Val Val Asp Val
         35                  40                  45

Ser Gln Glu Asp Pro Glu Val Gln Phe Asn Trp Tyr Val Asp Gly Val
 50                  55                  60

Glu Val His Asn Ala Lys Thr Lys Pro Arg Glu Glu Gln Phe Asn Ser
 65                  70                  75                  80

Thr Tyr Arg Val Val Ser Val Leu Thr Val Leu His Gln Asp Trp Leu
                 85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
210                 215                 220

Leu Ser Leu Gly Lys
225

<210> SEQ ID NO 96
<211> LENGTH: 232
<212> TYPE: PRT
<213> ORGANISM: Artificial sequence
<220> FEATURE:
<223> OTHER INFORMATION: polypeptide linker

<400> SEQUENCE: 96

Glu Pro Lys Ser Cys Asp Lys Thr His Thr Cys Pro Pro Cys Pro Ala
1               5                  10                  15

Pro Glu Ala Ala Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
 50                  55                  60

Asp Gly Val Glu Val His Asn Ala Lys Thr Lys Pro Arg Glu Glu Gln
 65                  70                  75                  80

Tyr Asn Ser Thr Tyr Arg Val Val Ser Val Leu Thr Val Leu His Gln
                 85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
130                 135                 140

Lys Asn Gln Val Ser Leu Thr Cys Leu Val Lys Gly Phe Tyr Pro Ser
145                 150                 155                 160

-continued

```
Asp Ile Ala Val Glu Trp Glu Ser Asn Gly Gln Pro Glu Asn Asn Tyr
                165                 170                 175
Lys Thr Thr Pro Pro Val Leu Asp Ser Asp Gly Ser Phe Phe Leu Tyr
            180                 185                 190
Ser Lys Leu Thr Val Asp Lys Ser Arg Trp Gln Gln Gly Asn Val Phe
        195                 200                 205
Ser Cys Ser Val Met His Glu Ala Leu His Asn His Tyr Thr Gln Lys
    210                 215                 220
Ser Leu Ser Leu Ser Pro Gly Lys
225                 230

<210> SEQ ID NO 97
<211> LENGTH: 8
<212> TYPE: PRT
<213> ORGANISM: Artificial sequence
<220> FEATURE:
<223> OTHER INFORMATION: polypeptide linker

<400> SEQUENCE: 97

Gly Leu Pro Ser Pro Arg Ser Glu
1               5

<210> SEQ ID NO 98
<211> LENGTH: 23
<212> TYPE: PRT
<213> ORGANISM: Artificial sequence
<220> FEATURE:
<223> OTHER INFORMATION: polypeptide linker

<400> SEQUENCE: 98

Ala Cys Pro Trp Ala Val Ser Gly Ala Arg Ala Ser Pro Gly Ser Ala
1               5                   10                  15

Ala Ser Pro Arg Leu Arg Glu
            20

<210> SEQ ID NO 99
<211> LENGTH: 19
<212> TYPE: PRT
<213> ORGANISM: Artificial sequence
<220> FEATURE:
<223> OTHER INFORMATION: polypeptide linker

<400> SEQUENCE: 99

Met Gly Trp Ser Leu Ile Leu Leu Phe Leu Val Ala Val Ala Thr Arg
1               5                   10                  15

Val Leu Ser

<210> SEQ ID NO 100
<211> LENGTH: 4
<212> TYPE: PRT
<213> ORGANISM: Artificial sequence
<220> FEATURE:
<223> OTHER INFORMATION: Predicted proteolytic sites in DSP107 SIRP-
      alpha-4-1BBL fusion protein

<400> SEQUENCE: 100

Thr Cys Gln Val
1

<210> SEQ ID NO 101
<211> LENGTH: 4
<212> TYPE: PRT
<213> ORGANISM: Artificial sequence
<220> FEATURE:
```

```
<223> OTHER INFORMATION: Predicted proteolytic sites in DSP107 SIRP-
      alpha-4-1BBL fusion protein

<400> SEQUENCE: 101

Glu His Asp Gly
1

<210> SEQ ID NO 102
<211> LENGTH: 4
<212> TYPE: PRT
<213> ORGANISM: Artificial sequence
<220> FEATURE:
<223> OTHER INFORMATION: Predicted proteolytic sites in DSP107 SIRP-
      alpha-4-1BBL fusion protein

<400> SEQUENCE: 102

Gln Pro Ala Val
1

<210> SEQ ID NO 103
<211> LENGTH: 4
<212> TYPE: PRT
<213> ORGANISM: Artificial sequence
<220> FEATURE:
<223> OTHER INFORMATION: Predicted proteolytic sites in DSP107 SIRP-
      alpha-4-1BBL fusion protein

<400> SEQUENCE: 103

Ser Lys Ser His
1

<210> SEQ ID NO 104
<211> LENGTH: 4
<212> TYPE: PRT
<213> ORGANISM: Artificial sequence
<220> FEATURE:
<223> OTHER INFORMATION: Predicted proteolytic sites in DSP107 SIRP-
      alpha-4-1BBL fusion protein

<400> SEQUENCE: 104

His Asp Leu Lys
1

<210> SEQ ID NO 105
<211> LENGTH: 4
<212> TYPE: PRT
<213> ORGANISM: Artificial sequence
<220> FEATURE:
<223> OTHER INFORMATION: Predicted proteolytic sites in DSP107 SIRP-
      alpha-4-1BBL fusion protein

<400> SEQUENCE: 105

Val Ser Ala His
1

<210> SEQ ID NO 106
<211> LENGTH: 4
<212> TYPE: PRT
<213> ORGANISM: Artificial sequence
<220> FEATURE:
<223> OTHER INFORMATION: Predicted proteolytic sites in DSP107 SIRP-
      alpha-4-1BBL fusion protein

<400> SEQUENCE: 106

Ser Ala His Pro
1
```

```
<210> SEQ ID NO 107
<211> LENGTH: 4
<212> TYPE: PRT
<213> ORGANISM: Artificial sequence
<220> FEATURE:
<223> OTHER INFORMATION: Predicted proteolytic sites in DSP107 SIRP-
      alpha-4-1BBL fusion protein

<400> SEQUENCE: 107

Lys Glu Gln Gly
1

<210> SEQ ID NO 108
<211> LENGTH: 4
<212> TYPE: PRT
<213> ORGANISM: Artificial sequence
<220> FEATURE:
<223> OTHER INFORMATION: Predicted proteolytic sites in DSP107 SIRP-
      alpha-4-1BBL fusion protein

<400> SEQUENCE: 108

Thr Ala Ala Glu
1

<210> SEQ ID NO 109
<211> LENGTH: 4
<212> TYPE: PRT
<213> ORGANISM: Artificial sequence
<220> FEATURE:
<223> OTHER INFORMATION: Predicted proteolytic sites in DSP107 SIRP-
      alpha-4-1BBL fusion protein

<400> SEQUENCE: 109

Asn Thr Gly Ser
1

<210> SEQ ID NO 110
<211> LENGTH: 4
<212> TYPE: PRT
<213> ORGANISM: Artificial sequence
<220> FEATURE:
<223> OTHER INFORMATION: Predicted proteolytic sites in DSP107 SIRP-
      alpha-4-1BBL fusion protein

<400> SEQUENCE: 110

Asn Glu Arg Asn
1

<210> SEQ ID NO 111
<211> LENGTH: 4
<212> TYPE: PRT
<213> ORGANISM: Artificial sequence
<220> FEATURE:
<223> OTHER INFORMATION: Predicted proteolytic sites in DSP107 SIRP-
      alpha-4-1BBL fusion protein

<400> SEQUENCE: 111

Ile Tyr Gly Ala
1

<210> SEQ ID NO 112
<211> LENGTH: 4
<212> TYPE: PRT
<213> ORGANISM: Artificial sequence
<220> FEATURE:
<223> OTHER INFORMATION: Predicted proteolytic sites in DSP107 SIRP-
      alpha-4-1BBL fusion protein

<400> SEQUENCE: 112
```

```
Met Phe Ala Gln
1

<210> SEQ ID NO 113
<211> LENGTH: 4
<212> TYPE: PRT
<213> ORGANISM: Artificial sequence
<220> FEATURE:
<223> OTHER INFORMATION: Predicted proteolytic sites in DSP107 SIRP-
      alpha-4-1BBL fusion protein

<400> SEQUENCE: 113

Leu Val Ala Gln
1

<210> SEQ ID NO 114
<211> LENGTH: 4
<212> TYPE: PRT
<213> ORGANISM: Artificial sequence
<220> FEATURE:
<223> OTHER INFORMATION: Predicted proteolytic sites in DSP107 SIRP-
      alpha-4-1BBL fusion protein

<400> SEQUENCE: 114

Leu Val Ala Gln
1

<210> SEQ ID NO 115
<211> LENGTH: 4
<212> TYPE: PRT
<213> ORGANISM: Artificial sequence
<220> FEATURE:
<223> OTHER INFORMATION: Predicted proteolytic sites in DSP107 SIRP-
      alpha-4-1BBL fusion protein

<400> SEQUENCE: 115

Asn Val Leu Leu
1

<210> SEQ ID NO 116
<211> LENGTH: 4
<212> TYPE: PRT
<213> ORGANISM: Artificial sequence
<220> FEATURE:
<223> OTHER INFORMATION: Predicted proteolytic sites in DSP107 SIRP-
      alpha-4-1BBL fusion protein

<400> SEQUENCE: 116

Val Ala Gln Asn
1

<210> SEQ ID NO 117
<211> LENGTH: 4
<212> TYPE: PRT
<213> ORGANISM: Artificial sequence
<220> FEATURE:
<223> OTHER INFORMATION: Predicted proteolytic sites in DSP107 SIRP-
      alpha-4-1BBL fusion protein

<400> SEQUENCE: 117

Val Leu Leu Ile
1

<210> SEQ ID NO 118
<211> LENGTH: 4
<212> TYPE: PRT
<213> ORGANISM: Artificial sequence
```

```
<220> FEATURE:
<223> OTHER INFORMATION: Predicted proteolytic sites in DSP107 SIRP-
      alpha-4-1BBL fusion protein

<400> SEQUENCE: 118

Gln Asn Val Leu
1

<210> SEQ ID NO 119
<211> LENGTH: 4
<212> TYPE: PRT
<213> ORGANISM: Artificial sequence
<220> FEATURE:
<223> OTHER INFORMATION: Predicted proteolytic sites in DSP107 SIRP-
      alpha-4-1BBL fusion protein

<400> SEQUENCE: 119

Leu Ile Asp Gly
1

<210> SEQ ID NO 120
<211> LENGTH: 4
<212> TYPE: PRT
<213> ORGANISM: Artificial sequence
<220> FEATURE:
<223> OTHER INFORMATION: Predicted proteolytic sites in DSP107 SIRP-
      alpha-4-1BBL fusion protein

<400> SEQUENCE: 120

Asn Val Leu Leu
1

<210> SEQ ID NO 121
<211> LENGTH: 4
<212> TYPE: PRT
<213> ORGANISM: Artificial sequence
<220> FEATURE:
<223> OTHER INFORMATION: Predicted proteolytic sites in DSP107 SIRP-
      alpha-4-1BBL fusion protein

<400> SEQUENCE: 121

Ile Asp Gly Pro
1

<210> SEQ ID NO 122
<211> LENGTH: 4
<212> TYPE: PRT
<213> ORGANISM: Artificial sequence
<220> FEATURE:
<223> OTHER INFORMATION: Predicted proteolytic sites in DSP107 SIRP-
      alpha-4-1BBL fusion protein

<400> SEQUENCE: 122

Asp Gly Pro Leu
1

<210> SEQ ID NO 123
<211> LENGTH: 4
<212> TYPE: PRT
<213> ORGANISM: Artificial sequence
<220> FEATURE:
<223> OTHER INFORMATION: Predicted proteolytic sites in DSP107 SIRP-
      alpha-4-1BBL fusion protein

<400> SEQUENCE: 123

Ser Trp Tyr Ser
1
```

```
<210> SEQ ID NO 124
<211> LENGTH: 4
<212> TYPE: PRT
<213> ORGANISM: Artificial sequence
<220> FEATURE:
<223> OTHER INFORMATION: Predicted proteolytic sites in DSP107 SIRP-
      alpha-4-1BBL fusion protein

<400> SEQUENCE: 124

Asp Gly Pro Leu
1

<210> SEQ ID NO 125
<211> LENGTH: 4
<212> TYPE: PRT
<213> ORGANISM: Artificial sequence
<220> FEATURE:
<223> OTHER INFORMATION: Predicted proteolytic sites in DSP107 SIRP-
      alpha-4-1BBL fusion protein

<400> SEQUENCE: 125

Ser Trp Tyr Ser
1

<210> SEQ ID NO 126
<211> LENGTH: 4
<212> TYPE: PRT
<213> ORGANISM: Artificial sequence
<220> FEATURE:
<223> OTHER INFORMATION: Predicted proteolytic sites in DSP107 SIRP-
      alpha-4-1BBL fusion protein

<400> SEQUENCE: 126

Gly Pro Leu Ser
1

<210> SEQ ID NO 127
<211> LENGTH: 4
<212> TYPE: PRT
<213> ORGANISM: Artificial sequence
<220> FEATURE:
<223> OTHER INFORMATION: Predicted proteolytic sites in DSP107 SIRP-
      alpha-4-1BBL fusion protein

<400> SEQUENCE: 127

Trp Tyr Ser Asp
1

<210> SEQ ID NO 128
<211> LENGTH: 4
<212> TYPE: PRT
<213> ORGANISM: Artificial sequence
<220> FEATURE:
<223> OTHER INFORMATION: Predicted proteolytic sites in DSP107 SIRP-
      alpha-4-1BBL fusion protein

<400> SEQUENCE: 128

Leu Ser Trp Tyr
1

<210> SEQ ID NO 129
<211> LENGTH: 4
<212> TYPE: PRT
<213> ORGANISM: Artificial sequence
<220> FEATURE:
<223> OTHER INFORMATION: Predicted proteolytic sites in DSP107 SIRP-
      alpha-4-1BBL fusion protein
```

```
<400> SEQUENCE: 129

Ser Asp Pro Gly
1

<210> SEQ ID NO 130
<211> LENGTH: 4
<212> TYPE: PRT
<213> ORGANISM: Artificial sequence
<220> FEATURE:
<223> OTHER INFORMATION: Predicted proteolytic sites in DSP107 SIRP-
      alpha-4-1BBL fusion protein

<400> SEQUENCE: 130

Leu Ser Trp Tyr
1

<210> SEQ ID NO 131
<211> LENGTH: 4
<212> TYPE: PRT
<213> ORGANISM: Artificial sequence
<220> FEATURE:
<223> OTHER INFORMATION: Predicted proteolytic sites in DSP107 SIRP-
      alpha-4-1BBL fusion protein

<400> SEQUENCE: 131

Ser Asp Pro Gly
1
```